(12) United States Patent
Yin et al.

(10) Patent No.: US 10,953,036 B2
(45) Date of Patent: Mar. 23, 2021

(54) COMPOSITIONS AND METHODS OF MODULATING HIF-2A TO IMPROVE MUSCLE GENERATION AND REPAIR

(71) Applicant: University of Georgia Research Foundation, Inc., Athens, GA (US)

(72) Inventors: Hang Yin, Watkinsville, GA (US); Liwei Xie, Athens, GA (US); Amelia Yao-Ye Yin, Watkinsville, GA (US)

(73) Assignee: UNIVERSITY OF GEORGIA RESEARCH FOUNDATION, INC., Athens, GA (US)

(*) Notice: Subject to any disclaimer, the term of this patent is extended or adjusted under 35 U.S.C. 154(b) by 0 days.

(21) Appl. No.: 16/197,023

(22) Filed: Nov. 20, 2018

(65) Prior Publication Data

US 2019/0151347 A1    May 23, 2019

Related U.S. Application Data

(60) Provisional application No. 62/588,786, filed on Nov. 20, 2017.

(51) Int. Cl.
| | |
|---|---|
| *A61K 31/7105* | (2006.01) |
| *A61K 31/015* | (2006.01) |
| *A61K 31/277* | (2006.01) |
| *A61P 25/14* | (2006.01) |
| *A61P 21/04* | (2006.01) |
| *A61K 9/00* | (2006.01) |
| *C12Q 1/6876* | (2018.01) |

(52) U.S. Cl.
CPC ........ *A61K 31/7105* (2013.01); *A61K 9/0019* (2013.01); *A61K 31/015* (2013.01); *A61K 31/277* (2013.01); *A61P 21/04* (2018.01); *A61P 25/14* (2018.01); *C12Q 1/6876* (2013.01)

(58) Field of Classification Search
CPC .......... A61K 35/34; A61P 21/00; A61P 35/00; A61P 43/00; C12N 15/111; C12N 15/8257
USPC ........... 514/1, 2, 44 A; 435/6.1, 91.1, 91.31, 435/455, 458; 536/23.1, 24.5
See application file for complete search history.

(56) References Cited

U.S. PATENT DOCUMENTS

| | | |
|---|---|---|
| 5,034,506 A | 7/1991 | Summerton |
| 5,142,047 A | 8/1992 | Summerton |
| 5,166,315 A | 11/1992 | Summerton |
| 5,217,866 A | 6/1993 | Summerton |
| 5,356,802 A | 10/1994 | Chandrasegaran |
| 5,436,150 A | 7/1995 | Chandrasegaran |
| 5,487,994 A | 1/1996 | Chandrasegaran |
| 5,506,337 A | 4/1996 | Summerton |
| 5,521,063 A | 5/1996 | Summerton |
| 5,527,675 A | 6/1996 | Coull |
| 5,539,082 A | 7/1996 | Nielsen |
| 5,623,049 A | 4/1997 | Lobberding |
| 5,698,685 A | 12/1997 | Summerton |
| 5,714,331 A | 2/1998 | Buchardt |
| 5,736,336 A | 4/1998 | Buchardt |
| 5,773,571 A | 6/1998 | Nielsen |
| 5,786,571 A | 7/1998 | Bethel |
| 5,948,433 A | 9/1999 | Burton |
| 5,985,311 A | 11/1999 | Cordes |
| 6,140,081 A | 10/2000 | Barbas |
| 6,453,242 B1 | 9/2002 | Eisenburg |
| 6,461,644 B1 | 10/2002 | Jackson |
| 6,534,261 B1 | 3/2003 | Cox, III |
| 6,610,512 B1 | 8/2003 | Barbas |
| 6,676,961 B1 | 1/2004 | Lichter |
| 6,746,838 B1 | 6/2004 | Choo |
| 6,866,997 B1 | 3/2005 | Choo |
| 7,067,617 B2 | 6/2006 | Barbas, III |
| 2002/0165356 A1 | 11/2002 | Barbas |
| 2004/0197892 A1 | 10/2004 | Moore |
| 2007/0154989 A1 | 7/2007 | Barbas |
| 2007/0213269 A1 | 9/2007 | Barbas |

(Continued)

FOREIGN PATENT DOCUMENTS

| | | |
|---|---|---|
| WO | 98/53059 | 11/1998 |
| WO | 9853059 | 11/1998 |

(Continued)

OTHER PUBLICATIONS

Scheuermann et al, Nature Chem. Biol., vol. 9, pp. 271-276. (Year: 2013).*

(Continued)

*Primary Examiner* — Jane J Zara

(74) *Attorney, Agent, or Firm* — Pabst Patent Group LLP

(57) ABSTRACT

Compositions and methods for modulating HIF-2α to meditate of hypoxia signaling in satellite cells and applications thereof for improving skeletal muscle generation and repair are provided. For example, methods of enhancing, increasing, accelerating or/and otherwise improving skeletal muscle generation or regeneration in a subject in need thereof are disclosed. In some embodiments, the methods include administering the subject an effective amount of HIF-2α inhibitor. The HIF-2α inhibitor can be effective to, for example, increase muscle satellite cell proliferation, differentiation, or a combination thereof in a subject. Composition and methods for improving respiration, and reducing or preventing the development or progression of fibrosis are also provided. The disclosed compositions and methods are particularly useful for treating muscular dystrophies, myopathies, and other muscle-related diseases and disorders.

20 Claims, 19 Drawing Sheets

Specification includes a Sequence Listing.

(56) References Cited

U.S. PATENT DOCUMENTS

| | | | |
|---|---|---|---|
| 2009/0176745 | A1 | 7/2009 | Arbiser |
| 2011/0145940 | A1 | 6/2011 | Voytas |
| 2011/0301122 | A1 | 12/2011 | Haerter |
| 2011/0312930 | A1 | 12/2011 | Haerter |
| 2013/0196964 | A1 | 8/2013 | Haerter |
| 2015/0125427 | A1 | 5/2015 | Rudnicki |
| 2015/0218098 | A1 | 8/2015 | Gardner |
| 2016/0251307 | A1 | 9/2016 | Dixon |
| 2016/0362390 | A1 | 12/2016 | Wehn |
| 2016/0368893 | A1 | 12/2016 | Dixon |
| 2017/0217891 | A1 | 8/2017 | Dixon |
| 2018/0042884 | A1 | 2/2018 | Josey |
| 2018/0049995 | A1 | 2/2018 | Dixon |
| 2018/0140569 | A1 | 5/2018 | Josey |
| 2018/0148413 | A1 | 5/2018 | Wehn |
| 2018/0155279 | A1 | 6/2018 | Dixon |
| 2018/0162807 | A1 | 6/2018 | Dixon |
| 2018/0177754 | A1 | 6/2018 | Josey |

FOREIGN PATENT DOCUMENTS

| | | |
|---|---|---|
| WO | 02/44321 | 6/2002 |
| WO | 0244321 | 6/2002 |
| WO | 2003/016496 | 2/2003 |
| WO | 2003016496 | 2/2003 |
| WO | 2010/0054762 | 5/2010 |
| WO | 2010/0054763 | 5/2010 |
| WO | 2010/0054764 | 5/2010 |
| WO | 2010054762 | 5/2010 |
| WO | 2010054763 | 5/2010 |
| WO | 2010054764 | 5/2010 |
| WO | 2011/072246 | 7/2010 |
| WO | 2011072246 | 6/2011 |
| WO | 2013/176772 | 11/2013 |
| WO | 2013176772 | 11/2013 |
| WO | 2014/018423 | 1/2014 |
| WO | 2014018423 | 1/2014 |
| WO | 2015/035223 | 3/2015 |
| WO | 2015035223 | 3/2015 |
| WO | 2015/095048 | 6/2015 |
| WO | 2015095048 | 6/2015 |
| WO | 2016/144825 | 9/2016 |
| WO | 2016/144826 | 9/2016 |
| WO | 2016/145032 | 9/2016 |
| WO | 2016/145045 | 9/2016 |
| WO | 2016/145236 | 9/2016 |
| WO | 2016144825 | 9/2016 |
| WO | 2016144826 | 9/2016 |
| WO | 2016145032 | 9/2016 |
| WO | 2016145045 | 9/2016 |
| WO | 2016145236 | 9/2016 |
| WO | 2016/168510 | 10/2016 |
| WO | 2016168510 | 10/2016 |

OTHER PUBLICATIONS

Xu et al, J. Medicinal Chem., vol. 62, pp. 6876-6893. (Year: 2019).*
Abou-Khalil et al., "Autocrine and paracrine angiopoietin 1/Tie-2 signaling promotes muscle satellite cell self-renewal", Cell Stem Cell, 5(3):298-309 (2009).
Agrawal et al., "Cell-cycle kinetics and VSV-G pseudotyped retrovirus-mediated gene transfer in blood-derived CD34+ cells", Exper. Hematol., 24:738-747 (1996).
Bareja et al., "Human and mouse skeletal muscle stem cells: convergent and divergent mechanisms of myogenesis", PLoS ONE., 9(2):e90398 (2014).
Barka et al., "Transduction of TAT-HA-beta-galactosidase fusion protein into salivary gland-derived cells and organ cultures of the developing gland, and into rat submandibular gland in vivo", Histochem. Cytochem., 48(11):1453-60 (2000).
Bernstein et al., "Role for a bidentate ribonuclease in the initiation step of RNA interference", Nature, 409:363-6 (2001).
Boekstegers, et al., "Oxygen partial pressure distribution within skeletal muscle: indicator of whole body oxygen delivery in patients", Adv. Exp. Med. Biol., 277:507-14 (1990).
Bonnemann, "The collagen VI-related myopathies: muscle meets its matrix", Nat. Rev. Neurol. 7(7):379-390 (2011).
Braasch, et al., "Locked nucleic acid (LNA): fine-tuning the recognition of DNA and RNA", Chem. Biol., 8(1):1-7 (2001).
Burns et al., "Sensorimotor control of breathing in the mdx mouse model of Duchenne muscular dystrophy", J Physiol. 595(21):6653-6672 (2017).
Call et al., "Eccentric Contraction-Induced Muscle Injury: Reproducible, Quantitative, Physiological Models to Impair Skeletal Muscle's Capacity to Generate Force", Methods Mol. Biol., 1460:3-18 (2016).
Carillo et al., "The Multiple Sequence Alignment Problem in Biology", SIAM J Applied Math., 48(5):1073-1082 (1988).
Castiglioni et al., "Isolation of progenitors that exhibit myogenic/osteogenic bipotency in vitro by fluorescence-activated cell sorting from human fetal muscle", Stem Cell Reports, 2(1):92-106 (2014).
Cermak et al, "Efficient design and assembly of custom TALEN and other TAL effector-based constructs for DNA targeting", Nucl. Acids Res., 39(12)e82 (2011).
Chaillou et al., "Ambient hypoxia enhances the loss of muscle mass after extensive injury", Pflugers Arch 466:587-598 (2014).
Chaillou et al., "Regulation of myogenesis and skeletal muscle regeneration: effects of oxygen levels on satellite cell activity", FASEB J., 30(12):3929-41 (2016).
Chakkalakal et al., "The aged niche disrupts muscle stem cell quiescence", Nature, 490(7420):355-60 (2012).
Chen et al., "Early onset of inflammation and later involvement of TGFbeta in Duchenne muscular dystrophy", Neurology, 65(6):826-834 (2005).
Chen et al., "Expression profiling in the muscular dystrophies: identification of novel aspects of molecular pathophysiology", J. Cell Biol., 151(6):1321-36 (2000).
Chen et al., "EAF2 suppresses hypoxia-induced factor 1 α transcriptional activity by disrupting its interaction with coactivator CBP/p300", Mol. Cell Biol., 34(6):1085-99 (2014).
Chen et al., "Targeting renal cell carcinoma with a HIF-2 antagonist", Nature, 539(7627):112-117 (2016).
Cheung et al., "Maintenance of muscle stem-cell quiescence by microRNA-489", Nature, 482(7386):524-8 (2012).
Cho et al., "On-target efficacy of a HIF-2α antagonist in preclinical kidney cancer models", Nature, 539(7627):107-111 (2016).
Christov et al., "Muscle satellite cells and endothelial cells: close neighbors and privileged partners", Mol. Biol. Cell, 18(4):1397-409 (2007).
Cong, "Multiplex genome engineering using CRISPR/Cas systems", Science, 339(6121):819-823 (2013).
Cosgrove et al., "Rejuvenation of the muscle stem cell population restores strength to injured aged muscles", Nat Med., 20(3):255-64 (2014).
Crist, et al., "Muscle satellite cells are primed for myogenesis but maintain quiescence with sequestration of Myf5 mRNA targeted by microRNA-31 in mRNP granules", Cell Stem Cell, 11(1):118-26 (2012).
Dadgar et al., "Asynchronous remodeling is a driver of failed regeneration in Duchenne muscular dystrophy", J Cell Biol., 207(1)139-158 (2014).
Darabi et al., "Human ES- and iPS-derived myogenic progenitors restore Dystrophin and improve contractility upon transplantation in dystrophic mice", Cell Stem Cell., 10:610-619 (2012).
Darby et al., "Hypoxia in tissue repair and fibrosis", Cell Tissue Res 365,553-562, doi:10.1007/s00441-016-2461-3 (2016).
Das et al., "HIF-2α suppresses p53 to enhance the stemness and regenerative potential of human embryonic stem cells", Stem Cells, 30(8):1685-95 (2012).
Deal et al., "A simple method for gene expression and chromatin profiling of individual cell types within a tissue", Dev Cell, 18(6):1030-40 (2010).
Dempsey et al., "Humans in Hypoxia: A Conspiracy of Maladaptation", Physiology (Bethesda) 30(4):304-316 (2015).

(56) References Cited

OTHER PUBLICATIONS

Derossi et al., "The third helix of the Antennapedia homeodomain translocates through biological membranes", *J Biol Chem.*, 269(14):10444-50 (1994).
Ehrhardt et al., "Human muscle precursor cells give rise to functional satellite cells in vivo.", *Neuromuscul. Disord.*, 17(8):631-638 (2007).
Elbashir, et al. "RNA interference is mediated by 21- and 22-nucleotide RNAs", *Genes Dev.*, 15:188-200 (2001).
Elbashir, et al. "Duplexes of 21-nucleotide RNAs mediate RNA interference in cultured mammalian cells", *Nature*, 411:494-498 (2001).
Farkas, et al., "Episodic hypoxia exacerbates respiratory muscle dysfunction in DMD(mdx) mice", *Muscle Nerve*, 36:708-710 (2007).
Fire, et al. "Potent and specific genetic interference by double-stranded RNA in Caenorhabditis elegans ", *Nature*, 391:806-811 (1998).
Fox, et al., "Transdermal Drug Delivery Enhancement by Compounds of Natural Origin", *Molecules*, 16(12):10507-10540 (2011).
Frankel, et al., "Cellular uptake of the tat protein from human immunodeficiency virus", *Cell*, 55(6):1189-93(1988).
Fu, et al., "Combination of inflammation-related cytokines promotes long-term muscle stem cell expansion", *Cell Res.*, 25(6):655-73 (2015).
Fukada, et al., "Genetic background affects properties of satellite cells and mdx phenotypes", *Am J Pathol.*, 176:2414-2424 (2010).
Gage, et al., "Whole animal perfusion fixation for rodents", *J Vis Exp.*, (65) pii: 3564., (2012).
Goodell, et al., "Stem cells and healthy aging", *Science*, 350(6265); 1199-204 (2015).
Goodman, et al., "Recombinant adeno-associated virus-mediated gene transfer into hematopoietic progenitor cells", *Blood*, 84(5):1492-1500 (1994).
Hammond, et al. "An RNA-directed nuclease mediates post-transcriptional gene silencing in Drosophila cells ", *Nature*, 404:293-296 (2000).
Hannon, "RNA interference", *Nature*, 418:244-251 (2002).
Hardy, et al., "Comparative Study of Injury Models for Studying Muscle Regeneration in Mice", *PLoS One*, 11(1):e0147198 (2016).
Haslett, et al., "Gene expression comparison of biopsies from Duchenne muscular dystrophy (DMD) and normal skeletal muscle", *PNAS*, 99(23):15000-5 (2002).
Hausburg, et al., "Post-transcriptional regulation of satellite cell quiescence by TTP-mediated mRNA decay", *Elife*, 4:e03390 doi: 10.7554/eLife.03390 (2015).
Hirotani, et al., "Hyperbaric oxygen therapy for muscular dystrophy", *Nihon Geka Hokan*, 43(2):161-167 (1974).
Ho, et al., "Synthetic protein transduction domains: enhanced transduction potential in vitro and in vivo", *Cancer Res.*, 61(2):474-7 (2001).
Holmquist-Mengelbier, et al., "Recruitment of HIF-1alpha and HIF-2alpha to common target genes is differentially regulated in neuroblastoma: HIF-2alpha promotes an aggressive phenotype", *Cancer Cell*, 10(5):413-23 (2006).
Horie et al., "Enhancement of satellite cell differentiation and functional recovery in injured skeletal muscle by hyperbaric oxygen treatment", *J Appl Physiol.*, 116(2):149-155 (1985).
Hu, et al., "The N-terminal transactivation domain confers target gene specificity of hypoxia-inducible factors HIF-1alpha and HIF-2alpha", Mol. Biol. Cell, 18(11):4528-42 (2007).
Ikemoto, et al., "Autologous transplantation of SM/C-2.6(+) satellite cells transduced with micro-dystrophin CS1 cDNA by lentiviral vector into mdx mice", *Mol. Ther.*, 15(12):2178-85 (2007).
Ikossi, et al., "Continuous muscle tissue oxygenation in critically injured patients: a prospective observational study", *J Trauma*, 61(4):780-8; Discussion 788-790 (2006).
Ito, et al, "Enhancement of Satellite Cell Transplantation Efficiency by Leukemia Inhibitory Factor", *Journal of Neuromuscular Diseases*, 3(2):201-207 (2016).
Jinek, et al., "A programmable dual-RNA-guided DNA endonuclease in adaptive bacterial immunity", *Science*, 337(6096):816-821 (2012).
Jones, et al., "The p38alpha/beta MAPK functions as a molecular switch to activate the quiescent satellite cell", *J Cell Biol.*, 169(1):105-16 (2005).
Kabouridis, "Biological applications of protein transduction technology", *Trends in Biotechnology*, 21(11):498-503 (2003).
Keith, et al., "HIF1α and HIF2α: sibling rivalry in hypoxic tumour growth and progression", Nat. Rev. Cancer, 12(1):9-22 (2011).
Kim, et al., "Insertion and Deletion Mutatns of FokI Restriction Endonuclease", *J. Biol. Chem.*, 269(50):31978-31982 (1994b).
Kim, et al., "Chimeric restriction endonuclease ", *Proc. Natl. Acad. Sci.*, 91(3):883-887 (1994a).
Klingler, et al., "The role of fibrosis in Duchenne muscular dystrophy", *Acta Myol*, 31(3):184-195 (2012).
Koh, et al., "The hypoxia-associated factor switches cells from HIF-1α- to HIF-2α-dependent signaling promoting stem cell characteristics, aggressive tumor growth and invasion", Cancer Res., 71(11):4015-27 (2011).
Latil, et al., "Skeletal muscle stem cells adopt a dormant cell state post mortem and retain regenerative capacity", Nat. Commun., 3:903 (2012).
Lewis, et al., "Diaphragm Muscle Adaptation to Sustained Hypoxia: Lessons from Animal Models with Relevance to High Altitude and Chronic Respiratory Diseases", *Front Physiol.* 7:623, doi:10.3389/fphys.2016.00623 (2016).
Li, et al., "Alteration of the cleavage distance of Fok I restriction endonuclease by insertion mutagenesis", *Proc. Natl. Acad. Sci.*, 90(7):2764-2768 (1993).
Li, et al., "Functional domains in Fok I restriction endonuclease", *Proc., Natl. Acad. Sci.*,89:4275-4279 (1992).
Li, "Recent advances in Developing Novel Anti-Cancer Drugs Targeting Tumor Hypoxic and Acidic Microenvironments", *Recent Patents on Anti-Cancer Drug Discovery*, 13(4):455-468 (2018).
Liu, et al., "Hypoxia promotes satellite cell self-renewal and enhances the efficiency of myoblast transplantation", *Development*, 139(16):2857-2865 (2012).
Lo Mauro, et al., "Physiology of respiratory disturbances in muscular dystrophies", *Breathe (Sheff)* 12(4):318-327, doi:10.1183/20734735.012716 (2016).
Majmundar, et al., "HIF modulation of Wnt signaling regulates skeletal myogenesis in vivo", *Development*, 142(14):2405-12 (2015).
Majmundar, et al., "O(2) regulates skeletal muscle progenitor differentiation through phosphatidylinositol 3-kinase/AKT signaling", Mol. Cell Biol., 32(1):36-49 (2012).
Martinez, et al., "Single-stranded antisense siRNAs guide target RNA cleavage in RNAi", Cell, 110:563-574 (2002).
Mathieu, et al., "Hypoxia-inducible factors have distinct and stage-specific roles during reprogramming of human cells to pluripotency", *Cell Stem Cell*, 14(5):592-605 (2014).
Meng, et al., "Human skeletal muscle-derived CD133(+) cells form functional satellite cells after intramuscular transplantation in immunodeficient host mice", *Mol. Ther.*, 22:1008-1017 (2014).
Miller, et al., "A TALE nuclease architecture for efficient genome editing", *Nature Biotechnol.*, 29: 143 (2011).
Miller, et al., "Redesign of retrovirus packaging cell lines to avoid recombination leading to helper virus production", *Mol. Cell. Biol.*, 6:2895 (1986).
Miller, et al., "Myoblast implantation in Duchenne muscular dystrophy: the San Francisco study", *Muscle Nerve.*, 20:469-478 (1997).
Mitani, et al., "Transduction of human bone marrow by adenoviral vector", *Hum. Gene Ther.*, 5(8):941-948 (1994).
Mohlin, et al., "PI3K-mTORC2 but not PI3K-mTORC1 regulates transcription of HIF2A/EPAS1 and vascularization in neuroblastoma", *Cancer Res.*, 75(21):4617-28 (2015).
Mohyeldin, et al., "Oxygen in stem cell biology: a critical component of the stem cell niche", *Cell Stem Cell*, 7(2):150-61 (2010).
Mosqueira, et al., "Chronic hypoxia impairs muscle function in the Drosophila model of Duchenne's muscular dystrophy (DMD)", *PLoS One*, 5(10): e13450, doi:10.1371/journal.pone.0013450 (2010).
Motohashi, et al., "Isolation, Culture, and Transplantation of Muscle Satellite Cells", *J Vis. Exp.*, 8(86):doi: 10.3791/50846 (2014).

(56) References Cited

OTHER PUBLICATIONS

Murphy, et al., "Satellite cells, connective tissue fibroblasts and their interactions are crucial for muscle regeneration", *Development*, 138(17):3625-37 (2011).

Naldini, et al., "In Vivo Gene Delivery and Stable Transduction of Nondividing Cells by a Lentiviral Vector", *Science*, 272:263-267 (1996).

Nakazawa, et al., "Epigenetic re-expression of HIF-2α suppresses soft tissue sarcoma growth", *Nat Commun.*, 7:10539 (2016).

Napoli, et al., "Introduction of a Chimeric Chalcone Synthase Gene into Petunia Results in Reversible Co-Suppression of Homologous Genes in trans", *Plant Cell*, 2:279-89 (1990).

Needelman, "A general method applicable to the search for similarities in the amino acid sequence of two proteins", J. Mol. Biol., 48: 443-453 (1970).

Nykanen, et al. "ATP requirements and small interfering RNA structure in the RNA interference pathway ", *Cell*, 107:309-321 (2001).

Papadopoulous, et al., "A first-in-human phase 1 dose-escalation trial of the oral HIF-2a inhibitor PT2977 in patients with advanced solid tumors", *An American Society of Clinical Oncology Journal*, 36(15_suppl):2508-2508 (2018).

Partridge, "Myoblast transplantation", *Neuromuscul. Disord.*, 12(Suppl 1):S3-S6 (2002).

Pastan et al., "A retrovirus carrying an MDR1 cDNA confers multidrug resistance and polarized expression of P-glycoprotein in MDCK cells", *Proc. Natl. Acad. Sci.*, 85(12):4486-4490 (1988).

Pasut, et al., "Isolation and culture of individual myofibers and their satellite cells from adult skeletal muscle", *J Vis Exp.*, (73):e50074 (2013).

Pathan, et al., "Chemical Penetration Enhancers for Transdermal Drug Delivery Systems", *Tropical Journal of Pharmaceutical Research*, 8(2):173-179 (2009).

Pawlus, et al., "A retrovirus carrying an MDR1 cDNA confers multidrug resistance and polarized expression of P-glycoprotein in MDCK cells", *Oncogene*, 33(13):1670-9 (2014).

Pisani, et al., "Isolation of a highly myogenic CD34-negative subset of human skeletal muscle cells free of adipogenic potential", *Stem Cells*, 28:753-764 (2010).

Qu, et al., "Hypoxia-inducible transcription factor 2α, promotes steatohepatitis through augmenting lipid accumulation, inflammation, and fibrosis", *Hepatology*, 54:472-483, doi:10.1002/hep.24400 (2011).

Quarta, "Mimicking the niche: cytokines expand muscle stem cells", *Cell Res.*, 25(7):761-2 (2015).

Rasbach, et al., "PGC-1alpha regulates a HIF2alpha-dependent switch in skeletal muscle fiber types", *Proc. Natl. Acad. Sci. U S A*, 107(50):21866-71 (2010).

Rodgers, et al., "mTORC1 controls the adaptive transition of quiescent stem cells from G0 to G(Alert)", *Nature*, 510(7505):393-6 (2014).

Ryall, et al., "The NAD(+)-dependent SIRT1 deacetylase translates a metabolic switch into regulatory epigenetics in skeletal muscle stem cells", *Cell Stem Cell*, 16(2):171-83 (2015).

Sacco, et al., "Short telomeres and stem cell exhaustion model Duchenne muscular dystrophy in mdx/mTR mice", *Cell*, 143(7):1059-1071, doi:10.1016/j.cell.2010.11.039 (2010).

Sato, et al., "Respiratory management of patients with Fukuyama congenital muscular dystrophy", *Brain Dev*, 38(3):324-330 doi:10.1016/j.braindev.2015.08.010 (2016).

Scheuermann, et al., "Allosteric inhibition of hypoxia inducible factor-2 with small molecules", *Nat Chem Biol.*, 9(4):271-6 (2013).

Schwarzenberger, et al., "Targeted gene transfer to human hematopoietic progenitor cell lines through the c-kit receptor", *Blood*, 87(2):472-478 (1996).

Seale, et al., "Pax7 is required for the specification of myogenic satellite cells", *Cell*, 102(6):777-86 (2000).

Semenza, "Hypoxia-inducible factors in physiology and medicine", *Cell*, 148(3):399-408 (2012).

Serrano, et al., "Cellular and molecular mechanisms regulating fibrosis in skeletal muscle repair and disease", *Curr. Top. Dev. Biol.* 96:167-201, doi:10.1016/B978-0-12-385940-2.00007-3 (2011).

Shahrizaila et al., "Respiratory involvement in inherited primary muscle conditions", *J Neurol. Neurosurg. Psychiatry*, 77:1108-1115, doi:10.1136/jnnp.2005.078881 (2006).

Shea, et al., "Sprouty1 regulates reversible quiescence of a self-renewing adult muscle stem cell pool during regeneration", *Cell Stem Cell*, 6(2):117-29 (2010).

Shu et al., "Inhibition of the CXCL12/CXCR4-axis as preventive therapy for radiation-induced pulmonary fibrosis", *PLoS One* 8(11):e79768, doi:10.1371/journal.pone.0079768 (2013).

Silva-Barbosa, et al., "Comparative analysis of genetically engineered immunodeficient mouse strains as recipients for human myoblast transplantation", *Cell Transplant*, 14(7):457-467 (2005).

Skuk et al., "Intramuscular transplantation of human postnatal myoblasts generates functional donor-derived satellite cells", *Mol. Ther.*, 18:1689-1697 (2010).

Stanford, et al., "Erratum. Exercise Effects on White Adipose Tissue: Beiging and Metabolic Adaptations", *Diabetes*, 64:2361-2638 (2015).

Stirchak, et al., "Uncharged stereoregular nucleic acid analogs. 1. Synthesis of a cytosine-containing oligomer with carbamate internucleoside linkages", *Organic. Chem.*, 52:4202 (1987).

Takeda, et al., "Endothelial PAS domain protein 1 gene promotes angiogenesis through the transactivation of both vascular endothelial growth factor and its receptor, Flt-1", *Circ. Res.*, 95(2):146-53 (2004).

Tian, et al., "Endothelial PAS domain protein 1 (EPAS1), a transcription factor selectively expressed in endothelial cells", *Genes Dev.*, 11(1):72-82 (1997).

Toschi, et al., "Differential dependence of hypoxia-inducible factors 1 alpha and 2 alpha on mTORC1 and mTORC2", *J Biol. Chem.*, 283(50):34495-9 (2008).

Troy, et al., "Coordination of satellite cell activation and self-renewal by Par-complex-dependent asymmetric activation of p38α/β MAPK", *Cell Stem Cell*, 11(4):541-53 (2012).

Ui-Tei, et al. "Sensitive assay of RNA interference in Drosophila and Chinese hamster cultured cells using firefly luciferase gene as target ", *FEBS Lett.*, 479:79-82 (2000).

Wadia, et al., "Transducible TAT-HA fusogenic peptide enhances escape of TAT-fusion proteins after lipid raft macropinocytosis", *Nat. Med.*, 10(3):310-5 (2004).

Wald, et al., "Involvement of the CXCL12/CXCR4 pathway in the advanced liver disease that is associated with hepatitis C virus or hepatitis B virus", *Eur. J Immunol.*, 34(4):1164-1174, doi:10.1002/eji.200324441 (2004).

Wallace, "PT2385:First-In-Class HIF-2α Antagonist for the Treatment of Renal Cell Carcinoma", *AACR 106th Annual Meeting*, 75(15) (2015).

Wender, et al., "The design, synthesis, and evaluation of molecules that enable or enhance cellular uptake: peptoid molecular transporters", *Proc. Natl. Acad. Sci. U S A.*, 97(24):13003-8 (2000).

Xie, et al., "Transient HIF2A inhibition promotes satellite cell proliferation and muscle regeneration", *J Clin. Invest.*, 128(6):2339-2355 (2018).

Xu, et al., "Human Satellite Cell Transplantation and Regeneration from Diverse Skeletal Muscles", *Stem Cell Reports*, 5(3): 419-434 (2015).

Yamaguchi, et al., "Calcitonin Receptor Signaling Inhibits Muscle Stem Cells from Escaping the Quiescent State and the Niche", *Cell Rep.*, 13(2):302-14 (2015).

Yang, et al., "The hypoxia-inducible factors HIF1α and HIF2α are dispensable for embryonic muscle development but essential for postnatal muscle regeneration", *J Biol. Chem.*, 292(14):5981-91 (2017).

Yin, et al., "Satellite cells and the muscle stem cell niche", *Physiol. Rev.*, 93(1):23-67 (2013).

Zammit, et al., "Muscle satellite cells adopt divergent fates: a mechanism for self-renewal", J Cell. Biol., 166(3):347-57 (2004).

International Search Report PCT/US2018/061971 dated Feb. 15, 2019.

(56) References Cited

OTHER PUBLICATIONS

Kim, et al., "Insertion and Deletion Mutatns of FokI Restriction Endonuclease", J. Biol. Chem., 269(50):31978-31982 (1994b).
Rasbach, et al., "PGC-1alpha regulates a HIF2alpha-dependent switch in skeletal muscle fiber types", Proc. Natl. Acad. Sci. U S A, 107(50):21866-71 (2010).

* cited by examiner

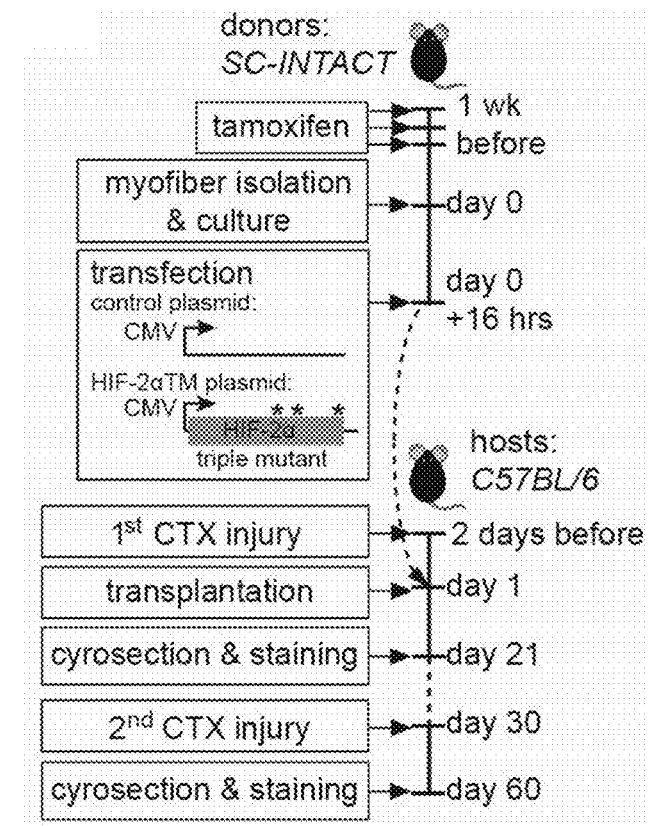
FIG. 3G
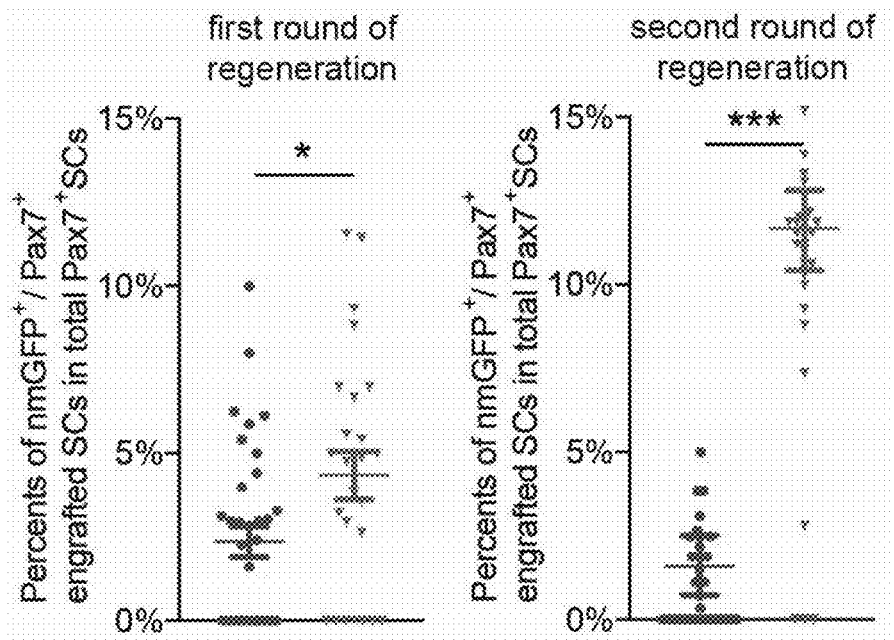
FIG. 3H
FIG. 3I

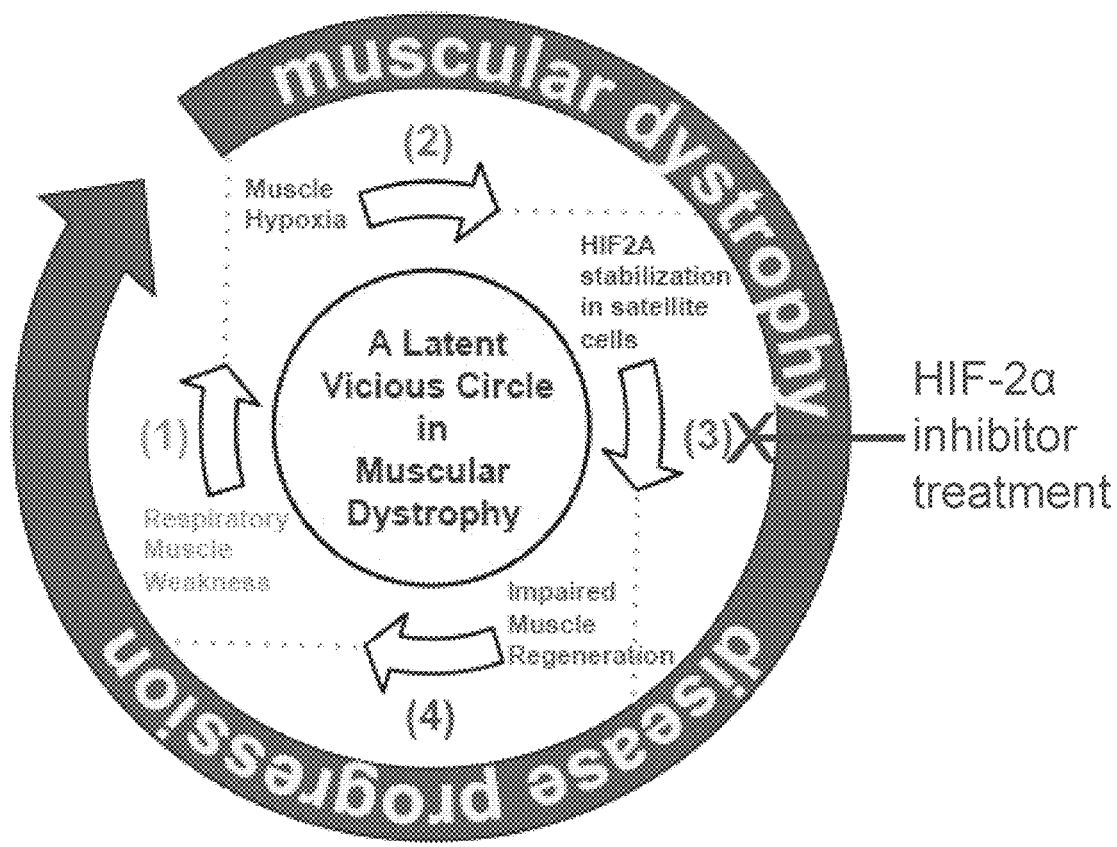
FIG. 7
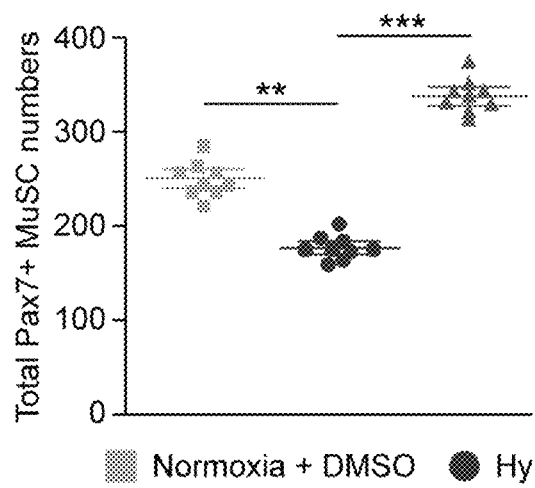
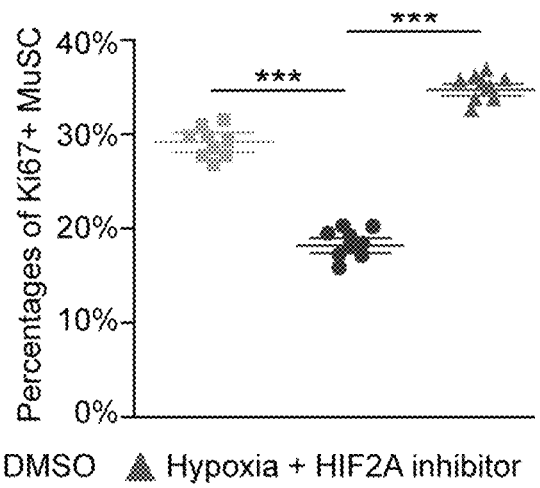
FIG. 8A
FIG. 8B

SEQUENCE LISTING

<160> NUMBER OF SEQ ID NOS: 39

<210> SEQ ID NO 1
<211> LENGTH: 5184
<212> TYPE: DNA
<213> ORGANISM: Homo sapiens

<400> SEQUENCE: 1

| | | | | | |
|---|---|---|---|---|---|
| gctttacact | cgcgagcgga | ccgccacacg | ggtccggtgc | ccgctgcgct | tccgcccag | 60 |
| cgctcctgag | gcggccgtac | aatcctcggc | agtgtcctga | gactgtatgg | tcagctcagc | 120 |
| ccggcctccg | actccttccg | actcccagca | ttcgagccac | ttttttttt | ctttgaaaac | 180 |
| tcagaaaagt | gactcctttt | ccagggaaaa | aggaacttgg | gttcccttct | ctccgtcctc | 240 |
| ttttcgggtc | tgacagcctc | cacccactcc | ttccccggac | cccgcctccg | cgcgcaggtt | 300 |
| cctcccagtc | acctttctcc | accccgccc | ccgcacctag | cccgccgcgc | gccaccttcc | 360 |
| acctgactgc | gcggggcgct | cgggacctgc | gcgcacctcg | gaccttcacc | acccgccgg | 420 |
| gccgcgggga | gcggacgagg | gccacagccc | cccacccgcc | agggagccca | ggtgctcggc | 480 |
| gtctgaacgt | ctcaaagggc | cacagcgaca | atgacagctg | acaaggagaa | gaaaaggagt | 540 |
| agctcggaga | ggaggaagga | gaagtcccgg | gatgctgcgc | ggtgccggcg | gagcaaggag | 600 |
| acggaggtgt | tctatgagct | ggcccatgag | ctgcctctgc | ccacagtgt | gagctcccat | 660 |
| ctggacaagg | cctccatcat | gcgactggca | atcagcttcc | tgcgaacaca | caagctcctc | 720 |
| tcctcagttt | gctctgaaaa | cgagtccgaa | gccgaagctg | accagcagat | ggacaacttg | 780 |
| tacctgaaag | ccttggaggg | tttcattgcc | gtggtgaccc | aagatggcga | catgatcttt | 840 |
| ctgtcagaaa | acatcagcaa | gttcatggga | cttacacagg | tggagctaac | aggacatagt | 900 |
| atctttgact | tcactcatcc | ctgcgaccat | gaggagattc | gtgagaacct | gagtctcaaa | 960 |
| aatggctctg | gttttgggaa | aaaaagcaaa | gacatgtcca | cagagcggga | cttcttcatg | 1020 |
| aggatgaagt | gcacggtcac | caacagaggc | cgtactgtca | acctcaagtc | agccacctgg | 1080 |
| aaggtcttgc | actgcacggg | ccaggtgaaa | gtctacaaca | actgccctcc | tcacaatagt | 1140 |
| ctgtgtggct | acaaggagcc | cctgctgtcc | tgcctcatca | tcatgtgtga | accaatccag | 1200 |
| cacccatccc | acatggacat | cccccctggat | agcaagacct | tcctgagccg | ccacagcatg | 1260 |
| gacatgaagt | tcacctactg | tgatgacaga | atcacagaac | tgattggtta | ccaccctgag | 1320 |
| gagctgcttg | gccgctcagc | ctatgaattc | taccatgcgc | tagactccga | gaacatgacc | 1380 |
| aagagtcacc | agaacttgtg | caccaagggt | caggtagtaa | gtggccagta | ccggatgctc | 1440 |
| gcaaagcatg | ggggctacgt | gtggctggag | acccagggga | cggtcatcta | caaccctcgc | 1500 |
| aacctgcagc | cccagtgcat | catgtgtgtc | aactacgtcc | tgagtgagat | tgagaagaat | 1560 |
| gacgtggtgt | tctccatgga | ccagactgaa | tccctgttca | agccccacct | gatggccatg | 1620 |
| aacagcatct | ttgatagcag | tggcaagggg | gctgtgtctg | agaagagtaa | cttcctattc | 1680 |
| accaagctaa | aggaggagcc | cgaggagctg | gcccagctgg | ctcccacccc | aggagacgcc | 1740 |
| atcatctctc | tggatttcgg | gaatcagaac | ttcgaggagt | cctcagccta | tggcaaggcc | 1800 |
| atcctgcccc | cgagccagcc | atgggccacg | gagttgagga | gccacagcac | ccagagcgag | 1860 |
| gctgggagcc | tgcctgcctt | caccgtgccc | caggcagctg | cccggggcag | caccacccc | 1920 |
| agtgccacca | gcagcagcag | cagctgctcc | acgcccaata | gccctgaaga | ctattacaca | 1980 |
| tctttggata | cgaccgtgaa | gattgaagtg | attgagaagc | tcttcgccat | ggacacagag | 2040 |
| gccaaggacc | aatgcagtac | ccagacggat | ttcaatgagc | tggacttgga | gacactggca | 2100 |

```
ccctatatcc ccatggacgg ggaagacttc cagctaagcc ccatctgccc cgaggagcgg    2160
ctcttggcgg agaacccaca gtccacccccc cagcactgct tcagtgccat gacaaacatc   2220
ttccagccac tggcccctgt agcccgcac agtcccttcc tcctggacaa gtttcagcag     2280
cagctggaga gcaagaagac agagcccgag caccggccca tgtcctccat cttctttgat    2340
gccggaagca aagcatccct gccaccgtgc tgtggccagg ccagcacccc tctctcttcc    2400 atgggggca gatccaatac ccagtggccc ccagatccac cattacattt tgggcccaca    2460
aagtgggccg tcgggatca gcgcacagag ttcttgggag cagcgccgtt ggggccccct    2520
gtctctccac cccatgtctc caccttcaag acaaggtctg caaagggttt tggggctcga    2580
ggcccagacg tgctgagtcc ggccatggta gccctctcca caagctgaa gctgaagcga     2640 cagctggagt atgaagagca agccttccag gacctgagcg gggggaccc acctggtggc     2700 agcacctcac atttgatgtg gaaacggatg aagaacctca ggggtgggag ctgccctttg    2760
atgccggaca agccactgag cgcaaatgta cccaatgata agttcaccca aaaccccatg    2820
aggggcctgg gccatcccct gagacatctg ccgctgccac agcctccatc tgccatcagt    2880
cccggggaga cagcaagag caggttcccc ccacagtgct acgccaccca gtaccaggac     2940
tacagcctgt cgtcagccca aaggtgtca ggcatggcaa gccggctgct cgggccctca     3000
tttgagtcct acctgctgcc cgaactgacc agatatgact gtgaggtgaa cgtgcccgtg    3060
ctgggaagct ccacgctcct gcaaggaggg gacctcctca gagccctgga ccaggccacc    3120
tgagccaggc cttctacctg ggcagcacct ctgccgacgc cgtcccacca gcttcactct    3180
ctccgtctgt ttttgcaact aggtatttct aacgccagca cactatttac aagatggact    3240
tacctggcag acttgcccag gtcaccaagc agtggccttt ttctgagatg ctcactttat    3300
tatccctatt tttaaagtac acaattgttt tacctgttct gaaatgttct taaattttgt    3360
aggatttttt tcctccccac cttcaatgac ttctaattta tattatccat aggtttctct    3420
ccctccttct ccttctcaca cacaactgtc catactaaca agtttggtgc atgtctgttc    3480
ttctgtaggg agaagcttta gcttcatttt actaaaaaga ttcctcgtta ttgttgttgc     3540
caaagagaaa caaaaatgat tttgctttcc aagcttggtt tgtggcgtct ccctcgcaga     3600
gcccttctcg tttctttttt aaactaatca ccatattgta aatttcaggg ttttttttt      3660 tttgtttaag ctgactcttt gctctaattt tggaaaaaaa gaaatgtgaa gggtcaactc     3720
caacgtatgt ggttatctgt gaaagttgca cagcgtggct tttcctaaac tggtgttttt    3780
cccccgcatt tggtggattt tttattatta ttcaaaaaca taactgagtt tttttaaaga    3840
ggagaaaatt tatatctggg ttaagtgttt atcatatata tgggtacttt gtaatatcta    3900
aaaacttaga aacggaaatg gaatcctgct cacaaaatca ctttaagatc ttttcgaagc    3960
tgttaatttt tcttagtgtt gtggacactg cagacttgtc cagtgctccc acggcctgta    4020
cggacactgt ggaaggcctc cctctgtcgg cttttttgcca tctgtgatat gccataggtg    4080
tgacaatccg agcagtggag tcattcagcg ggagcactgc gcgctatccc ctcacattct    4140
ctatgtacta tgtatgtatg tattattatt attgctgcca agagggtctg atggcacgtt    4200
gtggggtcgg ggggtggggc ggggaagtgc tctaacttttt cttaaggttt tgttgctagc    4260
ccttcaagtg cactgagcta tgtgactcgg atggtctttc acacggcaca tttggacatt    4320
tccagaacta ccatgagatg gtttagacgg gaattcatgc aaatgagggg tcaaaaatgg    4380
tatagtgacc ccgtccacgt cctccaagct cacgaccttg agcccgtg gagctggact       4440
```

-continued

```
gaggaggagg ctgcacagcg ggagagcagc tggtccagac cagccctgca gcccccactc    4500
agccggcagc cagatggccc cgcaaggcct ccagggatgg cccctagcca caggccctgg    4560
ctgaggtctc tgggtcggtc agtgacatgt aggtaggaag cactgaaaat agtgttccca    4620
gagcactttg caactccctg gtaagaggg acgacacctc tggttttca ataccaatta    4680 catggaactt ttctgtaatg ggtacaatga agaagtttct aaaaacacac acaaagcaca    4740
ttgggccaac tatttagtaa gcccggatag acttattgcc aaaaacaaaa aatagctttc    4800
aaaagaaatt taagttctat gagaaattcc ttagtcatgg tgttgcgtaa atcatatttt    4860
agctgcacgg cattacccca cacagggtgg cagaacttga agggttactg acgtgtaaat    4920
gctggtattt gatttcctgt gtgtgttgcc ctggcattaa gggcatttta cccttgcagt    4980
tttactaaaa cactgaaaaa tattccaagc ttcatattaa ccctacctgt caacgtaacg    5040
atttcatgaa cgttattata ttgtcgaatt cctactgaca acattataac tgtatgggag    5100
cttaacttta taaggaaatg tattttgaca ctggtatctt attaaagtat tctgatccta    5160
ccactgaaaa aaaaaaaaaa aaaa                                           5184
```

<210> SEQ ID NO 2
<211> LENGTH: 870
<212> TYPE: PRT
<213> ORGANISM: Homo sapiens

<400> SEQUENCE: 2

```
Met Thr Ala Asp Lys Glu Lys Arg Ser Ser Glu Arg Arg Lys
1               5                   10                  15

Glu Lys Ser Arg Asp Ala Ala Arg Cys Arg Arg Ser Lys Glu Thr Glu
                20                  25                  30

Val Phe Tyr Glu Leu Ala His Glu Leu Pro Leu Pro His Ser Val Ser
            35                  40                  45

Ser His Leu Asp Lys Ala Ser Ile Met Arg Leu Ala Ile Ser Phe Leu
        50                  55                  60

Arg Thr His Lys Leu Leu Ser Ser Val Cys Ser Glu Asn Glu Ser Glu
65                  70                  75                  80

Ala Glu Ala Asp Gln Gln Met Asp Asn Leu Tyr Leu Lys Ala Leu Glu
                85                  90                  95

Gly Phe Ile Ala Val Val Thr Gln Asp Gly Asp Met Ile Phe Leu Ser
            100                 105                 110

Glu Asn Ile Ser Lys Phe Met Gly Leu Thr Gln Val Glu Leu Thr Gly
        115                 120                 125

His Ser Ile Phe Asp Phe Thr His Pro Cys Asp His Glu Glu Ile Arg
    130                 135                 140

Glu Asn Leu Ser Leu Lys Asn Gly Ser Gly Phe Gly Lys Lys Ser Lys
145                 150                 155                 160

Asp Met Ser Thr Glu Arg Asp Phe Phe Met Arg Met Lys Cys Thr Val
                165                 170                 175

Thr Asn Arg Gly Arg Thr Val Asn Leu Lys Ser Ala Thr Trp Lys Val
            180                 185                 190

Leu His Cys Thr Gly Gln Val Lys Val Tyr Asn Asn Cys Pro Pro His
        195                 200                 205

Asn Ser Leu Cys Gly Tyr Lys Glu Pro Leu Leu Ser Cys Leu Ile Ile
    210                 215                 220

Met Cys Glu Pro Ile Gln His Pro Ser His Met Asp Ile Pro Leu Asp
225                 230                 235                 240
```

```
Ser Lys Thr Phe Leu Ser Arg His Ser Met Asp Lys Phe Thr Tyr
            245                 250                 255

Cys Asp Asp Arg Ile Thr Glu Leu Ile Gly Tyr His Pro Glu Leu
        260                 265                 270

Leu Gly Arg Ser Ala Tyr Glu Phe Tyr His Ala Leu Asp Ser Glu Asn
            275                 280                 285

Met Thr Lys Ser His Gln Asn Leu Cys Thr Lys Gly Gln Val Val Ser
    290                 295                 300

Gly Gln Tyr Arg Met Leu Ala Lys His Gly Tyr Val Trp Leu Glu
305                 310                 315                 320

Thr Gln Gly Thr Val Ile Tyr Asn Pro Arg Asn Leu Gln Pro Gln Cys
                325                 330                 335

Ile Met Cys Val Asn Tyr Val Leu Ser Glu Ile Glu Lys Asn Asp Val
                340                 345                 350

Val Phe Ser Met Asp Gln Thr Glu Ser Leu Phe Lys Pro His Leu Met
            355                 360                 365

Ala Met Asn Ser Ile Phe Asp Ser Ser Gly Lys Gly Ala Val Ser Glu
    370                 375                 380

Lys Ser Asn Phe Leu Phe Thr Lys Leu Lys Glu Glu Pro Glu Glu Leu
385                 390                 395                 400

Ala Gln Leu Ala Pro Thr Pro Gly Asp Ala Ile Ile Ser Leu Asp Phe
                405                 410                 415

Gly Asn Gln Asn Phe Glu Glu Ser Ser Ala Tyr Gly Lys Ala Ile Leu
            420                 425                 430

Pro Pro Ser Gln Pro Trp Ala Thr Glu Leu Arg Ser His Ser Thr Gln
            435                 440                 445

Ser Glu Ala Gly Ser Leu Pro Ala Phe Thr Val Pro Gln Ala Ala Ala
    450                 455                 460

Pro Gly Ser Thr Thr Pro Ser Ala Thr Ser Ser Ser Ser Cys Ser
465                 470                 475                 480

Thr Pro Asn Ser Pro Glu Asp Tyr Tyr Thr Ser Leu Asp Asn Asp Leu
            485                 490                 495

Lys Ile Glu Val Ile Glu Lys Leu Phe Ala Met Asp Thr Glu Ala Lys
        500                 505                 510

Asp Gln Cys Ser Thr Gln Thr Asp Phe Asn Glu Leu Asp Leu Glu Thr
    515                 520                 525

Leu Ala Pro Tyr Ile Pro Met Asp Gly Glu Asp Phe Gln Leu Ser Pro
    530                 535                 540

Ile Cys Pro Glu Glu Arg Leu Leu Ala Glu Asn Pro Gln Ser Thr Pro
545                 550                 555                 560

Gln His Cys Phe Ser Ala Met Thr Asn Ile Phe Gln Pro Leu Ala Pro
                565                 570                 575

Val Ala Pro His Ser Pro Phe Leu Leu Asp Lys Phe Gln Gln Gln Leu
            580                 585                 590

Glu Ser Lys Lys Thr Glu Pro Glu His Arg Pro Met Ser Ser Ile Phe
        595                 600                 605

Phe Asp Ala Gly Ser Lys Ala Ser Leu Pro Pro Cys Cys Gly Gln Ala
    610                 615                 620

Ser Thr Pro Leu Ser Ser Met Gly Gly Arg Ser Asn Thr Gln Trp Pro
625                 630                 635                 640

Pro Asp Pro Pro Leu His Phe Gly Pro Thr Lys Trp Ala Val Gly Asp
                645                 650                 655

Gln Arg Thr Glu Phe Leu Gly Ala Ala Pro Leu Gly Pro Pro Val Ser
```

-continued

```
                    660                 665                 670
Pro Pro His Val Ser Thr Phe Lys Thr Arg Ser Ala Lys Gly Phe Gly
                675                 680                 685
Ala Arg Gly Pro Asp Val Leu Ser Pro Ala Met Val Ala Leu Ser Asn
            690                 695                 700
Lys Leu Lys Leu Lys Arg Gln Leu Glu Tyr Glu Gln Ala Phe Gln
705                 710                 715                 720
Asp Leu Ser Gly Gly Asp Pro Pro Gly Gly Ser Thr Ser His Leu Met
                725                 730                 735
Trp Lys Arg Met Lys Asn Leu Arg Gly Gly Ser Cys Pro Leu Met Pro
                740                 745                 750
Asp Lys Pro Leu Ser Ala Asn Val Pro Asn Asp Lys Phe Thr Gln Asn
            755                 760                 765
Pro Met Arg Gly Leu Gly His Pro Leu Arg His Leu Pro Leu Pro Gln
        770                 775                 780
Pro Pro Ser Ala Ile Ser Pro Gly Glu Asn Ser Lys Ser Arg Phe Pro
785                 790                 795                 800
Pro Gln Cys Tyr Ala Thr Gln Tyr Gln Asp Tyr Ser Leu Ser Ser Ala
                805                 810                 815
His Lys Val Ser Gly Met Ala Ser Arg Leu Leu Gly Pro Ser Phe Glu
                820                 825                 830
Ser Tyr Leu Leu Pro Glu Leu Thr Arg Tyr Asp Cys Glu Val Asn Val
            835                 840                 845
Pro Val Leu Gly Ser Ser Thr Leu Leu Gln Gly Gly Asp Leu Leu Arg
        850                 855                 860
Ala Leu Asp Gln Ala Thr
865                 870

<210> SEQ ID NO 3
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 3

Tyr Gly Arg Lys Lys Arg Arg Gln Arg Arg
1               5                   10

<210> SEQ ID NO 4
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 4

Arg Lys Lys Arg Arg Gln Arg Arg Arg
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 5

Arg Arg Arg Arg Arg Arg Arg
1               5
```

<210> SEQ ID NO 6
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 6

Arg Arg Gln Arg Arg Thr Ser Lys Leu Met Lys Arg
1               5                   10

<210> SEQ ID NO 7
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 7

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 8
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 8

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 9
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 10

Pro Lys Lys Lys Arg Lys Val
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic polypeptide

```
<400> SEQUENCE: 11

Gly Lys Lys Arg Ser Lys Val
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 12

Lys Ser Arg Lys Arg Lys Leu
1               5

<210> SEQ ID NO 13
<211> LENGTH: 19
<212> TYPE: PRT
<213> ORGANISM: Artificial Sequence
<220> FEATURE:
<223> OTHER INFORMATION: synthetic polypeptide

<400> SEQUENCE: 13

Lys Arg Pro Ala Ala Thr Lys Lys Ala Gly Gln Ala Lys Lys Lys
1               5                   10                  15

Leu Asp Lys

<210> SEQ ID NO 14
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 14

Arg Lys Lys Arg Lys Thr Glu Glu Glu Ser Pro Leu Lys Asp Lys Ala
1               5                   10                  15

Lys Lys Ser Lys
            20

<210> SEQ ID NO 15
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 15

Lys Asp Cys Val Met Asn Lys His His Arg Asn Arg Cys Gln Tyr Cys
1               5                   10                  15

Arg Leu Gln Arg
            20

<210> SEQ ID NO 16
<211> LENGTH: 9
<212> TYPE: PRT
<213> ORGANISM: Artificial Sequence
<220> FEATURE:
<223> OTHER INFORMATION: syntehtic polypeptide

<400> SEQUENCE: 16

Pro Ala Ala Lys Arg Val Lys Leu Asp
1               5
```

<210> SEQ ID NO 17
<211> LENGTH: 20
<212> TYPE: PRT
<213> ORGANISM: Artificial Sequence
<220> FEATURE:
<223> OTHER INFORMATION: syntehtic polypeptide

<400> SEQUENCE: 17

Lys Lys Tyr Glu Asn Val Val Ile Lys Arg Ser Pro Arg Lys Arg Gly
1               5                   10                  15

Arg Pro Arg Lys
            20

<210> SEQ ID NO 18
<211> LENGTH: 97
<212> TYPE: DNA
<213> ORGANISM: Artificial Sequence
<220> FEATURE:
<223> OTHER INFORMATION: synthetic polynucleotide

<400> SEQUENCE: 18
tgctgttgac agtgagcgaa cacttgatgt ggaaacgtat tagtgaagcc acagatgtaa     60
tacgtttcca catcaagtgt gtgcctactg cctcgga                             97

<210> SEQ ID NO 19
<211> LENGTH: 97
<212> TYPE: DNA
<213> ORGANISM: Artificial Sequence
<220> FEATURE:
<223> OTHER INFORMATION: synthetic polynucleotide

<400> SEQUENCE: 19
tgctgttgac agtgagcgat ccaacaagct gaagctaaag tagtgaagcc acagatgtac     60
tttagcttca gcttgttgga ctgcctactg cctcgga                             97

<210> SEQ ID NO 20
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 20
gagtgtcctg ggttccttgc                                                20

<210> SEQ ID NO 21
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 21
ggcataatgc atttgcaagc                                                20

<210> SEQ ID NO 22
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 22
cccgtcactc aaccatttca                                                20

<210> SEQ ID NO 23
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 23
cttatcaatg ggggctctgg                                          20

<210> SEQ ID NO 24
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 24
agatatggct ggctttgtgc                                          20

<210> SEQ ID NO 25
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 25
gaactcgctc aggttctgc                                           19

<210> SEQ ID NO 26
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 26
acatggcccc cgatgaat                                            18

<210> SEQ ID NO 27
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 27
caggtaaggc tcgaacgatg                                          20

<210> SEQ ID NO 28
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 28
ggatttggcc gagagttgtt                                          20

<210> SEQ ID NO 29
<211> LENGTH: 20
<212> TYPE: DNA
<213> ORGANISM: Artificial Sequence
<220> FEATURE:

<223> OTHER INFORMATION: synthetic polynucleotide

<400> SEQUENCE: 29
cggctaggag aaggacacta                                                    20

<210> SEQ ID NO 30
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 30
cggcgggatc ctataagttg                                                    20

<210> SEQ ID NO 31
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 31
gcgtggataa tggttggca                                                     19

<210> SEQ ID NO 32
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 32
tcctctgaca tttgcaggtc                                                    20

<210> SEQ ID NO 33
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 33
aaggcattgg ctggaaga                                                      18

<210> SEQ ID NO 34
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 34
cgccatgtct ctagtgatcc                                                    20

<210> SEQ ID NO 35
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 35
ggtcgatgtc tgctttcctc                                                    20

```
<210> SEQ ID NO 36
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 36
acttcgtgca agaaatgctg a                                              21

<210> SEQ ID NO 37
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 37
tctggattgt tcttcactct tgg                                            23

<210> SEQ ID NO 38
<211> LENGTH: 5011
<212> TYPE: DNA
<213> ORGANISM: Homo sapiens

<400> SEQUENCE: 38
cttttccagg gaaaaggaa cttgggttcc cttctctccg tcctcttttc gggtctgaca      60
gcctccaccc actccttccc cggaccccgc ctccgcgcgc aggttcctcc cagtcacctt    120
tctccacccc cgcccccgca cctagcccgc cgcgcgccac cttccacctg actgcgcggg    180
gcgctcggga cctgcgcgca cctcggacct tcaccacccg cccgggccgc ggggagcgga    240
cgagggccac agcccccccac ccgccaggga gcccaggtgc tcggcgtctg aacgtctcaa    300
agggccacag cgacaatgac agctgacaag gagaagaaaa ggagtagctc ggagaggagg    360
aaggagaagt cccgggatgc tgcgcggtgc cggcggagca aggagacgga ggtgttctat    420
gagctggccc atgagctgcc tctgccccac agtgtgagct cccatctgga caaggcctcc    480
atcatgcgac tggcaatcag cttcctgcga acacacaagc tcctctcctc agtttgctct    540
gaaaacgagt ccgaagccga agctgaccag cagatggaca acttgtacct gaaagccttg    600
gagggtttca ttgccgtggt gacccaagat ggcgacatga tctttctgtc agaaaacatc    660
agcaagttca tgggacttac acaggtggag ctaacaggac atagtatctt tgacttcact    720
catccctgcg accatgagga gattcgtgag aacctgagtc tcaaaaatgg ctctggtttt    780
gggaaaaaa gcaaagacat gttccacagag cgggacttct tcatgaggat gaagtgcacg    840
gtcaccaaca gaggccgtac tgtcaacctc aagtcagcca cctggaaggt cttgcactgc    900
acgggccagg tgaaagtcta caacaactgc cctcctcaca atagtctgtg tggctacaag    960
gagcccctgc tgtcctgcct catcatcatg tgtgaaccaa tccagcaccc atcccacatg   1020
gacatccccc tggatagcaa gaccttcctg agccgccaca gcatggacat gaagttcacc   1080
tactgtgatg acagaatcac agaactgatt ggttaccacc ctgaggagct gcttggccgc   1140
tcagcctatg aattctacca tgcgctagac tccgagaaca tgaccaagag tcaccagaac   1200
ttgtgcacca aggtcaggt agtaagtggc cagtaccgga tgctcgcaaa gcatgggggc   1260
tacgtgtggc tggagaccca ggggacggtc atctacaacc ctcgcaacct gcagccccag   1320
tgcatcatgt gtgtcaacta cgtcctgagt gagattgaga agaatgacgt ggtgttctcc   1380
atggaccaga ctgaatccct gttcaagccc cacctgatgg ccatgaacag catctttgat   1440
```

-continued

```
agcagtggca agggggctgt gtctgagaag agtaacttcc tattcaccaa gctaaaggag    1500
gagcccgagg agctggccca gctggctccc accccaggag acgccatcat ctctctggat    1560
ttcgggaatc agaacttcga ggagtcctca gcctatggca aggccatcct gcccccgagc    1620
cagccatggg ccacggagtt gaggagccac agcacccaga gcgaggctgg gagcctgcct    1680
gccttcaccg tgccccaggc agctgccccg ggcagcacca ccccagtgc caccagcagc     1740 agcagcagct gctccacgcc caatagccct gaagactatt acacatcttt ggataacgac    1800
ctgaagattg aagtgattga aagctcttc gccatggaca cagaggccaa ggaccaatgc     1860
agtacccaga cggatttcaa tgagctggac ttggagacac tggcacccta tatccccatg    1920
gacggggaag acttccagct aagccccatc tgccccgagg agcggctctt ggcggagaac    1980
ccacagtcca ccccccagca ctgcttcagt gccatgacaa acatcttcca gccactggcc    2040
cctgtagccc cgcacagtcc cttcctcctg acaagtttc agcagcagct ggagagcaag     2100
aagacagagc ccgagcaccg gcccatgtcc tccatcttct ttgatgccgg aagcaaagca    2160
tccctgccac cgtgctgtgg ccaggccagc accectctct cttccatggg gggcagatcc    2220
aatacccagt ggcccccaga tccaccatta cattttgggc ccacaaagtg ggccgtcggg    2280
gatcagcgca cagagttctt gggagcagcg ccgttggggc ccctgtctc tccaccccat     2340 gtctccacct tcaagacaag gtctgcaaag ggttttgggg ctcgaggccc agacgtgctg    2400
agtccggcca tggtagccct ctccaacaag ctgaagctga gcgcagct ggagtatgaa      2460 gagcaagcct tccaggacct gagcgggggg acccacctg gtggcagcac ctcacatttg     2520
atgtggaaac ggatgaagaa cctcaggggt gggagctgcc ctttgatgcc ggacaagcca    2580
ctgagcgcaa atgtacccaa tgataagttc acccaaaacc ccatgagggg cctgggccat    2640
cccctgagac atctgccgct gccacagcct ccatctgcca tcagtcccgg ggagaacagc    2700
aagagcaggt tcccccccaca gtgctacgcc acccagtacc aggactacag cctgtcgtca    2760
gcccacaagg tgtcaggcat ggcaagccgg ctctcgggc cctcatttga gtcctacctg    2820
ctgcccgaac tgaccagata tgactgtgag gtgaacgtgc ccgtgctggg aagctccacg    2880
ctcctgcaag gagggaccct cctcagagcc ctggaccagg ccacctgagc caggccttct    2940
acctgggcag cacctctgcc gacgccgtcc caccagcttc actctctccg tctgtttttg    3000
caactaggta tttctaacgc cagcacacta tttacaagat ggacttacct ggcagacttg    3060
cccaggtcac caagcagtgg ccttttttctg agatgctcac tttattatcc ctattttaa    3120 agtacacaat tgtttacct gttctgaaat gttcttaaat tttgtaggat ttttttcctc     3180
cccaccttca atgacttcta atttatatta tccataggtt tctctccctc cttctccttc    3240
tcacacacaa ctgtccatac taacaagttt ggtgcatgtc tgttcttctg tagggagaag    3300
ctttagcttc attttactaa aaagattcct cgttattgtt gttgccaaag agaaacaaaa    3360
atgattttgc tttccaagct tggtttgtgg cgtctccctc gcagagccct tctcgtttct    3420
tttttaaact aatcaccata ttgtaaattt cagggttttt ttttttgttt aagctgactc    3480
tttgctctaa ttttggaaaa aaagaaatgt gaagggtcaa ctccaacgta tgtggttatc    3540
tgtgaaagtt gcacagcgtg cttttcccta aactggtgtt tttccccgc atttggtgga    3600 tttttatta ttattcaaaa acataactga gttttttaaa agaggagaaa atttatatct     3660
gggttaagtg tttatcatat atatgggtac tttgtaatat ctaaaaactt agaaacggaa    3720
atggaatcct gctcacaaaa tcactttaag atcttttcga agctgttaat ttttcttagt    3780
gttgtggaca ctgcagactt gtccagtgct cccacggcct gtacggacac tgtggaaggc    3840
```

-continued

```
ctccctctgt cggcttttg ccatctgtga tatgccatag gtgtgacaat ccgagcagtg    3900
gagtcattca gcgggagcac tgcgcgctat ccctcacat tctctatgta ctatgtatgt    3960
atgtattatt attattgctg ccaagagggt ctgatggcac gttgtggggt cggggggtgg    4020
ggcggggaag tgctctaact tttcttaagg ttttgttgct agcccttcaa gtgcactgag    4080
ctatgtgact cggatggtct ttcacacggc acatttggac atttccagaa ctaccatgag    4140
atggtttaga cggaattca tgcaaatgag gggtcaaaaa tggtatagtg accccgtcca     4200
cgtcctccaa gctcacgacc ttggagcccc gtggagctgg actgaggagg aggctgcaca    4260
gcgggagagc agctggtcca gaccagccct gcagccccca ctcagccggc agccagatgg    4320
ccccgcaagg cctccaggga tggcccctag ccacaggccc tggctgaggt ctctgggtcg    4380
gtcagtgaca tgtaggtagg aagcactgaa aatagtgttc ccagagcact ttgcaactcc    4440
ctgggtaaga gggacgacac ctctggtttt tcaataccaa ttacatggaa cttttctgta    4500
atgggtacaa tgaagaagtt tctaaaaaca cacacaaagc acattgggcc aactatttag    4560
taagcccgga tagacttatt gccaaaaaca aaaaatagct ttcaaaagaa atttaagttc    4620
tatgagaaat tccttagtca tggtgttgcg taaatcatat tttagctgca cggcattacc    4680
ccacacaggg tggcagaact tgaagggtta ctgacgtgta aatgctggta tttgatttcc    4740
tgtgtgtgtt gccctggcat taagggcatt ttacccttgc agtttactaa aacactgaa    4800 aaatattcca agcttcatat taaccctacc tgtcaacgta acgatttcat gaacgttatt    4860
atattgtcga attcctactg acaacattat aactgtatgg gagcttaact ttataaggaa    4920
atgtattttg acactggtat cttattaaag tattctgatc ctaaaaaaaa aaaaaaaaa    4980 aaaaaaaaa aaaaaaaaa aaaaaaaaa a                                     5011
```

<210> SEQ ID NO 39
<211> LENGTH: 883
<212> TYPE: PRT
<213> ORGANISM: Homo sapiens

<400> SEQUENCE: 39

```
Met Leu Gly Leu Phe Val Phe Lys Thr Gly Thr Gln Arg Arg Asn Arg
1               5                   10                  15

Arg Leu Pro Tyr Ala Arg Ser Ser Glu Arg Lys Glu Lys Ser
            20                  25                  30

Arg Asp Ala Ala Arg Cys Arg Ser Lys Glu Thr Glu Val Phe Tyr
        35                  40                  45

Glu Leu Ala His Glu Leu Pro Leu Pro His Ser Val Ser Ser His Leu
    50                  55                  60

Asp Lys Ala Ser Ile Met Arg Leu Ala Ile Ser Phe Leu Arg Thr His
65                  70                  75                  80

Lys Leu Leu Ser Ser Val Cys Ser Glu Asn Glu Ser Glu Ala Glu Ala
                85                  90                  95

Asp Gln Gln Met Asp Asn Leu Tyr Leu Lys Ala Leu Glu Gly Phe Ile
            100                 105                 110

Ala Val Val Thr Gln Asp Gly Asp Met Ile Phe Leu Ser Glu Asn Ile
        115                 120                 125

Ser Lys Phe Met Gly Leu Thr Gln Val Glu Leu Thr Gly His Ser Ile
    130                 135                 140

Phe Asp Phe Thr His Pro Cys Asp His Glu Glu Ile Arg Glu Asn Leu
145                 150                 155                 160
```

```
Ser Leu Lys Asn Gly Ser Gly Phe Gly Lys Lys Ser Lys Asp Met Ser
            165                 170                 175

Thr Glu Arg Asp Phe Phe Met Arg Met Lys Cys Thr Val Thr Asn Arg
        180                 185                 190

Gly Arg Thr Val Asn Leu Lys Ser Ala Thr Trp Lys Val Leu His Cys
    195                 200                 205

Thr Gly Gln Val Lys Val Tyr Asn Asn Cys Pro Pro His Asn Ser Leu
210                 215                 220

Cys Gly Tyr Lys Glu Pro Leu Leu Ser Cys Leu Ile Ile Met Cys Glu
225                 230                 235                 240

Pro Ile Gln His Pro Ser His Met Asp Ile Pro Leu Asp Ser Lys Thr
                245                 250                 255

Phe Leu Ser Arg His Ser Met Asp Met Lys Phe Thr Tyr Cys Asp Asp
            260                 265                 270

Arg Ile Thr Glu Leu Ile Gly Tyr His Pro Glu Glu Leu Leu Gly Arg
        275                 280                 285

Ser Ala Tyr Glu Phe Tyr His Ala Leu Asp Ser Glu Asn Met Thr Lys
    290                 295                 300

Ser His Gln Asn Leu Cys Thr Lys Gly Gln Val Val Ser Gly Gln Tyr
305                 310                 315                 320

Arg Met Leu Ala Lys His Gly Gly Tyr Val Trp Leu Glu Thr Gln Gly
                325                 330                 335

Thr Val Ile Tyr Asn Pro Arg Asn Leu Gln Pro Gln Cys Ile Met Cys
            340                 345                 350

Val Asn Tyr Val Leu Ser Glu Ile Glu Lys Asn Asp Val Val Phe Ser
        355                 360                 365

Met Asp Gln Thr Glu Ser Leu Phe Lys Pro His Leu Met Ala Met Asn
    370                 375                 380

Ser Ile Phe Asp Ser Ser Gly Lys Gly Ala Val Ser Glu Lys Ser Asn
385                 390                 395                 400

Phe Leu Phe Thr Lys Leu Lys Glu Glu Pro Glu Glu Leu Ala Gln Leu
                405                 410                 415

Ala Pro Thr Pro Gly Asp Ala Ile Ile Ser Leu Asp Phe Gly Asn Gln
            420                 425                 430

Asn Phe Glu Glu Ser Ser Ala Tyr Gly Lys Ala Ile Leu Pro Pro Ser
        435                 440                 445

Gln Pro Trp Ala Thr Glu Leu Arg Ser His Ser Thr Gln Ser Glu Ala
    450                 455                 460

Gly Ser Leu Pro Ala Phe Thr Val Pro Gln Ala Ala Ala Pro Gly Ser
465                 470                 475                 480

Thr Thr Pro Ser Ala Thr Ser Ser Ser Ser Cys Ser Thr Pro Asn
                485                 490                 495

Ser Pro Glu Asp Tyr Tyr Thr Ser Leu Asp Asn Asp Leu Lys Ile Glu
            500                 505                 510

Val Ile Glu Lys Leu Phe Ala Met Asp Thr Glu Ala Lys Asp Gln Cys
        515                 520                 525

Ser Thr Gln Thr Asp Phe Asn Glu Leu Asp Leu Glu Thr Leu Ala Pro
    530                 535                 540

Tyr Ile Pro Met Asp Gly Glu Asp Phe Gln Leu Ser Pro Ile Cys Pro
545                 550                 555                 560

Glu Glu Arg Leu Leu Ala Glu Asn Pro Gln Ser Thr Pro Gln His Cys
                565                 570                 575

Phe Ser Ala Met Thr Asn Ile Phe Gln Pro Leu Ala Pro Val Ala Pro
```

-continued

```
                580                    585                    590
His Ser Pro Phe Leu Leu Asp Lys Phe Gln Gln Gln Leu Glu Ser Lys
        595                    600                    605

Lys Thr Glu Pro Glu His Arg Pro Met Ser Ser Ile Phe Phe Asp Ala
        610                    615                    620

Gly Ser Lys Ala Ser Leu Pro Pro Cys Cys Gly Gln Ala Ser Thr Pro
625                    630                    635                    640

Leu Ser Ser Met Gly Gly Arg Ser Asn Thr Gln Trp Pro Pro Asp Pro
                645                    650                    655

Pro Leu His Phe Gly Pro Thr Lys Trp Ala Val Gly Asp Gln Arg Thr
            660                    665                    670

Glu Phe Leu Gly Ala Ala Pro Leu Gly Pro Pro Val Ser Pro Pro His
        675                    680                    685

Val Ser Thr Phe Lys Thr Arg Ser Ala Lys Gly Phe Gly Ala Arg Gly
        690                    695                    700

Pro Asp Val Leu Ser Pro Ala Met Val Ala Leu Ser Asn Lys Leu Lys
705                    710                    715                    720

Leu Lys Arg Gln Leu Glu Tyr Glu Glu Gln Ala Phe Gln Asp Leu Ser
                725                    730                    735

Gly Gly Asp Pro Pro Gly Gly Ser Thr Ser His Leu Met Trp Lys Arg
            740                    745                    750

Met Lys Asn Leu Arg Gly Gly Ser Cys Pro Leu Met Pro Asp Lys Pro
        755                    760                    765

Leu Ser Ala Asn Val Pro Asn Asp Lys Phe Thr Gln Asn Pro Met Arg
    770                    775                    780

Gly Leu Gly His Pro Leu Arg His Leu Pro Leu Pro Gln Pro Pro Ser
785                    790                    795                    800

Ala Ile Ser Pro Gly Glu Asn Ser Lys Ser Arg Phe Pro Pro Gln Cys
                805                    810                    815

Tyr Ala Thr Gln Tyr Gln Asp Tyr Ser Leu Ser Ser Ala His Lys Val
            820                    825                    830

Ser Gly Met Ala Ser Arg Leu Leu Gly Pro Ser Phe Glu Ser Tyr Leu
        835                    840                    845

Leu Pro Glu Leu Thr Arg Tyr Asp Cys Glu Val Asn Val Pro Val Leu
    850                    855                    860

Gly Ser Ser Thr Leu Leu Gln Gly Gly Asp Leu Leu Arg Ala Leu Asp
865                    870                    875                    880

Gln Ala Thr
```

COMPOSITIONS AND METHODS OF MODULATING HIF-2A TO IMPROVE MUSCLE GENERATION AND REPAIR

CROSS-REFERENCE TO RELATED APPLICATIONS

This application claims the benefit of and priority to U.S. Ser. No. 62/588,786 filed Nov. 20, 2017, and which is incorporated by reference in its entirety.

STATEMENT REGARDING FEDERALLY SPONSORED RESEARCH

This invention was made with government support under Grant 1R01AR070178 awarded by the National Institutes of Health. The government has certain rights in the invention.

REFERENCE TO SEQUENCE LISTING

The Sequence Listing submitted as a text file named "UGA_2017_198_ST25.txt," created on Nov. 19, 2018, and having a size of 36,643 bytes is hereby incorporated by reference pursuant to 37 C.F.R. § 1.52(e)(5).

FIELD OF THE INVENTION

The invention is generally related to compositions and methods for increasing skeletal muscle generation and regeneration.

BACKGROUND OF THE INVENTION

The coordinated proliferation and differentiation of adult stem cells that reside in many adult tissues provide sustainable cell sources for tissue repair and regeneration. In support of long-term tissue homeostasis, many adult stem cell populations fine-tune the balance between proliferative and quiescent states to both meet the need for tissue repair and lessen cell cycle-associated stresses. Ineffective reversal of proliferation/quiescence in adult stem cells has been implicated in aging and many diseases (Goodell, et al., *Science*, 350(6265); 1199-204 (2015)).

Adult muscle stem cells, also called satellite cells (SCs), are important for skeletal muscle regeneration. SCs and their undifferentiated progeny universally express Pax7, a character that has been utilized to manipulate gene expression specifically in SCs (Murphy, et al., *Development*, 138(17): 3625-37 (2011); Seale, et al., *Cell*, 102(6):777-86 (2000)). In uninjured muscle, SCs reside closely juxtaposed with contractile myofibers beneath the basal lamina and are mitotically quiescent (G0). SC quiescence is jointly maintained by multiple mechanisms, but not limited to, TTP-mediated RNA decay, SIRT1-dependent histone deacetylation, restraint of myogenic and proliferation-associated gene expression by microRNAs (Cheung, et al., Nature, 482 (7386):524-8 (2012); Crist, et al., *Cell Stem Cell*, 11(1):118-26 (2012); Hausburg, et al., Elife, 4:e03390 doi: 10.7554/eLife.03390 (2015); Ryall, et al., *Cell Stem Cell*, 16(2):171-83 (2015)). Upon muscle injury, SCs transit through a $G_{(Alert)}$ phase and enter the cell cycle in response to the activation of HGF/FGF-mediated receptor tyrosine kinase (RTK) signaling and p38/MAPK signaling (Rodgers, et al., *Nature*, 510(7505):393-6 (2014); Jones, et al., *J Cell Biol.*, 169(1):105-16 (2005); Troy, et al., *Cell Stem Cell*, 11(4): 541-53 (2012)).

After limited rounds of proliferation, a subset of SCs return to quiescence and the niche location adjacent to myofibers (self-renewal), whereas many SCs undergo myogenic differentiation and eventually repair damaged myofibers. Angiopoietin-1/Tie2 RTK signaling, RTK negative regulator Spry1, and inactivation of p38/MAPK signaling promote SC self-renewal (Troy, et al., Cell Stem Cell, 11(4):541-53 (2012); Abou-Khalil, et al., *Cell Stem Cell*, 5(3):298-309 (2009); Shea, et al., *Cell Stem Cell*, 6(2):117-29 (2010)). Dynamic remodeling of the muscle microenvironment also plays a pivotal role to direct SC behaviors during muscle repair (Yin, et al., *Physiol Rev.*, 93(1):23-67 (2013)). However, how SCs fine-tune quiescence vs. activation and balance self-renewal vs. differentiation in response to niche cues remains incompletely understood.

Oxygen ($O_2$) is important for mitochondrial respiration and bioenergetic homeostasis; low oxygen tension (hypoxia) underlies many disease conditions (Semenza, *Cell*, 148(3): 399-408 (2012)). The cellular responses to hypoxia are mainly mediated by hypoxia-inducible factors, which are bHLH-PAS transcription factors that form heterodimeric complexes between an $O_2$-sensitive α-subunit (HIF-1α, HIF-2α, HIF-3α) and a stable β-subunit (HIF-1β). The $O_2$-dependent degradation of HIF α-subunits serves as an $O_2$-sensing mechanism. Under normoxia, HIFα is hydroxylated by HIF prolyl-hydroxylases, recognized by von Hippel-Lindau tumor suppressor protein and targeted to proteasome degradation. Under hypoxia, limited $O_2$ (a substrate for HIFα hydroxylation) stabilizes HIFα/HIF1β transcription factor complex, which binds hypoxia-responsive elements (HREs; 5'-RCGTG-3') and activate target gene expression. Intriguingly, many types of adult stem cells prefer hypoxic niches to maintain their quiescent and/or undifferentiated states (Mohyeldin, et al., Cell Stem Cell, 7(2):150-61 (2010)). Hypoxia has a profound impact on proliferation and differentiation of cultured myogenic cells in vitro (Chaillou, et al., *FASEB J.*, 30(12):3929-41 (2016)). Yet, it remains elusive whether hypoxia is of any physiological relevance to SC in vivo, and if so, whether a hypoxia-inducible factor plays a role in SC quiescence/self-renewal. Thus, there remains a need for characterizing muscle SC pathways and modulating them to improve muscle repair.

It is an object of the invention to provide compositions and methods of use thereof for the increasing muscle generation and regeneration.

SUMMARY OF THE INVENTION

It has been discovered that muscle satellite cells (SCs) are maintained in a hypoxic state in the stem cell niche in vivo. Quiescent SCs express HIF-2α and this is important for the maintenance of their quiescence and homeostasis. Stabilization of HIF-2α promotes self-renewal and stemness of cultured SCs and improves the transplantation efficiency of these cells in injured muscle. The experiments below also show that transient inhibition of HIF-2α after muscle injury improves muscle regeneration by augmenting the proliferation of SCs and accelerating their differentiation.

Thus, compositions and methods for modulating HIF-2α to meditate of hypoxia signaling in SCs and applications thereof for improving skeletal muscle generation and repair are provided. For example, methods of enhancing, increasing, accelerating or/and otherwise improving skeletal muscle generation or regeneration in a subject in need thereof are disclosed. In some embodiments, the methods include administering the subject an effective amount of a HIF-2α inhibitor. The HIF-2α inhibitor can be effective to, for example, increase muscle satellite cell proliferation, differentiation, or a combination thereof in a subject. The HIF-2α inhibitor can be effective to increase or accelerate differentiation of satellite cells into myoblasts and mature muscle cells in the subject.

Exemplary HIF-2α inhibitors including small molecule and functional nucleic acids, and formulations and pharmaceutical compositions formed therefrom are also provided. In some embodiments, the HIF-2α inhibitor is PT2385 or PT2977 (Peloton Therapeutics).

The HIF-2α inhibitor can be targeted to skeletal muscle.

The inhibitors can be locally or systemically administered. Means of administration include, but are not limited to oral, parenteral, transdermal, or transmucosal.

Bandages, wraps and other dressings including an effective amount of a HIF-2α inhibitor to increase muscle satellite cell proliferation, differentiation, or a combination thereof in the underlying muscle when the bandage or wrap or other dressing is applied to a subject, and their use in the disclosed methods are also provided.

In some embodiments, the methods include administering to a subject an effective amount of muscle tissue having muscle satellite cells treated ex vivo with an effective amount of a compound that increases the bioavailability or expression of HIF-2α. The compound can effective to, for example, increase or maintain the stemness of SC cells and/or their self-renewal ex vivo and before delivery to the subject. In some embodiments, the compound is wildtype HIF-2α protein, or a functional fragment or variant thereof, or a nucleic acid encoding a wildtype HIF-2α protein, or a functional fragment or variant thereof. A preferred variant is one that has increased resistance to oxygen-induced hydroxylation and/or proteasome degradation relative to wildtype HIF-2α protein.

The compositions and methods can be used to treat subjects with healthy muscle to enhance the size or performance thereof, as well as improve the recovery, repair, or regeneration of muscle in subjects with a muscle injury, atrophy, or muscle disease or disorder.

In some embodiments the muscle disease or disorder is a muscular dystrophy or myopathic disorder. For example, the subject can have one or more of a dystrophin-glycoprotein complex (DGC)-related dystrophy, a congenital muscular dystrophy, a facioscapulohumeral dystrophy, a limb-girdle muscular dystrophy, a myotonic dystrophy an oculopharyngeal muscular dystrophy, a congenital myopathy, a toxic myopathy, an inflammatory myopathy, an endocrine or metabolic myopathy, a vitamin D deficiency, a mitochondrial myopathy, glycogenoses, a lipid storage myopathy, a myotonic disease, and periodic paralyses. In particular embodiments, the muscular dystrophy or myopathic disorder is Bethlem myopathy, Duchenne Muscular Dystrophy, Becker dystrophy, limb-girdle muscular dystrophy 2 (2A-2L), myotonic dystrophy type 1, myotonic dystrophy type 2, or myasthenia gravis. The dystrophy can also be a congenital muscular dystrophy (CMD) (including Bethlem CMD, Fukuyama CMD, Muscle-eye-brain diseases, Rigid spine syndromes, Ullrich CMD, Walker-Warburg syndromes), or Emery-Dreifuss muscular dystrophy.

In some embodiments, the method increases myofiber number, length, density, cross sectional area, or a combination thereof, increases muscle strength, volume, and/or mass, reduces or slows the progression or development of fibrosis, or a combination thereof in the subject. In some embodiments, the compositions and methods reduce the effects of hypoxia, improve respiration, or a combination thereof.

BRIEF DESCRIPTION OF THE DRAWINGS

FIG. 3G is a diagram depicting the experimental scheme for transplanting HIF-2α-stabilized SCs and tracing their cell fates in vivo. FIGS. 3H-3I are dot plots showing the percents of engrafted self-renewed SCs (nmGFP$^+$/Pax7$^+$) in total SC pool after the 1$^{st}$ round of regeneration (at 21 days post injury (dpi); n>30 sections from n=5 mice/group) (3H) and after the 2$^{nd}$ round of regeneration (at 30 dpi; n>30 sections from n=6 mice/group) (3I) ((-●-) control, (-▼-) HIF-2α OE).

FIG. 7 is a diagram showing a circular model for muscular dystrophy progression including (1) respiratory muscle weakness, (2) muscle hypoxia, (3) HIF-2α stabilization, and (4) impaired muscle regeneration, and how a HIF-2α inhibitor (such as PT2385 or PT2977) may disrupt this circle by targeting HIF-2α.

FIGS. 8A and 8B are dot plots showing total numbers of Pax7$^{+pos}$ SCs (8A) and percentages of Ki67$^{+pos}$ SCs (8B) at 10 dpi in tibialis anterior (TA) muscle samples FROM control and hypoxia-exposed mice treated with HIF-C2 or vehicle (DMSO).

DETAILED DESCRIPTION OF THE INVENTION

I. Definitions

Figure 1A:
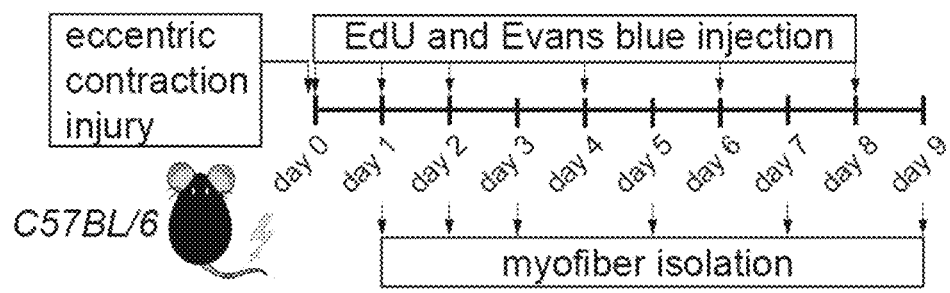
FIG. 1A is a diagram depicting the experimental scheme for characterizing SC dynamics after eccentric contraction-induced injury. For each time point, EdU and Evans blue were injected 24-hrs before myofiber isolation.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a nontoxic material that does not interfere with the effectiveness of the biological activity of the active ingredients.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

As used herein, the term "identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "inhibit" or other forms of the word such as "inhibiting" or "inhibition" means to hinder or restrain a particular characteristic. It is understood that this is typically in relation to some standard or expected value, in other words it is relative, but that it is not always necessary for the standard or relative value to be referred to. For example, "inhibits HIF-2α" means hindering or restraining the activity of the protein relative to a standard or a control. HIF-2α is a transcription factor. Thus, inhibiting HIF-2α includes, but it not limited to, hindering or restraining or otherwise interfering with the ability of HIF-2α to bind to DNA. "Inhibits HIF-2α" can also mean to hinder or restrain the synthesis or expression of the protein, or mRNA encoding the protein, relative to a standard or control.

As used herein, the terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, the term "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "localization signal or sequence or domain or ligand" or "targeting signal or sequence or domain or ligand" are used interchangeably and refer to a signal that directs a molecule to a specific cell, tissue, organelle, or intracellular region. The signal can be polynucleotide, polypeptide, or carbohydrate moiety or can be an organic or inorganic compound sufficient to direct an attached molecule to a desired location.

As used herein, the term "microparticles" refers to particles having a diameter between one micron and 1000 microns, typically less than 400 microns, more typically less than 100 microns, most preferably for the uses described herein in the range of less than 10 microns in diameter. Microparticles include microcapsules and microspheres unless otherwise specified.

As used herein, the term "nanoparticles" refers to particles having a diameter of less than one micron, more typically between 50 and 1000 nanometers, preferably in the range of 100 to 300 nanometers.

II. Methods of Use

Skeletal muscle injury occurs upon eccentric contraction often during exercise, sports and daily locomotion. The proliferation and differentiation of muscle stem cells (also called satellite cells) is important for the tissue repair following muscle injury. Muscle regeneration is often compromised after severe muscle injury, which happens when the major body of muscle is physically damaged (e.g. in traumatic accidents or battlefields) or under some disease conditions (e.g. chronic obstructive pulmonary disease, peripheral artery disease, etc.). Impaired muscle regeneration leads to muscle fibrosis (replacement of functional muscle tissue by the scar tissue) as well as poor life-quality due to prolonged pain and limited muscle function. The impairment of muscle regeneration attributes to the limited capability of satellite cells to proliferate, which is pivotal for providing sufficient cell source for myogenic differentiation.

The Examples below illustrate that stem cells are maintained in a hypoxic state in the stem cell niche in vivo. Quiescent satellite cells (SCs) express HIF-2α and this is important for the maintenance of their quiescence and homeostasis.

Compositions and methods of use thereof for modulating HIF-2α activity to enhance, increase, accelerate or/and otherwise improve muscle generation or regeneration are provided. In some embodiments, the subject has or had or is at risk of developing a muscle disease or disorder, muscle atrophy, or a muscle injury. In some embodiments, clinical symptoms of muscle disease, injury or atrophy are reduced. In some embodiments, muscle size, muscle volume, muscle mass, and/or muscle strength is increased. For example, the compositions and methods can increase myofiber number, length, density, cross sectional area, or a combination thereof. The methods can increase muscle strength. The methods can increase contractile function by, for example, increasing maximal torque that can be generated by the muscle.

As discussed in more detail below, the methods can include administering to a subject in need thereof an effective amount of hypoxia-inducible factor 2α (HIF-2α) inhibitor, or a derivative thereof, or a pharmaceutically acceptable salt thereof to increase satellite cell (SC) proliferation, differentiation, or a combination thereof in a subject. Exemplary HIF-2α inhibitors and formulations formed therefrom are also provided.

In some embodiments, SC cells are treated ex vivo with a compound that increases or stabilizes bioavailability or expression of HIF-2α in an effective amount to enhance or maintain self-renewal and/or stemness (e.g., reduce or prevent differentiation) of SC cells. The compound that increases or stabilizes bioavailability or expression of HIF-2α can be, for example, a HIF-2α protein or variant thereof, or a nucleic acid encoding the same. As provided are methods of using the treated cells in regenerative medicine and transplantation applications for enhancing, increasing, accelerating or/and otherwise improving muscle generation or regeneration.

A. Methods of Treatment

Adult muscle stem cells, also called satellite cells (SCs) or myosatellite cells, are important for skeletal muscle regeneration. They are small multipotent cells with virtually no cytoplasm found in mature muscle. Satellite cells are precursors to skeletal muscle cells, able to give rise to satellite cells (e.g., self-renew) or differentiated skeletal muscle cells. They can provide additional myonuclei to their parent muscle fiber, or return to a quiescent state. Upon activation, satellite cells can re-enter the cell cycle to proliferate and differentiate into myoblasts. SCs and their undifferentiated progeny universally express Pax7, a character that has been utilized to manipulate gene expression specifically in SCs (Murphy, et al., Development, 138(17):3625-37 (2011); Seale, et al., Cell, 102(6):777-86 (2000)). Another marker that has been used to identify SCs is Pax3.

In some embodiments, the effect of the disclosed compositions and methods on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based on measuring the symptom, pharmacologic, or physiologic indicator in one or more subjects that do not have the disease or condition to be treated (e.g., healthy subjects). In some embodiments, the effect of the treatment is compared to a conventional treatment that is known the art, such as one of those discussed herein.

In some embodiments, disclosed methods include a combination of transplanting into a subject satellite cells primed by ex vivo treatment with an effective amount of a compound that increases the bioavailability or expression of HIF-2α, and treatment of the subject and an effective amount of HIF-2α inhibitor before, during, and/or after transplantation to drive satellite cell differentiation in vivo.

1. Methods of Inhibiting HIF-2α

Within generating or regenerating muscles it can be desirable to increase the differentiation of satellite cells into myoblasts and subsequently into fully differentiated myofibers. Thus, methods of increasing satellite cell proliferation, differentiation, or a combination thereof in a subject are provided. The methods typically include administering a subject in need thereof an effective amount of a HIF-2α inhibitor. The subject can be administered the HIF-2α inhibitor in a dosage and for a duration sufficient to improve muscle generation or regeneration by augmenting the proliferation of SCs and/or accelerating their differentiation compared to a control. In some embodiments, the composition increases or accelerates differentiation of SCs into myoblasts.

The route of administration can be oral, parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In certain embodiments, the compositions are administered locally, for example by injection or other application directly into or onto a site to be treated. In some embodiments, the compositions are injected, topically applied, or otherwise administered directly into muscle or musculature at or adjacent to a site of injury, surgery, or implantation. For example, in some embodiments, the compositions are topically applied to muscle tissue that is exposed, for example as a result of injury or during a surgical or implantation, or transplantation procedure. Typically, local administration causes an increased localized concentration of the compositions which is greater than that which can be achieved by systemic administration.

In some embodiments the route of administration is transdermal, for example, a transdermal patch or gel that is contacted with the skin of the subject. In some embodiments the HIF-2α inhibitor directly or indirectly contacts muscle through an injury, for example, an open wound. The composition can be included or impregnated into or onto a bandage or other wrap or dressing for increasing muscle repair while the bandage protects the wound.

Suitable HIF-2α inhibitors are known in the art, and exemplary compounds and formulations thereof are discussed in more detail below.

The precise dosage will vary according to a variety of factors including but not limited to the inhibitor that is selected and subject-dependent variables (e.g., age, immune system health, clinical symptoms etc.).

In cases of a solid dosage form, examples of daily dosages of the compounds described herein which can be used are an effective amount within the dosage range of about 0.001 mg to about 2 mg per kilogram of body weight, about 0.001 mg to about 5 mg per kilogram of body weight, about 0.001 mg to about 10 mg per kilogram of body weight, about 0.001 mg to about 20 mg per kilogram of body weight, about 0.001 mg to about 50 mg per kilogram of body weight, about 0.001 mg to about 100 mg per kilogram of body weight, about 0.001 mg to about 200 mg per kilogram of body weight, or about 0.001 mg to about 300 mg per kilogram of body weight.

When administered orally or by inhalation, examples of daily dosages are an effective amount within the dosage range of about 0.1 mg to about 10 mg, or about 0.1 mg to about 20 mg, or about 0.1 mg to about 30 mg, or about 0.1 mg to about 40 mg, or about 0.1 mg to about 50 mg, or about 0.1 mg to about 60 mg, or about 0.1 mg to about 70 mg, or about 0.1 mg to about 80 mg, or about 0.1 mg to about 90 mg, or about 0.1 mg to about 100 mg, or about 0.1 mg to about 200 mg, or about 0.1 mg to about 300 mg, or about 0.1 mg to about 400 mg, or about 0.1 mg to about 500 mg, or about 0.1 mg to about 600 mg, or about 0.1 mg to about 700 mg, or about 0.1 mg to about 800 mg, or about 0.1 mg to about 900 mg, or about 0.1 mg to about 1 g, or about 20 mg to 300 mg, or about 20 mg to 500 mg, or about 20 mg to 700 mg, or about 20 mg to 1000 mg, or about 50 mg to 1500 mg, or about 50 mg to 2000 mg.

Exemplary fixed daily doses include about 1 mg, about 2 mg, about 3 mg, about 4 mg, about 5 mg, about 6 mg, about 7 mg, about 8 mg, about 9 mg, about 10 mg, about 12 mg, about 15 mg, about 18 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, about 1200 mg, about 1500 mg, or about 2000 mg, independently of body weight. However, it is understood that pediatric patients may require smaller dosages, and depending on the severity of the disease and condition of the patient, dosages may vary.

When formulated as a liquid, the concentration of the compounds described herein may be about 0.01 mg/ml to about 0.1 mg/ml or about 0.1 mg/ml to about 1 mg/ml, but can also be about 1 mg/ml to about 10 mg/ml or about 10 mg/ml to about 100 mg/ml. The liquid formulation could be a solution or a suspension. When formulated as a solid, for example as a tablet or as a powder for inhalation, the concentration, expressed as the weight of a compound divided by total weight, will typically be about 0.01% to about 0.1%, about 0.1% to about 1%, about 1% to about 10%, about 10% to about 20%, about 20% to about 40%, about 40% to about 60%, about 60% to about 80%, or about 80% to about 100%.

The timing of the administration of the composition will also depend on the formulation and/or route of administration used. The compound may be administered once daily, but may also be administered two, three or four times daily, or every other day, or once or twice per week. For example, the subject can be administered one or more treatments 1, 2, 3, 4, 5, 6, 7, 8, 9, 10, 11, 12, 13, 14, 15, 16, 17, 18, 19, 20, 21, 22, 23, or 24 hours, days, weeks, or months apart.

In some embodiments, the compositions are formulated for extended release. For example, the formulation can be suitable for administration once daily or less. In some embodiments, the composition is only administered to the subject once every 24-48 hours.

In some embodiments, administration of the composition will be given as a long-term treatment regimen whereby pharmacokinetic steady state conditions will be reached.

2. Methods of Increasing HIF-2α Bioavailability

Satellite cells are stem cells in skeletal muscle and represent an important cell source for transplantation therapy, because their depletion leads to complete impairment of muscle regeneration (see, e.g., Ito, et al., *Journal of Neuromuscular Diseases,* 3 (2016) 201-207, DOI 10.3233/JND-160156, and references cited therein). Although primary satellite cells immediately after isolation show high levels of stemness, culturing and passaging of satellite cells results in loss of their undifferentiated state, and gradual reductions in transplantation efficiency (Ikemoto, et al., *Mol Ther.,* 2007; 15(12):2178-85, and Quarta, *Cell Res.,* 2015; 25(7):761-2). However, the culture and expansion of human skeletal muscle cells in vitro is needed to obtain adequate cell numbers for transplantation therapy. Although growth factors, cytokines and chemicals have been used in muscle cell cultures Fu, et al., *Cell Res.* 2015; 25(6):655-73, and Cosgrove, et al., *Nat Med.,* 2014; 20(3):255-64, the improved culture conditions for maintaining the undifferentiated state, inhibiting differentiation, and enhancing eventual transplantation efficiency are needed.

The Examples below show that stabilization of HIF-2α promotes self-renewal and stemness of cultured SCs and improves the transplantation efficiency of these cells in a muscle injury model. Thus, in some embodiments, stemness of SC cells and/or their self-renewal is maintained or increased, preferably without increasing their differentiation and proliferation, by contacting (e.g., transfecting) the cells with HIF-2α protein or nucleic acids expressing HIF-2α.

Methods of treatment can include administering the subject the cells to increase muscle generation or regeneration. Thus, in some embodiments, muscle cells or muscle tissue are cultured ex vivo with an effective amount of HIF-2α, or transfected with a nucleic acid expressing HIF-2α, to maintain or increase SC self-renewal, maintain or increase stemness, reduce or otherwise impair myogenic differentiation, reduce or temporarily block SC activation or proliferation, or a combination thereof, of SCs prior implantation of the muscle cells or precursors. In some embodiments, the compositions reduce, delay or prevent differentiation of SCs into myoblasts.

In some embodiments, the method increases the number or percentage of Pax7+ cells in a population of cells relative to an untreated control population.

HIF-2α nucleic acid and protein sequences that can be used in the disclosed methods are known in the art and exemplified herein. The HIF-2α can be wildtype HIF-2α, such as the HIF-2α of SEQ ID NOS:1, 2, 38, and 39 or functional fragment thereof or variant thereof having at least 50, 60, 70, 80, 85, 90, 95, 96, 97, 98, 99 sequence identity to SEQ ID NOS: 1, 2, 38, or 39. In some embodiments, the HIF-2α is a variant of wildtype HIF-2α that stabilizes HIF-2α expression or activity within the cell, for example by increasing resistance to oxygen-induced hydroxylation and/or proteasome degradation. Such variants are known in the art and include, for example, a triple mutated form of HIF-2α (HIF-2αTM, carrying P405A, P530V and N851A mutations of mouse HIF-2α) (Hu, et al., Mol Biol Cell, 18(11):4528-42 (2007)).

The disclosed methods of stabilizing HIF-2α and/or increasing expression of HIF-2α are particularly useful in the context of muscle transplantation and muscle stem cell therapy. For example, in some embodiments, the methods are applied in the context of personalized therapy, for example, to generate tissue or cells for introduction into a subject in need thereof. Increasing the expression or stabilization of HIF-2α in vitro or ex vivo can be carried out on a variety of different starting muscle tissue and cell populations and allows fast and safe generation of muscle SC's that are self-renewable and maintained in their undifferentiated state.

In an exemplary protocol, target cells first isolated from a donor using methods known in the art can be contacted with HIF-2α protein or nucleic acid encoding HIF-2α (e.g., mRNA or a vector encoding HIF-2α) in an effective amount to cause HIF-2α expression or stabilization. Additionally or alternatively, cells can be treated with a histone deacetylases (HDAC) inhibitor. For example, Nakazawa, et al., reported that the HDAC inhibitor Vorinostat can reverse the epigenetic silencing of HIF-2α, but not HIF-1a (Nakazawa, et al., *Nat Commun.,* 7:10539 (2016) doi: 10.1038/ncomms10539).

The cells can be optionally stored and administered to a patient in need thereof. Sources or cells include, but are not limited to muscle cells, or a mixed population of cells including muscle cells. Preferably the muscle cells include satellite cells. In some embodiments, the satellite cells culture ex vivo independent of muscle fiber. In some embodiments, the satellite cells are associated with muscle fiber. In some embodiments, a marker such as Pax7 and/or Pax3 is used to identify muscle SCs or confirm that a population contains SCs. The cells can be harvested directly from the patient or an allographic donor.

In preferred embodiments, the target cells to be administered to a subject will be autologous, e.g. derived from the subject, or syngenic. Allogenic cells can also be isolated from antigenically matched, genetically unrelated donors (identified through a national registry), or by using target cells obtained or derived from a genetically related sibling or parent.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to or after treatment with HIF-2α protein or nucleic acid encoding HIF-2α. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200 or 1000 orders of magnitude. Once target cells have been isolated, they may be propagated by growing in suitable medium according to established methods known in the art. Established cell lines may also be useful in for the disclosed methods. The cells can be stored frozen before transfection, if necessary.

Next the cells are contacted with HIF-2α protein or nucleic acid encoding HIF-2α in vitro, for example using a transfection technique known in the art. Status of the cells can be monitored, and the desired cell type, for example quiescent satellite cells, can be selected for therapeutic administration.

Following treatment, the cells can be administered to a patient in need thereof. The cells can be isolated from and administered back to the same patient. In alternative embodiments, the cells are isolated from one patient, and administered to a second patient. The method can also be used to produce frozen stocks of quiescent SCs stored long-term, for later use.

Muscles transplantation and regenerative medicine protocols are known in the art and include, for example, cultured derivatives of endogenous or induced muscle cells, and freshly isolated or prospectively identified cells (see, e.g., Xu, et al., *Stem Cell Reports.* 2015 Sep. 8; 5(3): 419-434, and references cited therein). Culture-expanded human myoblasts (Skuk et al., *Mol. Ther.* 2010; 18:1689-1697) and CD133+ cells (Meng et al., *Mol. Ther.* 2014; 22:1008-1017.) can engraft and generate functional satellite cells after xenotransplantation of large numbers of cells, indicating the potential for regenerative applications. Advances were gained through clinical trials (Miller et al., *Muscle Nerve.* 1997; 20:469-478; Partridge, *Neuromuscul. Disord.* 2002; 12(Suppl 1):S3-S6.) and xenotransplantation experiments (Bareja et al., *PLoS ONE.* 2014; 9:e90398.; Castiglioni et al., *Stem Cell Reports.* 2014; 2:92-106; Darabi et al., *Cell Stem Cell.* 2012; 10:610-619.; Ehrhardt et al., *Neuromuscul. Disord.* 2007; 17:631-638.; Miller et al., *Muscle Nerve.* 1997; 20:469-478; Partridge, *Neuromuscul. Disord.* 2002; 12(Suppl 1):S3-S6.; Pisani et al., *Stem Cells.* 2010; 28:753-764.; Silva-Barbosa et al., *Cell Transplant.* 2005; 14:457-467). Although results collectively showed low transplantation efficiency, and satellite stem cell functions of self-renewal or expansion in vivo after injury, Xu, et al., *Stem Cell Reports.* 2015 Sep. 8; 5(3): 419-434 characterized, isolated, and transplanted endogenous human satellite stem cells that can engraft, differentiate, replenish the niche, self-renew, and respond to injury. Any of these methods can be modified to include the techniques disclosed herein.

For example, in some embodiments, the methods disclosed herein include transplantation and regenerative cell therapy approaches such as fiber grafting and satellite cell isolation (e.g., based on surface marker expression phenotype).

In some embodiments, the methods include culturing the cells with leukemia inhibitory factor (LIF) (Ito, et al, *Journal of Neuromuscular Diseases,* 3 (2016) 201-207).

B. Conditions to be Treated

The disclosed methods can be used to increase muscle development, growth, strengthening, repair, recovery or combination thereof in a subject in need there of. In some embodiments the subject has healthy muscle and the compositions and methods are used for enhancement of the healthy muscle. In some embodiments, the subject diseased or deficient muscle and the compositions and methods are used to improve the diseased or deficient muscle. In some embodiments, the subject has injured muscle are the compositions and methods are used to increase or improve repair of the injured muscle. In some embodiments, clinical symptoms of muscle disease, injury or atrophy are reduced. In some embodiments, muscle size, volume, mass, strength, or a combination thereof is increased compared to a control.

The subject can have a diseases and disorders that results from direct abnormalities of the muscles (i.e., primary muscle diseases), or one that can be traced as symptoms or manifestations of disorders of nerves or other systems are not properly classified as primary muscle diseases. Because muscles and nerves (neurons) supplying muscle operate as a functional unit, disease of both systems can result in muscular atrophy (wasting) and paralysis.

In some embodiments, the subject has or had muscular atrophy, weakness, pain, cramps, inflammation, or a combination thereof, which are also symptoms of muscle disease and injury. In some embodiments, HIF-2α inhibitor is administered to a subject in an effective amount to protect muscle from or otherwise reduce the effects, progression, or speed of hypoxia-induced muscle wasting and/or atrophy.

In some embodiments, the subject has or had a muscle injury. The injury can be an acute injury or chronic injury. Acute injuries are usually the result of a single traumatic event and cause a macro-trauma to the muscle. There is typically a link between the cause and noticeable symptoms. They common in contact sports and trauma. Overuse, chronic or exercise-induced injuries are subtler and usually occur over a longer period of time. They result from repetitive micro-trauma to the muscle. Diagnosing can by more challenging than for acute injuries because the link between the cause of the injury and the symptoms can be less clear.

Exemplary, non-limiting injuries include, for example, muscle strains, tears, and pulls, (e.g., grade I, grade II, or grade III) muscle contusions, cramps, and soreness. Common strains include hamstring, quadriceps, calf, groin, rotator cuff, rupture long head bicep, and Achilles rupture.

The experiments described below support the conclusion that hypoxia in dystrophic muscle stabilizes HIF-2A in muscle satellite cells and hence compromise the regeneration capacity; and 2) HIF-2α inhibition benefits the regeneration in dystrophic muscle and ameliorate dystrophic phenotypes. Thus, the disclosed compositions and methods can be used to treat dystrophic and myopathic diseases, disorders, and conditions.

Thus, in some embodiments, the subject has or had a muscular dystrophy and/or a myopathic disease. Muscular dystrophies include, but are not limited to, Duchenne, Becker, Congenital (CMD) (including Bethlem CMD, Fukuyama CMD, Muscle-eye-brain diseases, Rigid spine syndromes, Ullrich CMD, Walker-Warburg syndromes), Emery-Dreifuss, facioscapulohumeral, limb-girdle, myotonic, ocular, and oculpharyngeal; myasthenia gravis, a toxic myopathy, an inflammatory myopathy, an endocrine or metabolic myopathy, a vitamin D deficiency, a mitochondrial myopathy, glycogenoses, a lipid storage myopathy, a myotonic disease, periodic paralyses, or fatigue.

Muscular dystrophies are a heterogeneous group of genetic disorders characterized by progressive muscle wasting. The dystrophin-glycoprotein complex (DGC) links the extracellular matrix to the actin cytoskeleton in the muscle fiber. In DGC-related muscular dystrophies, DGC function is compromised due to mutations in genes encoding DGC components (e.g. dystrophin) or enzymes needed for glycosylation of DGC component α-dystroglycan (e.g., fukutin [FKTN]). Impaired DGC function makes the muscle fiber membrane (sarcolemma) susceptible to contraction-induced damage.

Duchenne muscular dystrophy (DMD), which affects 1 in 3,500 boys/males, is caused by dystrophin deficiency. DMD is highly progressive—the patients develop muscle function deficit in the age of 5-8 and survive only to the late second or early third decades of life.

Muscle satellite cells are important stem cells for muscle regeneration (Yin et al., *Physiol Rev* 93, 23-67, doi:10.1152/physrev.00043.2011 (2013)). Regenerative mechanisms mediated by satellite cells can repair the sarcolemma damage in dystrophic muscle and hence delay the progression of muscular dystrophy. Satellite cell-dependent muscle regeneration is robust in young DMD patients yet progressively fails in most muscles with age (Chen et al., *Neurology* 65, 826-834, doi:10.1212/01.wnl.0000173836.09176.c4 (2005)). Regeneration failure commensurates with the loss of muscle function and muscle fibrosis/fat infiltration. In contrast to the debilitating and lethal outcome of DMD in humans, dystrophin-deficient mdx mice usually have delayed progression and mild manifestation of dystrophic pathologies, which is coincident with the long-term maintenance of regeneration capacity in most muscles. Intriguingly, muscular dystrophy in mdx mice is much aggravated by DBA/2 genetic background or a telomerase RNA null mutation (Fukada et al., *Am J Pathol* 176, 2414-2424, doi:10.2353/ajpath.2010.090887 (2010), Sacco et al., *Cell* 143, 1059-1071, doi:10.1016/j.cell.2010.11.039 (2010)), either of which impairs satellite cell function. The above correlations strongly support that boosting satellite cell function can improve the quality of life and extend the lifespan of DMD patients.

The molecular underpinning of regeneration deterioration in DMD patients has not been fully understood. A prevailing explanation points to the muscle microenvironment in DMD patients—excessive and ill-timed TGF-β signaling (due to chronic inflammation) impairs satellite cell proliferation and myogenic differentiation (Dadgar et al., *J Cell Biol* 207, 139-158, doi:10.1083/jcb.201402079 (2014), Serrano et al., *Curr Top Dev Biol* 96, 167-201, doi:10.1016/B978-0-12-385940-2.00007-3 (2011)). When satellite cell function is overwhelmed by the excessive damage in dystrophic muscle, sustained damage of the myofiber leads to chronic inflammation and triggers muscle degeneration, fibrosis, and fat infiltration (dystrophic pathologies), which cause progressive muscle weakness and further impairs satellite cell function.

It is noteworthy that respiratory muscles (diaphragm and intercostal muscles) are particularly affected in many types of muscular dystrophies and myopathic diseases (e.g., DMD, congenital muscular dystrophy, facioscapulohumeral dystrophy, limb-girdle muscular dystrophy 2 (2A-2L), myotonic dystrophy type 1 and type 2, oculopharyngeal muscular dystrophy, Bethlem myopathy, and congenital myopathies) (Lo Mauro, and Aliverti, *Breathe (Sheff)* 12, 318-327, doi:10.1183/20734735.012716 (2016), Burns et al., *J Physiol* 595, 6653-6672, doi:10.1113/JP274792 (2017), Sato et al., *Brain Dev* 38, 324-330, doi:10.1016/j.braindev.2015.08.010 (2016), Shahrizaila et al., *J Neurol Neurosurg Psychiatry* 77, 1108-1115, doi:10.1136/jnnp.2005.078881 (2006)). This susceptibility is owing to the repetitive contraction and damage of respiratory muscles during respiratory activity as well as increased respiratory load secondary to kyphosis/rib cage deformation. Respiratory failure (deficiency in gas exchange) resulting from respiratory muscle weakness is a common comorbidity and a leading cause of death for many severe types of muscular dystrophies in both patients and animal models (e.g., DMD patients, mdx/utrn "double knockout" (dKO) mice, and skeletal muscle-specific Myf5-cre;FktnL/L knockout mice). For human patients, mechanical ventilation has been the survival-affecting intervention in the late stage of severe muscular dystrophies/myopathies, which has been shown to extend the lifespan significantly. However, an underappreciated notion is that respiratory insufficiency and the secondary pathophysiology (i.e., hypoxemia and tissue hypoxia) in the early stage of disease can impair muscle function and contribute to the disease progression. For example, previous studies demonstrated that hypoxic environments exacerbate muscle (particularly diaphragm) dysfunction and pathology in dystrophic animal models (Farkas et al., *Muscle Nerve* 36, 708-710, doi:10.1002/mus.20858 (2007), Mosqueira et al., *PLoS One* 5, e13450, doi:10.1371/journal.pone.0013450 (2010), Lewis et al., *Front Physiol* 7, 623, doi:10.3389/fphys.2016.00623 (2016)). However, the underlying molecular mechanism and hence the therapeutic target previously remained unclear.

The data presented herein show that hypoxia-induced hypoxia-inducible factor 2 alpha (HIF-2α) signaling has profound impacts on satellite cell behaviors. Using mouse muscle injury models that is complicated by blood vessel damage and muscle hypoxia, HIF-2α stabilization in satellite cells was demonstrated to impair the activation, proliferation, and myogenic differentiation of this muscle stem cell population, which impairs the overall muscle regeneration process. The data also shows that the pharmacological inhibition of HIF-2α reversed the adverse effects of hypoxia on satellite cell function, and accelerated muscle regeneration and functional recovery under hypoxia.

These findings support a disease mechanism that explains the progressive deterioration of muscle regeneration in many severe types of muscular dystrophies/myopathies. This latent mechanism is basically a self-driving vicious circle with four critical cause-effect components (FIG. 7). Component 1: Respiratory muscle weakness and respiratory failure in muscular dystrophy patients cause hypoxemia and muscle hypoxia. Component 2: Muscle hypoxia induces HIF-2α stabilization in satellite cells. Component 3: HIF-2α impairs the activation, proliferation, and myogenic differentiation of satellite cells. Component 4: Impaired satellite cell function reduces regeneration capacity in respiratory muscles, which further exacerbates hypoxia and drives the vicious circle. The above mechanism corroborates well with the current understanding of muscular dystrophy. For example, the poorly-understood species- and age-specific progressions of DMD might reflect differential responses and tolerance to hypoxia in humans vs. small mammals or young vs. aged individuals (Dempsey et al., *Physiology (Bethesda)* 30, 304-316, doi:10.1152/physiol.00007.2015 (2015), which involve multiple organs/tissues and are beyond local lesions in dystrophic muscle. The experimental data present below support this latent disease mechanism in muscular dystrophies and demonstrate the efficacy of a HIF-2α inhibitor in ameliorating muscle dystrophic pathologies. HIF-2α inhibitor was therapeutic in a disease model for muscular dystrophy that involves diaphragm dystrophy and muscle hypoxia. The inhibitor remarkably increased the total and proliferative satellite cell numbers, as well as the number of central nuclei in dystrophic muscles. These observations are highly consistent with observations in wildtype injured muscles that HIF-2α inhibition promotes satellite cell proliferation and myogenic differentiation. Improving muscle satellite cell function and regeneration ameliorates muscular dystrophy pathology. Consistently with this proposition, HIF-2α inhibitor-treated dystrophic muscle showed much better maintenance of myofiber calibers than the control muscle that received the vehicle treatment.

Thus, in particularly preferred embodiments, a subject with muscular dystrophy or another myopathic disease or disorder is treated with an effective amount of a HIF-2α inhibitor to treat one or more symptoms of the dystrophy or myopathy.

Fibrosis is an important indicator of dystrophic severity and a major contributing factor to the progressive weakness and loss of contractibility in dystrophic muscles (Bonnemann, *Nat Rev Neurol* 7, 379-390, doi:10.1038/nrneurol.2011.81 (2011). The data below shows that a HIF-2α drastically repressed tissue fibrosis, which overtly developed in vehicle-treated dystrophic muscle. The reduced fibrosis and better maintenance of myofiber calibers after HIF-2α inhibitor treatment indicates that HIF-2α inhibition improves muscle contractile functions. Fibrosis is both a cause and a result of impaired satellite cell function in muscle. An imbalance of muscle satellite cells and fibroadipogenic progenitor (FAP) cells have been implicated in muscle injury-induced fibrosis. HIF-2α inhibiton may indirectly inhibit fibrosis by promoting satellite cell proliferation, resulting in repressed FAP proliferation in dystrophic muscle.

As discussed herein CXCL12 is a downstream target of HIF-2α. It is noteworthy that both HIF-2α and CXCL12 have been impinged in hypoxia-induced fibrosis development in liver and lung (Darby and Hewitson, *Cell Tissue Res* 365, 553-562, doi:10.1007/s00441-016-2461-3 (2016), Qu et al., *Hepatology* 54, 472-483, doi:10.1002/hep.24400 (2011), Shu et al., *PLoS One* 8, e79768, doi:10.1371/journal.pone.0079768 (2013), Wald et al., *Eur J Immunol* 34, 1164-1174, doi:10.1002/eji.200324441 (2004)). Therefore, HIF-2α inhibition may also have a direct effect on FAP cells and inflammatory cells that infiltrate frequently-damaged dystrophic muscles and repress the proliferation/recruitment of these fibrogenic cell populations.

Thus, in some embodiments, a HIF-2α inhibitor is administered to a subject in need thereof in an effective amount to reduce or inhibit fibrosis. In some embodiments, treatment reduces the amount of collagen, or reduces the onset or progression thereof, in the endomysial space.

Hypoxia commonly results from exercise and many environmental and disease conditions such as insufficient ventilation (e.g., sleep apnea, respiratory disorders), reduced partial pressure of oxygen (e.g., high altitude, flight travel), and decreased oxygen delivery to the tissue (e.g., anemia, atherosclerosis), all of which may occur in muscular dystrophy patients and trigger the entry into the vicious circle of disease progression. Respiratory failure is the primary cause of morbidity and mortality in many severe types of muscular dystrophy and myopathic diseases, none of which has a conventional cure (Shahrizaila et al., *J Neurol Neurosurg Psychiatry* 77, 1108-1115, doi:10.1136/jnnp.2005.078881 (2006).

Hyperbaric oxygen treatment (HBOT) has been shown to benefit muscular dystrophy (Hirotani and Kuyama, *Nihon Geka Hokan* 43, 161-167 (1974). and been recently advocated by DMD patient families (Stanford et al., *Diabetes* 64, 3334-3334, doi:10.2337/db15-er09 (2015). However, repetitive/prolonged HBOT has well-known side effects (e.g., cataracts, inner ear damage, and lung damage) and its therapeutic efficacy in muscular dystrophy has not been proved. Thus, in some embodiments, a HIF-2α inhibitor is administered to a subject in need thereof in an effective amount to improve respiration, reduce the effects of hypoxia, or a combination thereof. In some embodiments, the subject has a respiratory-related deficiency or disorder. The respiratory-related deficiency or disorder can be related or unrelated to a dystrophic or myopathic disease or disorder.

In some embodiments, the subject of the disclosed treatments does not have cancer. In some embodiments, the subject does not have a tumor. In some embodiments, the subject does not have an infection.

III. Compositions

HIF-2α, also referred to as HIF2A, HIF-2a, HIP-2 alpha, and endothelial PAS domain-containing protein 1, is a transcription factor involved in the induction of oxygen regulated genes. It binds to core DNA sequence 5'-[AG]CGTG-3' within the hypoxia response element (HRE) of target gene promoters. HIF-2α regulates the vascular endothelial growth factor (VEGF) expression and a potent activator of the Tie-2 tyrosine kinase expression.

A. HIF-2α Sequences

Nucleic acid and amino acid sequences for HIF-2α are known in the art. See, for example, *Homo sapiens* endothelial PAS domain protein 1 (EPAS1), mRNA NCBI Reference Sequence: NM_001430.4; endothelial PAS domain-containing protein 1 [*Homo sapiens*] NCBI Reference Sequence: NP_001421.2; NCBI Reference Sequence: *Homo sapiens* endothelial PAS domain protein 1, mRNA (cDNA clone MGC:59860 IMAGE:6305604), complete cds; and UniProtKB—Q99814 (EPAS1_HUMAN); and U.S. Pat. No. 8,114,983.

An exemplary nucleic acid sequence for human HIF-2α is:

GCTTTACACTCGCGAGCGGACCGCCACACGGGTCCGGTGCCCGCTGCGCT

TCCGCCCCAGCGCTCCTGAGGCGGCCGTACAATCCTCGGCAGTGTCCTGA

GACTGTATGGTCAGCTCAGCCCGGCCTCCGACTCCTTCCGACTCCCAGCA

TTCGAGCCACTTTTTTTTTCTTTGAAAACTCAGAAAAGTGACTCCTTTT

CCAGGGAAAAAGGAACTTGGGTTCCCTTCTCTCCGTCCTCTTTTCGGGTC

TGACAGCCTCCACCCACTCCTTCCCCGGACCCCGCCTCCGCGCGCAGGTT

CCTCCCAGTCACCTTTCTCCACCCCCGCCCCCGCACCTAGCCCGCCGCGC

GCCACCTTCCACCTGACTGCGCGGGGCGCTCGGGACCTGCGCGCACCTCG

GACCTTCACCACCCGCCCGGGCCGCGGGGAGCGGACGAGGGCCACAGCCC

CCCACCCGCCAGGGAGCCCAGGTGCTCGGCGTCTGAACGTCTCAAAGGGC

CACAGCGACAATGACAGCTGACAAGGAGAAGAAAAGGAGTAGCTCGGAGA

GGAGGAAGGAGAAGTCCCGGGATGCTGCGCGGTGCCGGCGGAGCAAGGAG

ACGGAGGTGTTCTATGAGCTGGCCCATGAGCTGCCTCTGCCCCACAGTGT

GAGCTCCCATCTGGACAAGGCCTCCATCATGCGACTGGCAATCAGCTTCC

TGCGAACACACAAGCTCCTCTCCTCAGTTTGCTCTGAAAACGAGTCCGAA

GCCGAAGCTGACCAGCAGATGGACAACTTGTACCTGAAAGCCTTGGAGGG

TTTCATTGCCGTGGTGACCCAAGATGGCGACATGATCTTTCTGTCAGAAA

ACATCAGCAAGTTCATGGGACTTACACAGGTGGAGCTAACAGGACATAGT

ATCTTTGACTTCACTCATCCCTGCGACCATGAGGAGATTCGTGAGAACCT

GAGTCTCAAAAATGGCTCTGGTTTTGGGAAAAAAAGCAAAGACATGTCCA

CAGAGCGGGACTTCTTCATGAGGATGAAGTGCACGGTCACCAACAGAGGC

-continued

CGTACTGTCAACCTCAAGTCAGCCACCTGGAAGGTCTTGCACTGCACGGG
CCAGGTGAAAGTCTACAACAACTGCCCTCCTCACAATAGTCTGTGTGGCT
ACAAGGAGCCCCTGCTGTCCTGCCTCATCATCATGTGTGAACCAATCCAG
CACCCATCCCACATGGACATCCCCCTGGATAGCAAGACCTTCCTGAGCCG
CCACAGCATGGACATGAAGTTCACCTACTGTGATGACAGAATCACAGAAC
TGATTGGTTACCACCCTGAGGAGCTGCTTGGCCGCTCAGCCTATGAATTC
TACCATGCGCTAGACTCCGAGAACATGACCAAGAGTCACCAGAACTTGTG
CACCAAGGGTCAGGTAGTAAGTGGCCAGTACCGGATGCTCGCAAAGCATG
GGGGCTACGTGTGGCTGGAGACCCAGGGGACGGTCATCTACAACCCTCGC
AACCTGCAGCCCCAGTGCATCATGTGTGTCAACTACGTCCTGAGTGAGAT
TGAGAAGAATGACGTGGTGTTCTCCATGGACCAGACTGAATCCCTGTTCA
AGCCCCACCTGATGGCCATGAACAGCATCTTTGATAGCAGTGGCAAGGGG
GCTGTGTCTGAGAAGAGTAACTTCCTATTCACCAAGCTAAAGGAGGAGCC
CGAGGAGCTGGCCCAGCTGGCTCCCACCCCAGGAGACGCCATCATCTCTC
TGGATTTCGGGAATCAGAACTTCGAGGAGTCCTCAGCCTATGGCAAGGCC
ATCCTGCCCCCGAGCCAGCCATGGGCCACGGAGTTGAGGAGCCACAGCAC
CCAGAGCGAGGCTGGGAGCCTGCCTGCCTTCACCGTGCCCCAGGCAGCTG
CCCCGGGCAGCACCACCCCAGTGCCACCAGCAGCAGCAGCAGCTGCTCC
ACGCCCAATAGCCCTGAAGACTATTACACATCTTTGGATAACGACCTGAA
GATTGAAGTGATTGAGAAGCTCTTCGCCATGGACACAGAGGCCAAGGACC
AATGCAGTACCCAGACGGATTTCAATGAGCTGGACTTGGAGACACTGGCA
CCCTATATCCCCATGGACGGGGAAGACTTCCAGCTAAGCCCCATCTGCCC
CGAGGAGCGGCTCTTGGCGGAGAACCCACAGTCCACCCCCCAGCACTGCT
TCAGTGCCATGACAAACATCTTCCAGCCACTGGCCCCTGTAGCCCCGCAC
AGTCCCTTCCTCCTGGACAAGTTTCAGCAGCAGCTGGAGAGCAAGAAGAC
AGAGCCCGAGCACCGGCCCATGTCCTCCATCTTCTTTGATGCCGGAAGCA
AAGCATCCCTGCCACCGTGCTGTGGCCAGGCCAGCACCCCTCTCTCTTCC
ATGGGGGGCAGATCCAATACCCAGTGGCCCCCAGATCCACCATTACATTT
TGGGCCCACAAAGTGGGCCGTCGGGGATCAGCGCACAGAGTTCTTGGGAG
CAGCGCCGTTGGGGCCCCCTGTCTCTCCACCCCATGTCTCCACCTTCAAG
ACAAGGTCTGCAAAGGGTTTTGGGGCTCGAGGCCCAGACGTGCTGAGTCC
GGCCATGGTAGCCCTCTCCAACAAGCTGAAGCTGAAGCGACAGCTGGAGT
ATGAAGAGCAAGCCTTCCAGGACCTGAGCGGGGGGGACCCACCTGGTGGC
AGCACCTCACATTTGATGTGGAAACGGATGAAGAACCTCAGGGGTGGGAG
CTGCCCTTTGATGCCGACAAGCCACTGAGCGCAAATGTACCCAATGATA
AGTTCACCCAAAACCCCATGAGGGGCCTGGGCCATCCCCTGAGACATCTG
CCGCTGCCACAGCCTCCATCTGCCATCAGTCCCGGGGAGAACAGCAAGAG
CAGGTTCCCCCCACAGTGCTACGCCACCCAGTACCAGGACTACAGCCTGT
CGTCAGCCCACAAGGTGTCAGGCATGGCAAGCCGGCTGCTCGGGCCCTCA
TTTGAGTCCTACCTGCTGCCCGAACTGACCAGATATGACTGTGAGGTGAA
CGTGCCCGTGCTGGGAAGCTCCACGCTCCTGCAAGGAGGGGACCTCCTCA

-continued

GAGCCCTGGACCAGGCCACCTGAGCCAGGCCTTCTACCTGGGCAGCACCT
CTGCCGACGCCGTCCCACCAGCTTCACTCTCTCCGTCTGTTTTTGCAACT
AGGTATTTCTAACGCCAGCACACTATTTACAAGATGGACTTACCTGGCAG
ACTTGCCCAGGTCACCAAGCAGTGGCCTTTTTCTGAGATGCTCACTTTAT
TATCCCTATTTTTAAAGTACACAATTGTTTTACCTGTTCTGAAATGTTCT
TAAATTTTGTAGGATTTTTTTCCTCCCCACCTTCAATGACTTCTAATTTA
TATTATCCATAGGTTTCTCTCCCTCCTTCTCCTTCTCACACACAACTGTC
CATACTAACAAGTTTGGTGCATGTCTGTTCTTCTGTAGGGAGAAGCTTTA
GCTTCATTTTACTAAAAAGATTCCTCGTTATTGTTGTTGCCAAAGAGAAA
CAAAAATGATTTTGCTTTCCAAGCTTGGTTTGTGGCGTCTCCCTCGCAGA
GCCCTTCTCGTTTCTTTTTTAAACTAATCACCATATTGTAAATTTCAGGG
TTTTTTTTTTTTGTTTAAGCTGACTCTTTGCTCTAATTTTGGAAAAAAA
GAAATGTGAAGGGTCAACTCCAACGTATGTGGTTATCTGTGAAAGTTGCA
CAGCGTGGCTTTTCCTAAACTGGTGTTTTTCCCCGCATTTGGTGGATTT
TTTATTATTATTCAAAAACATAACTGAGTTTTTTAAAAGAGGAGAAAATT
TATATCTGGGTTAAGTGTTTATCATATATATGGGTACTTTGTAATATCTA
AAAACTTAGAAACGGAAATGGAATCCTGCTCACAAAATCACTTTAAGATC
TTTTCGAAGCTGTTAATTTTTCTTAGTGTTGTGGACACTGCAGACTTGTC
CAGTGCTCCCACGGCCTGTACGGACACTGTGGAAGGCCTCCCTCTGTCGG
CTTTTTGCCATCTGTGATATGCCATAGGTGTGACAATCCGAGCAGTGGAG
TCATTCAGCGGGAGCACTGCGCGCTATCCCCTCACATTCTCTATGTACTA
TGTATGTATGTATTATTATTATTGCTGCCAAGAGGGTCTGATGGCACGTT
GTGGGGTCGGGGGTGGGCGGGGAAGTGCTCTAACTTTTCTTAAGGTTT
TGTTGCTAGCCCTTCAAGTGCACTGAGCTATGTGACTCGGATGGTCTTTC
ACACGGCACATTTGGACATTTCCAGAACTACCATGAGATGGTTTAGACGG
GAATTCATGCAAATGAGGGGTCAAAAATGGTATAGTGACCCCGTCCACGT
CCTCCAAGCTCACGACCTTGGAGCCCCGTGGAGCTGGACTGAGGAGGAGG
CTGCACAGCGGGAGAGCAGCTGGTCCAGACCAGCCCTGCAGCCCCCACTC
AGCCGGCAGCCAGATGGCCCCGCAAGGCCTCCAGGGATGGCCCCTAGCCA
CAGGCCCTGGCTGAGGTCTCTGGGTCGGTCAGTGACATGTAGGTAGGAAG
CACTGAAAATAGTGTTCCCAGAGCACTTTGCAACTCCCTGGGTAAGAGGG
ACGACACCTCTGGTTTTTCAATACCAATTACATGGAACTTTTCTGTAATG
GGTACAATGAAGAAGTTTCTAAAAACACACACAAAGCACATTGGGCCAAC
TATTTAGTAAGCCCGGATAGACTTATTGCCAAAAACAAAAAATAGCTTTC
AAAAGAAATTTAAGTTCTATGAGAAATTCCTTAGTCATGGTGTTGCGTAA
ATCATATTTTAGCTGCACGGCATTACCCCACACAGGGTGGCAGAACTTGA
AGGGTTACTGACGTGTAAATGCTGGTATTTGATTTCCTGTGTGTGTTGCC
CTGGCATTAAGGGCATTTTACCCTTGCAGTTTTACTAAAACACTGAAAAA
TATTCCAAGCTTCATATTAACCCTACCTGTCAACGTAACGATTTCATGAA
CGTTATTATATTGTCGAATTCCTACTGACAACATTATAACTGTATGGGAG

CTTAACTTTATAAGGAAATGTATTTTGACACTGGTATCTTATTAAAGTAT
TCTGATCCTACCACTGAAAAAAAAAAAAAAAAAA (SEQ ID NO: 1,
NCBI Reference Sequence: NM_001430.4).

Another exemplary nucleic acid sequence from human HIF-2α is:

CTTTTCCAGGGAAAAAGGAACTTGGGTTCCCTTCTCTCCGTCCTCTTTTC
GGGTCTGACAGCCTCCACCCACTCCTTCCCCGGACCCCGCCTCCGCGCGC
AGGTTCCTCCCAGTCACCTTTCTCCACCCCCGCCCCCGCACCTAGCCCGC
CGCGCGCCACCTTCCACCTGACTGCGCGGGGCGCTCGGGACCTGCGCGCA
CCTCGGACCTTCACCACCCGCCCGGGCCGCGGGGAGCGGACGAGGGCCAC
AGCCCCCCACCCGCCAGGGAGCCCAGGTGCTCGGCGTCTGAACGTCTCAA
AGGGCCACAGCGACAATGACAGCTGACAAGGAGAAGAAAAGGAGTAGCTC
GGAGAGGAGGAAGGAGAAGTCCCGGGATGCTGCGCGGTGCCGGCGGAGCA
AGGAGACGGAGGTGTTCTATGAGCTGGCCCATGAGCTGCCTCTGCCCCAC
AGTGTGAGCTCCCATCTGGACAAGGCCTCCATCATGCGACTGGCAATCAG
CTTCCTGCGAACACACAAGCTCCTCTCCTCAGTTTGCTCTGAAAACGAGT
CCGAAGCCGAAGCTGACCAGCAGATGGACAACTTGTACCTGAAAGCCTTG
GAGGGTTTCATTGCCGTGGTGACCCAAGATGGCGACATGATCTTTCTGTC
AGAAAACATCAGCAAGTTCATGGGACTTACACAGGTGGAGCTAACAGGAC
ATAGTATCTTTGACTTCACTCATCCCTGCGACCATGAGGAGATTCGTGAG
AACCTGAGTCTCAAAAATGGCTCTGGTTTTGGGAAAAAAAGCAAAGACAT
GTCCACAGAGCGGGACTTCTTCATGAGGATGAAGTGCACGGTCACCAACA
GAGGCCGTACTGTCAACCTCAAGTCAGCCACCTGGAAGGTCTTGCACTGC
ACGGGCCAGGTGAAAGTCTACAACAACTGCCCTCCTCACAATAGTCTGTG
TGGCTACAAGGAGCCCCTGCTGTCCTGCCTCATCATCATGTGTGAACCAA
TCCAGCACCCATCCCACATGGACATCCCCCTGGATAGCAAGACCTTCCTG
AGCCGCCACAGCATGGACATGAAGTTCACCTACTGTGATGACAGAATCAC
AGAACTGATTGGTTACCACCCTGAGGAGCTGCTTGGCCGCTCAGCCTATG
AATTCTACCATGCGCTAGACTCCGAGAACATGACCAAGAGTCACCAGAAC
TTGTGCACCAAGGGTCAGGTAGTAAGTGGCCAGTACCGGATGCTCGCAAA
GCATGGGGGCTACGTGTGGCTGGAGACCCAGGGGACGGTCATCTACAACC
CTCGCAACCTGCAGCCCCAGTGCATCATGTGTGTCAACTACGTCCTGAGT
GAGATTGAGAAGAATGACGTGGTGTTCTCCATGGACCAGACTGAATCCCT
GTTCAAGCCCCACCTGATGGCCATGAACAGCATCTTTGATAGCAGTGGCA
AGGGGGCTGTGTCTGAGAAGAGTAACTTCCTATTCACCAAGCTAAAGGAG
GAGCCCGAGGAGCTGGCCCAGCTGGCTCCCACCCCAGGAGACGCCATCAT
CTCTCTGGATTTCGGGAATCAGAACTTCGAGGAGTCCTCAGCCTATGGCA
AGGCCATCCTGCCCCCGAGCCAGCCATGGGCCACGGAGTTGAGGAGCCAC
AGCACCCAGAGCGAGGCTGGGAGCCTGCCTGCCTTCACCGTGCCCCAGGC
AGCTGCCCCGGGCAGCACCACCCCCAGTGCCACCAGCAGCAGCAGCAGCT

GCTCCACGCCCAATAGCCCTGAAGACTATTACACATCTTTGGATAACGAC
CTGAAGATTGAAGTGATTGAGAAGCTCTTCGCCATGGACACAGAGGCCAA
GGACCAATGCAGTACCCAGACGGATTTCAATGAGCTGGACTTGGAGACAC
TGGCACCCTATATCCCCATGGACGGGGAAGACTTCCAGCTAAGCCCCATC
TGCCCCGAGGAGCGGCTCTTGGCGGAGAACCCACAGTCCACCCCCCAGCA
CTGCTTCAGTGCCATGACAAACATCTTCCAGCCACTGGCCCCTGTAGCCC
CGCACAGTCCCTTCCTCCTGGACAAGTTTCAGCAGCAGCTGGAGAGCAAG
AAGACAGAGCCCGAGCACCGGCCCATGTCCTCCATCTTCTTTGATGCCGG
AAGCAAAGCATCCCTGCCACCGTGCTGTGGCCAGGCCAGCACCCCTCTCT
CTTCCATGGGGGGCAGATCCAATACCCAGTGGCCCCCAGATCCACCATTA
CATTTTGGGCCCACAAAGTGGGCCGTCGGGGATCAGCGCACAGAGTTCTT
GGGAGCAGCGCCGTTGGGGCCCCCTGTCTCTCCACCCCATGTCTCCACCT
TCAAGACAAGGTCTGCAAAGGGTTTTGGGGCTCGAGGCCCAGACGTGCTG
AGTCCGGCCATGGTAGCCCTCTCCAACAAGCTGAAGCTGAAGCGACAGCT
GGAGTATGAAGAGCAAGCCTTCCAGGACCTGAGCGGGGGGACCCACCTG
GTGGCAGCACCTCACATTTGATGTGGAAACGGATGAAGAACCTCAGGGGT
GGGAGCTGCCCTTTGATGCCGGACAAGCCACTGAGCGCAAATGTACCCAA
TGATAAGTTCACCCAAAACCCCATGAGGGGCCTGGGCCATCCCCTGAGAC
ATCTGCCGCTGCCACAGCCTCCATCTGCCATCAGTCCCGGGGAGAACAGC
AAGAGCAGGTTCCCCCCACAGTGCTACGCCACCCAGTACCAGGACTACAG
CCTGTCGTCAGCCCACAAGGTGTCAGGCATGGCAAGCCGGCTGCTCGGGC
CCTCATTTGAGTCCTACCTGCTGCCCGAACTGACCAGATATGACTGTGAG
GTGAACGTGCCCGTGCTGGGAAGCTCCACGCTCCTGCAAGGAGGGGACCT
CCTCAGAGCCCTGGACCAGGCCACCTGAGCCAGGCCTTCTACCTGGGCAG
CACCTCTGCCGACGCCGTCCCACCAGCTTCACTCTCTCCGTCTGTTTTTG
CAACTAGGTATTTCTAACGCCAGCACACTATTTACAAGATGGACTTACCT
GGCAGACTTGCCCAGGTCACCAAGCAGTGGCCTTTTCTGAGATGCTCAC
TTTATTATCCCTATTTTTAAAGTACACAATTGTTTTACCTGTTCTGAAAT
GTTCTTAAATTTTGTAGGATTTTTTTCCTCCCCACCTTCAATGACTTCTA
ATTTATATTATCCATAGGTTTCTCTCCCTCCTTCTCCTTCTCACACACAA
CTGTCCATACTAACAAGTTTGGTGCATGTCTGTTCTTCTGTAGGGAGAAG
CTTTAGCTTCATTTTACTAAAAGATTCCTCGTTATTGTTGTTGCCAAAG
AGAAACAAAATGATTTTGCTTTCCAAGCTTGGTTTGTGGCGTCTCCCTC
GCAGAGCCCTTCTCGTTTCTTTTTTAAACTAATCACCATATTGTAAATTT
CAGGGTTTTTTTTTTGTTTAAGCTGACTCTTTGCTCTAATTTTGGAAAA
AAAGAAATGTGAAGGGTCAACTCCAACGTATGTGGTTATCTGTGAAAGTT
GCACAGCGTGGCTTTTCCTAAACTGGTGTTTTTCCCCCGCATTTGGTGGA
TTTTTTATTATTATTCAAAAACATAACTGAGTTTTTTAAAAGAGGAGAAA
ATTTATATCTGGGTTAAGTGTTTATCATATATATGGGTACTTTGTAATAT
CTAAAAACTTAGAAACGGAAATGGAATCCTGCTCACAAAATCACTTTAAG
ATCTTTTCGAAGCTGTTAATTTTTCTTAGTGTTGTGGACACTGCAGACTT

-continued

```
GTCCAGTGCTCCCACGGCCTGTACGGACACTGTGGAAGGCCTCCCTCTGT

CGGCTTTTTGCCATCTGTGATATGCCATAGGTGTGACAATCCGAGCAGTG

GAGTCATTCAGCGGGAGCACTGCGCGCTATCCCCTCACATTCTCTATGTA

CTATGTATGTATGTATTATTATTATTGCTGCCAAGAGGGTCTGATGGCAC

GTTGTGGGGTCGGGGGTGGGGCGGGAAGTGCTCTAACTTTTCTTAAGG

TTTTGTTGCTAGCCCTTCAAGTGCACTGAGCTATGTGACTCGGATGGTCT

TTCACACGGCACATTTGGACATTTCCAGAACTACCATGAGATGGTTTAGA

CGGGAATTCATGCAAATGAGGGGTCAAAAATGGTATAGTGACCCCGTCCA

CGTCCTCCAAGCTCACGACCTTGGAGCCCCGTGGAGCTGGACTGAGGAGG

AGGCTGCACAGCGGGAGAGCAGCTGGTCCAGACCAGCCCTGCAGCCCCA

CTCAGCCGGCAGCCAGATGGCCCCGCAAGGCCTCCAGGGATGGCCCCTAG

CCACAGGCCCTGGCTGAGGTCTCTGGGTCGGTCAGTGACATGTAGGTAGG

AAGCACTGAAAATAGTGTTCCCAGAGCACTTTGCAACTCCCTGGGTAAGA

GGGACGACACCTCTGGTTTTTCAATACCAATTACATGGAACTTTTCTGTA

ATGGGTACAATGAAGAAGTTTCTAAAAACACACACAAAGCACATTGGGCC

AACTATTTAGTAAGCCCGGATAGACTTATTGCCAAAAACAAAAAATAGCT

TTCAAAAGAAATTTAAGTTCTATGAGAAATTCCTTAGTCATGGTGTTGCG

TAAATCATATTTTAGCTGCACGGCATTACCCCACACAGGGTGGCAGAACT

TGAAGGGTTACTGACGTGTAAATGCTGGTATTTGATTTCCTGTGTGTGTT

GCCCTGGCATTAAGGGCATTTTACCCTTGCAGTTTTACTAAAACACTGAA

AAATATTCCAAGCTTCATATTAACCCTACCTGTCAACGTAACGATTTCAT

GAACGTTATTATATTGTCGAATTCCTACTGACAACATTATAACTGTATGG

GAGCTTAACTTTATAAGGAAATGTATTTTGACACTGGTATCTTATTAAAG

TATTCTGATCCTAAAAAAAAAAAAAAAAAAAAAAAAAAAAAAAAAAAAA

AAAAAAAAAAA (SEQ ID NO: 38, GenBank: BC051338.1).
```

An exemplary amino acid sequence for HIF-2α is:

```
MTADKEKKRSSSERRKEKSRDAARCRRSKETEVFYELAHELPLPHSVSSH

LDKASIMRLAISFLRTHKLLSSVCSENESEAEADQQMDNLYLKALEGFIA

VVTQDGDMIFLSENISKFMGLTQVELTGHSIFDFTHPCDHEEIRENLSLK

NGSGFGKKSKDMSTERDFFMRMKCTVTNRGRTVNLKSATWKVLHCTGQVK

VYNNCPPHNSLCGYKEPLLSCLIIMCEPIQHPSHMDIPLDSKTFLSRHSM

DMKFTYCDDRITELIGYHPEELLGRSAYEFYHALDSENMTKSHQNLCTKG

QVVSGQYRMLAKHGGYVWLETQGTVIYNPRNLQPQCIMCVNYVLSEIEKN

DVVFSMDQTESLFKPHLMAMNSIFDSSGKGAVSEKSNFLFTKLKEEPEEL

AQLAPTPGDAIISLDFGNQNFEESSAYGKAILPPSQPWATELRSHSTQSE

AGSLPAFTVPQAAAPGSTTPSATSSSSSCSTPNSPEDYYTSLDNDLKIEV

IEKLFAMDTEAKDQCSTQTDFNELDLETLAPYIPMDGEDFQLSPICPEER

LLAENPQSTPQHCFSAMTNIFQPLAPVAPHSPFLLDKFQQQLESKKTEPE

HRPMSSIFFDAGSKASLPPCCGQASTPLSSMGGRSNTQWPPDPPLHFGPT

KWAVGDQRTEFLGAAPLGPPVSPPHVSTFKTRSAKGFGARGPDVLSPAMV

ALSNKLKLKRQLEYEEQAFQDLSGGDPPGGSTSHLMWKRMKNLRGGSCPL

MPDKPLSANVPNDKFTQNPMRGLGHPLRHLPLPQPPSAISPGENSKSRFP

PQCYATQYQDYSLSSAHKVSGMASRLLGPSFESYLLPELTRYDCEVNVPV

LGSSTLLQGGDLLRALDQAT (SEQ ID NO: 2, NCBI

Reference Sequence: NM_001430.4 and NP_001421.2).
```

Another exemplary amino acid sequence for HIF-2α is

```
MLGLFVFKTGTQRRNRRLPYARSSSERRKEKSRDAARCRRSKETEVFYEL

AHELPLPHSVSSHLDKASIMRLAISFLRTHKLLSSVCSENESEAEADQQM

DNLYLKALEGFIAVVTQDGDMIFLSENISKFMGLTQVELTGHSIFDFTHP

CDHEEIRENLSLKNGSGFGKKSKDMSTERDFFMRMKCTVTNRGRTVNLKS

ATWKVLHCTGQVKVYNNCPPHNSLCGYKEPLLSCLIIMCEPIQHPSHMDI

PLDSKTFLSRHSMDMKFTYCDDRITELIGYHPEELLGRSAYEFYHALDSE

NMTKSHQNLCTKGQVVSGQYRMLAKHGGYVWLETQGTVIYNPRNLQPQCI

MCVNYVLSEIEKNDVVFSMDQTESLFKPHLMAMNSIFDSSGKGAVSEKSN

FLFTKLKEEPEELAQLAPTPGDAIISLDFGNQNFEESSAYGKAILPPSQP

WATELRSHSTQSEAGSLPAFTVPQAAAPGSTTPSATSSSSSCSTPNSPED

YYTSLDNDLKIEVIEKLFAMDTEAKDQCSTQTDFNELDLETLAPYIPMDG

EDFQLSPICPEERLLAENPQSTPQHCFSAMTNIFQPLAPVAPHSPFLLDK

FQQQLESKKTEPEHRPMSSIFFDAGSKASLPPCCGQASTPLSSMGGRSNT

QWPPDPPLHFGPTKWAVGDQRTEFLGAAPLGPPVSPPHVSTFKTRSAKGF

GARGPDVLSPAMVALSNKLKLKRQLEYEEQAFQDLSGGDPPGGSTSHLMW

KRMKNLRGGSCPLMPDKPLSANVPNDKFTQNPMRGLGHPLRHLPLPQPPS

AISPGENSKSRFPPQCYATQYQDYSLSSAHKVSGMASRLLGPSFESYLLP

ELTRYDCEVNVPVLGSSTLLQGGDLLRALDQAT (SEQ ID NO: 39,

NCBI Reference Sequence: XP_011531000.1).
```

B. HIF-2α Inhibitors

Compounds for decreasing the bioactivity of HIF-2α, and formulations formed therewith are provided. In some embodiments, the compound is an inhibitory polypeptide; a small molecule or peptidomimedic, or an inhibitory nucleic acid that targets genomic or expressed HIF-2α nucleic acids (e.g., HIF-2α mRNA), or a vector that encodes an inhibitory nucleic acid. The compound can reduce the expression or bioavailability of HIF-2α. HIF-2α inhibition can be competitive, non-competitive, uncompetitive, or product inhibition. Thus, an HIF-2α inhibitor can directly inhibit HIF-2α, a HIF-2α inhibitor can inhibit another factor in a pathway that leads to induction, persistence, or amplification of HIF-2α expression, or a combination thereof.

In other embodiments, muscle repair and regeneration is modulated by targeting a target of HIF-2α. The Examples below show that HIF-2α induces satellite cell quiescence by binding HREs in the Spry1 promoter and impedes SC proliferation by activating Spry1 transcription. Thus, in some embodiments the compound for use in the disclosed methods is a Spry1 inhibitor.

Exemplary inhibitors are described below. See also, U.S. Published Application Nos. 2011/0312930 (see also WO/2010/0054762), 2013/0196964 (see also WO/2010/ 0054763), 2011/0301122 (see also WO/2010/0054764), 2015/0218098, 2016/0251307 (see also WO/2015/035223), 2016/0362390, 2016/0368893 (see also WO/2015/095048), 2017/0217891 (see also WO/2015/035223), 2017/0217892 (see also WO/2015/035223), 2018/0042884 (see also WO/2016/145045), 2018/0049995 (see also WO/2016/ 145236), 20180148413 (see also WO/2016/144826), 2018/ 0155279 (WO/2015/035223), 2018/0140569 (see also WO/2016/168510), 2018/0162807 (see also WO/2016/ 144825), 20180177754 (see also WO/2016/145032), each of which is specifically incorporated by reference herein in its entirety.

In a preferred embodiment, the HIF-2α inhibitor is PT2385 or PT2977 (Peloton Therapeutics). PT2385 demonstrated clinical activity in patients (pts) with clear cell renal cell carcinoma (ccRCC). PT2977 is an orally administerable selective small molecule HIF-2α inhibitor with improved potency compared to PT2385. PT2977 inhibited expression of HIF-2α target genes in tumor cells and induced regression in mouse xenograft models. Papadopoulous, et al., *Journal of Clinical Oncology*, 36, no. 15_suppl (May 2018) 2508-2508. DOI: 10.1200/ JCO.2018.36.15_suppl.2508; Clinical trial information: NCT02974738.

In the experiments described below, HIF-c2, CAS #:1422955-31-4; was exemplified as the of HIF-2α inhibitor and administered at a dosage of 5 mg/injection/day for 3 consecutive days.

The disclosed compounds also includes tautomers, isomers, epimers, diastereoisomer, as well as any form of the compounds, such as the base (zwitter ion), pharmaceutically acceptable salts, e.g., pharmaceutically acceptable acid addition salts, hydrates or solvates of the base or salt, as well as anhydrates, and also amorphous, or crystalline forms thereof.

1. Pharmacological HIF-2α Inhibitors

Pharmacological inhibitors of HIF-2α include, but are not limited to the compounds described below.

a. Aryl Ether Compounds

In some embodiments, the HIF-2α inhibitor is a compound (as disclosed in U.S. Published Application 2016/ 0251307 which is specifically incorporated by reference herein in its entirety) defined according to the following paragraphs found in this subheading:

Paragraph 1a: A compound of Formula:

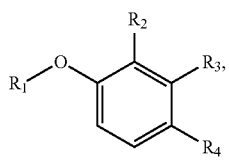

or a pharmaceutically acceptable salt thereof, wherein:

$R_1$ is monocyclic aryl or monocyclic heteroaryl;

$R_2$ is nitro, carboxaldehyde, carboxylic acid, ester, amido, cyano, halo, sulfonyl or alkyl;

$R_3$ is hydrogen, halo, cyano, alkyl, heteroalkyl, alkenyl, alkynyl, alkylamino, carboxaldehyde, carboxylic acid, ester, amido or acyl, or $R_2/R_3$ and atoms they are attached to form a 5- or 6-membered carbocycle with at least one sp³ hybridized carbon; and $R_4$ is halo, cyano, fluoroalkyl, sulfinyl, alkylsulfonamide, sulfonyl or sulfoximinyl;

with the proviso that when $R_3$ is H, $R_4$ is $-S(=O)_2R_a$ or $-S(=O)(=NR_b)R_a$, wherein $R_a$ is fluoroalkyl and $R_b$ is hydrogen or alkyl; and $R_1$ is selected from the group consisting of

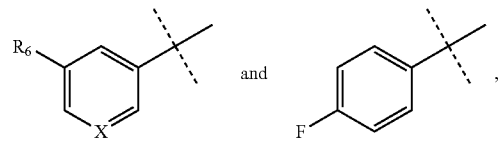

wherein X is N or $CR_7$, $R_6$ is cyano, halo, alkyl or alkoxy, and $R_7$ is hydrogen, cyano, halo, alkyl or alkoxy; and

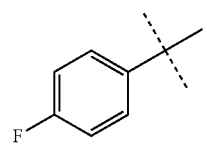

may optionally be substituted with one or more substituents selected from the group consisting of cyano, halo, alkyl and alkoxy.

Paragraph 2a: The compound of paragraph 1a, wherein $R_1$ is phenyl or pyridyl.

Paragraph 3a: The compound of paragraph 2a, wherein said phenyl or pyridyl is substituted with one or more substituents selected from the group consisting of halo, alkyl, alkoxy and cyano.

Paragraph 4a: The compound of paragraph 1a, having the structure of Formula:

or a pharmaceutically acceptable salt thereof, wherein:

n is 0, 1, 2, 3 or 4;

$R_8$ is hydrogen, hydroxy, alkoxy or amino;

$R_9$ is hydrogen, alkyl, alkenyl or alkynyl, or $R_8$ and $R_9$ in combination form oxo; and each of $R_{10}$ is independently selected from the group consisting of fluoro, hydroxy, alkyl, and heteroalkyl, with the proviso that when $R_{10}$ is hydroxy, n is 1 or 2.

Paragraph 5a: The compound of paragraph 4a, wherein $R_8$ is hydroxy or amino.

Paragraph 6a: The compound of paragraph 4a, wherein $R_9$ is hydrogen.

Paragraph 7a: The compound of paragraph 4a, wherein n is 1 or 2 and $R_{10}$ is fluoro.

Paragraph 8a: The compound of paragraph 4a, having the structure of Formula:

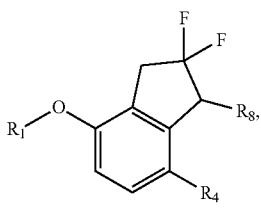

or a pharmaceutically acceptable salt thereof, wherein $R_8$ is hydroxy or amino.

Paragraph 9a: The compound of claim 8, having the structure of Formula:

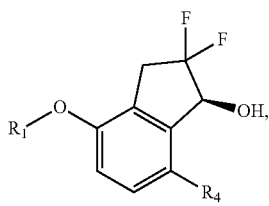

or a pharmaceutically acceptable salt thereof.

Paragraph 10a: The compound of paragraph 4a, wherein $R_4$ is fluoroalkyl, sulfonyl or sulfoximinyl.

Paragraph 11a: The compound of paragraph 9a, wherein enantiomeric excess of said compound is at least about 85%.

Paragraph 12a: The compound of paragraph 1a, wherein said compound is (S)-3-((2,2-difluoro-1-hydroxy-7-(methylsulfonyl)-2,3-dihydro-1H-inden-4-yl)oxy)-5-fluorobenzonitrile, represented by the formula:

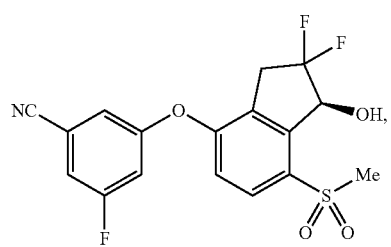 [SMILES: CS(=O)(=O)c1ccc(Oc2cc(F)cc(C#N)c2)c2c1[C@H](O)C(F)(F)C2]

or a pharmaceutically acceptable salt thereof.

Paragraph 13a: A compound of Formula:

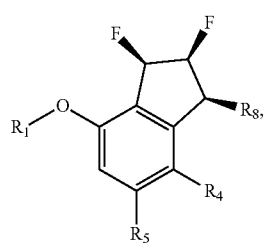

or a pharmaceutically acceptable salt thereof, wherein:
$R_1$ is aryl or heteroaryl;
$R_4$ is halo, cyano, alkyl, sulfonamide, sulfinyl, sulfonyl or sulfoximinyl;
$R_5$ is hydrogen, halo or alkyl; and
$R_8$ is hydroxy, alkylamino, alkoxy or amino.

Paragraph 14a: The compound of paragraph 13a, wherein $R_1$ is phenyl or pyridyl.

Paragraph 15a: The compound of paragraph 14a, wherein said phenyl or pyridyl is substituted with at least one substituent selected from the group consisting of halo, C1-C4 alkyl, C1-C4 alkoxy, and cyano.

Paragraph 16a: The compound of paragraph 13a, wherein $R_8$ is hydroxy or amino.

Paragraph 17a: The compound of paragraph 13a, wherein said compound is:

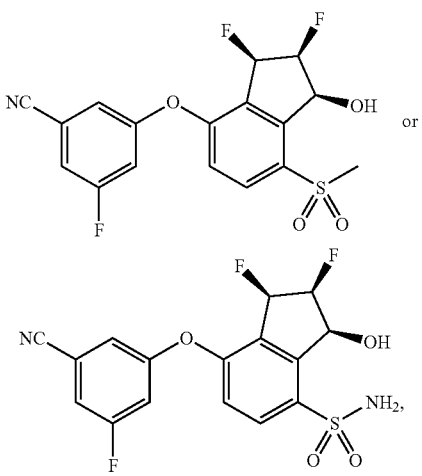

or a pharmaceutically acceptable salt thereof.

Paragraph 18a: A compound of Formula:

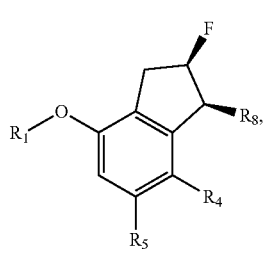

or a pharmaceutically acceptable salt thereof, wherein:
$R_1$ is aryl or heteroaryl;
$R_4$ is halo, cyano, alkyl, sulfonamide, sulfinyl, sulfonyl or sulfoximinyl;
$R_5$ is hydrogen, halo or alkyl; and
$R_8$ is hydroxy, alkylamino, alkoxy or amino.

Paragraph 19a: The compound of paragraph 18a, wherein $R_1$ is phenyl or pyridyl.

Paragraph 20a: The compound of paragraph 19a, wherein said phenyl or pyridyl is substituted with at least one substituent selected from the group consisting of halo, C1-C4 alkyl, C1-C4 alkoxy, and cyano.

Paragraph 21a: The compound of paragraph 18a, wherein $R_8$ is hydroxy or amino.

Paragraph 22a: The compound of paragraph 18a, wherein said compound is:

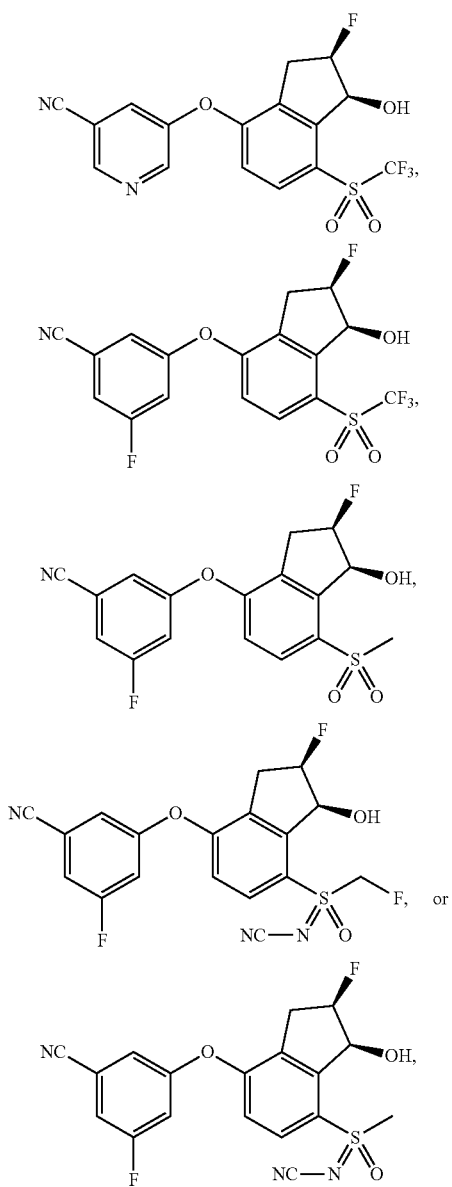

or a pharmaceutically acceptable salt thereof.

Paragraph 23a: A compound of the following structure:

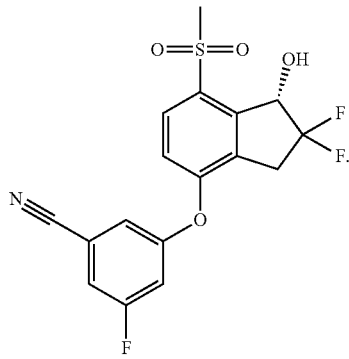 [SMILES: CS(=O)(=O)c1ccc(Oc2cc(F)cc(C#N)c2)c2c1[C@H](O)C(F)(F)C2]

The compound of paragraph 23a, also referred to PT-2385, is being investigated for the treatment of cancer in clinical trials.

Paragraph 24a: A compound of the structure:

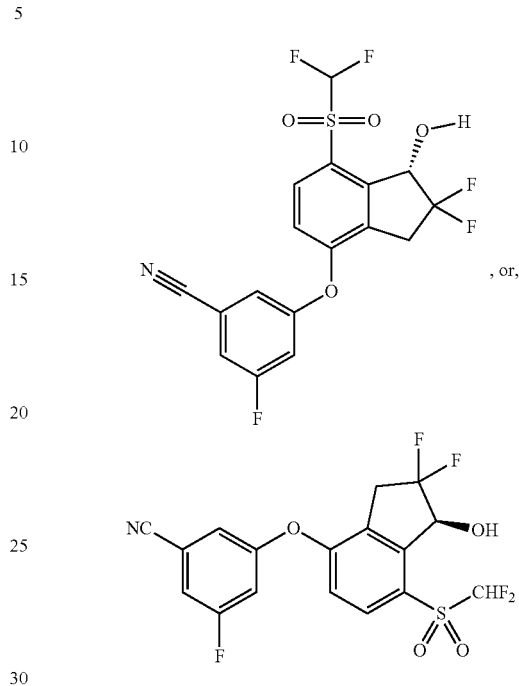

or another stereoisomer thereof. The foregoing compound, also referred to PT-2399, is a HIF-2α antagonist, pharmacologically indistinguishable from PT-2385 in mice (Wallace, *PT2385: First-In-Class HIF-2α Antagonist for the Treatment of Renal Cell Carcinoma*; Chen, et al., *Nature*. 539(7627):112-117 (2016). doi: 10.1038/nature19796. Epub 2016 Sep. 5; Cho, et al., *Nature,* 539, 107-111 (3 Nov. 2016)) doi:10.1038/nature19795.

b. Cyclic Sulfone and Sulfoximine Compounds

In some embodiments, the HIF-2α inhibitor is a compound (as disclosed in U.S. Published Application No. 2016/0368893 which is specifically incorporated by reference herein in its entirety) defined according to the following paragraphs found in this subheading:

Paragraph 1b: A compound of Formula:

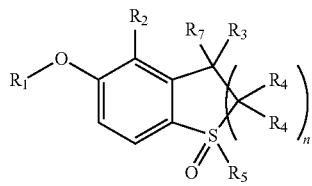

or a pharmaceutically acceptable salt thereof,
wherein:
$R_1$ is alkyl, heteroalkyl, cycloalkyl, heterocycloalkyl, aryl or heteroaryl;
$R_2$ is hydrogen, nitro, cyano, halo, alkyl, heteroalkyl, alkynyl or alkenyl;
$R_3$ is hydrogen, hydroxy or amino;
each of $R_4$ is independently selected from the group consisting of hydrogen, halo, alkyl, heteroalkyl and cycloalkyl, or two $R_4$ groups and the carbon(s) to which they are attached form C3-C8 cycloalkyl or C5-C8 heterocycloalkyl;

$R_5$ is O or $NR_6$, wherein $R_6$ is selected from the group consisting of hydrogen, alkyl, and cyano;

$R_7$ is hydrogen, deuterium, or alkyl, or $R_3$ and $R_7$ in combination form oxo; and n is 1 or 2.

Paragraph 2b: The compound of paragraph 1b, wherein $R_1$ is aryl or heteroaryl.

Paragraph 3b: The compound of paragraph 1b, wherein $R_2$ is cyano, halo, fluoroalkyl or alkyl.

Paragraph 4b: The compound of paragraph 1b, wherein $R_3$ is hydroxy or amino, $R_2$ is fluoroalkyl, at least one $R_4$ is fluoro, and n is 1.

Paragraph 5b: The compound of paragraph 1b, wherein at least one $R_4$ is fluoro.

Paragraph 6b: The compound of paragraph 1b, having the structure of Formula:

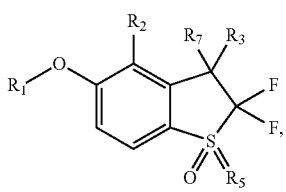

or a pharmaceutically acceptable salt thereof.

Paragraph 7b: The compound of paragraph 6b, wherein $R_1$ is aryl or heteroaryl.

Paragraph 8b: The compound of paragraph 6b, wherein $R_2$ is cyano, halo, fluoroalkyl or alkyl.

Paragraph 9b: The compound of paragraph 6b, wherein $R_3$ is hydroxy or amino.

Paragraph 10b: The compound of paragraph 6b, wherein $R_5$ is O, N—CN or NH.

Paragraph 11b: The compound of paragraph 10b, wherein $R_7$ is hydrogen or deuterium and $R_3$ is hydroxy.

Paragraph 12b: The compound of paragraph 1b, having the structure of Formula:

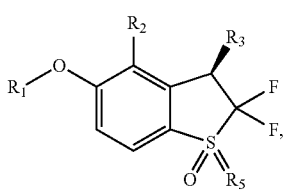

or a pharmaceutically acceptable salt thereof.

Paragraph 13b: The compound of paragraph 12b, wherein $R_1$ is aryl or heteroaryl.

Paragraph 14b: The compound of paragraph 12b, wherein $R_3$ is hydroxy or $NH_2$.

Paragraph 15b: The compound of paragraph 14b, wherein $R_5$ is O, N—CN or NH.

Paragraph 16b: The compound of paragraph 14b, wherein $R_5$ is O and said compound has an enantiomeric excess of at least about 80%.

Paragraph 17b: A compound selected from the group consisting of:

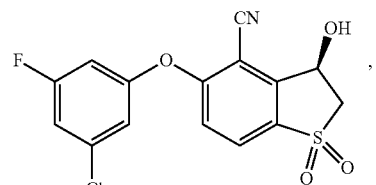

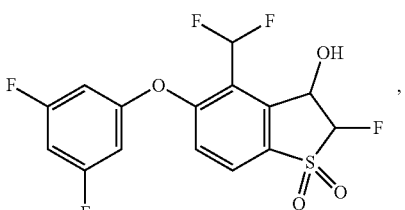

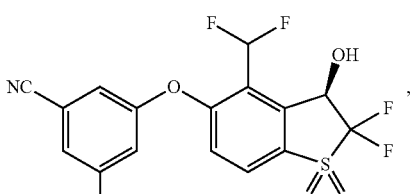

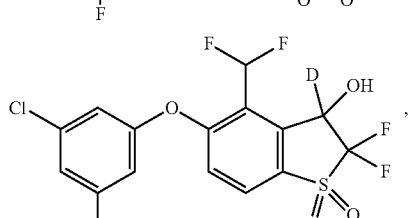

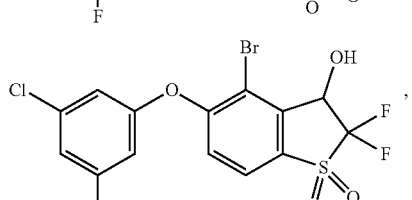

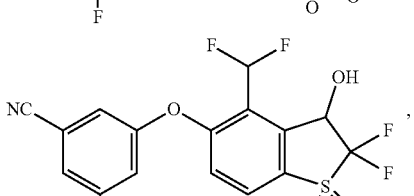

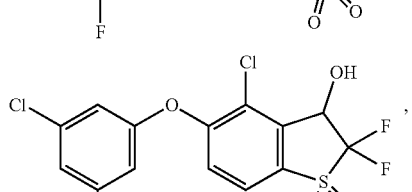

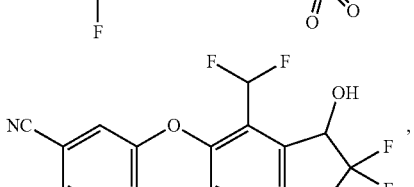

-continued
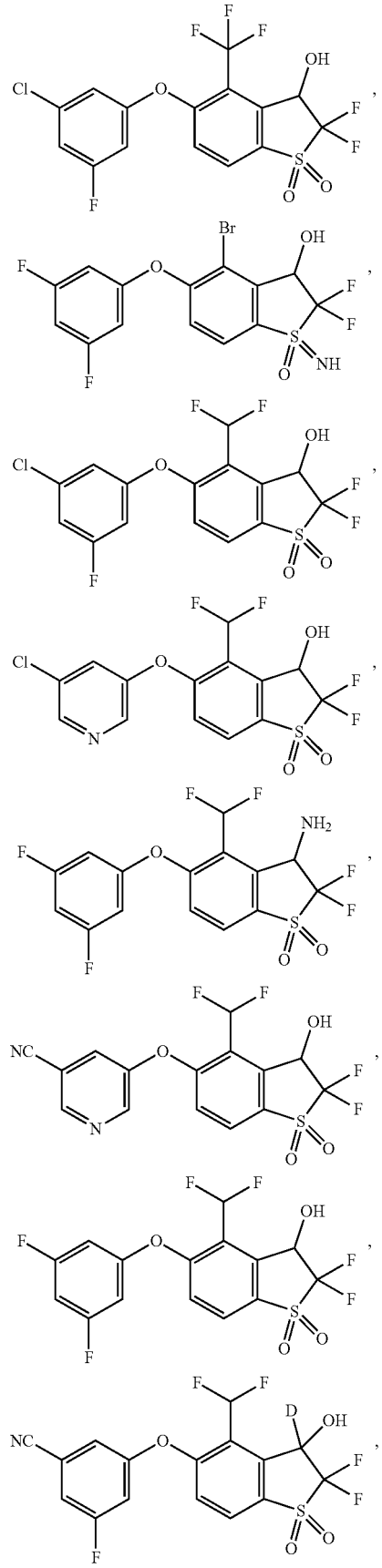
-continued
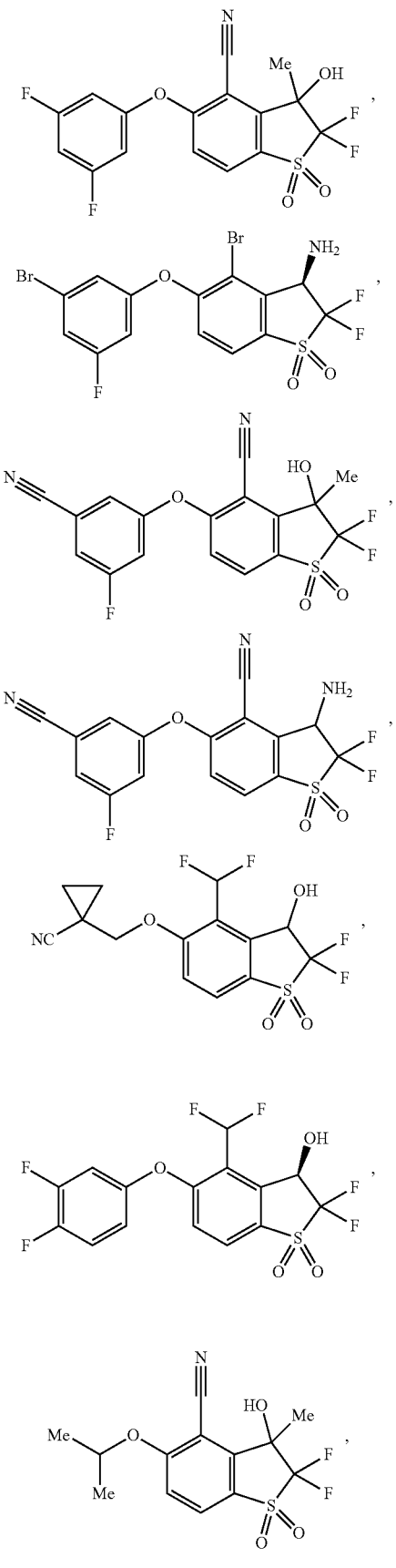

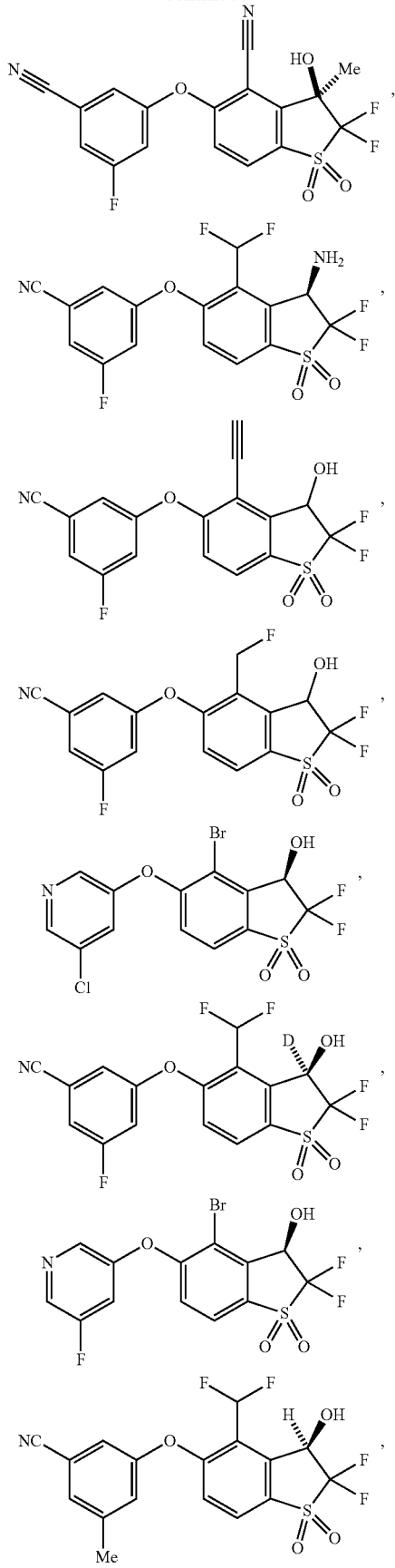
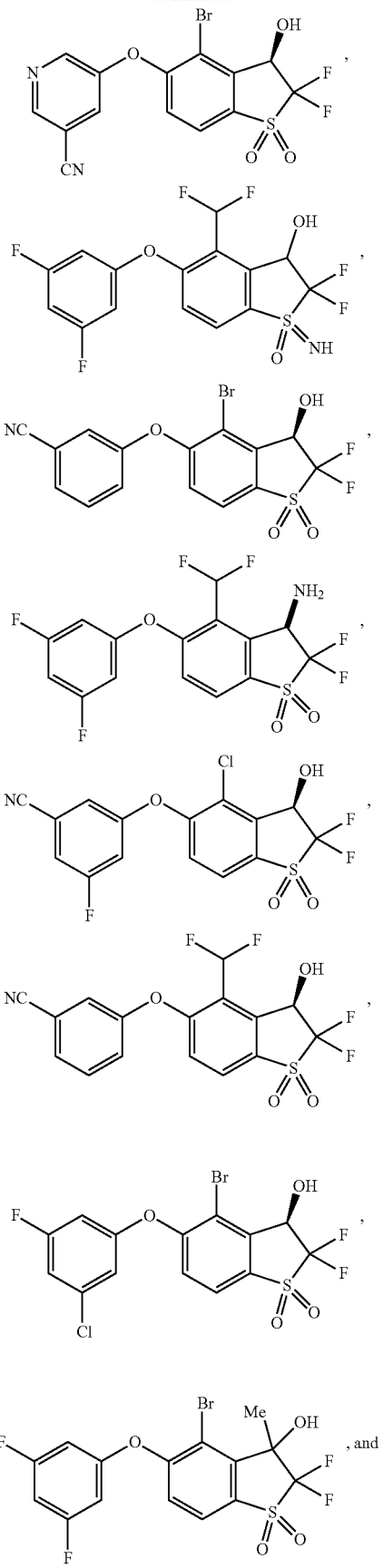

-continued

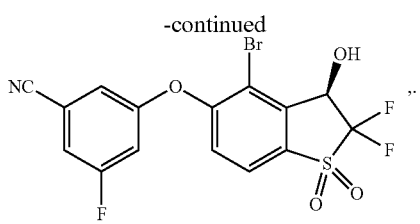

c. Aryl Compounds with Aminoalkyl Substituents

In some embodiments, the HIF-2α inhibitor is a compound (as disclosed in U.S. Published Application No. 2011/0312930 which is specifically incorporated by reference herein in its entirety) defined according to the following paragraphs found in this subheading:

Paragraph 1c: A compound of the formula

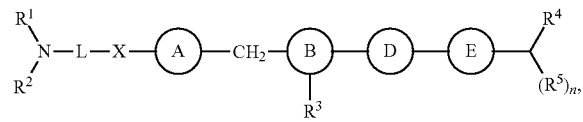

in which
the ring

represents a phenyl or pyridyl ring,
the ring

with the substituent $R^3$ represents a heteroaryl ring of the formula

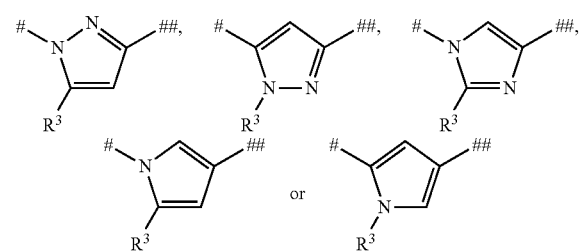

wherein
\# designates the linkage point with the adjacent $CH_2$ group
and
\#\# designates the linkage point with the ring

the ring

represents a heteroaryl ring of the formula

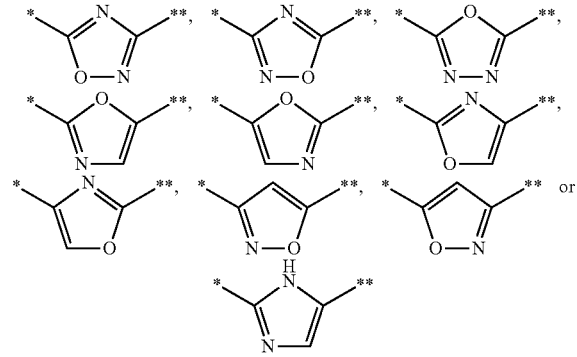

wherein
\* designates the linkage point with the ring

and
\*\* designates the linkage point with the ring

the ring

represents a phenyl or pyridyl ring,
X represents a bond or represents —N($R^6$)—, —O—, —S—, —S(═O)$_2$—, ♦-C(═O)—N($R^6$)-♦♦ or ♦-N($R^6$)—C(═O)-♦♦, wherein
♦ designates the linkage point with the group L
and
♦♦ designates the linkage point with the ring

and
$R^6$ denotes hydrogen, ($C_1$-$C_6$)-alkyl or ($C_3$-$C_6$)-cycloalkyl, wherein ($C_1$-$C_6$)-alkyl and ($C_3$-$C_6$)-cycloalkyl can each be substituted by hydroxyl or ($C_1$-$C_4$)-alkoxy,
L represents straight-chain ($C_1$-$C_4$)-alkanediyl if X denotes a bond or the group —S(═O)$_2$— or ♦-C(═O)N($R^6$)-♦♦, and
represents straight-chain $(C_2-C_4)$-alkanediyl if X denotes the group —N(R$^6$)—, —O—, —S— or ♦-N(R$^6$)C(=O)-♦♦, R$^1$ represents hydrogen, $(C_1-C_6)$-alkyl, $(C_1-C_6)$-alkylcarbonyl, $(C_1-C_6)$-alkoxycarbonyl, $(C_1-C_6)$-alkylsulphonyl or $(C_3-C_6)$-cycloalkyl, wherein the alkyl group in $(C_1-C_6)$-alkyl, $(C_1-C_6)$-alkylcarbonyl, $(C_1-C_6)$-alkoxycarbonyl and $(C_1-C_6)$-alkylsulphonyl can be substituted up to three times by fluorine and up to two times by identical or different radicals selected from the group consisting of hydroxyl, $(C_1-C_4)$-alkoxy, amino, mono-$(C_1-C_4)$-alkylamino and di-$(C_1-C_4)$-alkylamino and $(C_3-C_6)$-cycloalkyl can be substituted up to two times by identical or different radicals selected from the group consisting of fluorine, $(C_1-C_4)$-alkyl, hydroxyl, $(C_1-C_4)$-alkoxy, amino, mono-$(C_1-C_4)$-alkylamino and di-$(C_1-C_4)$-alkylamino, R$^2$ represents hydrogen, $(C_1-C_6)$-alkyl or $(C_3-C_6)$-cycloalkyl, where $(C_1-C_6)$-alkyl can be substituted up to three times by fluorine and up to two times by identical or different radicals selected from the group consisting of hydroxyl, $(C_1-C_4)$-alkoxy, amino, mono-$(C_1-C_4)$-alkylamino and di-$(C_1-C_4)$-alkylamino and $(C_3-C_6)$-cycloalkyl can be substituted up to two times by identical or different radicals selected from the group consisting of fluorine, $(C_1-C_4)$-alkyl, hydroxyl, $(C_1-C_4)$-alkoxy, amino, mono-$(C_1-C_4)$-alkylamino and di-$(C_1-C_4)$-alkylamino, or R$^1$ and R$^2$ together with the nitrogen atom to which they are attached form a saturated 4- to 7-membered heterocycle which can contain a further ring heteroatom from the group consisting of N, O, S and S(O)$_2$ and which can be substituted up to two times by identical or different radicals selected from the group consisting of fluorine, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino, $(C_1-C_4)$-alkylcarbonyl, $(C_1-C_4)$-alkylsulphonyl and $(C_3-C_6)$-cycloalkyl, wherein the $(C_1-C_4)$-alkyl and $(C_3-C_6)$-cycloalkyl for their part can be substituted by hydroxyl or $(C_1-C_4)$-alkoxy, R$^3$ represents methyl, ethyl or trifluoromethyl, R$^4$ represents hydrogen or a substituent chosen from the group consisting of halogen, cyano, pentafluorothio, $(C_1-C_6)$-alkyl, tri-$(C_1-C_4)$-alkylsilyl, —OR$^7$, —NR$^7$R$^8$, —N(R$^7$)—C(=O)—R$^8$, —N(R$^7$)—C(=O)—OR$^8$, —N(R$^7$)—S(=O)$_2$—R$^8$, —C(=O)—OR$^7$, —C(=O)—NR$^7$R$^8$, —SR$^7$, —S(=O)—R$^7$, —S(=O)$_2$—R$^7$, —S(=O)$_2$—NR$^7$R$^8$, $(C_3-C_6)$-cycloalkyl, 4- to 6-membered heterocyclyl and 5- or 6-membered heteroaryl, where $(C_1-C_6)$-alkyl for its part can be substituted up to three times by fluorine and up to two times by identical or different radicals selected from the group consisting of —OR$^7$, —NR$^7$R$^8$, —N(R$^7$)—C(=O)—R$^8$, —N(R$^7$)—C(=O)—OR$^8$, —C(=O)—OR$^7$, —C(=O)—NR$^7$R$^8$, $(C_3-C_6)$-cycloalkyl, 4- to 6-membered heterocyclyl and 5- or 6-membered heteroaryl and where the cycloalkyl and heterocyclyl groups mentioned for their part can be substituted up to two times by identical or different radicals selected from the group consisting of fluorine, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, $(C_1-C_4)$-alkylcarbonylamino, $(C_1-C_4)$-alkoxycarbonylamino, $(C_1-C_4)$-alkylcarbonyl and $(C_1-C_4)$-alkoxycarbonyl and the heteroaryl groups mentioned for their part can be substituted up to two times by identical or different radicals selected from the group consisting of fluorine, chlorine, cyano, $(C_1-C_4)$-alkyl, trifluoromethyl, $(C_1-C_4)$-alkoxy and trifluoromethoxy, and wherein R$^7$ and R$^8$ independently of each other for each individual occurrence denote hydrogen, $(C_1-C_6)$-alkyl, $(C_3-C_6)$-cycloalkyl or 4- to 6-membered heterocyclyl, where $(C_1-C_6)$-alkyl can be substituted up to three times by fluorine and up to two times by identical or different radicals selected from the group consisting of hydroxyl, $(C_1-C_4)$-alkoxy, trifluoromethoxy, amino, mono-$(C_1-C_4)$-alkylamino, di-$(C_1-C_4)$-alkylamino, $(C_1-C_4)$-alkoxycarbonyl, $(C_3-C_6)$-cycloalkyl and 4- to 6-membered heterocyclyl and the cycloalkyl and heterocyclyl groups mentioned can be substituted up to two times by identical or different radicals selected from the group consisting of fluorine, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, $(C_1-C_4)$-alkylcarbonyl and $(C_1-C_4)$-alkoxycarbonyl, or R$^7$ and R$^8$ in the case where both are bonded to a nitrogen atom form a 4- to 6-membered heterocycle together with this nitrogen atom, which can contain a further ring heteroatom from the group consisting of N, O, S and S(O)$_2$ and which can be substituted up to two times by identical or different radicals selected from the group consisting of fluorine, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino, $(C_1-C_4)$-alkylcarbonyl and $(C_1-C_4)$-alkoxycarbonyl, R$^5$ represents a substituent selected from the group consisting of fluorine, chlorine, cyano, methyl, trifluoromethyl and hydroxyl and n represents the number 0, 1 or 2, where, if the substituent R$^5$ occurs twice, its meanings can be identical or different, or a salt thereof.

Paragraph 2c: The compound of the formula according to paragraph 1c in which the ring

represents a phenyl or pyridyl ring and the adjacent groups X and CH$_2$ are bonded to ring carbon atoms of

in 1,3 or 1,4 relation to one another and the ring

with the substituents $R^4$ and $R^5$ represents a phenyl ring of the formula

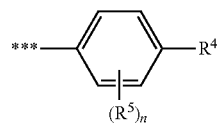

wherein
*** designates the linkage point with the ring

, or a salt thereof.

Paragraph 3c: The compound of the formula according to paragraph 1c in which
the ring

represents a pyridyl ring and the adjacent groups X and $CH_2$ are bonded to ring carbon atoms of this pyridyl ring in 1,3 or 1,4 relation to one another
and the ring

with the substituents $R^4$ and $R^5$ represents a phenyl ring of the formula

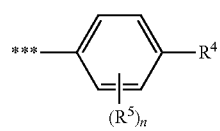

wherein
*** designates the linkage point with the ring

, or a salt thereof.

Paragrah 4: The compound of the formula according to paragraph 1c in which
the ring

represents a phenyl ring and the adjacent groups X and $CH_2$ are bonded to this phenyl ring in 1,3 or 1,4 relation to one another, the ring

with the substituent $R^3$ represents a heteroaryl ring of the formula

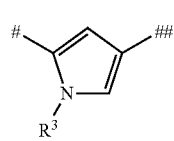

wherein
designates the linkage point with the adjacent $CH_2$ group
and
designates the linkage point with the ring

, and
the ring

with the substituents $R^4$ and $R^5$ represents a phenyl ring of the formula

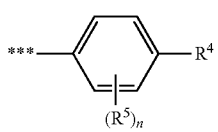

wherein
*** designates the linkage point with the ring

, or a salt thereof.

Paragraph 5c: The compound of the formula according to paragraph 1c in which the ring

represents a phenyl ring and the adjacent groups X and CH$_2$ are bonded to this phenyl ring in 1,3 or 1,4 relation to one another, the ring

with the substituents R$^4$ and R$^5$ represents a phenyl ring of the formula

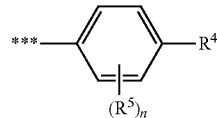

wherein
*** designates the linkage point with the ring
and
R$^1$ and R$^2$ together with the nitrogen atom to which they are attached form a saturated 4- to 7-membered heterocycle which can contain a further ring heteroatom from the group consisting of N, O, S and S(O)$_2$ and which can be substituted up to two times by identical or different radicals selected from the group consisting of fluorine, (C$_1$-C$_4$)-alkyl, trifluoromethyl, hydroxyl, (C$_1$-C$_4$)-alkoxy, oxo, amino, mono-(C$_1$-C$_4$)-alkylamino, di-(C$_1$-C$_4$)-alkylamino, (C$_1$-C$_4$)-alkylcarbonyl, (C$_1$-C$_4$)-alkylsulphonyl and (C$_3$-C$_6$)-cycloalkyl, wherein (C$_1$-C$_4$)-alkyl and (C$_3$-C$_6$)-cycloalkyl for their part can be substituted by hydroxyl or (C$_1$-C$_4$)-alkoxy,
or a salt thereof.

Paragraph 6c: The compound of the formula according to paragraph 1c in which
the ring

represents a pyridyl ring and the adjacent groups X and CH$_2$ are bonded to ring carbon atoms of this pyridyl ring in 1,3 or 1,4 relation to one another,
the ring

with the substituent R$^3$ represents a heteroaryl ring of the formula

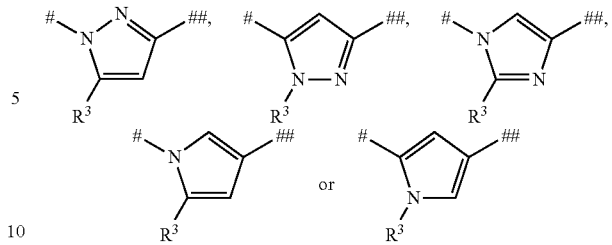

wherein
designates the linkage point with the adjacent CH$_2$ group
and
designates the linkage point with the ring

the ring

represents a heteroaryl ring of the formula

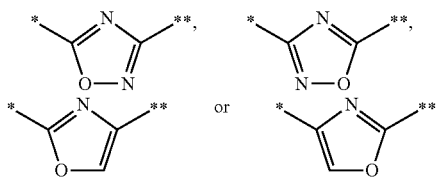

wherein
* designates the linkage point with the ring

and
** designates the linkage point with the ring

the ring

with the substituents R$^4$ and R$^5$ represents a phenyl ring of the formula

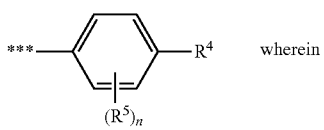 wherein

\*\*\* designates the linkage point with the ring

X represents a bond or represents —N(R$^6$)—, —O—, —S—, ♦-C(═O)—N(R$^6$)-♦♦ or ♦-N(R$^6$)—C(═O)-♦♦, wherein ♦ designates the linkage point with the group L and ♦♦ designates the linkage point with the ring and R$^6$ denotes hydrogen, (C$_1$-C$_4$)-alkyl or (C$_3$-C$_6$)-cycloalkyl, L represents straight-chain (C$_1$-C$_4$)-alkanediyl if X denotes a bond or the group ♦-C(═O)—N(R$^6$)-♦♦, and represents straight-chain (C$_2$-C$_4$)-alkanediyl if X denotes the group —N(R$^6$)—, —O—, —S— or ♦-N(R$^6$)—C(═O)-♦♦, R$^1$ represents hydrogen, (C$_1$-C$_4$)-alkyl, (C$_1$-C$_4$)-alkylcarbonyl, (C$_1$-C$_4$)-alkylsulphonyl or (C$_3$-C$_6$)-cycloalkyl, where the alkyl group in (C$_1$-C$_4$)-alkyl, (C$_1$-C$_4$)-alkylcarbonyl and (C$_1$-C$_4$)-alkylsulphonyl can be substituted up to three times by fluorine and up to two times by identical or different radicals selected from the group consisting of hydroxyl and (C$_1$-C$_4$)-alkoxy and (C$_3$-C$_6$)-cycloalkyl can be substituted up to two times by identical or different radicals selected from the group consisting of fluorine, (C$_1$-C$_4$)-alkyl, hydroxyl and (C$_1$-C$_4$)-alkoxy, R$^2$ represents hydrogen, (C$_1$-C$_4$)-alkyl or (C$_3$-C$_6$)-cycloalkyl, where (C$_1$-C$_4$)-alkyl may be substituted up to three times by fluorine and (C$_3$-C$_6$)-cycloalkyl can be substituted up to two times by identical or different radicals selected from the group consisting of fluorine and (C$_1$-C$_4$)-alkyl, or R$^1$ and R$^2$ together with the nitrogen atom to which they are attached form a saturated 4- to 6-membered heterocycle which can contain a further ring heteroatom from the group consisting of N, O, S and S(O)$_2$ and which can be substituted up to two times by identical or different radicals selected from the group consisting of fluorine, (C$_1$-C$_4$)-alkyl, trifluoromethyl, hydroxyl, (C$_1$-C$_4$)-alkoxy, oxo, amino, mono-(C$_1$-C$_4$)-alkylamino, di-(C$_1$-C$_4$)-alkylamino, (C$_1$-C$_4$)-alkylcarbonyl, (C$_1$-C$_4$)-alkylsulphonyl and (C$_3$-C$_6$)-cycloalkyl, R$^3$ represents methyl, ethyl or trifluoromethyl, R$^4$ represents a substituent selected from the group consisting of fluorine, chlorine, cyano, pentafluorothio, (C$_1$-C$_6$)-alkyl, tri-(C$_1$-C$_4$)-alkylsilyl, —OR$^7$, —NR$^7$R$^8$, —SR$^7$, —S(═O)—R$^7$, —S(═O)$_2$—R$^7$, (C$_3$-C$_6$)-cycloalkyl and 4- to 6-membered heterocyclyl, where (C$_1$-C$_6$)-alkyl for its part can be substituted up to three times by fluorine and up to two times by identical or different radicals selected from the group consisting of —OR$^7$, —NR$^7$R$^8$, —N(R$^7$)—C(═O)—R$^8$, —C(═O)—NR$^7$R$^8$, (C$_3$-C$_6$)-cycloalkyl, 4- to 6-membered heterocyclyl and 5- or 6-membered heteroaryl and where the cycloalkyl and heterocyclyl groups mentioned for their part can be substituted up to two times by identical or different radicals selected from the group consisting of fluorine, (C$_1$-C$_4$)-alkyl, trifluoromethyl, hydroxyl, (C$_1$-C$_4$)-alkoxy, trifluoromethoxy, oxo and (C$_1$-C$_4$)-alkylcarbonyl and the heteroaryl groups mentioned for their part can be substituted up to two times by identical or different radicals selected from the group consisting of fluorine, chlorine, cyano, (C$_1$-C$_4$)-alkyl, trifluoromethyl, (C$_1$-C$_4$)-alkoxy and trifluoromethoxy, and wherein R$^7$ and R$^8$ independently of each other for each individual occurrence denote hydrogen, (C$_1$-C$_4$)-alkyl, (C$_3$-C$_6$)-cycloalkyl or 4- to 6-membered heterocyclyl, where (C$_1$-C$_4$)-alkyl can be substituted up to three times by fluorine and up to two times by identical or different radicals selected from the group consisting of hydroxyl, (C$_1$-C$_4$)-alkoxy, trifluoromethoxy, (C$_3$-C$_6$)-cycloalkyl and 4- to 6-membered heterocyclyl and the cycloalkyl and heterocyclyl groups mentioned can be substituted up to two times by identical or different radicals selected from the group consisting of fluorine, (C$_1$-C$_4$)-alkyl, trifluoromethyl, hydroxyl, (C$_1$-C$_4$)-alkoxy, trifluoromethoxy, oxo and (C$_1$-C$_4$)-alkylcarbonyl or R$^7$ and R$^8$ in the case where both are bonded to a nitrogen atom form a 4- to 6-membered heterocycle together with this nitrogen atom, which can contain a further ring heteroatom from the group consisting of N, O, S and S(O)$_2$ and which can be substituted up to two times by identical or different radicals selected from the group consisting of fluorine, (C$_1$-C$_4$)-alkyl, trifluoromethyl, hydroxyl, (C$_1$-C$_4$)-alkoxy, oxo and (C$_1$-C$_4$)-alkylcarbonyl, R$^5$ represents a substituent selected from the group consisting of fluorine, chlorine and methyl and n represents the number 0 or 1, or a salt thereof.

Paragraph 7c: The compound of the formula according to paragraph 1c in which the ring

represents a phenyl ring and the adjacent groups X and CH$_2$ are bonded to this phenyl ring in 1,3 or 1,4 relation to one another, the ring

with the substituent R³ represents a heteroaryl ring of the formula

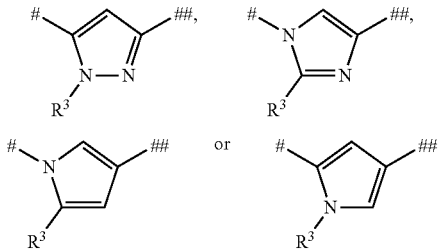

wherein
designates the linkage point with the adjacent CH₂ group
and
designates the linkage point with the ring

the ring

represents a heteroaryl ring of the formula

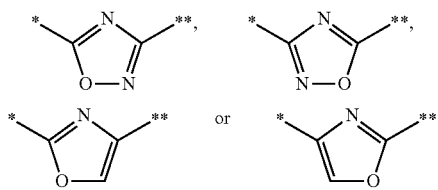

wherein
* designates the linkage point with the ring

and
** designates the linkage point with the ring

the ring

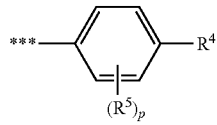

with the substituents R⁴ and R⁵ represents a phenyl ring of the formula

wherein
*** designates the linkage point with the ring

D ,

X represents a bond or represents —N(R⁶)—, —O—, —S—, ♦-C(=O)—N(R⁶)-♦♦ or ♦-N(R⁶)—C(=O)-♦♦,
wherein
♦ designates the linkage point with the group L
and
♦♦ designates the linkage point with the ring

A and
R⁶ denotes hydrogen, ($C_1$-$C_4$)-alkyl or ($C_3$-$C_6$)-cycloalkyl,
L represents straight-chain ($C_1$-$C_4$)-alkanediyl if X denotes a bond or the group ♦-C(=O)—N(R⁶)-♦♦,
and
represents straight-chain ($C_2$-$C_4$)-alkanediyl if X denotes the group —N(R⁶)—, —O—, —S— or ♦-N(R⁶)—C(=O)-♦♦,
R¹ represents hydrogen, ($C_1$-$C_4$)-alkyl, ($C_1$-$C_4$)-alkylcarbonyl, ($C_1$-$C_4$)-alkylsulphonyl or ($C_3$-$C_6$)-cycloalkyl,
where the alkyl group in ($C_1$-$C_4$)-alkyl, ($C_1$-$C_4$)-alkylcarbonyl and ($C_1$-$C_4$)-alkylsulphonyl can be substituted up to three times by fluorine and up to two times by identical or different radicals selected from the group consisting of hydroxyl and ($C_1$-$C_4$)-alkoxy
and
($C_3$-$C_6$)-cycloalkyl can be substituted up to two times by identical or different radicals selected from the group consisting of fluorine, ($C_1$-$C_4$)-alkyl, hydroxyl and ($C_1$-$C_4$)-alkoxy,
R² represents hydrogen, ($C_1$-$C_4$)-alkyl or ($C_3$-$C_6$)-cycloalkyl,
where ($C_1$-$C_4$)-alkyl may be substituted up to three times by fluorine
and
($C_3$-$C_6$)-cycloalkyl can be substituted up to two times by identical or different radicals selected from the group consisting of fluorine and ($C_1$-$C_4$)-alkyl,
R³ represents methyl, ethyl or trifluoromethyl,
R⁴ represents a substituent selected from the group consisting of fluorine, chlorine, cyano, pentafluorothio, ($C_1$-$C_6$)-alkyl, tri-($C_1$-$C_4$)-alkylsilyl, —OR⁷, —NR⁷R⁸, —SR⁷, —S(=O)—R⁷, —S(=O)₂—R⁷, (C₃-C₆)-cycloalkyl and 4- to 6-membered heterocyclyl,
where (C₁-C₆)-alkyl for its part can be substituted up to three times by fluorine and up to two times by identical or different radicals selected from the group consisting of —OR⁷, —NR⁷R⁸, —N(R⁷)—C(=O)—R⁸, —C(=O)—NR⁷R⁸, (C₃-C₆)-cycloalkyl, 4- to 6-membered heterocyclyl and 5- or 6-membered heteroaryl
and where
the cycloalkyl and heterocyclyl groups mentioned for their part can be substituted up to two times by identical or different radicals selected from the group consisting of fluorine, (C₁-C₄)-alkyl, trifluoromethyl, hydroxyl, (C₁-C₄)-alkoxy, trifluoromethoxy, oxo and (C₁-C₄)-alkylcarbonyl
and
the heteroaryl groups mentioned for their part can be substituted up to two times by identical or different radicals selected from the group consisting of fluorine, chlorine, cyano, (C₁-C₄)-alkyl, trifluoromethyl, (C₁-C₄)-alkoxy and trifluoromethoxy,
and wherein
R⁷ and R⁸ independently of each other for each individual occurrence denote hydrogen, (C₁-C₄)-alkyl, (C₃-C₆)-cycloalkyl or 4- to 6-membered heterocyclyl, where (C₁-C₄)-alkyl can be substituted up to three times by fluorine and up to two times by identical or different radicals selected from the group consisting of hydroxyl, (C₁-C₄)-alkoxy, trifluoromethoxy, (C₃-C₆)-cycloalkyl and 4- to 6-membered heterocyclyl
and
the cycloalkyl and heterocyclyl groups mentioned can be substituted up to two times by identical or different radicals selected from the group consisting of fluorine, (C₁-C₄)-alkyl, trifluoromethyl, hydroxyl, (C₁-C₄)-alkoxy, trifluoromethoxy, oxo and (C₁-C₄)-alkylcarbonyl
or
R⁷ and R⁸ in the case where both are bonded to a nitrogen atom form a 4- to 6-membered heterocycle together with this nitrogen atom, which can contain a further ring heteroatom from the group consisting of N, O, S and S(O)₂ and which can be substituted up to two times by identical or different radicals selected from the group consisting of fluorine, (C₁-C₄)-alkyl, trifluoromethyl, hydroxyl, (C₁-C₄)-alkoxy, oxo and (C₁-C₄)-alkylcarbonyl,
R⁵ represents a substituent selected from the group consisting of fluorine, chlorine and methyl
and
n represents the number 0 or 1,
or a salt thereof.

Paragraph 8c: The compound of the formula according to paragraph 1c in which
the ring (A)

represents a phenyl ring and the adjacent groups X and CH₂ are bonded to this phenyl ring in 1,3 or 1,4 relation to one another,
the ring (B)

with the substituent R³ represents a heteroaryl ring of the formula wherein
designates the linkage point with the adjacent CH₂ group
and
designates the linkage point with the ring (D), the ring (D)

represents a heteroaryl ring of the formula wherein
* designates the linkage point with the ring (B)

and
** designates the linkage point with the ring (E), the ring (E)

with the substituents R⁴ and R⁵ represents a phenyl ring of the formula

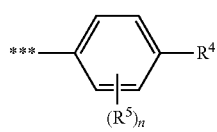

wherein
*** designates the linkage point with the ring

X represents a bond or represents —N(R⁶)—, —O—, —S—, ♦-C(=O)—N(R⁶)-♦♦ or ♦-N(R⁶)—C(=O)-♦♦,
wherein
♦ designates the linkage point with the group L
and
♦♦ designates the linkage point with the ring

and
R⁶ denotes hydrogen, $(C_1-C_4)$-alkyl or $(C_3-C_6)$-cycloalkyl,
L represents straight-chain $(C_1-C_4)$-alkanediyl if X denotes a bond or the group ♦-C(=O)—N(R⁶)-♦♦,
and
represents straight-chain $(C_2-C_4)$-alkanediyl if X denotes the group —N(R⁶)—, —O—, —S— or ♦-N(R⁶)—C(=O)-♦♦,
R¹ and R² together with the nitrogen atom to which they are attached form a saturated 4- to 6-membered heterocycle which can contain a further ring heteroatom from the group consisting of N, O, S and $S(O)_2$ and which can be substituted up to two times by identical or different radicals selected from the group consisting of fluorine, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino, $(C_1-C_4)$-alkylcarbonyl, $(C_1-C_4)$-alkylsulphonyl and $(C_3-C_6)$-cycloalkyl,
R³ represents methyl, ethyl or trifluoromethyl,
R⁴ represents a substituent selected from the group consisting of fluorine, chlorine, cyano, pentafluorothio, $(C_1-C_6)$-alkyl, tri-$(C_1-C_4)$-alkylsilyl, —OR⁷, —NR⁷R⁸, —SR⁷, —S(=O)—R⁷, —S(=O)₂—R⁷, $(C_3-C_6)$-cycloalkyl and 4- to 6-membered heterocyclyl,
where $(C_1-C_6)$-alkyl for its part can be substituted up to three times by fluorine and up to two times by identical or different radicals selected from the group consisting of —OR⁷, —NR⁷R⁸, —N(R⁷)—C(=O)—R⁸, —C(=O)—NR⁷R⁸, $(C_3-C_6)$-cycloalkyl, 4- to 6-membered heterocyclyl and 5- or 6-membered heteroaryl
and where
the cycloalkyl and heterocyclyl groups mentioned for their part can be substituted up to two times by identical or different radicals selected from the group consisting of fluorine, $(C_1-C_4)$-alkyl, trifluoromethyl, hydroxyl, $(C_1-C_4)$-alkoxy, trifluoromethoxy, oxo and $(C_1-C_4)$-alkylcarbonyl
and
the heteroaryl groups mentioned for their part can be substituted up to two times by identical or different radicals selected from the group consisting of fluorine, chlorine, cyano, $(C_1-C_4)$-alkyl, trifluoromethyl, $(C_1-C_4)$-alkoxy and trifluoromethoxy, and wherein
R⁷ and R⁸ independently of each other for each individual occurrence denote hydrogen, $(C_1-C_4)$-alkyl, $(C_3-C_6)$-cycloalkyl or 4- to 6-membered heterocyclyl, where $(C_1-C_4)$-alkyl can be substituted up to three times by fluorine and up to two times by identical or different radicals selected from the group consisting of hydroxyl, $(C_1-C_4)$-alkoxy, trifluoromethoxy, $(C_3-C_6)$-cycloalkyl and 4- to 6-membered heterocyclyl
and
the cycloalkyl and heterocyclyl groups mentioned can be substituted up to two times by identical or different radicals selected from the group consisting of fluorine, $(C_1-C_4)$-alkyl, trifluoromethyl, hydroxyl, $(C_1-C_4)$-alkoxy, trifluoromethoxy, oxo and $(C_1-C_4)$-alkylcarbonyl
or
R⁷ and R⁸ in the case where both are bonded to a nitrogen atom form a 4- to 6-membered heterocycle together with this nitrogen atom, which can contain a further ring heteroatom from the group consisting of N, O, S and $S(O)_2$ and which can be substituted up to two times by identical or different radicals selected from the group consisting of fluorine, $(C_1-C_4)$-alkyl, trifluoromethyl, hydroxyl, $(C_1-C_4)$-alkoxy, oxo and $(C_1-C_4)$-alkylcarbonyl,
R⁵ represents a substituent selected from the group consisting of fluorine, chlorine and methyl
and
n represents the number 0 or 1,
or a salt thereof.

Paragraph 9c: The compound of the formula according to paragraph 1c in which
the ring

represents a phenyl ring and the adjacent groups X and CH₂ are bonded to this phenyl ring in 1,3 or 1,4 relation to one another,
the ring

with the substituent R³ represents a heteroaryl ring of the formula

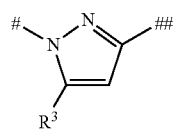

wherein
\# designates the linkage point with the adjacent CH$_2$ group and
\#\# designates the linkage point with the ring the ring $$\boxed{D}$$

represents a heteroaryl ring of the formula wherein
\* designates the linkage point with the ring $$\boxed{B}$$

and
\*\* designates the linkage point with the ring $$\boxed{E}$$

the ring $$\boxed{E}$$

with the substituents R$^4$ and R$^5$ represents a phenyl ring of the formula wherein
\*\*\* designates the linkage point with the ring $$\boxed{D}$$

X represents a bond or represents —N(R$^6$)—, —O—, —S—, ♦-C(=O)—N(R$^6$)-♦♦ or ♦-N(R$^6$)—C(=O)-♦♦,
wherein
♦ designates the linkage point with the group L
and
♦♦ designates the linkage point with the ring $$\boxed{A}$$

and
R$^6$ denotes hydrogen, (C$_1$-C$_4$)-alkyl or (C$_3$-C$_6$)-cycloalkyl,
L represents straight-chain (C$_1$-C$_4$)-alkanediyl if X denotes a bond or the group ♦-C(=O)—N(R$^6$)-♦♦,
and
represents straight-chain (C$_2$-C$_4$)-alkanediyl if X denotes the group —N(R$^6$)—, —O—, —S— or ♦-N(R$^6$)—C(=O)-♦♦,
R$^1$ represents hydrogen, (C$_1$-C$_4$)-alkyl or (C$_3$-C$_6$)-cycloalkyl,
where (C$_1$-C$_4$)-alkyl can be substituted up to three times by fluorine and up to two times by identical or different radicals selected from the group consisting of hydroxyl and (C$_1$-C$_4$)-alkoxy,
R$^2$ represents hydrogen, (C$_1$-C$_4$)-alkyl or (C$_3$-C$_6$)-cycloalkyl,
R$^3$ represents methyl, ethyl or trifluoromethyl,
R$^4$ represents a substituent selected from the group consisting of fluorine, chlorine, cyano, pentafluorothio, (C$_1$-C$_6$)-alkyl, tri-(C$_1$-C$_4$)-alkylsilyl, —OR$^7$, —NR$^7$R$^8$, —SR$^7$, —S(=O)—R$^7$, —S(=O)$_2$—R$^7$, (C$_3$-C$_6$)-cycloalkyl and 4- to 6-membered heterocyclyl,
where (C$_1$-C$_6$)-alkyl for its part can be substituted up to three times by fluorine and up to two times by identical or different radicals selected from the group consisting of —OR$^7$, —NR$^7$R$^8$, —N(R$^7$)—C(=O)—R$^8$, —C(=O)—NR$^7$R$^8$, (C$_3$-C$_6$)-cycloalkyl, 4- to 6-membered heterocyclyl and 5- or 6-membered heteroaryl
and where
the cycloalkyl and heterocyclyl groups mentioned for their part can be substituted up to two times by identical or different radicals selected from the group consisting of fluorine, (C$_1$-C$_4$)-alkyl, trifluoromethyl, hydroxyl, (C$_1$-C$_4$)-alkoxy, trifluoromethoxy, oxo and (C$_1$-C$_4$)-alkylcarbonyl
and
the heteroaryl groups mentioned for their part can be substituted up to two times by identical or different radicals selected from the group consisting of fluorine, chlorine, cyano, (C$_1$-C$_4$)-alkyl, trifluoromethyl, (C$_1$-C$_4$)-alkoxy and trifluoromethoxy,
and wherein
R$^7$ and R$^8$ independently of each other for each individual occurrence denote hydrogen, (C$_1$-C$_4$)-alkyl, (C$_3$-C$_6$)-cycloalkyl or 4- to 6-membered heterocyclyl, where (C$_1$-C$_4$)-alkyl can be substituted up to three times by fluorine and up to two times by identical or different radicals selected from the group consisting of hydroxyl, (C$_1$-C$_4$)-alkoxy, trifluoromethoxy, (C$_3$-C$_6$)-cycloalkyl and 4- to 6-membered heterocyclyl
and
the cycloalkyl and heterocyclyl groups mentioned can be substituted up to two times by identical or different radicals selected from the group consisting of fluorine, ($C_1$-$C_4$)-alkyl, trifluoromethyl, hydroxyl, ($C_1$-$C_4$)-alkoxy, trifluoromethoxy, oxo and ($C_1$-$C_4$)-alkylcarbonyl
or
$R^7$ and $R^8$ in the case where both are bonded to a nitrogen atom form a 4- to 6-membered heterocycle together with this nitrogen atom, which can contain a further ring heteroatom from the group consisting of N, O, S and $S(O)_2$ and which can be substituted up to two times by identical or different radicals selected from the group consisting of fluorine, ($C_1$-$C_4$)-alkyl, trifluoromethyl, hydroxyl, ($C_1$-$C_4$)-alkoxy, oxo and ($C_1$-$C_4$)-alkylcarbonyl,
$R^5$ represents a substituent selected from the group consisting of fluorine, chlorine and methyl
and
n represents the number 0 or 1,
or a salt thereof.

Paragraph 10c: The compound of the formula according to paragraph 1c in which
the ring

represents a pyridyl ring of the formula

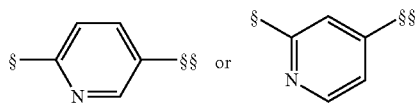

wherein
§ designates the linkage point with the adjacent group X
and
§§ designates the linkage point with the adjacent $CH_2$ group,
the ring

with the substituent $R^3$ represents a heteroaryl ring of the formula

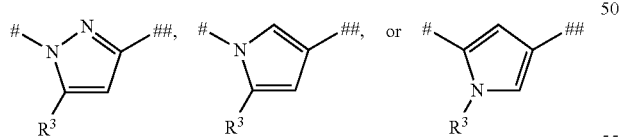

wherein
\# designates the linkage point with the adjacent $CH_2$ group
and
\#\# designates the linkage point with the ring

the ring

represents a heteroaryl ring of the formula

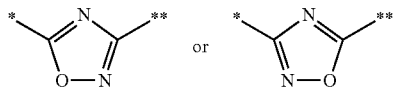

wherein
\* designates the linkage point with the ring

and
\*\* designates the linkage point with the ring

the ring

with the substituents $R^4$ and $R^5$ represents a phenyl ring of the formula

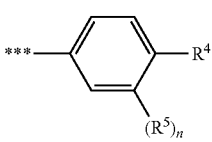

wherein
\*\*\* designates the linkage point with the ring

X represents —N($R^6$)—, —O—, —S— or ♦-N($R^6$)—C(=O)-♦♦ wherein
♦ designates the linkage point with the group L
and
♦♦ designates the linkage point with the ring

A and
$R^6$ denotes hydrogen, methyl, ethyl, isopropyl, cyclopropyl or cyclobutyl, L represents ethane-1,2-diyl or propane-1,3-diyl,
$R^1$ represents hydrogen, $(C_1-C_4)$-alkyl, $(C_1-C_4)$-alkylcarbonyl, $(C_1-C_4)$-alkylsulphonyl or $(C_3-C_6)$-cycloalkyl,
where the alkyl group in $(C_1-C_4)$-alkyl, $(C_1-C_4)$-alkylcarbonyl and $(C_1-C_4)$-alkylsulphonyl may be substituted by hydroxyl or $(C_1-C_4)$-alkoxy or up to three times by fluorine
and
$(C_3-C_6)$-cycloalkyl can be substituted up to two times by identical or different radicals selected from the group consisting of fluorine, $(C_1-C_4)$-alkyl, hydroxyl and $(C_1-C_4)$-alkoxy,
$R^2$ represents hydrogen, $(C_1-C_4)$-alkyl or cyclopropyl,
where $(C_1-C_4)$-alkyl may be substituted up to three times by fluorine,
or
$R^1$ and $R^2$ together with the nitrogen atom to which they are attached form a saturated 4- to 6-membered heterocycle which can contain a further ring heteroatom from the group consisting of N, O, S and $S(O)_2$ and which can be substituted up to two times by identical or different radicals selected from the group consisting of fluorine, $(C_1-C_4)$-alkyl, trifluoromethyl, hydroxyl, $(C_1-C_4)$-alkoxy, oxo and $(C_3-C_6)$-cycloalkyl,
$R^3$ represents methyl,
$R^4$ represents a substituent selected from the group consisting of chlorine, $(C_1-C_6)$-alkyl, trimethylsilyl, $-OR^7$, $-SR^7$, $-S(=O)-R^7$, $-S(=O)_2-R^7$, $(C_3-C_6)$-cycloalkyl and 4- to 6-membered heterocyclyl,
wherein $(C_1-C_6)$-alkyl for its part can be substituted by a radical selected from the group consisting of $-OR^7$, $-NR^7R^8$, $-C(=O)-NR^7R^8$, $(C_3-C_6)$-cycloalkyl and 4- to 6-membered heterocyclyl and up to three time by fluorine
and
the cycloalkyl and heterocyclyl groups mentioned for their part can be substituted up to two times by identical or different radicals selected from the group consisting of fluorine, $(C_1-C_4)$-alkyl, trifluoromethyl, hydroxyl, $(C_1-C_4)$-alkoxy, trifluoromethoxy, oxo and $(C_1-C_4)$-alkylcarbonyl
and wherein
$R^7$ and $R^8$ independently of each other for each individual occurrence denote hydrogen, $(C_1-C_4)$-alkyl or $(C_3-C_6)$-cycloalkyl,
where $(C_1-C_4)$-alkyl can be substituted by hydroxyl, $(C_1-C_4)$-alkoxy, trifluoromethoxy or $(C_3-C_6)$-cycloalkyl and up to three times by fluorine
and
the cycloalkyl groups mentioned can be substituted up to two times by identical or different radicals selected from the group consisting of fluorine, $(C_1-C_4)$-alkyl, trifluoromethyl, hydroxyl, $(C_1-C_4)$-alkoxy and trifluoromethoxy,
or
$R^7$ and $R^8$ in the case where both are bonded to a nitrogen atom form a 4- to 6-membered heterocycle together with this nitrogen atom, which can contain a further ring heteroatom from the group consisting of N, O, S and $S(O)_2$ and which can be substituted up to two times by identical or different radicals selected from the group consisting of fluorine, $(C_1-C_4)$-alkyl, trifluoromethyl, hydroxyl, $(C_1-C_4)$-alkoxy, oxo and $(C_1-C_4)$-alkylcarbonyl,
$R^5$ represents fluorine,
and
n represents the number 0 or 1,
or a salt thereof.

Paragraph 11c: The compound of the formula according to paragraph 1c in which
the ring

represents a phenyl ring and the adjacent groups X and $CH_2$ are bonded to this phenyl ring in 1,3 or 1,4 relation to one another,
the ring

with the substituent $R^3$ represents a heteroaryl ring of the formula

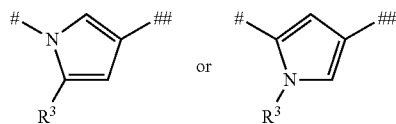

wherein
designates the linkage point with the adjacent $CH_2$ group
and
designates the linkage point with the ring

, the ring

represents a heteroaryl ring of the formula

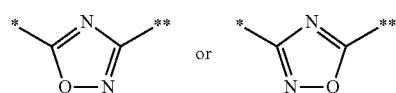

wherein
* designates the linkage point with the ring

And
** designates the linkage point with the ring

, the ring

, with the substituents $R^4$ and $R^5$ represents a phenyl ring of the formula

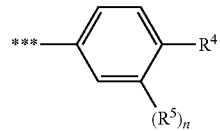

wherein
*** designates the linkage point with the ring

,

X represents —N($R^6$)—, —O—, —S— or ♦-N($R^6$)—C(=O)-♦♦ wherein
♦ designates the linkage point with the group L
and
♦♦ designates the linkage point with the ring

and
$R^6$ denotes hydrogen, methyl, ethyl, isopropyl, cyclopropyl or cyclobutyl,
L represents ethane-1,2-diyl or propane-1,3-diyl,
$R^1$ represents hydrogen, $(C_1\text{-}C_4)$-alkyl, $(C_1\text{-}C_4)$-alkylcarbonyl, $(C_1\text{-}C_4)$-alkylsulphonyl or $(C_3\text{-}C_6)$-cycloalkyl,
where the alkyl group in $(C_1\text{-}C_4)$-alkyl, $(C_1\text{-}C_4)$-alkylcarbonyl and $(C_1\text{-}C_4)$-alkylsulphonyl may be substituted by hydroxyl or $(C_1\text{-}C_4)$-alkoxy or up to three times by fluorine
and
$(C_3\text{-}C_6)$-cycloalkyl can be substituted up to two times by identical or different radicals selected from the group consisting of fluorine, $(C_1\text{-}C_4)$-alkyl, hydroxyl and $(C_1\text{-}C_4)$-alkoxy,
$R^2$ represents hydrogen, $(C_1\text{-}C_4)$-alkyl or cyclopropyl,
where $(C_1\text{-}C_4)$-alkyl may be substituted up to three times by fluorine,
$R^3$ represents methyl,
$R^4$ represents a substituent selected from the group consisting of chlorine, $(C_1\text{-}C_6)$-alkyl, trimethylsilyl, —$OR^7$, —$SR^7$, —S(=O)—$R^7$, —S(=O)$_2R^7$, $(C_3\text{-}C_6)$-cycloalkyl and 4- to 6-membered heterocyclyl,
wherein $(C_1\text{-}C_6)$-alkyl for its part can be substituted by a radical selected from the group consisting of —$OR^7$, —$NR^7R^8$, —C(=O)—$NR^7R^8$, $(C_3\text{-}C_6)$-cycloalkyl and 4- to 6-membered heterocyclyl and up to three times by fluorine
and
the cycloalkyl and heterocyclyl groups mentioned for their part can be substituted up to two times by identical or different radicals selected from the group consisting of fluorine, $(C_1\text{-}C_4)$-alkyl, trifluoromethyl, hydroxyl, $(C_1\text{-}C_4)$-alkoxy, trifluoromethoxy, oxo and $(C_1\text{-}C_4)$-alkylcarbonyl
and wherein
$R^7$ and $R^8$ independently of each other for each individual occurrence denote hydrogen, $(C_1\text{-}C_4)$-alkyl or $(C_3\text{-}C_6)$-cycloalkyl,
where $(C_1\text{-}C_4)$-alkyl can be substituted by hydroxyl, $(C_1\text{-}C_4)$-alkoxy, trifluoromethoxy or $(C_3\text{-}C_6)$-cycloalkyl and up to three times by fluorine
and
the cycloalkyl groups mentioned can be substituted up to two times by identical or different radicals selected from the group consisting of fluorine, $(C_1\text{-}C_4)$-alkyl, trifluoromethyl, hydroxyl, $(C_1\text{-}C_4)$-alkoxy and trifluoromethoxy,
or
$R^7$ and $R^8$ in the case where both are bonded to a nitrogen atom form a 4- to 6-membered heterocycle together with this nitrogen atom, which can contain a further ring heteroatom from the group consisting of N, O, S and $S(O)_2$ and which can be substituted up to two times by identical or different radicals selected from the group consisting of fluorine, $(C_1\text{-}C_4)$-alkyl, trifluoromethyl, hydroxyl, $(C_1\text{-}C_4)$-alkoxy, oxo and $(C_1\text{-}C_4)$-alkylcarbonyl,
$R^5$ represents fluorine,
and
n represents the number 0 or 1,
or a salt thereof.

Paragraph 12c: The compound of the formula according to paragraph 1c in which
the ring

represents a phenyl ring and the adjacent groups X and $CH_2$ are bonded to this phenyl ring in 1, 3 or 1,4 relation to one another,
the ring

with the substituent $R^3$ represents a heteroaryl ring of the formula

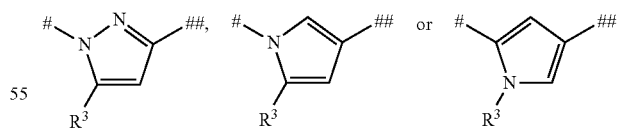

wherein
designates the linkage point with the adjacent $CH_2$ group
and
designates the linkage point with the ring

, the ring

, represents a heteroaryl ring of the formula

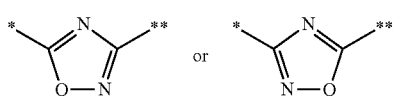

wherein
* designates the linkage point with the ring

and
** designates the linkage point with the ring

, the ring

, with the substituents $R^4$ and $R^5$ represents a phenyl ring of the formula

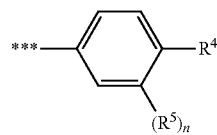

wherein
*** designates the linkage point with the ring

,

X represents —N($R^6$)—, —O—, —S— or ♦-N($R^6$)—C(=O)-♦♦ wherein
♦ designates the linkage point with the group L
and
♦♦ designates the linkage point with the ring

and
$R^6$ denotes hydrogen, methyl, ethyl, isopropyl, cyclopropyl or cyclobutyl,
L represents ethane-1,2-diyl or propane-1,3-diyl, $R^1$ and $R^2$ together with the nitrogen atom to which they are attached form a saturated 4- to 6-membered heterocycle which can contain a further ring heteroatom from the group consisting of N, O, S and $S(O)_2$ and which can be substituted up to two times by identical or different radicals selected from the group consisting of fluorine, $(C_1$-$C_4)$-alkyl, trifluoromethyl, hydroxyl, $(C_1$-$C_4)$-alkoxy, oxo and $(C_3$-$C_6)$-cycloalkyl, $R^3$ represents methyl, $R^4$ represents a substituent selected from the group consisting of chlorine, $(C_1$-$C_6)$-alkyl, trimethylsilyl, —$OR^7$, —$SR^7$, —S(=O)—$R^7$, —$S(=O)_2$—$R^7$, $(C_3$-$C_6)$-cycloalkyl and 4- to 6-membered heterocyclyl, wherein $(C_1$-$C_6)$-alkyl for its part can be substituted by a radical selected from the group consisting of —$OR^7$, —$NR^7R^8$, —C(=O)—$NR^7R^8$, $(C_3$-$C_6)$-cycloalkyl and 4- to 6-membered heterocyclyl and up to three times by fluorine and the cycloalkyl and heterocyclyl groups mentioned for their part can be substituted up to two times by identical or different radicals selected from the group consisting of fluorine, $(C_1$-$C_4)$-alkyl, trifluoromethyl, hydroxyl, $(C_1$-$C_4)$-alkoxy, trifluoromethoxy, oxo and $(C_1$-$C_4)$-alkylcarbonyl and wherein $R^7$ and $R^8$ independently of each other for each individual occurrence denote hydrogen, $(C_1$-$C_4)$-alkyl or $(C_3$-$C_6)$-cycloalkyl, where $(C_1$-$C_4)$-alkyl can be substituted by hydroxyl, $(C_1$-$C_4)$-alkoxy, trifluoromethoxy or $(C_3$-$C_6)$-cycloalkyl and up to three times by fluorine and the cycloalkyl groups mentioned can be substituted up to two times by identical or different radicals selected from the group consisting of fluorine, $(C_1$-$C_4)$-alkyl, trifluoromethyl, hydroxyl, $(C_1$-$C_4)$-alkoxy and trifluoromethoxy, or $R^7$ and $R^8$ in the case where both are bonded to a nitrogen atom form a 4- to 6-membered heterocycle together with this nitrogen atom, which can contain a further ring heteroatom from the group consisting of N, O, S and $S(O)_2$ and which can be substituted up to two times by identical or different radicals selected from the group consisting of fluorine, $(C_1$-$C_4)$-alkyl, trifluoromethyl, hydroxyl, $(C_1$-$C_4)$-alkoxy, oxo and $(C_1$-$C_4)$-alkylcarbonyl, $R^5$ represents fluorine, and n represents the number 0 or 1, or a salt thereof.

Paragraph 13c: The compound of the formula according to paragraph 1c in which the ring

represents a phenyl ring and the adjacent groups X and CH₂ are bonded to this phenyl ring in 1,3 or 1,4 relation to one another, the ring (B)

with the substituent R³ represents a heteroaryl ring of the formula

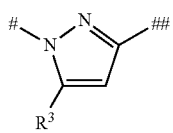

wherein
designates the linkage point with the adjacent CH₂ group
and
designates the linkage point with the ring (D), the ring (D), represents a heteroaryl ring of the formula

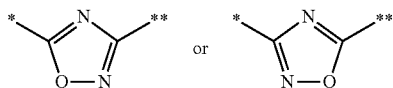

wherein
* designates the linkage point with the ring (B)

and
** designates the linkage point with the ring (E), the ring (E), with the substituents R⁴ and R⁵ represents a phenyl ring of the formula

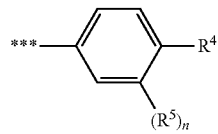

wherein
*** designates the linkage point with the ring (D),

X represents —N(R⁶)—, —O—, —S— or ♦-N(R⁶)—C(=O)-♦♦ wherein
♦ designates the linkage point with the group L
and
♦♦ designates the linkage point with the ring (A)

and
R⁶ denotes hydrogen, methyl, ethyl, isopropyl, cyclopropyl or cyclobutyl,
L represents ethane-1,2-diyl or propane-1,3-diyl,
R¹ represents hydrogen, methyl, ethyl, 2-hydroxyethyl, 2-methoxyethyl, isopropyl, cyclopropyl or cyclobutyl,
R² represents hydrogen, methyl or cyclopropyl,
R³ represents methyl,
R⁴ represents a substituent selected from the group consisting of chlorine, $(C_1\text{-}C_6)$-alkyl, trimethylsilyl, —OR⁷, —SR⁷, —S(=O)—R⁷, —S(=O)₂—R⁷, $(C_3\text{-}C_6)$-cycloalkyl and 4- to 6-membered heterocyclyl,
wherein $(C_1\text{-}C_6)$-alkyl for its part can be substituted by a radical selected from the group consisting of —OR⁷, —NR⁷R⁸, —C(=O)—NR⁷R⁸, $(C_3\text{-}C_6)$-cycloalkyl and 4- to 6-membered heterocyclyl and up to three times by fluorine
and
the cycloalkyl and heterocyclyl groups mentioned for their part can be substituted up to two times by identical or different radicals selected from the group consisting of fluorine, $(C_1\text{-}C_4)$-alkyl, trifluoromethyl, hydroxyl, $(C_1\text{-}C_4)$-alkoxy, trifluoromethoxy, oxo and $(C_1\text{-}C_4)$-alkylcarbonyl
and wherein
R⁷ and R⁸ independently of each other for each individual occurrence denote hydrogen, $(C_1\text{-}C_4)$-alkyl or $(C_3\text{-}C_6)$-cycloalkyl,
where $(C_1\text{-}C_4)$-alkyl can be substituted by hydroxyl, $(C_1\text{-}C_4)$-alkoxy, trifluoromethoxy or $(C_3\text{-}C_6)$-cycloalkyl and up to three times by fluorine
and
the cycloalkyl groups mentioned can be substituted up to two times by identical or different radicals selected from the group consisting of fluorine, $(C_1\text{-}C_4)$-alkyl, trifluoromethyl, hydroxyl, $(C_1\text{-}C_4)$-alkoxy and trifluoromethoxy, or
R⁷ and R⁸ in the case where both are bonded to a nitrogen atom form a 4- to 6-membered heterocycle together with this nitrogen atom, which can contain a further ring heteroatom from the group consisting of N, O, S and $S(O)_2$ and which can be substituted up to two times by identical or different radicals selected from the group consisting of fluorine, $(C_1-C_4)$-alkyl, trifluoromethyl, hydroxyl, $(C_1-C_4)$-alkoxy, oxo and $(C_1-C_4)$-alkylcarbonyl, R⁵ represents fluorine,
and
n represents the number 0 or 1,
or a salt thereof.

d. Heterocyclically Substituted Aryl Compounds

In some embodiments, the HIF-2α inhibitor is a compound (as disclosed in U.S. Published Application No. 2013/0196964 which is specifically incorporated by reference herein in its entirety) defined according to the following paragraphs found in this subheading:

Paragraph 1d: A compound of formula in which
the ring (A)

represents a phenyl or pyridyl ring,
the ring (B)

with the substituent R³ represents a heteroaryl ring of the formula wherein
designates the linkage point with the adjacent CH₂ group
and
designates the linkage point with the ring (D), the ring (D), represents a heteroaryl ring of the formula wherein
* designates the linkage point with the ring (B)

and
** designates the linkage point with the ring (E), the ring (E), represents a phenyl or pyridyl ring,
the ring (N)

represents a saturated 4- to 10-membered aza-heterocycle, which contains at least one N atom as a ring member and in addition can contain one or two further hetero ring members from the series N, O, S and/or $S(O)_2$, X represents a bond or ♦-$(CH_2)_q$—N(R⁶)-♦♦, ♦-N(R⁶)—$(CH_2)_q$-♦♦, —O—, —S—, —C(=O)—, —S(=O)₂—, ♦-C(=O)—N(R⁶)-♦♦ or ♦-N(R⁶)—C(=O)-♦♦,
wherein
♦ designates the linkage point with the ring (N)

and

♦♦ designates the linkage point with the ring

, q denotes the number 0, 1 or 2
and
$R^6$ denotes hydrogen, $(C_1-C_6)$-alkyl or $(C_3-C_6)$-cycloalkyl,
wherein $(C_1-C_6)$-alkyl and $(C_3-C_6)$-cycloalkyl can each be substituted by hydroxyl or $(C_1-C_4)$-alkoxy,
$R^1$ represents a substituent bonded to a carbon atom of the ring

, chosen from the series fluorine, cyano, $(C_1-C_6)$-alkyl, hydroxyl, $(C_1-C_6)$-alkoxy, oxo, amino, mono-$(C_1-C_6)$-alkylamino, di-$(C_1-C_6)$-alkylamino and $(C_3-C_6)$-cycloalkyl,
wherein $(C_1-C_6)$-alkyl in its turn can be substituted up to three times by fluorine and up to two times in an identical or different manner by a radical chosen from the series hydroxyl, $(C_1-C_4)$-alkoxy, amino, mono-$(C_1-C_4)$-alkylamino and di-$(C_1-C_4)$-alkylamino
and
$(C_3-C_6)$-cycloalkyl in its turn can be substituted up to two times in an identical or different manner by a radical chosen from the series fluorine, $(C_1-C_4)$-alkyl, hydroxyl, $(C_1-C_4)$-alkoxy, amino, mono-$(C_1-C_4)$-alkylamino and di-$(C_1-C_4)$-alkylamino,
m represents the number 0, 1, 2, 3 or 4,
wherein in the case where the substituent $R^5$ occurs several times, its meanings can be identical or different,
$R^2$ represents a substituent bonded to a nitrogen atom of the ring

, chosen from the series $(C_1-C_6)$-alkyl, $(C_1-C_6)$-alkylcarbonyl, $(C_1-C_6)$-alkoxycarbonyl, $(C_1-C_6)$-alkylsulfonyl and $(C_3-C_6)$-cycloalkyl,
wherein the alkyl group in $(C_1-C_6)$-alkyl, $(C_1-C_6)$-alkylcarbonyl, $(C_1-C_6)$-alkoxycarbonyl and $(C_1-C_6)$-alkylsulfonyl in its turn can be substituted up to three times by fluorine and up to two times in an identical or different manner by a radical chosen from the series hydroxyl, $(C_1-C_4)$-alkoxy, amino, mono-$(C_1-C_4)$-alkylamino, di-$(C_1-C_4)$-alkylamino $(C_3-C_6)$-cycloalkyl and 4- to 6-membered heterocyclyl
and
$(C_3-C_6)$-cycloalkyl in its turn can be substituted up to two times in an identical or different manner by a radical chosen from the series fluorine, $(C_1-C_4)$-alkyl, hydroxyl, $(C_1-C_4)$-alkoxy, amino, mono-$(C_1-C_4)$-alkylamino and di-$(C_1-C_4)$-alkylamino,
n represents the number 0 or 1 or also, if the aza-heterocycle

, contains further N atoms as ring members, the number 2, wherein in the case where the substituent $R^2$ occurs twice, its meanings can be identical or different,
$R^3$ represents methyl, ethyl or trifluoromethyl,
$R^4$ represents hydrogen or a substituent chosen from the series halogen, cyano, pentafluorothio, $(C_1-C_6)$-alkyl, tri-$(C_1-C_4)$-alkylsilyl, —$OR^7$, —$NR^7R^8$, —$N(R^7)$—C(=O)—$R^8$, —$N(R^7)$—C(=O)—$OR^8$, —$N(R^7)$—S(=O)$_2$—$R^8$, —C(=O)—$OR^7$, —C(=O)—$NR^7R^8$, —$SR^7$, —S(=O)—$R^7$, —S(=O)$_2$—$R^7$, —S(=O)$_2$—$NR^7R^8$, —S(=O)(=NH)—$R^7$, —S(=O)(=NCH$_3$)—$R^7$, $(C_3-C_6)$-cycloalkyl, 4- to 6-membered heterocyclyl and 5- or 6-membered heteroaryl,
wherein $(C_1-C_6)$-alkyl in its turn can be substituted up to three times by fluorine and up to two times in an identical or different manner by a radical chosen from the series —$OR^7$, —$NR^7R^8$, —$N(R^7)$—C(=O)—$R^8$, —$N(R^7)$—C(=O)—$OR^8$, —C(=O)—$OR^7$, —C(=O)—$NR^7R^8$, $(C_3-C_6)$-cycloalkyl, 4- to 6-membered heterocyclyl and 5- or 6-membered heteroaryl
and wherein
the cycloalkyl and heterocyclyl groups mentioned in their turn can be substituted up to two times in an identical or different manner by a radical chosen from the series fluorine, $(C_1-C_4)$-alkyl, hydroxyl, $(C_1-C_4)$-alkoxy, trifluoromethoxy, oxo, amino, mono-$(C_1-C_4)$-alkylamino, di-$(C_1-C_4)$-alkylamino, $(C_1-C_4)$-alkylcarbonylamino, $(C_1-C_4)$-alkoxycarbonylamino, $(C_1-C_4)$-alkylcarbonyl and $(C_1-C_4)$-alkoxycarbonyl
and
the heteroaryl groups mentioned in their turn can be substituted up to two times in an identical or different manner by a radical chosen from the series fluorine, chlorine, cyano, $(C_1-C_4)$-alkyl, $(C_1-C_4)$-alkoxy and trifluoromethoxy wherein the $(C_1-C_4)$-alkyl substituents mentioned herein in their turn can be substituted by hydroxyl, $(C_1-C_4)$-alkoxy, trifluoromethoxy, $(C_1-C_4)$-alkylcarbonyloxy, aminocarbonyl, mono-$(C_1-C_4)$-alkylaminocarbonyl or di-$(C_1-C_4)$-alkylaminocarbonyl or up to three times by fluorine,
and wherein
$R^7$ and $R^8$ independently of each other for each individual occurrence denote hydrogen, $(C_1-C_6)$-alkyl, $(C_3-C_6)$-cycloalkyl or 4- to 6-membered heterocyclyl, wherein $(C_1-C_6)$-alkyl can be substituted up to three times by fluorine and up to two times in an identical or different manner by a radical chosen from the series hydroxyl, $(C_1-C_4)$-alkoxy, trifluoromethoxy, amino, mono-$(C_1-C_4)$-alkylamino, di-$(C_1-C_4)$-alkylamino, $(C_1-C_4)$-alkoxycarbonyl, $(C_3-C_6)$-cycloalkyl and 4- to 6-membered heterocyclyl
and
the cycloalkyl and heterocyclyl groups mentioned can be substituted up to two times in an identical or different manner by a radical chosen from the series fluorine, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, $(C_1-C_4)$-alkylcarbonyl and $(C_1-C_4)$-alkoxycarbonyl,
or
$R^7$ and $R^8$ in the case where both are bonded to a nitrogen atom form a 4- to 6-membered heterocycle together with this nitrogen atom, which can contain a further ring hetero atom from the series N, O, S or S(O)$_2$ and which can be substituted up to two times in an identical or different manner by a radical chosen from the series fluorine, $(C_1-C_4)$-alkyl, trifluoromethyl, hydroxyl, $(C_1-C_4)$-alkoxy, oxo, amino, mono-$(C_1$-$C_4)$-alkylamino, di-$(C_1$-$C_4)$-alkylamino, $(C_1$-$C_4)$-alkylcarbonyl and $(C_1$-$C_4)$-alkoxycarbonyl, $R^5$ represents a substituent chosen from the series fluorine, chlorine, cyano, methyl, trifluoromethyl and hydroxyl and p represents the number 0, 1 or 2, wherein in the case where the substituent $R^5$ occurs twice, its meanings can be identical or different, or a salt thereof.

Paragraph 2d: The compound of the formula according to paragraph 1d, in which the ring (A)

represents a phenyl or pyridyl ring and the adjacent groups X and $CH_2$ are bonded to ring carbon atoms (A)

in 1, 3 or 1,4 relation to one another and the ring (E)

with the substituents $R^4$ and $R^5$ represents a phenyl ring of the formula

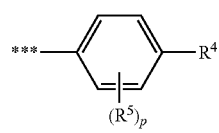

wherein

*** designates the linkage point with the ring (D), or a salt thereof.

Paragraph 3d: The compound of the formula according to paragraph 1d, in which the ring (A)

represents a pyridyl ring and the adjacent groups X and $CH_2$ are bonded to ring carbon atoms of this pyridyl ring in 1, 3 or 1,4 relation to one another and the ring (E)

with the substituents $R^4$ and $R^5$ represents a phenyl ring of the formula

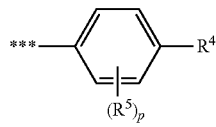

wherein

*** designates the linkage point with the ring (D), or a salt thereof.

Paragraph 4d: The compound of the formula according to paragraph 1d, in which the ring (A)

represents a phenyl ring and the adjacent groups X and $CH_2$ are bonded to this phenyl ring in 1, 3 or 1,4 relation to one another, the ring (B)

with the substituent $R^3$ represents a heteroaryl ring of the formula

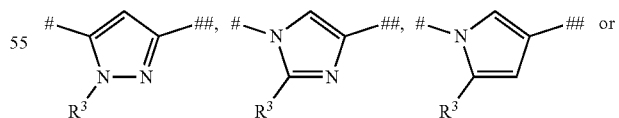

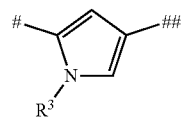

wherein
\# designates the linkage point with the adjacent CH$_2$ group
and
\#\# designates the linkage point with the ring

and
the ring

with the substituents R$^4$ and R$^5$ represents a phenyl ring of the formula

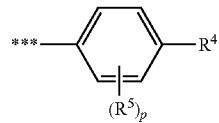

wherein
*** designates the linkage point with the ring

or a salt thereof.

Paragraph 5d: The compound of the formula according to paragraph 1d, in which
the ring

represents a phenyl ring and the adjacent groups X and CH$_2$ are bonded to this phenyl ring in 1, 3 or 1,4 relation to one another,
the ring

with the substituent R$^3$ represents a heteroaryl ring of the formula

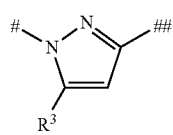

wherein
\# designates the linkage point with the adjacent CH$_2$ group
and
\#\# designates the linkage point with the ring

the ring

with the substituents R$^4$ and R$^5$ represents a phenyl ring of the formula

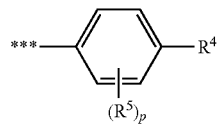

wherein
*** designates the linkage point with the ring

R$^1$ represents a substituent bonded to a carbon atom of the ring

chosen from the series cyano, (C$_1$-C$_6$)-alkyl, oxo and (C$_3$-C$_6$)-cycloalkyl, wherein (C$_1$-C$_6$)-alkyl in its turn can be substituted up to three times by fluorine and up to two times in an identical or different manner by a radical chosen from the series hydroxyl, (C$_1$-C$_4$)-alkoxy, amino, mono-(C$_1$-C$_4$)-alkylamino and di-(C$_1$-C$_4$)-alkylamino
and
(C$_3$-C$_6$)-cycloalkyl in its turn can be substituted up to two times in an identical or different manner by a radical chosen from the series fluorine, (C$_1$-C$_4$)-alkyl, hydroxyl, (C$_1$-C$_4$)-alkoxy, amino, mono-(C$_1$-C$_4$)-alkylamino and di-(C$_1$-C$_4$)-alkylamino,
R$^2$ represents a substituent bonded to a nitrogen atom of the ring

chosen from the series (C$_1$-C$_6$)-alkyl, (C$_1$-C$_6$)-alkylcarbonyl, (C$_1$-C$_6$)-alkoxycarbonyl, (C$_1$-C$_4$-alkylsulfonyl and (C$_3$-C$_6$)-cycloalkyl,
wherein the alkyl group in (C$_1$-C$_6$)-alkyl, (C$_1$-C$_6$)-alkylcarbonyl, (C$_1$-C$_6$)-alkoxycarbonyl and (C$_1$-C$_6$)-alkylsulfonyl in its turn can be substituted up to three times by fluorine and up to two times in an identical or different manner by a radical chosen from the series hydroxyl, $(C_1-C_4)$-alkoxy, amino, mono-$(C_1-C_4)$-alkylamino, di-$(C_1-C_4)$-alkylamino $(C_3-C_6)$-cycloalkyl and 4- to 6-membered heterocyclyl
and
$(C_3-C_6)$-cycloalkyl in its turn can be substituted up to two times in an identical or different manner by a radical chosen from the series fluorine, $(C_1-C_4)$-alkyl, hydroxyl, $(C_1-C_4)$-alkoxy, amino, mono-$(C_1-C_4)$-alkylamino and di-$(C_1-C_4)$-alkylamino,
m represents the number 0, 1, 2, 3 or 4,
wherein in the case where the substituent $R^5$ occurs several times, its meanings can be identical or different,
and
n represents the number 0 or 1 or also, if the aza-heterocycle

contains further N atoms as ring members, the number 2, wherein in the case where the substituent $R^2$ occurs twice, its meanings can be identical or different,
wherein the sum of m and n does not equal the number 0, or a salt thereof.

Paragraph 6d: The compound of the formula according to paragraph 1d, in which
the ring

represents a pyridyl ring and the adjacent groups X and $CH_2$ are bonded to ring carbon atoms of this pyridyl ring in 1, 3 or 1,4 relation to one another,
the ring

with the substituent $R^3$ represents a heteroaryl ring of the formula

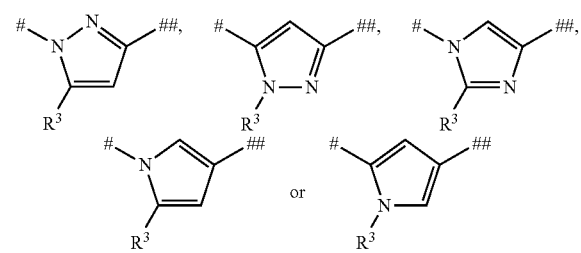

wherein
designates the linkage point with the adjacent $CH_2$ group
and
designates the linkage point with the ring

the ring

represents a heteroaryl ring of the formula

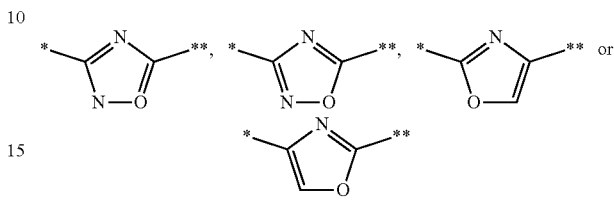

wherein
* designates the linkage point with the ring

and
** designates the linkage point with the ring

the ring

with the substituents $R^4$ and $R^5$ represents a phenyl ring of the formula

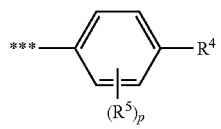

wherein
*** designates the linkage point with the ring

the ring

represents a saturated 4- to 10-membered aza-heterocycle, which contains at least one N atom as a ring member and in addition can contain a further hetero ring member from the series N, O, S or S(O)$_2$, X represents a bond or ♦-(CH$_2$)$_q$—N(R$^6$)-♦♦, —O—, —S—, —C(=O)—, —S(=O)$_2$— or ♦-N(R$^6$)—C(=O)-♦♦, wherein ♦ designates the linkage point with the ring

and

♦♦ designates the linkage point with the ring

q denotes the number 0, 1 or 2 and

R$^6$ denotes hydrogen, (C$_1$-C$_4$)-alkyl or (C$_3$-C$_6$)-cycloalkyl,

R$^1$ represents a substituent bonded to a carbon atom of the ring

chosen from the series fluorine, cyano, (C$_1$-C$_4$)-alkyl, hydroxyl, (C$_1$-C$_4$)-alkoxy, oxo, amino, mono-(C$_1$-C$_4$)-alkylamino, di-(C$_1$-C$_4$)-alkylamino and (C$_3$-C$_6$)-cycloalkyl, wherein (C$_1$-C$_4$)-alkyl in its turn can be substituted by a radical chosen from the series hydroxyl, (C$_1$-C$_4$)-alkoxy, amino, mono-(C$_1$-C$_4$)-alkylamino and di-(C$_1$-C$_4$)-alkylamino and up to three times by fluorine and (C$_3$-C$_6$)-cycloalkyl in its turn can be substituted up to two times in an identical or different manner by a radical chosen from the series fluorine, (C$_1$-C$_4$)-alkyl, hydroxyl, (C$_1$-C$_4$)-alkoxy, amino, mono-(C$_1$-C$_4$)-alkylamino and di-(C$_1$-C$_4$)-alkylamino, m represents the number 0, 1 or 2, wherein in the case where the substituent R$^1$ occurs twice, its meanings can be identical or different, R$^2$ represents a substituent bonded to a nitrogen atom of the ring

chosen from the series (C$_1$-C$_4$)-alkyl, (C$_1$-C$_4$)-alkylcarbonyl, (C$_1$-C$_4$)-alkoxycarbonyl, (C$_1$-C$_4$)-alkylsulfonyl and (C$_3$-C$_6$)-cycloalkyl, wherein the alkyl group in (C$_1$-C$_4$)-alkyl, (C$_1$-C$_4$)-alkylcarbonyl, (C$_1$-C$_4$)-alkoxycarbonyl and (C$_1$-C$_4$)-alkylsulfonyl in its turn can be substituted by a radical chosen from the series hydroxyl, (C$_1$-C$_4$)-alkoxy, amino, mono-(C$_1$-C$_4$)-alkylamino, di-(C$_1$-C$_4$)-alkylamino (C$_3$-C$_6$)-cycloalkyl and 4- to 6-membered heterocyclyl and up to three times by fluorine and (C$_3$-C$_6$)-cycloalkyl in its turn can be substituted up to two times in an identical or different manner by a radical chosen from the series fluorine, (C$_1$-C$_4$)-alkyl, hydroxyl, (C$_1$-C$_4$)-alkoxy, amino, mono-(C$_1$-C$_4$)-alkylamino and di-(C$_1$-C$_4$)-alkylamino, n represents the number 0 or 1, R$^3$ represents methyl, ethyl or trifluoromethyl, R$^4$ represents a substituent chosen from the series fluorine, chlorine, cyano, pentafluorothio, (C$_1$-C$_6$)-alkyl, tri-(C$_1$-C$_4$)-alkylsilyl, —OR$^7$, —NR$^7$R$^8$, —SR$^7$, —S(=O)—R$^7$, —S(=O)$_2$—R$^7$, —S(=O)(=NH)—R$^7$, —S(=O)(=NCH$_3$)—R$^7$, (C$_3$-C$_6$)-cycloalkyl and 4- to 6-membered heterocyclyl, wherein (C$_1$-C$_6$)-alkyl in its turn can be substituted up to three times by fluorine and up to two times in an identical or different manner by a radical chosen from the series —OR$^7$, —NR$^7$R$^8$, —N(R$^7$)—C(=O)—R$^8$, —C(=O)—NR$^7$R$^8$, (C$_3$-C$_6$)-cycloalkyl, 4- to 6-membered heterocyclyl and 5- or 6-membered heteroaryl and wherein the cycloalkyl and heterocyclyl groups mentioned in their turn can be substituted up to two times in an identical or different manner by a radical chosen from the series fluorine, (C$_1$-C$_4$)-alkyl, hydroxyl, (C$_1$-C$_4$)-alkoxy, trifluoromethoxy, oxo and (C$_1$-C$_4$)-alkylcarbonyl and the heteroaryl group mentioned in its turn can be substituted up to two times in an identical or different manner by a radical chosen from the series fluorine, chlorine, cyano, (C$_1$-C$_4$-alkyl, (C$_1$-C$_4$)-alkoxy and trifluoromethoxy wherein the (C$_1$-C$_4$)-alkyl substituents mentioned herein in their turn can be substituted by hydroxyl, methoxy, trifluoromethoxy, ethoxy, acetoxy, aminocarbonyl, methylaminocarbonyl or dimethylaminocarbonyl or up to three times by fluorine, and wherein R$^7$ and R$^8$ independently of each other for each individual occurrence denote hydrogen, (C$_1$-C$_4$)-alkyl, (C$_3$-C$_6$)-cycloalkyl or 4- to 6-membered heterocyclyl, wherein (C$_1$-C$_4$)-alkyl can be substituted up to three times by fluorine and up to two times in an identical or different manner by a radical chosen from the series hydroxyl, (C$_1$-C$_4$)-alkoxy, trifluoromethoxy, (C$_3$-C$_6$)-cycloalkyl and 4- to 6-membered heterocyclyl and the cycloalkyl and heterocyclyl groups mentioned can be substituted up to two times in an identical or different manner by a radical chosen from the series fluorine, (C$_1$-C$_4$)-alkyl, trifluoromethyl, hydroxyl, (C$_1$-C$_4$)-alkoxy, trifluoromethoxy, oxo and (C$_1$-C$_4$)-alkylcarbonyl or R$^7$ and R$^8$ in the case where both are bonded to a nitrogen atom form a 4- to 6-membered heterocycle together with this nitrogen atom, which can contain a further ring hetero atom from the series N, O, S or S(O)$_2$ and which can be substituted up to two times in an identical or different manner by a radical chosen from the series fluorine, (C$_1$-C$_4$)-alkyl, trifluoromethyl, hydroxyl, (C$_1$-C$_4$)-alkoxy, oxo and (C$_1$-C$_4$)-alkylcarbonyl, R$^5$ represents a substituent chosen from the series fluorine, chlorine and methyl and p represents the number 0 or 1, or a salt thereof.

Paragraph 7d: The compound of the formula according to paragraph 1d, in which
the ring

represents a phenyl ring and the adjacent groups X and CH$_2$ are bonded to this phenyl ring in 1,3 or 1,4 relation to one another,
the ring

with the substituent R$^3$ represents a heteroaryl ring of the formula

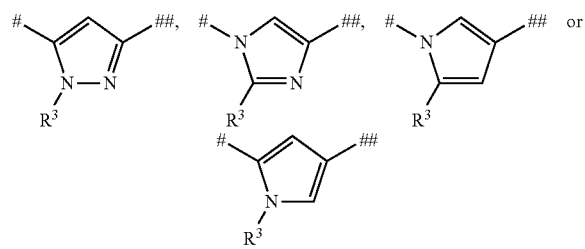

wherein
\# designates the linkage point with the adjacent CH$_2$ group
and
\#\# designates the linkage point with the ring

the ring

represents a heteroaryl ring of the formula

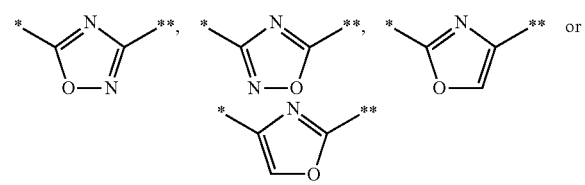

wherein
* designates the linkage point with the ring

and
** designates the linkage point with the ring

the ring

with the substituents R$^4$ and R$^5$ represents a phenyl ring of the formula

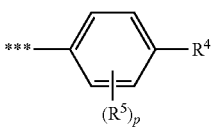

wherein
*** designates the linkage point with the ring

the ring

represents a saturated 4- to 10-membered aza-heterocycle, which contains at least one N atom as a ring member and in addition can contain a further hetero ring member from the series N, O, S or S(O)$_2$,
X represents a bond or ♦-(CH$_2$)$_q$—N(R$^6$)-♦♦, —O—, —S—, —C(=O)—, —S(=O)$_2$— or ♦-N(R$^6$)—C(=O)-♦♦, wherein
♦ designates the linkage point with the ring

and
♦♦ designates the linkage point with the ring

q denotes the number 0, 1 or 2
and
R$^6$ denotes hydrogen, (C$_1$-C$_4$)-alkyl or (C$_3$-C$_6$)-cycloalkyl,
R$^1$ represents a substituent bonded to a carbon atom of the ring

, chosen from the series fluorine, cyano, (C₁-C₄)-alkyl, hydroxyl, (C₁-C₄)-alkoxy, oxo, amino, mono-(C₁-C₄)-alkylamino, di-(C₁-C₄)-alkylamino and (C₃-C₆)-cycloalkyl, wherein (C₁-C₄)-alkyl in its turn can be substituted by a radical chosen from the series hydroxyl, (C₁-C₄)-alkoxy, amino, mono-(C₁-C₄)-alkylamino and di-(C₁-C₄)-alkylamino and up to three times by fluorine and (C₃-C₆)-cycloalkyl in its turn can be substituted up to two times in an identical or different manner by a radical chosen from the series fluorine, (C₁-C₄)-alkyl, hydroxyl, (C₁-C₄)-alkoxy, amino, mono-(C₁-C₄)-alkylamino and di-(C₁-C₄)-alkylamino, m represents the number 0, 1 or 2, wherein in the case where the substituent $R^1$ occurs twice, its meanings can be identical or different, $R^2$ represents a substituent bonded to a nitrogen atom of the ring

chosen from the series (C₁-C₄)-alkyl, (C₁-C₄)-alkylcarbonyl, (C₁-C₄)-alkoxycarbonyl, (C₁-C₄)-alkylsulfonyl and (C₃-C₆)-cycloalkyl, wherein the alkyl group in (C₁-C₄)-alkyl, (C₁-C₄)-alkylcarbonyl, (C₁-C₄)-alkoxycarbonyl and (C₁-C₄)-alkylsulfonyl in its turn can be substituted by a radical chosen from the series hydroxyl, (C₁-C₄)-alkoxy, amino, mono-(C₁-C₄)-alkylamino, di-(C₁-C₄)-alkylamino (C₃-C₆)-cycloalkyl and 4- to 6-membered heterocyclyl and up to three times by fluorine and (C₃-C₆)-cycloalkyl in its turn can be substituted up to two times in an identical or different manner by a radical chosen from the series fluorine, (C₁-C₄)-alkyl, hydroxyl, (C₁-C₄)-alkoxy, amino, mono-(C₁-C₄)-alkylamino and di-(C₁-C₄)-alkylamino, n represents the number 0 or 1, $R^3$ represents methyl, ethyl or trifluoromethyl, $R^4$ represents a substituent chosen from the series fluorine, chlorine, cyano, pentafluorothio, (C₁-C₆)-alkyl, tri-(C₁-C₄)-alkylsilyl, —OR⁷, —NR⁷R⁸, —SR⁷, —S(=O)—R⁷, —S(=O)₂—R⁷, —S(=O)(=NH)—R⁷, —S(=O)(=NCH₃)—R⁷, (C₃-C₆)-cycloalkyl and 4- to 6-membered heterocyclyl, wherein (C₁-C₆)-alkyl in its turn can be substituted up to three times by fluorine and up to two times in an identical or different manner by a radical chosen from the series —OR⁷, NR⁷R⁸, —N(R⁷)—C(=O)—R⁸, —C(=O)—NR⁷R⁸, (C₃-C₆)-cycloalkyl, 4- to 6-membered heterocyclyl and 5- or 6-membered heteroaryl and wherein the cycloalkyl and heterocyclyl groups mentioned in their turn can be substituted up to two times in an identical or different manner by a radical chosen from the series fluorine, (C₁-C₄)-alkyl, hydroxyl, (C₁-C₄)-alkoxy, trifluoromethoxy, oxo and (C₁-C₄)-alkylcarbonyl and the heteroaryl group mentioned in its turn can be substituted up to two times in an identical or different manner by a radical chosen from the series fluorine, chlorine, cyano, (C₁-C₄)-alkyl, (C₁-C₄)-alkoxy and trifluoromethoxy wherein the (C₁-C₄)-alkyl substituents mentioned herein in their turn can be substituted by hydroxyl, methoxy, trifluoromethoxy, ethoxy, acetoxy, aminocarbonyl, methylaminocarbonyl or dimethylaminocarbonyl or up to three times by fluorine, and wherein $R^7$ and $R^8$ independently of each other for each individual occurrence denote hydrogen, (C₁-C₄)-alkyl, (C₃-C₆)-cycloalkyl or 4- to 6-membered heterocyclyl, wherein (C₁-C₄)-alkyl can be substituted up to three times by fluorine and up to two times in an identical or different manner by a radical chosen from the series hydroxyl, (C₁-C₄)-alkoxy, trifluoromethoxy, (C₃-C₆)-cycloalkyl and 4- to 6-membered heterocyclyl and the cycloalkyl and heterocyclyl groups mentioned can be substituted up to two times in an identical or different manner by a radical chosen from the series fluorine, (C₁-C₄)-alkyl, trifluoromethyl, hydroxyl, (C₁-C₄)-alkoxy, trifluoromethoxy, oxo and (C₁-C₄)-alkylcarbonyl or $R^7$ and $R^8$ in the case where both are bonded to a nitrogen atom form a 4- to 6-membered heterocycle together with this nitrogen atom, which can contain a further ring hetero atom from the series N, O, S or S(O)₂ and which can be substituted up to two times in an identical or different manner by a radical chosen from the series fluorine, (C₁-C₄)-alkyl, trifluoromethyl, hydroxyl, (C₁-C₄)-alkoxy, oxo and (C₁-C₄)-alkylcarbonyl, $R^5$ represents a substituent chosen from the series fluorine, chlorine and methyl and p represents the number 0 or 1, or a salt thereof.

Paragraph 8d: The compound of the formula according to paragraph 1d, in which the ring

represents a phenyl ring and the adjacent groups X and CH₂ are bonded to this phenyl ring in 1, 3 or 1,4 relation to one another, the ring

with the substituent $R^3$ represents a heteroaryl ring of the formula

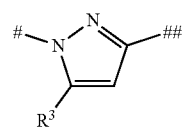

wherein
designates the linkage point with the adjacent CH$_2$ group
and
designates the linkage point with the ring

the ring

represents a heteroaryl ring of the formula

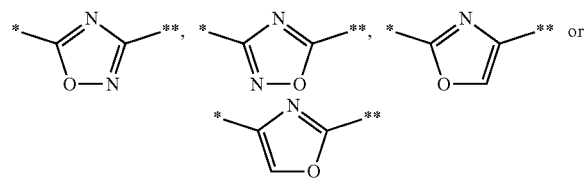

wherein
* designates the linkage point with the ring

and
** designates the linkage point with the ring

the ring

with the substituents R$^4$ and R$^5$ represents a phenyl ring of the formula

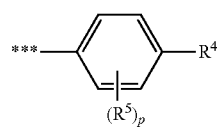

wherein
*** designates the linkage point with the ring

the ring

represents a saturated 4- to 10-membered aza-heterocycle, which contains at least one N atom as a ring member and in addition can contain a further hetero ring member from the series N, O, S or S(O)$_2$,
X represents a bond or ♦-(CH$_2$)$_q$—N(R$^6$)-♦♦, —O—, —S—, —C(=O)—, —S(=O)$_2$— or ♦-N(R$^6$)—C(=O)-♦♦, wherein
♦ designates the linkage point with the ring

and
♦♦ designates the linkage point with the ring

q denotes the number 0, 1 or 2
and
R$^6$ denotes hydrogen, (C$_1$-C$_4$)-alkyl or (C$_3$-C$_6$)-cycloalkyl,
R$^1$ represents a substituent bonded to a carbon atom of the ring

chosen from the series cyano, (C$_1$-C$_4$)-alkyl, oxo and (C$_3$-C$_6$)-cycloalkyl, wherein (C$_1$-C$_4$)-alkyl in its turn can be substituted by a radical chosen from the series hydroxyl, (C$_1$-C$_4$)-alkoxy, amino, mono-(C$_1$-C$_4$)-alkylamino and di-(C$_1$-C$_4$)-alkylamino and up to three times by fluorine
and
(C$_3$-C$_6$)-cycloalkyl in its turn can be substituted up to two times in an identical or different manner by a radical chosen from the series fluorine, (C$_1$-C$_4$)-alkyl, hydroxyl, (C$_1$-C$_4$)-alkoxy, amino, mono-(C$_1$-C$_4$)-alkylamino and di-(C$_1$-C$_4$)-alkylamino,
R$^2$ represents a substituent bonded to a nitrogen atom of the ring chosen from the series (C$_1$-C$_4$)-alkyl, (C$_1$-C$_4$)-alkylcarbonyl, (C$_1$-C$_4$)-alkoxycarbonyl, (C$_1$-C$_4$)-alkylsulfonyl and (C$_3$-C$_6$)-cycloalkyl, wherein the alkyl group in $(C_1-C_4)$-alkyl, $(C_1-C_4)$-alkylcarbonyl, $(C_1-C_4)$-alkoxycarbonyl and $(C_1-C_4)$-alkylsulfonyl in its turn can be substituted by a radical chosen from the series hydroxyl, $(C_1-C_4)$-alkoxy, amino, mono-$(C_1-C_4)$-alkylamino, di-$(C_1-C_4)$-alkylamino $(C_3-C_6)$-cycloalkyl and 4- to 6-membered heterocyclyl and up to three times by fluorine
and
$(C_3-C_6)$-cycloalkyl in its turn can be substituted up to two times in an identical or different manner by a radical chosen from the series fluorine, $(C_1-C_4)$-alkyl, hydroxyl, $(C_1-C_4)$-alkoxy, amino, mono-$(C_1-C_4)$-alkylamino and di-$(C_1-C_4)$-alkylamino,
m represents the number 0, 1 or 2,
wherein in the case where the substituent $R^1$ occurs twice, its meanings can be identical or different,
n represents the number 0 or 1,
wherein the sum of m and n equals the number 1, 2 or 3,
$R^3$ represents methyl, ethyl or trifluoromethyl,
$R^4$ represents a substituent chosen from the series fluorine, chlorine, cyano, pentafluorothio, $(C_1-C_6)$-alkyl, tri-$(C_1-C_4)$-alkylsilyl, —$OR^7$, —$NR^7R^8$, —$SR^7$, —$S(=O)-R^7$, —$S(=O)_2-R^7$, —$S(=O)(=NH)-R^7$, —$S(=O)(=NCH_3)-R^7$, $(C_3-C_6)$-cycloalkyl and 4- to 6-membered heterocyclyl,
wherein $(C_1-C_6)$-alkyl in its turn can be substituted up to three times by fluorine and up to two times in an identical or different manner by a radical chosen from the series —$OR^7$, —$NR^7R^8$, —$N(R^7)$—$C(=O)$—$R^8$, —$C(=O)$—$NR^7R^8$, $(C_3-C_6)$-cycloalkyl, 4- to 6-membered heterocyclyl and 5- or 6-membered heteroaryl
and wherein
the cycloalkyl and heterocyclyl groups mentioned in their turn can be substituted up to two times in an identical or different manner by a radical chosen from the series fluorine, $(C_1-C_4)$-alkyl, hydroxyl, $(C_1-C_4)$-alkoxy, trifluoromethoxy, oxo and $(C_1-C_4)$-alkylcarbonyl
and
the heteroaryl group mentioned in its turn can be substituted up to two times in an identical or different manner by a radical chosen from the series fluorine, chlorine, cyano, $(C_1-C_4)$-alkyl, $(C_1-C_4)$-alkoxy and trifluoromethoxy
wherein the $(C_1-C_4)$-alkyl substituents mentioned herein in their turn can be substituted by hydroxyl, methoxy, trifluoromethoxy, ethoxy, acetoxy, aminocarbonyl, methylaminocarbonyl or dimethylaminocarbonyl or up to three times by fluorine,
and wherein
$R^7$ and $R^8$ independently of each other for each individual occurrence denote hydrogen, $(C_1-C_4)$-alkyl, $(C_3-C_6)$-cycloalkyl or 4- to 6-membered heterocyclyl, wherein $(C_1-C_4)$-alkyl can be substituted up to three times by fluorine and up to two times in an identical or different manner by a radical chosen from the series hydroxyl, $(C_1-C_4)$-alkoxy, trifluoromethoxy, $(C_3-C_6)$-cycloalkyl and 4- to 6-membered heterocyclyl
and
the cycloalkyl and heterocyclyl groups mentioned can be substituted up to two times in an identical or different manner by a radical chosen from the series fluorine, $(C_1-C_4)$-alkyl, trifluoromethyl, hydroxyl, $(C_1-C_4)$-alkoxy, trifluoromethoxy, oxo and $(C_1-C_4)$-alkylcarbonyl
or
$R^7$ and $R^8$ in the case where both are bonded to a nitrogen atom form a 4- to 6-membered heterocycle together with this nitrogen atom, which can contain a further ring hetero atom from the series N, O, S or $S(O)_2$ and which can be substituted up to two times in an identical or different manner by a radical chosen from the series fluorine, $(C_1-C_4)$-alkyl, trifluoromethyl, hydroxyl, $(C_1-C_4)$-alkoxy, oxo and $(C_1-C_4)$-alkylcarbonyl,
$R^5$ represents a substituent chosen from the series fluorine, chlorine and methyl
and
p represents the number 0 or 1,
or a salt thereof.

Paragraph 9d: The compound of the formula according to paragraph 1d, in which
the ring

represents a pyridyl ring of the formula

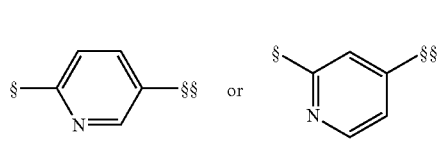

wherein
§ designates the linkage point with the adjacent group X
and
§§ designates the linkage point with the adjacent $CH_2$ group,
the ring

with the substituent $R^3$ represents a heteroaryl ring of the formula

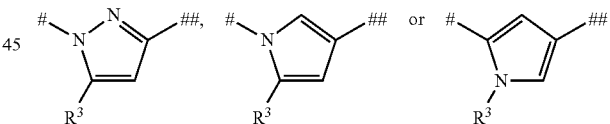

wherein
designates the linkage point with the adjacent $CH_2$ group
and
designates the linkage point with the ring

, the ring

represents a heteroaryl ring of the formula

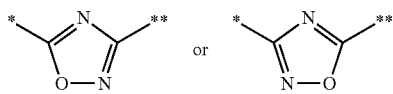

wherein
* designates the linkage point with the ring and
** designates the linkage point with the ring (B)

(E), the ring (E), with the substituents $R^4$ and $R^5$ represents a phenyl ring of the formula

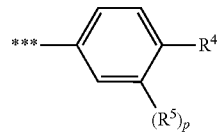

wherein
*** designates the linkage point with the ring (D), the ring (N)

represents a saturated 4- to 10-membered aza-heterocycle, which contains at least one N atom as a ring member and in addition can contain a further hetero ring member from the series N, O, S or $S(O)_2$,
X represents a bond or ♦-$(CH_2)_q$—$N(R^6)$-♦♦, —C(=O)— or ♦-$N(R^6)$—C(=O)-♦♦, wherein
♦ designates the linkage point with the ring (N)

And
♦♦ designates the linkage point with the ring (A)

q denotes the number 0 or 1
and
$R^6$ denotes hydrogen, methyl, ethyl, isopropyl, cyclopropyl or cyclobutyl,
$R^1$ represents a substituent bonded to a carbon atom of the ring (N)

chosen from the series fluorine, cyano, $(C_1-C_4)$-alkyl, hydroxyl, $(C_1-C_4)$-alkoxy, oxo, amino, mono-$(C_1-C_4)$-alkylamino, di-$(C_1-C_4)$-alkylamino, cyclopropyl and cyclobutyl, wherein $(C_1-C_4)$-alkyl in its turn can be substituted by a radical chosen from the series hydroxyl, $(C_1-C_4)$-alkoxy, amino, mono-$(C_1-C_4)$-alkylamino and di-$(C_1-C_4)$-alkylamino and up to three times by fluorine,
m represents the number 0 or 1,
$R^2$ represents a substituent bonded to a nitrogen atom of the ring (N)

chosen from the series $(C_1-C_4$-alkyl, $(C_1-C_4)$-alkylcarbonyl, $(C_1-C_4)$-alkoxycarbonyl, $(C_1-C_4)$-alkylsulfonyl, cyclopropyl and cyclobutyl,
wherein the alkyl group in $(C_1-C_4$-alkyl, $(C_1-C_4)$-alkylcarbonyl, $(C_1-C_4)$-alkoxycarbonyl and $(C_1-C_4)$-alkylsulfonyl in its turn can be substituted by a radical chosen from the series hydroxyl, $(C_1-C_4)$-alkoxy, amino, mono-$(C_1-C_4)$-alkylamino, di-$(C_1-C_4)$-alkylamino, (C3-05)-cycloalkyl and 4- or 5-membered heterocyclyl and up to three times by fluorine
n represents the number 0 or 1,
$R^3$ represents methyl,
$R^4$ represents a substituent chosen from the series chlorine, pentafluorothio, $(C_1-C_6)$-alkyl, trimethylsilyl, —$OR^7$, —$SR^7$, —$S(=O)$—$R^7$, —$S(=O)_2$—$R^7$, —$S(=O)$(=NCH_3)$—$CF_3$, $(C_3-C_6)$-cycloalkyl and 4- to 6-membered heterocyclyl,
wherein $(C_1-C_6)$-alkyl in its turn can be substituted by a radical chosen from the series —$OR^7$, —$NR^7R^8$, —C(=O)—$NR^7R^8$, $(C_3-C_6)$-cycloalkyl and 4- to 6-membered heterocyclyl and up to three time by fluorine
and
the cycloalkyl and heterocyclyl groups mentioned in their turn can be substituted up to two times in an identical or different manner by a radical chosen from the series fluorine, $(C_1-C_4)$-alkyl, trifluoromethyl, $(C_1-C_4)$-alkoxy, trifluoromethoxy and oxo,
wherein the $(C_1-C_4)$-alkyl substituent in its turn can be substituted by methoxy, trifluoromethoxy or ethoxy,
and wherein
$R^7$ and $R^8$ independently of each other for each individual occurrence denote hydrogen, $(C_1-C_4)$-alkyl or $(C_3-C_6)$-cycloalkyl, wherein $(C_1-C_4)$-alkyl can be substituted by a radical chosen from the series hydroxyl, $(C_1-C_4)$-alkoxy, trifluoromethoxy and $(C_3-C_6)$-cycloalkyl and up to three times by fluorine
and
the cycloalkyl groups mentioned can be substituted up to two times in an identical or different manner by a radical chosen from the series fluorine, $(C_1-C_4)$-alkyl, trifluoromethyl, hydroxyl, $(C_1-C_4)$-alkoxy and trifluoromethoxy,
or
$R^7$ and $R^8$ in the case where both are bonded to a nitrogen atom form a 4- to 6-membered heterocycle together with this nitrogen atom, which can contain a further ring hetero atom from the series N, O, S or $S(O)_2$ and which can be substituted up to two times in an identical or different manner by a radical chosen from the series fluorine, $(C_1-C_4)$-alkyl, trifluoromethyl, hydroxyl, $(C_1-C_4)$-alkoxy, oxo and $(C_1-C_4)$-alkylcarbonyl,
$R^5$ represents fluorine,
and
p represents the number 0 or 1,
or a salt thereof.

Paragraph 10d: The compound of the formula according to paragraph 1d, in which
the ring

represents a phenyl ring and the adjacent groups X and $CH_2$ are bonded to this phenyl ring in 1,3 or 1,4 relation to one another,
the ring

with the substituent $R^3$ represents a heteroaryl ring of the formula

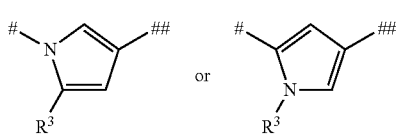

wherein
designates the linkage point with the adjacent $CH_2$ group
and
designates the linkage point with the ring

the ring

represents a heteroaryl ring of the formula

wherein
* designates the linkage point with the ring

and
** designates the linkage point with the ring

the ring

with the substituents $R^4$ and $R^5$ represents a phenyl ring of the formula

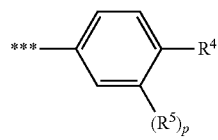

wherein
*** designates the linkage point with the ring

the ring

represents a saturated 4- to 10-membered aza-heterocycle, which contains at least one N atom as a ring member and in addition can contain a further hetero ring member from the series N, O, S or $S(O)_2$,
X represents a bond or ♦-$(CH_2)_q$—N($R^6$)-♦♦, —C(=O)— or ♦-N($R^6$)—C(=O)-♦♦, wherein
♦ designates the linkage point with the ring and ◆◆ designates the linkage point with the ring

, q denotes the number 0 or 1
and
R⁶ denotes hydrogen, methyl, ethyl, isopropyl, cyclopropyl or cyclobutyl,
R¹ represents a substituent bonded to a carbon atom of the ring

chosen from the series fluorine, cyano, $(C_1-C_4)$-alkyl, hydroxyl, $(C_1-C_4)$-alkoxy, oxo, amino, mono-$(C_1-C_4)$-alkylamino, di-$(C_1-C_4)$-alkylamino, cyclopropyl and cyclobutyl,
wherein $(C_1-C_4)$-alkyl in its turn can be substituted by a radical chosen from the series hydroxyl, $(C_1-C_4)$-alkoxy, amino, mono-$(C_1-C_4)$-alkylamino and di-$(C_1-C_4)$-alkylamino and up to three times by fluorine,
m represents the number 0 or 1,
R² represents a substituent bonded to a nitrogen atom of the ring

chosen from the series $(C_1-C_4)$-alkyl, $(C_1-C_4)$-alkylcarbonyl, $(C_1-C_4)$-alkoxycarbonyl, $(C_1-C_4)$-alkylsulfonyl, cyclopropyl and cyclobutyl,
wherein the alkyl group in $(C_1-C_4)$-alkyl, $(C_1-C_4)$-alkylcarbonyl, $(C_1-C_4)$-alkoxycarbonyl and $(C_1-C_4)$-alkylsulfonyl in its turn can be substituted by a radical chosen from the series hydroxyl, $(C_1-C_4)$-alkoxy, amino, mono-$(C_1-C_4)$-alkylamino, di-$(C_1-C_4)$-alkylamino $(C_3-C_5)$-cycloalkyl and 4- or 5-membered heterocyclyl and up to three times by fluorine,
n represents the number 0 or 1,
R³ represents methyl,
R⁴ represents a substituent chosen from the series chlorine, pentafluorothio, $(C_1-C_6)$-alkyl, trimethylsilyl, —OR⁷, —SR⁷, —S(=O)—R⁷, —S(=O)₂—R⁷, —S(=O)(=NCH₃)—CF₃, $(C_3-C_6)$-cycloalkyl and 4- to 6-membered heterocyclyl,
wherein $(C_1-C_6)$-alkyl in its turn can be substituted by a radical chosen from the series —OR⁷, —NR⁷R⁸, —C(=O)—NR⁷R⁸, $(C_3-C_6)$-cycloalkyl and 4- to 6-membered heterocyclyl and up to three time by fluorine
and
the cycloalkyl and heterocyclyl groups mentioned in their turn can be substituted up to two times in an identical or different manner by a radical chosen from the series fluorine, $(C_1-C_4)$-alkyl, trifluoromethyl, $(C_1-C_4)$-alkoxy, trifluoromethoxy and oxo,
wherein the $(C_1-C_4)$-alkyl substituent mentioned in its turn can be substituted by methoxy, trifluoromethoxy or ethoxy, and wherein
R⁷ and R⁸ independently of each other for each individual occurrence denote hydrogen, $(C_1-C_4)$-alkyl or $(C_3-C_6)$-cycloalkyl,
wherein $(C_1-C_4)$-alkyl can be substituted by a radical chosen from the series hydroxyl, $(C_1-C_4)$-alkoxy, trifluoromethoxy and $(C_3-C_6)$-cycloalkyl and up to three times by fluorine
and
the cycloalkyl groups mentioned can be substituted up to two times in an identical or different manner by a radical chosen from the series fluorine, $(C_1-C_4)$-alkyl, trifluoromethyl, hydroxyl, $(C_1-C_4)$-alkoxy and trifluoromethoxy,
or
R⁷ and R⁸ in the case where both are bonded to a nitrogen atom form a 4- to 6-membered heterocycle together with this nitrogen atom, which can contain a further ring hetero atom from the series N, O, S or S(O)₂ and which can be substituted up to two times in an identical or different manner by a radical chosen from the series fluorine, $(C_1-C_4)$-alkyl, trifluoromethyl, hydroxyl, $(C_1-C_4)$-alkoxy, oxo and $(C_1-C_4)$-alkylcarbonyl,
R⁵ represents fluorine,
and
p represents the number 0 or 1,
or a salt thereof.
Paragraph 11d: The compound of the formula according to paragraph 1d, in which
the ring

represents a phenyl ring and the adjacent groups X and CH₂ are bonded to this phenyl ring in 1, 3 or 1,4 relation to one another,
the ring

with the substituent R³ represents a heteroaryl ring of the formula

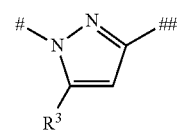

wherein
\# designates the linkage point with the adjacent CH₂ group
and
\#\# designates the linkage point with the ring

, the ring

, represents a heteroaryl ring of the formula

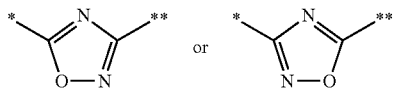

wherein
* designates the linkage point with the ring

and
** designates the linkage point with the ring

, the ring

with the substituents $R^4$ and $R^5$ represents a phenyl ring of the formula

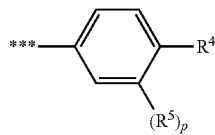

wherein
*** designates the linkage point with the ring

, the ring

represents a saturated 4- to 10-membered aza-heterocycle, which contains at least one N atom as a ring member and in addition can contain a further hetero ring member from the series N, O, S or $S(O)_2$,
X represents a bond or ♦-$(CH_2)_q$—N($R^6$)-♦♦, —C(=O)— or ♦-N($R^6$)—C(=O)-♦♦, wherein ♦ designates the linkage point with the ring

and
♦♦ designates the linkage point with the ring

, q denotes the number 0 or 1
and
$R^6$ denotes hydrogen, methyl, ethyl, isopropyl, cyclopropyl or cyclobutyl,
$R^1$ represents a substituent bonded to a carbon atom of the ring

chosen from the series cyano, ($C_1$-$C_4$)-alkyl, oxo, cyclopropyl and cyclobutyl, wherein ($C_1$-$C_4$)-alkyl in its turn can be substituted by a radical chosen from the series hydroxyl, ($C_1$-$C_4$)-alkoxy, amino, mono-($C_1$-$C_4$)-alkylamino and di-($C_1$-$C_4$)-alkylamino and up to three times by fluorine,
$R^2$ represents a substituent bonded to a nitrogen atom of the ring

chosen from the series ($C_1$-$C_4$)-alkyl, ($C_1$-$C_4$)-alkylcarbonyl, ($C_1$-$C_4$)-alkoxycarbonyl, ($C_1$-$C_4$)-alkylsulfonyl, cyclopropyl and cyclobutyl,
wherein the alkyl group in ($C_1$-$C_4$)-alkyl, ($C_1$-$C_4$)-alkylcarbonyl, ($C_1$-$C_4$)-alkoxycarbonyl and ($C_1$-$C_4$)-alkylsulfonyl in its turn can be substituted by a radical chosen from the series hydroxyl, ($C_1$-$C_4$)-alkoxy, amino, mono-($C_1$-$C_4$)-alkylamino, di-($C_1$-$C_4$)-alkylamino, (C3-05)-cycloalkyl and 4- or 5-membered heterocyclyl and up to three times by fluorine,
m represents the number 0 or 1,
n represents the number 0 or 1,
wherein the sum of m and n equals the number 1 or 2,
$R^3$ represents methyl,
$R^4$ represents a substituent chosen from the series chlorine, pentafluorothio, ($C_1$-$C_6$)-alkyl, trimethylsilyl, —$OR^7$, —$SR^7$, —S(=O)—$R^7$, —$S(=O)_2$—$R^7$, —S(=O)(=$NCH_3$)—$CF_3$, ($C_3$-$C_6$)-cycloalkyl and 4- to 6-membered heterocyclyl,
wherein ($C_1$-$C_6$)-alkyl in its turn can be substituted by a radical chosen from the series —$OR^7$, —$NR^7R^8$, —C(=O)—$NR^7R^8$, ($C_3$-$C_6$)-cycloalkyl and 4- to 6-membered heterocyclyl and up to three time by fluorine
and
the cycloalkyl and heterocyclyl groups mentioned in their turn can be substituted up to two times in an identical or different manner by a radical chosen from the series fluorine, ($C_1$-$C_4$)-alkyl, trifluoromethyl, ($C_1$-$C_4$)-alkoxy, trifluoromethoxy and oxo, wherein the $(C_1-C_4)$-alkyl substituent mentioned in its turn can be substituted by methoxy, trifluoromethoxy or ethoxy, and wherein $R^7$ and $R^8$ independently of each other for each individual occurrence denote hydrogen, $(C_1-C_4)$-alkyl or $(C_3-C_6)$-cycloalkyl, wherein $(C_1-C_4)$-alkyl can be substituted by a radical chosen from the series hydroxyl, $(C_1-C_4)$-alkoxy, trifluoromethoxy and $(C_3-C_6)$-cycloalkyl and up to three times by fluorine and the cycloalkyl groups mentioned can be substituted up to two times in an identical or different manner by a radical chosen from the series fluorine, $(C_1-C_4)$-alkyl, trifluoromethyl, hydroxyl, $(C_1-C_4)$-alkoxy and trifluoromethoxy, or $R^7$ and $R^8$ in the case where both are bonded to a nitrogen atom form a 4- to 6-membered heterocycle together with this nitrogen atom, which can contain a further ring hetero atom from the series N, O, S or $S(O)_2$ and which can be substituted up to two times in an identical or different manner by a radical chosen from the series fluorine, $(C_1-C_4)$-alkyl, trifluoromethyl, hydroxyl, $(C_1-C_4)$-alkoxy, oxo and $(C_1-C_4)$-alkylcarbonyl, $R^5$ represents fluorine, and p represents the number 0 or 1, or a salt thereof.

e. Heteroaromatic Compounds

In some embodiments, the HIF-2α inhibitor is a compound (as disclosed in U.S. Published Application No. 2011/0301122 which is specifically incorporated by reference herein in its entirety) defined according to the following paragraphs found in this subheading:

Paragraph 1e: A compound of formula

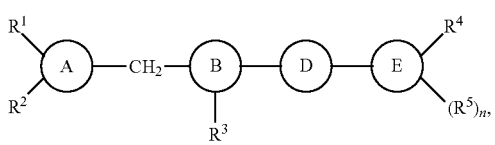

in which
either (a)
the ring

represents a pyridyl ring
and
the ring

with the substituent $R^3$ represents a heteroaryl ring of the formula

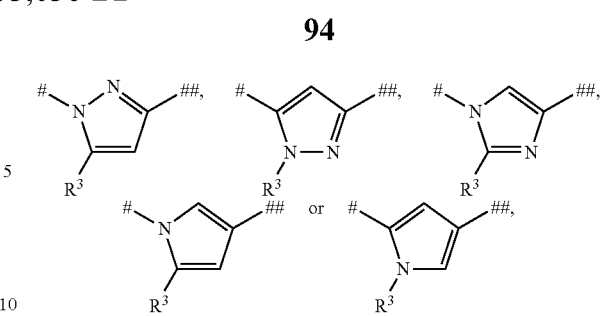

wherein

\# designates the linkage point with the adjacent $CH_2$ group and

\#\# designates the linkage point with the ring

or (b)
the ring

represents a phenyl ring
and
the ring

with the substituent $R^3$ represents a heteroaryl ring of the formula

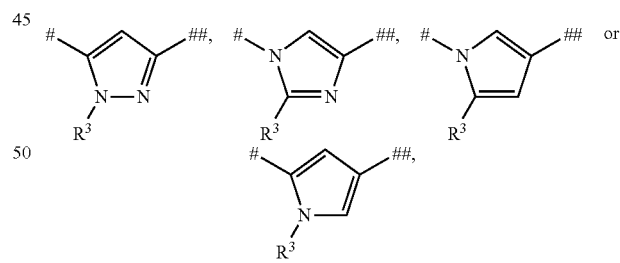

wherein

\# designates the linkage point with the adjacent $CH_2$ group and

\#\# designates the linkage point with the ring

the ring

, represents a heteroaryl ring of the formula

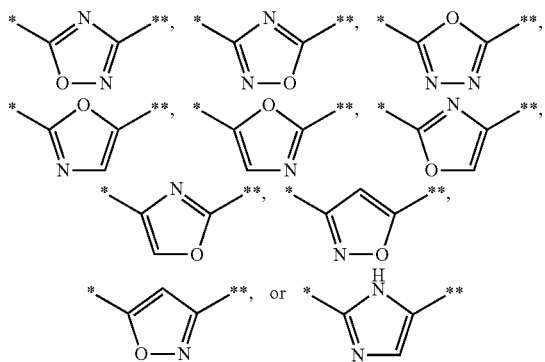

wherein
* designates the linkage point with the ring

and
** designates the linkage point with the ring

, the ring

represents a phenyl or pyridyl ring,
$R^1$ represents hydrogen or a substituent chosen from the series halogen, cyano, $(C_1-C_6)$-alkyl, $(C_2-C_6)$-alkenyl, $(C_2-C_6)$-alkynyl, $(C_3-C_6)$-cycloalkyl, oxetanyl, tetrahydrofuranyl, tetrahydropyranyl, —$OR^6$, —$SR^6$, —S(=O)—$R^6$, —S(=O)$_2$—$R^6$, —C(=O)—$OR^6$, —C(=O)—$NR^6R^7$, —S(=O)$_2$—$NR^6R^7$, —$NR^6R^8$, —N($R^6$)—C(=O)—$R^7$ and —N($R^6$)—S(=O)$_2$—$R^7$,
wherein $(C_1-C_6)$-alkyl, $(C_2-C_6)$-alkenyl and $(C_2-C_6)$-alkynyl in their turn can be substituted up to three times by fluorine and up to two times in an identical or different manner by a radical chosen from the series hydroxyl, $(C_1-C_4)$-alkoxy, trifluoromethoxy, tri-$(C_1-C_4)$-alkylsilyl, $(C_1-C_4)$-alkoxycarbonyl and $(C_3-C_6)$-cycloalkyl
and
oxetanyl, tetrahydrofuranyl, tetrahydropyranyl and the cycloalkyl groups mentioned in their turn can be substituted up to two times in an identical or different manner by a radical chosen from the series fluorine, $(C_1-C_4)$-alkyl, trifluoromethyl, hydroxyl, $(C_1-C_4)$-alkoxy, trifluoromethoxy and $(C_1-C_4)$-alkoxycarbonyl, and wherein
$R^6$ and $R^7$ independently of each other denote hydrogen, $(C_1-C_6)$-alkyl or $(C_3-C_6)$-cycloalkyl,
wherein $(C_1-C_6)$-alkyl can be substituted up to three times by fluorine and up to two times in an identical or different manner by a radical chosen from the series hydroxyl, $(C_1-C_4)$-alkoxy, trifluoromethoxy, $(C_1-C_4)$-alkoxycarbonyl and $(C_3-C_6)$-cycloalkyl
and
the cycloalkyl groups mentioned can be substituted up to two times in an identical or different manner by a radical chosen from the series fluorine, $(C_1-C_4)$-alkyl, trifluoromethyl, hydroxyl, $(C_1-C_4)$-alkoxy, trifluoromethoxy and $(C_1-C_4)$-alkoxycarbonyl,
and
$R^8$ denotes hydrogen, amino, $(C_1-C_6)$-alkyl, $(C_3-C_6)$-cycloalkyl or 5- or 6-membered heteroaryl,
wherein $(C_1-C_6)$-alkyl can be substituted up to three times by fluorine and up to two times in an identical or different manner by a radical chosen from the series hydroxyl, $(C_1-C_4)$-alkoxy, trifluoromethoxy, $(C_1-C_4)$-alkoxycarbonyl, $(C_3-C_6)$-cycloalkyl, oxetanyl, tetrahydrofuranyl, tetrahydropyranyl and 5- or 6-membered heteroaryl
and wherein
oxetanyl, tetrahydrofuranyl, tetrahydropyranyl and the cycloalkyl groups mentioned can be substituted up to two times in an identical or different manner by a radical chosen from the series fluorine, $(C_1-C_4)$-alkyl, trifluoromethyl, hydroxyl, $(C_1-C_4)$-alkoxy and $(C_1-C_4)$-alkoxycarbonyl,
and
the heteroaryl groups mentioned can be substituted up to two times in an identical or different manner by a radical chosen from the series fluorine, chlorine, cyano, $(C_1-C_4)$-alkyl, trifluoromethyl, $(C_1-C_4)$-alkoxy and trifluoromethoxy
$R^2$ represents hydrogen or a substituent chosen from the series fluorine, chlorine, cyano, methyl, trifluoromethyl, hydroxyl, methoxy and trifluoromethoxy,
$R^3$ represents methyl, ethyl or trifluoromethyl,
$R^4$ represents hydrogen or a substituent chosen from the series halogen, cyano, pentafluorothio, $(C_1-C_6)$-alkyl, tri-$(C_1-C_4)$-alkylsilyl, —$OR^9$, —$NR^9R^{10}$, —N($R^9$)—C(=O)—$R^{10}$, —N($R^9$)—C(=O)—$OR^{10}$, —N($R^9$)—S(=O)$_2$—$R^{10}$, —C(=O)—$OR^9$, —C(=O)—$NR^9R^{10}$, —$SR^9$, —S(=O)—$R^9$, —S(=O)$_2$—$R^9$, —S(=O)$_2$—$NR^9R^{10}$, —S(=O)(=NH)—$R^9$, —S(=O)(=NCH$_3$)—$R^9$, $(C_3-C_6)$-cycloalkyl, 4- to 6-membered heterocyclyl and 5- or 6-membered heteroaryl,
wherein $(C_1-C_6)$-alkyl in its turn can be substituted up to three times by fluorine and up to two times in an identical or different manner by a radical chosen from the series —$OR^9$, —$NR^9R^{10}$, —N($R^9$)—C(=O)—$R^{10}$, —N($R^9$)—C(=O)—$OR^{10}$, —C(=O)—$OR^9$, —C(=O)—$NR^9R^{10}$, $(C_3-C_6)$-cycloalkyl, 4- to 6-membered heterocyclyl and 5- or 6-membered heteroaryl
and wherein
the cycloalkyl and heterocyclyl groups mentioned in their turn can be substituted up to two times in an identical or different manner by a radical chosen from the series fluorine, $(C_1-C_4)$-alkyl, hydroxyl, $(C_1-C_4)$-alkoxy, oxo, amino, mono-$(C_1-C_4)$-alkylamino, di-$(C_1-C_4)$-alkylamino, $(C_1-C_4)$-alkylcarbonylamino, $(C_1-C_4)$-alkoxycarbonylamino, $(C_1-C_4)$-alkylcarbonyl, $(C_1-C_4)$-alkoxycarbonyl, aminocarbonyl, mono-$(C_1-C_4)$-alkylaminocarbonyl and di-$(C_1-C_4)$-alkylaminocarbonyl and
the heteroaryl groups mentioned in their turn can be substituted up to two times in an identical or different manner by a radical chosen from the series fluorine, chlorine, cyano, ($C_1$-$C_4$)-alkyl and ($C_1$-$C_4$)-alkoxy
wherein the ($C_1$-$C_4$)-alkyl substituents mentioned herein and the ($C_1$-$C_4$)-alkoxy substituents mentioned herein in their turn can be substituted by hydroxyl, ($C_1$-$C_4$)-alkoxy, trifluoromethoxy, ($C_1$-$C_4$)-alkylcarbonyloxy, ($C_1$-$C_4$)-alkoxycarbonyl, aminocarbonyl, mono-($C_1$-$C_4$)-alkylaminocarbonyl or di-($C_1$-$C_4$)-alkylaminocarbonyl or up to three times by fluorine,
and wherein
$R^9$ and $R^{10}$ independently of each other for each individual occurrence denote hydrogen, ($C_1$-$C_6$)-alkyl, ($C_3$-$C_6$)-cycloalkyl or 4- to 6-membered heterocyclyl, wherein ($C_1$-$C_6$)-alkyl can be substituted up to three times by fluorine and up to two times in an identical or different manner by a radical chosen from the series hydroxyl, ($C_1$-$C_4$)-alkoxy, trifluoromethoxy, amino, mono-($C_1$-$C_4$)-alkylamino, di-($C_1$-$C_4$)-alkylamino, ($C_1$-$C_4$)-alkoxycarbonyl, ($C_3$-$C_6$)-cycloalkyl and 4- to 6-membered heterocyclyl
and
the cycloalkyl and heterocyclyl groups mentioned can be substituted up to two times in an identical or different manner by a radical chosen from the series fluorine, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, ($C_1$-$C_4$)-alkylcarbonyl and ($C_1$-$C_4$)-alkoxycarbonyl,
or
$R^9$ and $R^{10}$ in the case where both are bonded to a nitrogen atom form a 4- to 6-membered heterocycle together with this nitrogen atom, which can contain a further ring hetero atom from the series N, O, S or $S(O)_2$ and which can be substituted up to two times in an identical or different manner by a radical chosen from the series fluorine, ($C_1$-$C_4$)-alkyl, trifluoromethyl, hydroxyl, ($C_1$-$C_4$)-alkoxy, oxo, amino, mono-($C_1$-$C_4$)-alkylamino, di-($C_1$-$C_4$)-alkylamino, ($C_1$-$C_4$)-alkylcarbonyl and ($C_1$-$C_4$)-alkoxycarbonyl,
$R^5$ represents a substituent chosen from the series fluorine, chlorine, cyano, methyl, trifluoromethyl and hydroxyl
and
n represents the number 0, 1 or 2,
wherein in the case where the substituent $R^5$ occurs twice, its meanings can be identical or different,
or a salt thereof.

Paragraph 2e: The compound according to paragraph 1e, in which
the ring

Ⓐ represents a phenyl or pyridyl ring and the adjacent groups $R^1$ and $CH_2$ are bonded to ring carbon atoms

Ⓐ in 1, 3 or 1,4 relation to one another and
the ring

Ⓔ with the substituents $R^4$ and $R^5$ represents a phenyl ring of the formula

***—⟨phenyl⟩—$R^4$
($R^5$)$_n$ wherein
designates the linkage point with the ring

Ⓓ, or a salt thereof.

Paragraph 3e: The compound according to paragraph 1e, in which
either (a)
the ring

Ⓐ represents a pyridyl ring and the adjacent groups $R^1$ and $CH_2$ are bonded to ring carbon atoms of this pyridyl ring in 1, 3 or 1,4 relation to one another
and
the ring

Ⓑ with the substituent $R^3$ represents a heteroaryl ring of the formula

—N(N)—##,  #—⟨pyrazole⟩—##,  #—N⟨imidazole⟩—##,
   |                  |                    |
   $R^3$              $R^3$                $R^3$

—N⟨pyrrole⟩—##   or   #—⟨pyrrole⟩N—##
   |                            |
   $R^3$                        $R^3$ wherein
designates the linkage point with the adjacent CH₂ group
and
designates the linkage point with the ring (D), or (b)
the ring (A)

represents a phenyl ring and the adjacent groups R¹ and CH₂ are bonded to this phenyl ring in 1,3 or 1,4 relation to one another,
and
the ring (B)

with the substituent R³ represents a heteroaryl ring of the formula

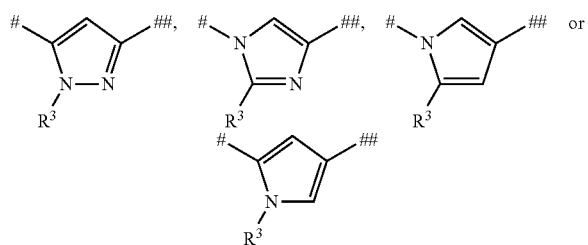

wherein
designates the linkage point with the adjacent CH₂ group
and
designates the linkage point with the ring (D), the ring (D), represents a heteroaryl ring of the formula

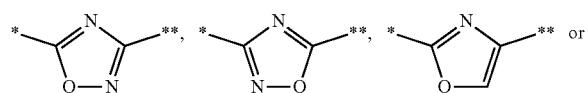

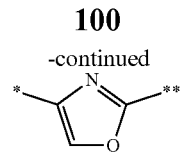

wherein
* designates the linkage point with the ring (B)

and
** designates the linkage point with the ring (E), the ring (E), with the substituents R⁴ and R⁵ represents a phenyl ring of the formula

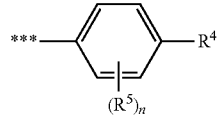

wherein
*** designates the linkage point with the ring (D),

R¹ represents hydrogen or a substituent chosen from the series fluorine, chlorine, bromine, cyano, $(C_1\text{-}C_4)$-alkyl, $(C_2\text{-}C_4)$-alkynyl, $(C_3\text{-}C_6)$-cycloalkyl, oxetanyl, tetrahydrofuranyl, tetrahydropyranyl, $-OR^6$, $-SR^6$, $-S(=O)-R^6$, $-S(=O)_2-R^6$, $-C(=O)-OR^6$, $-C(=O)-NR^6R^7$, $-S(=O)_2-NR^6R^7$ and $-NR^6R^8$,
wherein $(C_1\text{-}C_4)$-alkyl and $(C_2\text{-}C_4)$-alkynyl in their turn can be substituted by a radical chosen from the series hydroxyl, $(C_1\text{-}C_4)$-alkoxy, trifluoromethoxy, trimethylsilyl, $(C_1\text{-}C_4)$-alkoxycarbonyl and $(C_3\text{-}C_6)$-cycloalkyl and up to three times by fluorine
and
oxetanyl, tetrahydrofuranyl, tetrahydropyranyl and the cycloalkyl groups mentioned in their turn can be substituted up to two times in an identical or different manner by a radical chosen from the series fluorine, $(C_1\text{-}C_4)$-alkyl, trifluoromethyl, hydroxyl, $(C_1\text{-}C_4)$-alkoxy, trifluoromethoxy and $(C_1\text{-}C_4)$-alkoxycarbonyl,
and wherein
R⁶ and R⁷ independently of each other denote hydrogen, $(C_1\text{-}C_4)$-alkyl or $(C_3\text{-}C_6)$-cycloalkyl, wherein ($C_1$-$C_4$)-alkyl can be substituted by a radical chosen from the series hydroxyl, ($C_1$-$C_4$)-alkoxy, trifluoromethoxy and ($C_3$-$C_6$)-cycloalkyl and up to three times by fluorine
and
the cycloalkyl groups mentioned can be substituted up to two times in an identical or different manner by a radical chosen from the series fluorine, ($C_1$-$C_4$)-alkyl, trifluoromethyl, hydroxyl, ($C_1$-$C_4$)-alkoxy and trifluoromethoxy,
and
$R^8$ denotes hydrogen, amino, ($C_1$-$C_6$)-alkyl, ($C_3$-$C_6$)-cycloalkyl or 5- or 6-membered heteroaryl,
wherein ($C_1$-$C_6$)-alkyl can be substituted by a radical chosen from the series hydroxyl, ($C_1$-$C_4$)-alkoxy, trifluoromethoxy, ($C_1$-$C_4$)-alkoxycarbonyl, ($C_3$-$C_6$)-cycloalkyl, tetrahydrofuranyl, tetrahydropyranyl and 5- or 6-membered heteroaryl and up to three times by fluorine
and wherein
tetrahydrofuranyl, tetrahydropyranyl and the cycloalkyl groups mentioned can be substituted up to two times in an identical or different manner by a radical chosen from the series fluorine, ($C_1$-$C_4$)-alkyl, trifluoromethyl, hydroxyl, ($C_1$-$C_4$)-alkoxy and ($C_1$-$C_4$)-alkoxycarbonyl,
and
the heteroaryl groups mentioned can be substituted up to three times in an identical or different manner by a radical chosen from the series ($C_1$-$C_4$)-alkyl, trifluoromethyl, ($C_1$-$C_4$)-alkoxy and trifluoromethoxy
$R^2$ represents hydrogen or a substituent chosen from the series fluorine, chlorine, methyl, trifluoromethyl, methoxy and trifluoromethoxy,
$R^3$ represents methyl, ethyl or trifluoromethyl,
$R^4$ represents a substituent chosen from the series chlorine, cyano, pentafluorothio, ($C_1$-$C_6$)-alkyl, tri-($C_1$-$C_4$-)alkylsilyl, —$OR^9$, —$NR^9R^{10}$, —$SR^9$, —$S(=O)$—$R^9$, —$S(=O)_2$—$R^9$, —$S(=O)(=NH)$—$R^9$, —$S(=O)(=NCH_3)$—$R^9$, ($C_3$-$C_6$)-cycloalkyl and 4- to 6-membered heterocyclyl,
wherein ($C_1$-$C_6$)-alkyl in its turn can be substituted by a radical chosen from the series —$OR^9$, —$NR^9R^{10}$, —$N(R^9)$—$C(=O)$—$R^{10}$, —$C(=O)$—$NR^9R^{10}$, ($C_3$-$C_6$)-cycloalkyl, 4- to 6-membered heterocyclyl and 5- or 6-membered heteroaryl and up to three times by fluorine
and wherein
the cycloalkyl and heterocyclyl groups mentioned in their turn can be substituted up to two times in an identical or different manner by a radical chosen from the series fluorine, ($C_1$-$C_4$)-alkyl, hydroxyl, ($C_1$-$C_4$)-alkoxy, oxo, ($C_1$-$C_4$)-alkylcarbonyl, mono-($C_1$-$C_4$)-alkylaminocarbonyl and di-($C_1$-$C_4$)-alkylaminocarbonyl
and
the heteroaryl groups mentioned in their turn can be substituted up to two times in an identical or different manner by a radical chosen from the series fluorine, chlorine, cyano, ($C_1$-$C_4$)-alkyl and ($C_1$-$C_4$)-alkoxy
wherein the ($C_1$-$C_4$)-alkyl substituents mentioned herein and the ($C_1$-$C_4$)-alkoxy substituents mentioned herein in their turn can be substituted by hydroxyl, ($C_1$-$C_4$)-alkoxy, trifluoromethoxy, ($C_1$-$C_4$)-alkoxycarbonyl, mono-($C_1$-$C_4$)-alkylaminocarbonyl or di-($C_1$-$C_4$)-alkylaminocarbonyl or up to three times by fluorine,
and wherein
$R^9$ and $R^{10}$ independently of each other for each individual occurrence denote hydrogen, ($C_1$-$C_4$)-alkyl, ($C_3$-$C_6$)-cycloalkyl or 4- to 6-membered heterocyclyl, wherein ($C_1$-$C_4$)-alkyl can be substituted by a radical chosen from the series hydroxyl, ($C_1$-$C_4$)-alkoxy, trifluoromethoxy, ($C_3$-$C_6$)-cycloalkyl and 4- to 6-membered heterocyclyl and up to three times by fluorine
and
the cycloalkyl and heterocyclyl groups mentioned can be substituted up to two times in an identical or different manner by a radical chosen from the series fluorine, ($C_1$-$C_4$)-alkyl, trifluoromethyl, hydroxyl, ($C_1$-$C_4$)-alkoxy, trifluoromethoxy, oxo and ($C_1$-$C_4$)-alkylcarbonyl
or
$R^9$ and $R^{10}$ in the case where both are bonded to a nitrogen atom form a 4- to 6-membered heterocycle together with this nitrogen atom, which can contain a further ring hetero atom from the series N, O, S or $S(O)_2$ and which can be substituted up to two times in an identical or different manner by a radical chosen from the series fluorine, ($C_1$-$C_4$)-alkyl, trifluoromethyl, hydroxyl, ($C_1$-$C_4$)-alkoxy, oxo and ($C_1$-$C_4$)-alkylcarbonyl,
$R^5$ represents a substituent chosen from the series fluorine, chlorine and methyl
and
n represents the number 0 or 1,
or a salt thereof.
Paragraph 4e: The compound according to paragraph 1e, in which
the ring

with the substituents $R^1$ and $R^2$ represents a pyridyl ring of the formula

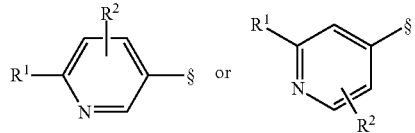

wherein
§ designates the linkage point with the adjacent $CH_2$ group,
the ring

with the substituent $R^3$ represents a heteroaryl ring of the formula

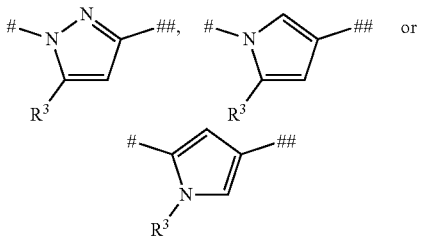

wherein
designates the linkage point with the adjacent CH₂ group
and
designates the linkage point with the ring

, the ring

represents a heteroaryl ring of the formula

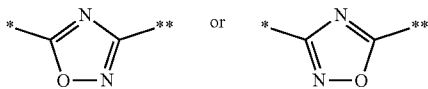

wherein
* designates the linkage point with the ring

and
** designates the linkage point with the ring

, the ring

, with the substituents R⁴ and R⁵ represents a phenyl ring of the formula

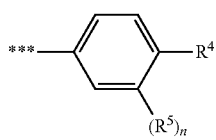

wherein
*** designates the linkage point with the ring

,

R¹ represents hydrogen or a substituent chosen from the series chlorine, cyano, $(C_1$-$C_4)$-alkyl, $(C_2$-$C_4)$-alkynyl, cyclopropyl, cyclobutyl, oxetanyl, tetrahydropyranyl, —OR⁶, —SR⁶, —S(=O)—R⁶, —S(=O)₂—R⁶, —C(=O)—OR⁶, —C(=O)—NR⁶R⁷, —S(=O)₂—NR⁶R⁷ and —NR⁶R⁸, wherein $(C_1$-$C_4)$-alkyl and $(C_2$-$C_4)$-alkynyl in their turn can be substituted by a radical chosen from the series hydroxyl, methoxy, ethoxy, trifluoromethoxy, cyclopropyl and cyclobutyl and up to three times by fluorine
and
oxetanyl and tetrahydropyranyl in their turn can be substituted by methyl, ethyl, hydroxyl, methoxy or ethoxy
and
the cyclopropyl and cyclobutyl groups mentioned in their turn can be substituted up to two times in an identical or different manner by a radical chosen from the series fluorine, methyl, ethyl and trifluoromethyl,
and wherein
R⁶ and R⁷ independently of each other denote hydrogen, $(C_1$-$C_4)$-alkyl or $(C_3$-$C_6)$-cycloalkyl,
wherein $(C_1$-$C_4)$-alkyl can be substituted by a radical chosen from the series hydroxyl, methoxy, ethoxy, trifluoromethoxy, cyclopropyl and cyclobutyl and up to three times by fluorine
and
R⁸ denotes hydrogen, $(C_1$-$C_4)$-alkyl, $(C_3$-$C_6)$-cycloalkyl or 5- or 6-membered heteroaryl,
wherein $(C_1$-$C_4)$-alkyl can be substituted by a radical chosen from the series hydroxyl, methoxy, ethoxy, trifluoromethoxy, $(C_3$-$C_6)$-cycloalkyl, tetrahydrofuranyl, tetrahydropyranyl and 5- or 6-membered heteroaryl and up to three times by fluorine
and wherein
tetrahydrofuranyl, tetrahydropyranyl and the cycloalkyl groups mentioned can be substituted up to two times in an identical or different manner by a radical chosen from the series fluorine, methyl, ethyl, trifluoromethyl, hydroxyl, methoxy and ethoxy
and
the heteroaryl groups mentioned can be substituted up to three times in an identical or different manner by a radical chosen from the series methyl, ethyl and trifluoromethyl
R² represents hydrogen or a substituent chosen from the series fluorine, chlorine, methyl and methoxy,
R³ represents methyl,
R⁴ represents a substituent chosen from the series chlorine, pentafluorothio, $(C_1$-$C_6)$-alkyl, trimethylsilyl, —OR⁹, —SR⁹, —S(=O)—R⁹, —S(=O)₂—R⁹, —S(=O)(=NH)—R⁹, —S(=O)(=NCH₃)—R⁹, $(C_3$-$C_6)$-cycloalkyl and 4- to 6-membered heterocyclyl,
wherein $(C_1$-$C_6)$-alkyl in its turn can be substituted by a radical chosen from the series —OR⁹, —NR⁹R¹⁰, —C(=O)—NR⁹R¹⁰, $(C_3$-$C_6)$-cycloalkyl and 4- to 6-membered heterocyclyl and up to three times by fluorine
and
the cycloalkyl and heterocyclyl groups mentioned in their turn can be substituted up to two times in an identical or different manner by a radical chosen from the series fluorine, $(C_1$-$C_4)$-alkyl, $(C_1$-$C_4)$-alkoxy and oxo,
wherein the $(C_1$-$C_4)$-alkyl substituent mentioned and the $(C_1$-$C_4)$-alkoxy substituent in their turn can be substituted by hydroxyl, methoxy, trifluoromethoxy, ethoxy, methoxycarbonyl, ethoxycarbonyl, tert-butoxycarbonyl, methylaminocarbonyl or dimethylaminocarbonyl or up to three times by fluorine, and wherein $R^9$ and $R^{10}$ independently of each other for each individual occurrence denote hydrogen, $(C_1-C_4)$-alkyl or $(C_3-C_6)$-cycloalkyl, wherein $(C_1-C_4)$-alkyl can be substituted by a radical chosen from the series hydroxyl, $(C_1-C_4)$-alkoxy, trifluoromethoxy and $(C_3-C_6)$-cycloalkyl and up to three times by fluorine and the cycloalkyl groups mentioned can be substituted up to two times in an identical or different manner by a radical chosen from the series fluorine, $(C_1-C_4)$-alkyl, trifluoromethyl, $(C_1-C_4)$-alkoxy and trifluoromethoxy, or $R^9$ and $R^{10}$ in the case where both are bonded to a nitrogen atom form a 4- to 6-membered heterocycle together with this nitrogen atom, which can contain a further ring hetero atom from the series N, O, S or $S(O)_2$ and which can be substituted up to two times in an identical or different manner by a radical chosen from the series fluorine, $(C_1-C_4)$-alkyl, hydroxyl, $(C_1-C_4)$-alkoxy, oxo, acetyl and propionyl, $R^5$ represents fluorine, and n represents the number 0 or 1, or a salt thereof.

Paragraph 5e: The compound according to paragraph 1e, in which the ring

with the substituents $R^1$ and $R^2$ represents a phenyl ring of the formula

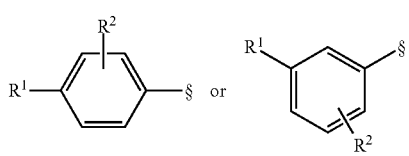

wherein

§ designates the linkage point with the adjacent CH$_2$ group, the ring

with the substituent $R^3$ represents a heteroaryl ring of the formula

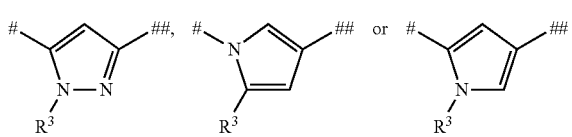

wherein designates the linkage point with the adjacent CH$_2$ group and designates the linkage point with the ring

, the ring

, represents a heteroaryl ring of the formula

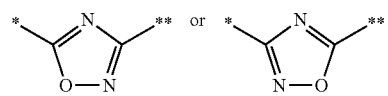

wherein

* designates the linkage point with the ring

and

** designates the linkage point with the ring

, the ring

, with the substituents $R^4$ and $R^5$ represents a phenyl ring of the formula

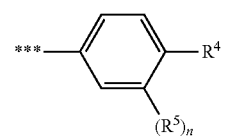

wherein

*** designates the linkage point with the ring

, $R^1$ represents hydrogen or a substituent chosen from the series chlorine, cyano, $(C_1-C_4)$-alkyl, $(C_2-C_4)$-alkynyl, cyclopropyl, cyclobutyl, oxetanyl, tetrahydropyranyl, —OR$^6$, —SR$^6$, —S(=O)—R$^6$, —S(=O)$_2$—R$^6$, —C(=O)—OR$^6$, —C(=O)—NR$^6$R$^7$, —S(=O)$_2$—NR$^6$R$^7$ and —NR$^6$R$^8$, wherein (C$_1$-C$_4$)-alkyl and (C$_2$-C$_4$)-alkynyl in their turn can be substituted by a radical chosen from the series hydroxyl, methoxy, ethoxy, trifluoromethoxy, cyclopropyl and cyclobutyl and up to three times by fluorine and oxetanyl and tetrahydropyranyl in their turn can be substituted by methyl, ethyl, hydroxyl, methoxy or ethoxy and the cyclopropyl and cyclobutyl groups mentioned in their turn can be substituted up to two times in an identical or different manner by a radical chosen from the series fluorine, methyl, ethyl and trifluoromethyl, and wherein R$^6$ and R$^7$ independently of each other denote hydrogen, (C$_1$-C$_4$)-alkyl or (C$_3$-C$_6$)-cycloalkyl, wherein (C$_1$-C$_4$)-alkyl can be substituted by a radical chosen from the series hydroxyl, methoxy, ethoxy, trifluoromethoxy, cyclopropyl and cyclobutyl and up to three times by fluorine and R$^8$ denotes hydrogen, (C$_1$-C$_4$)-alkyl, (C$_3$-C$_6$)-cycloalkyl or 5- or 6-membered heteroaryl, wherein (C$_1$-C$_4$)-alkyl can be substituted by a radical chosen from the series hydroxyl, methoxy, ethoxy, trifluoromethoxy, (C$_3$-C$_6$)-cycloalkyl, tetrahydrofuranyl, tetrahydropyranyl and 5- or 6-membered heteroaryl and up to three times by fluorine and wherein tetrahydrofuranyl, tetrahydropyranyl and the cycloalkyl groups mentioned can be substituted up to two times in an identical or different manner by a radical chosen from the series fluorine, methyl, ethyl, trifluoromethyl, hydroxyl, methoxy and ethoxy and the heteroaryl groups mentioned can be substituted up to three times in an identical or different manner by a radical chosen from the series methyl, ethyl and trifluoromethyl R$^2$ represents hydrogen or a substituent chosen from the series fluorine, chlorine, methyl and methoxy, R$^3$ represents methyl, R$^4$ represents a substituent chosen from the series chlorine, pentafluorothio, (C$_1$-C$_6$)-alkyl, trimethylsilyl, —OR$^9$, —SR$^9$, —S(=O)—R$^9$, —S(=O)$_2$—R$^9$, —S(=O)(=NH)—R$^9$, —S(=O)(=NCH$_3$)—R$^9$, (C$_3$-C$_6$)-cycloalkyl and 4- to 6-membered heterocyclyl, wherein (C$_1$-C$_6$)-alkyl in its turn can be substituted by a radical chosen from the series —OR$^9$, —NR$^9$R$^{10}$, —C(=O)—NR$^9$R$^{10}$, (C$_3$-C$_6$)-cycloalkyl and 4- to 6-membered heterocyclyl and up to three times by fluorine and the cycloalkyl and heterocyclyl groups mentioned in their turn can be substituted up to two times in an identical or different manner by a radical chosen from the series fluorine, (C$_1$-C$_4$)-alkyl, (C$_1$-C$_4$)-alkoxy and oxo, wherein the (C$_1$-C$_4$)-alkyl substituent mentioned and the (C$_1$-C$_4$)-alkoxy substituent in their turn can be substituted by hydroxyl, methoxy, trifluoromethoxy, ethoxy, methoxycarbonyl, ethoxycarbonyl, tert-butoxycarbonyl, methylaminocarbonyl or dimethylaminocarbonyl or up to three times by fluorine, and wherein R$^9$ and R$^{10}$ independently of each other for each individual occurrence denote hydrogen, (C$_1$-C$_4$)-alkyl or (C$_3$-C$_6$)-cycloalkyl, wherein (C$_1$-C$_4$)-alkyl can be substituted by a radical chosen from the series hydroxyl, (C$_1$-C$_4$)-alkoxy, trifluoromethoxy and (C$_3$-C$_6$)-cycloalkyl and up to three times by fluorine and the cycloalkyl groups mentioned can be substituted up to two times in an identical or different manner by a radical chosen from the series fluorine, (C$_1$-C$_4$)-alkyl, trifluoromethyl, (C$_1$-C$_4$)-alkoxy and trifluoromethoxy, or R$^9$ and R$^{10}$ in the case where both are bonded to a nitrogen atom form a 4- to 6-membered heterocycle together with this nitrogen atom, which can contain a further ring hetero atom from the series N, O, S or S(O)$_2$ and which can be substituted up to two times in an identical or different manner by a radical chosen from the series fluorine, (C$_1$-C$_4$)-alkyl, hydroxyl, (C$_1$-C$_4$)-alkoxy, oxo, acetyl and propionyl, R$^5$ represents fluorine, and n represents the number 0 or 1, or a salt thereof.

Paragraph 6e: The compound according to paragraph 1e, in which the ring

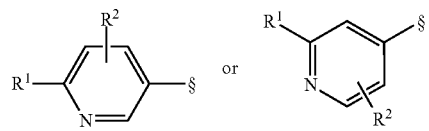

with the substituents R$^1$ and R$^2$ represents a pyridyl ring of the formula wherein § designates the linkage point with the adjacent CH$_2$ group, the ring

B with the substituent R$^3$ represents a heteroaryl ring of the formula

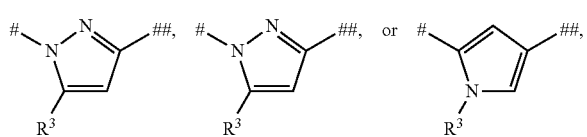

wherein
designates the linkage point with the adjacent CH$_2$ group
and
designates the linkage point with the ring

, the ring

represents a heteroaryl ring of the formula

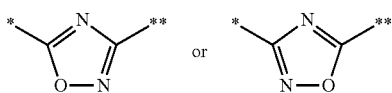

wherein
* designates the linkage point with the ring

and
** designates the linkage point with the ring

, the ring

, with the substituents R$^4$ and R$^5$ represents a phenyl ring of the formula

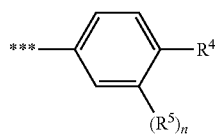

wherein
*** designates the linkage point with the ring

,

R$^1$ represents methyl or the group —NR$^6$R$^8$, wherein
R$^6$ denotes hydrogen, methyl, ethyl or cyclopropyl, and
R$^8$ denotes (C$_1$-C$_4$)-alkyl or (C$_3$-C$_6$)-cycloalkyl,
wherein (C$_1$-C$_4$)-alkyl can be substituted by a radical chosen from the series hydroxyl, methoxy, ethoxy, (C$_3$-C$_6$)-cycloalkyl, tetrahydrofuranyl, tetrahydropyranyl and 5- or 6-membered heteroaryl and up to three times by fluorine
and wherein
tetrahydrofuranyl, tetrahydropyranyl and the cycloalkyl groups mentioned can be substituted up to two times in an identical or different manner by a radical chosen from the series fluorine, methyl, ethyl, trifluoromethyl, hydroxyl, methoxy and ethoxy
and
the heteroaryl group mentioned can be substituted up to three times in an identical or different manner by a radical chosen from the series methyl, ethyl and trifluoromethyl
R$^2$ represents hydrogen,
R$^3$ represents methyl,
R$^4$ represents a substituent chosen from the series chlorine, pentafluorothio, (C$_1$-C$_6$)-alkyl, trimethylsilyl, —OR$^9$, —SR$^9$, —S(=O)—R$^9$, —S(=O)$_2$—R$^9$, —S(=O)(=NH)—CH$_3$, —S(=O)(=NH)—CF$_3$, —S(=O)(=NCH$_3$)—CH$_3$, —S(=O)(=NCH$_3$)—CF$_3$, (C$_3$-C$_6$)-cycloalkyl and 4- to 6-membered heterocyclyl,
wherein (C$_1$-C$_6$)-alkyl in its turn can be substituted by a radical chosen from the series —OR$^9$, —NR$^9$R$^{10}$, —C(=O)—NR$^9$R$^{10}$, (C$_3$-C$_6$)-cycloalkyl and 4- to 6-membered heterocyclyl and up to three times by fluorine
and
the cycloalkyl and heterocyclyl groups mentioned in their turn can be substituted up to two times in an identical or different manner by a radical chosen from the series fluorine, (C$_1$-C$_4$)-alkyl, trifluoromethyl, (C$_1$-C$_4$)-alkoxy, trifluoromethoxy and oxo,
wherein the (C$_1$-C$_4$)-alkyl substituent mentioned in its turn can be substituted by methoxy, trifluoromethoxy or ethoxy,
and wherein
R$^9$ and R$^{10}$ independently of each other for each individual occurrence denote hydrogen, (C$_1$-C$_4$)-alkyl or (C$_3$-C$_6$)-cycloalkyl,
wherein (C$_1$-C$_4$)-alkyl can be substituted by a radical chosen from the series hydroxyl, (C$_1$-C$_4$)-alkoxy, trifluoromethoxy and (C$_3$-C$_6$)-cycloalkyl and up to three times by fluorine
and
the cycloalkyl groups mentioned can be substituted up to two times in an identical or different manner by a radical chosen from the series fluorine, (C$_1$-C$_4$)-alkyl, trifluoromethyl, (C$_1$-C$_4$)-alkoxy and trifluoromethoxy,
or
R$^9$ and R$^{10}$ in the case where both are bonded to a nitrogen atom form a 4- to 6-membered heterocycle together with this nitrogen atom, which can contain a further ring heteroatom from the series N, O, S or S(O)$_2$ and which can be substituted up to two times in an identical or different manner by a radical chosen from the series fluorine, (C$_1$-C$_4$)-alkyl, hydroxyl, (C$_1$-C$_4$)-alkoxy, oxo, acetyl and propionyl,
R$^5$ represents fluorine,
and
n represents the number 0 or 1,
or a salt thereof.

Paragraph 7e: The compound according to paragraph 1e, in which the ring

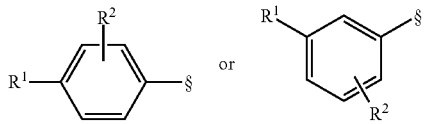

with the substituents $R^1$ and $R^2$ represents a phenyl ring of the formula

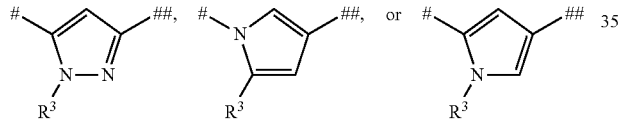

wherein
§ designates the linkage point with the adjacent CH$_2$ group,
the ring (B)

with the substituent $R^3$ represents a heteroaryl ring of the formula

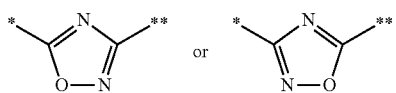

wherein
\# designates the linkage point with the adjacent CH$_2$ group
and
\#\# designates the linkage point with the ring (D), the ring (D)

represents a heteroaryl ring of the formula

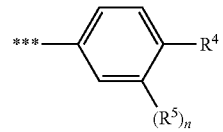

wherein
\* designates the linkage point with the ring (B)

and
\*\* designates the linkage point with the ring (E), the ring (E), with the substituents $R^4$ and $R^5$ represents a phenyl ring of the formula wherein
\*\*\* designates the linkage point with the ring (D), $R^1$ represents chlorine, cyano, methyl, ethyl, isopropyl, cyclopropyl, cyclobutyl, methoxy, ethoxy, methylsulphonyl, ethylsulphonyl, isopropylsulphonyl or the group —C(=O)—NR$^6$R$^7$, wherein
$R^6$ and $R^7$ independently of each other denote hydrogen, (C$_1$-C$_4$)-alkyl or (C$_3$-C$_6$)-cycloalkyl,
wherein (C$_1$-C$_4$)-alkyl can be substituted by a radical chosen from the series hydroxyl, methoxy, ethoxy, cyclopropyl and cyclobutyl and up to three times by fluorine
$R^2$ represents hydrogen,
$R^3$ represents methyl,
$R^4$ represents a substituent chosen from the series chlorine, pentafluorothio, (C$_1$-C$_6$)-alkyl, trimethylsilyl, —OR$^9$, —SR$^9$, —S(=O)—R$^9$, —S(=O)$_2$—R$^9$, —S(=O)(=NH)—CH$_3$, —S(=O)(=NH)—CF$_3$, —S(=O)(=NCH$_3$)—CH$_3$, —S(=O)(=NCH$_3$)—CF$_3$, (C$_3$-C$_6$)-cycloalkyl and 4- to 6-membered heterocyclyl,
wherein (C$_1$-C$_6$)-alkyl in its turn can be substituted by a radical chosen from the series —OR$^9$, —NR$^9$R$^{10}$, —C(=O)—NR$^9$R$^{10}$, (C$_3$-C$_6$)-cycloalkyl and 4- to 6-membered heterocyclyl and up to three times by fluorine
and
the cycloalkyl and heterocyclyl groups mentioned in their turn can be substituted up to two times in an identical or different manner by a radical chosen from the series fluorine, (C$_1$-C$_4$)-alkyl, trifluoromethyl, (C$_1$-C$_4$)-alkoxy, trifluoromethoxy and oxo, wherein the $(C_1-C_4)$-alkyl substituent mentioned in its turn can be substituted by methoxy, trifluoromethoxy or ethoxy,
and wherein
$R^9$ and $R^{10}$ independently of each other for each individual occurrence denote hydrogen, $(C_1-C_4)$-alkyl or $(C_3-C_6)$-cycloalkyl,
wherein $(C_1-C_4)$-alkyl can be substituted by a radical chosen from the series hydroxyl, $(C_1-C_4)$-alkoxy, trifluoromethoxy and $(C_3-C_6)$-cycloalkyl and up to three times by fluorine
and
the cycloalkyl groups mentioned can be substituted up to two times in an identical or different manner by a radical chosen from the series fluorine, $(C_1-C_4)$-alkyl, trifluoromethyl, $(C_1-C_4)$-alkoxy and trifluoromethoxy,
or
$R^9$ and $R^{10}$ in the case where both are bonded to a nitrogen atom form a 4- to 6-membered heterocycle together with this nitrogen atom, which can contain a further ring hetero atom from the series N, O, S or $S(O)_2$ and which can be substituted up to two times in an identical or different manner by a radical chosen from the series fluorine, $(C_1-C_4)$-alkyl, hydroxyl, $(C_1-C_4)$-alkoxy, oxo, acetyl and propionyl,
$R^5$ represents fluorine,
and
n represents the number 0 or 1,
or a salt thereof.

f. Triarylmethane Compounds

In some embodiments, the HIF-2α inhibitor is an triarylmethane compound, or prodrugs or metabolites thereof, or a pharmaceutically acceptable salt thereof (as disclosed in U.S. Published Application No. 2009/0176745 which is specifically incorporated by reference herein in its entirety) defined according to the following paragraphs found in this subheading.

For example, the HIF-2α inhibitor can be a triphenyl methane analog, which can be formed, for example, by reacting a diaryl ketone such as Mischler's ketone with an aromatic or heteroaromatic compound, such as a phenol or an aniline, in the presence of a Lewis acid such as phosphorus oxychloride or thionyl chloride. Typically, an electrophilic addition occurs at the ortho or para position to hydroxy or amine groups in the phenol or aniline compounds, or meta to nitro or carboxy groups, and is followed by dehydration to form the triphenyl methane compounds.

Representative compounds include triphenyl methane analogues of steroids and steroid precursors, such as cholesterol, progesterone, testosterone, or estrogen; dyes such as indigo, chrysin, and imipramine; benzophenones, nucleosides such as uracil, thymidine, adenine, cytosine, and guanine, aromatic amino acids such as phenylalanine; folic acid, and various tricyclic compounds, including various tricyclic dyes and tricyclic antidepressants, and include, but are not limited to, the compounds disclosed in U.S. Published Application No. 2009/0176745.

Triarylmethane compounds typically include a first carbon-carbon double bond linked at one end to two aryl or heteroaryl rings, and at the other end to a cyclohexadiene ring (forming a "first exocyclic double bond"), which optionally includes a second exocyclic double bond, typically in the form of an imine or ketone group. The two aryl or heteroaryl rings can be linked via a bridge, which can be, for example, an alkylene bridge, such as a methylene bridge, or a heteroatom, or a direct linkage between the rings.

The second exocyclic double bond in the cyclohexadiene can be at a position "ortho" or "para" to the first exocyclic double bond.

In one embodiment, the compounds generally fall within one of the formulas provided below:

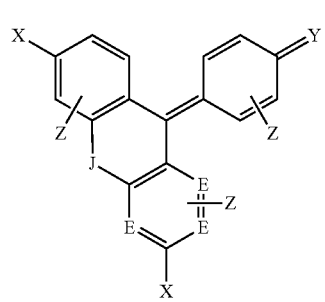

Formula 1

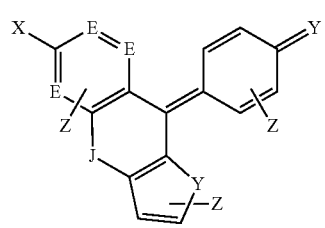

Formula 2

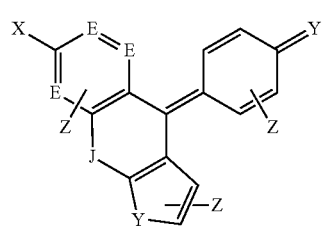

Formula 3

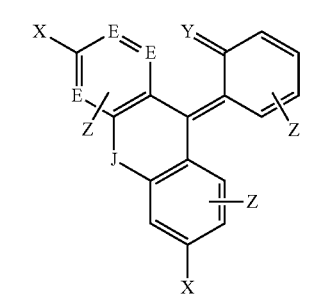

Formula 4 and counterparts to Formula 4 that include the heteroaryl rings in Formulas 2 and 3, wherein J represents a direct linkage between the two aryl rings, O, S, Se, NR, or $(CR_2)_n$
n=0-4, and, in one embodiment, is 1-4;
E is CH, C bonded to a substituent Z, as defined herein, or N,
R=H or substituted or unsubstituted alkyl, alkenyl, alkynyl, aryl, heteroaryl, alkylaryl, or arylalkyl,
X=H, amine, hydroxy, ether, thiol, or thiol ether, and is preferably selected from amine, hydroxy, ether, thiol, and thiol ether,
Y=O, S, or $NR_2$, where an amine can optionally link back to the ring in an ortho position via an alkyl, alkenyl, alkynyl, alkylaryl, or arylalkyl moiety,
Z=an optional substituent (e.g., halo, hydroxyl, thiol, ester, amide, carboxy, sulfoxy, nitrile, azido, alkyl, alkenyl, alkynyl, nitro, amino, aryl, heteroaryl, phosphonate, fulvene, and the like).

Z can also be a cyclic ring attached to the aryl ring, or a second aryl or heteroaryl ring attached to the benzene ring or cyclohexadiene ring.

wherein:

the aryl or heteroaryl rings can be substituted at any free position with H or a substituent, Z, as described herein.

Representative substituents, Z, include $C_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)OR", —SO$_2$R', —SO$_2$NR'R", and —NR'SO$_2$R", where R' and R" are individually hydrogen, C.sub.1-6 alkyl, cycloalkyl, heterocyclyl, aryl, or arylalkyl (such as benzyl);

Specific examples of compounds in which Z is a cyclic ring attached to the aryl ring, or a second aryl or heteroaryl ring attached to the benzene ring or cyclohexadiene ring, are shown below:

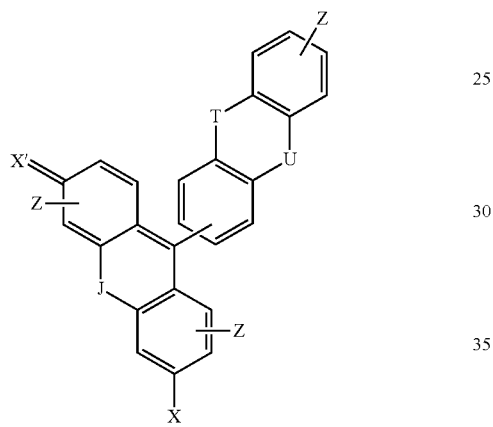

wherein

Z, X, and J are as defined above within this subsection,

X' is O, S, NR, or NR$_2^+$,

T is selected from the group consisting of —C(O)—, —C(O)—O—, —C(O)—S—, —C(O)—NR—, —O—C(O)—, —S—C(O)—, —NR—C(O)—, NR, O, S, (—CR$_2$)$_n$, (—CR$_2$)$_n$—NR—, (—CR$_2$)$_n$—O—, and (—CR$_2$)$_n$—S—; and U is selected from the group consisting of —C(O)—, NR, S, O, and (—CR$_2$)$_n$.

Representative tricyclic rings (i.e., including the U and T substituents described above within this subsection) include the following:

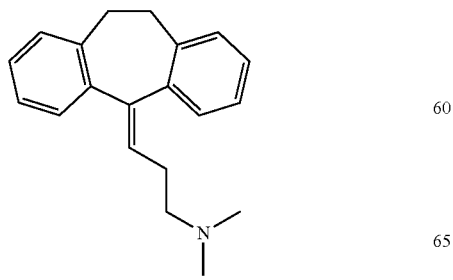

-continued

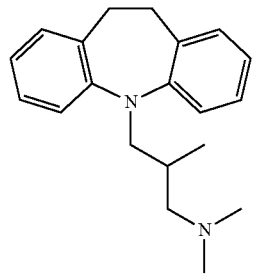

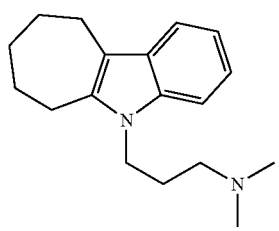

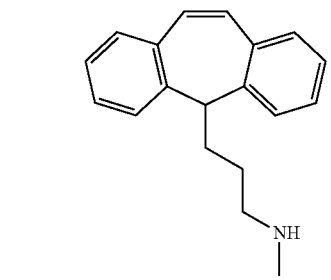

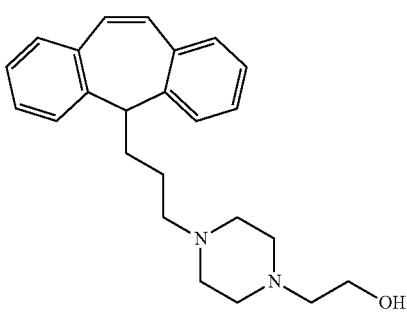

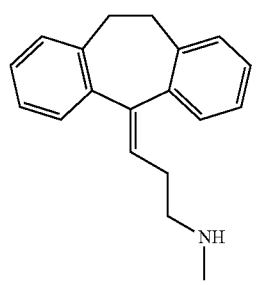

117
-continued
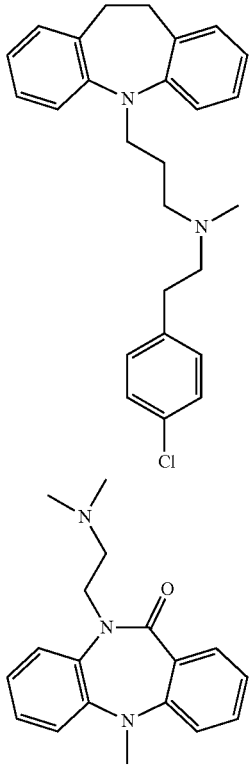
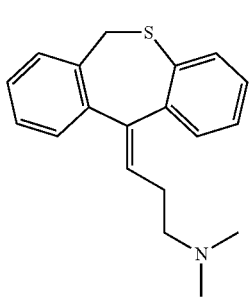
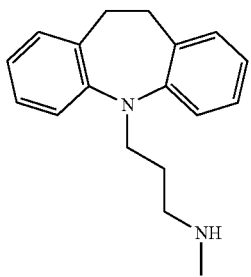
118
-continued
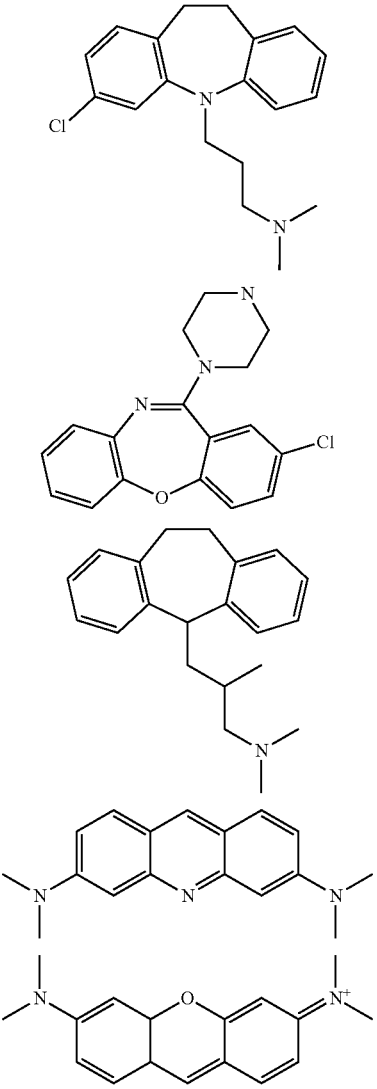
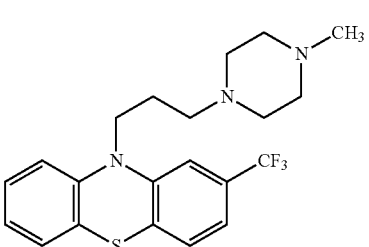
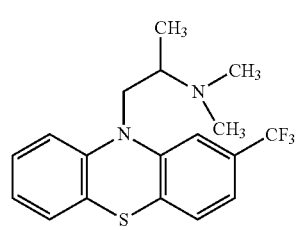

-continued

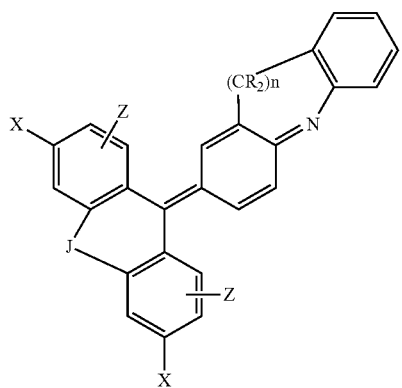

These compounds are, or are similar to, tricyclic antidepressants and triphenyl methane dyes. The aromatic rings in all of the above compounds within this subsection can optionally be functionalized with one or more substituents, Z, as defined above within this subsection.

The aryl rings described above within this subsection are typically attached to the other aryl rings primarily at a position dictated according to the conventional rules concerning electrophilic aromatic substitution reactions. That is, those rings with an electron donating substituent, such as alkyl, aryl, alkylaryl, arylalkyl, hydroxy, ether, and amine, will tend to be substituted at a position ortho or para to that substituent, and those rings with an electron withdrawing substituent, such as nitro or carboxy, will tend to be substituted at a position meta to that substituent. Positional isomers of these compounds can be separated, or, if desired, used in combination.

In one embodiment, the compounds are similar to those in Formula 1, except that there is not an exocyclic double bond to an oxygen or nitrogen atom in the cyclohexadiene moiety. Representative compounds for this embodiment are shown below, with the definitions for the various variables being the same as those described above within this subsection for Formula 1.

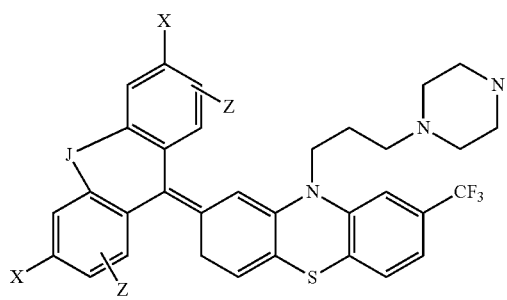
(Trifluoroperazine triaryl methanes)

-continued

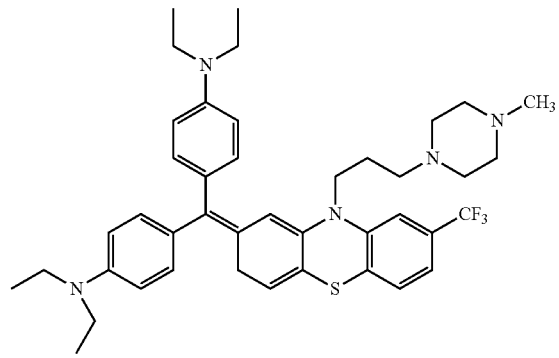

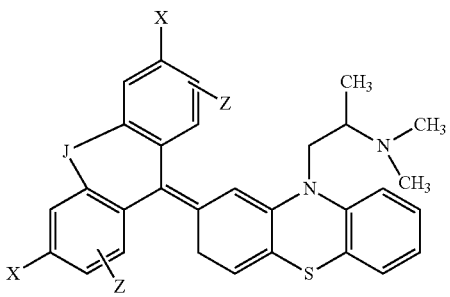
(Promethazine triaryl methanes)

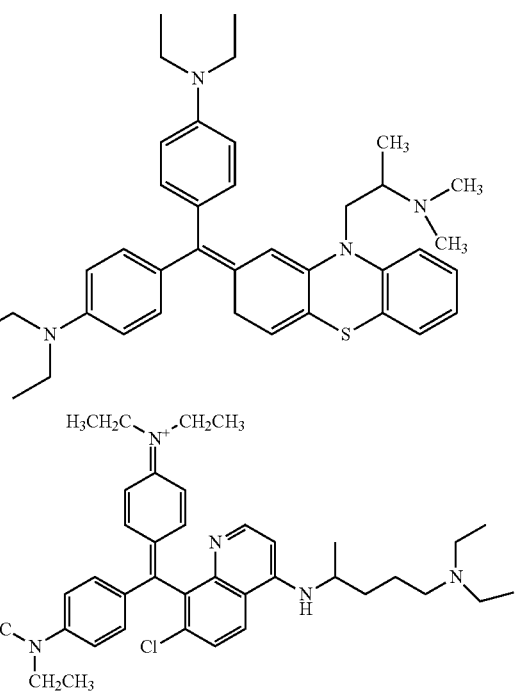

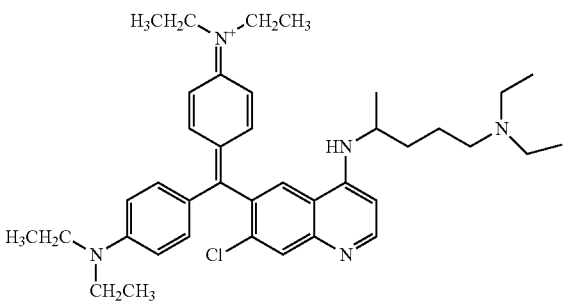
Chloroquine triaryl methanes

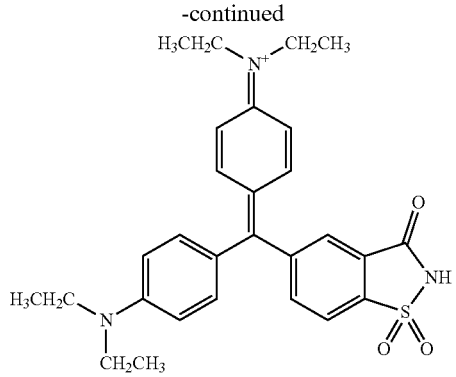

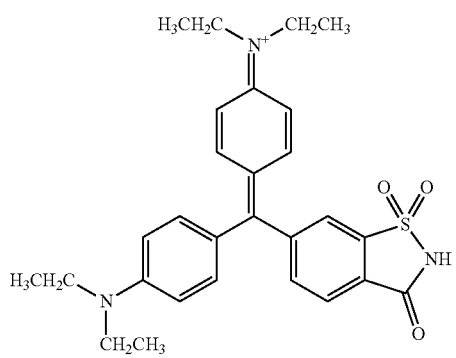

Saccharine triaryl methanes

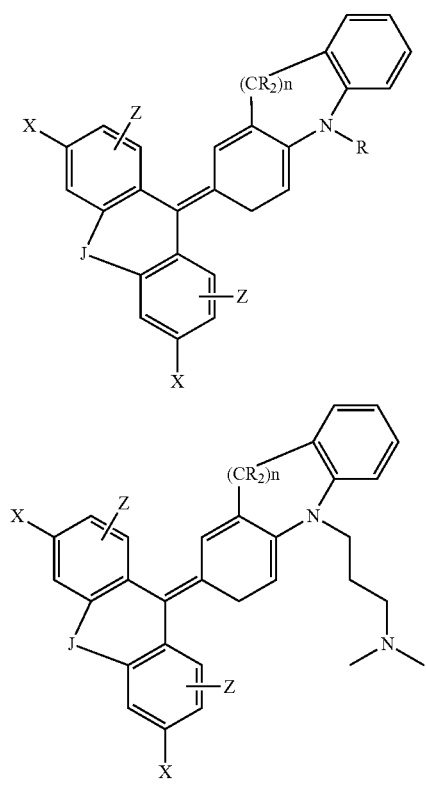

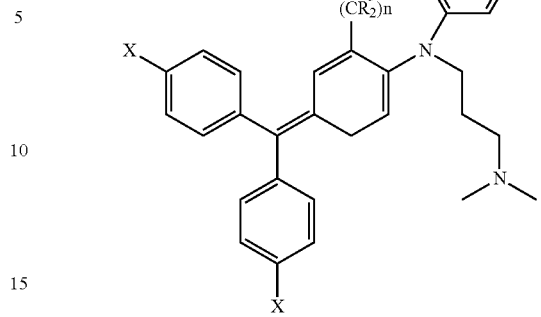

Where X, Z and R are as defined above within this subsection.

The compounds can occur in varying degrees of enantiomeric excess, and racemic mixtures can be purified using known chiral separation techniques.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

The following aryl/heteroaryl rings can be present in the compounds described herein, as one of the aryl rings in Formula 1.

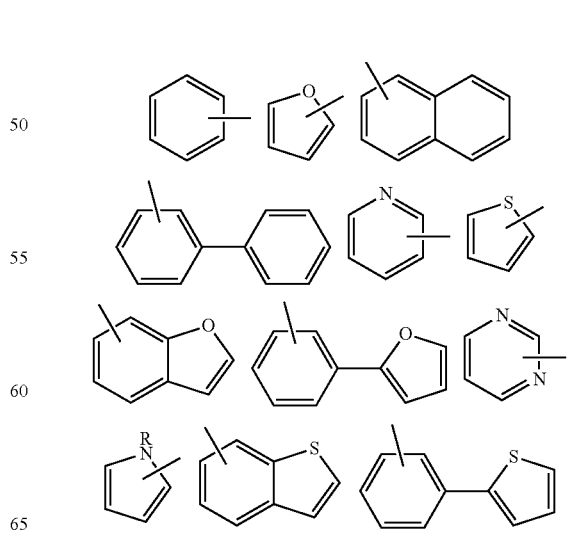

123
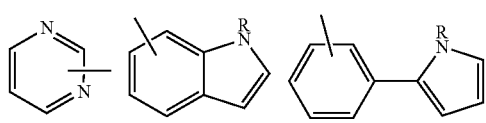
124
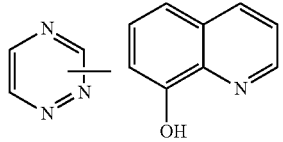
Representative compounds include the following:
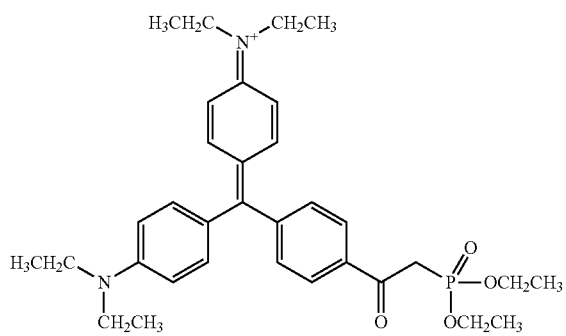
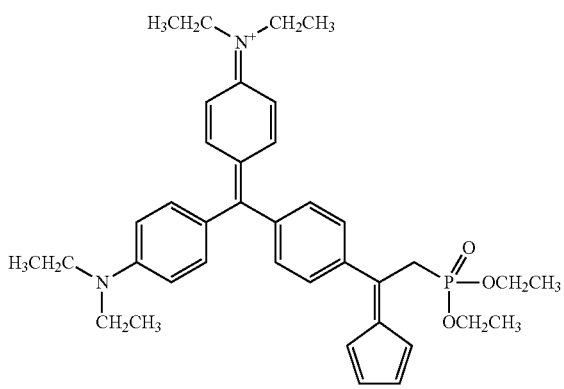
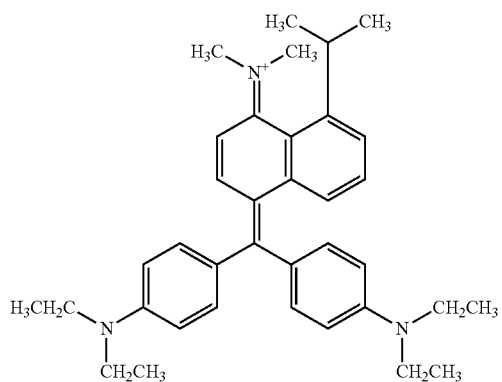
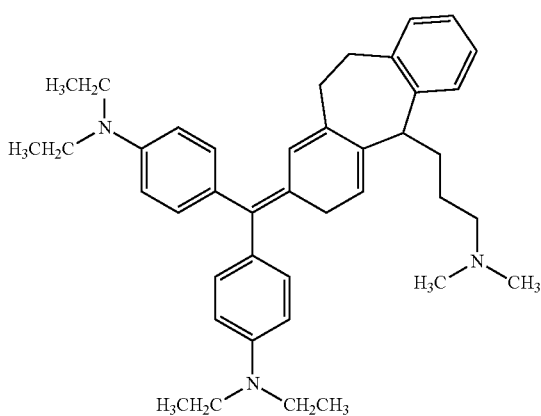
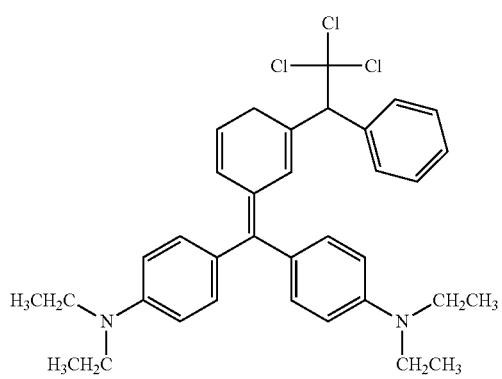
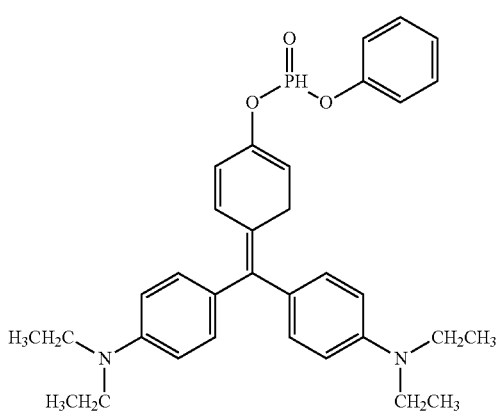

-continued
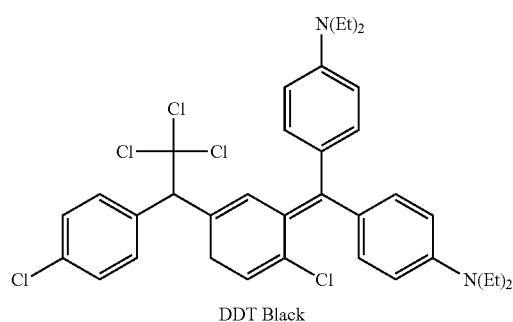
DDT Black
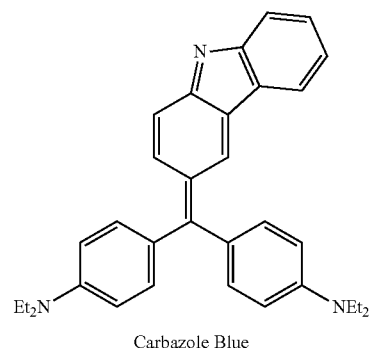
Carbazole Blue
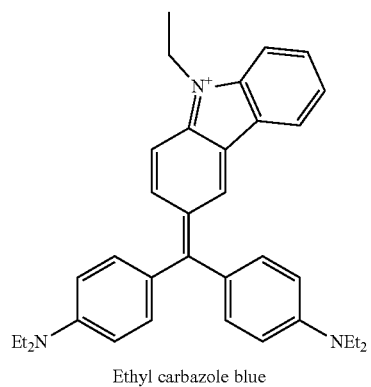
Ethyl carbazole blue
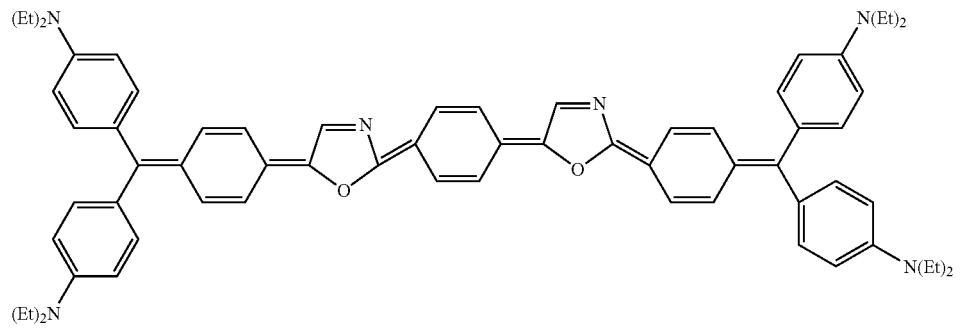
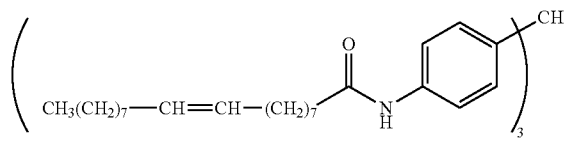
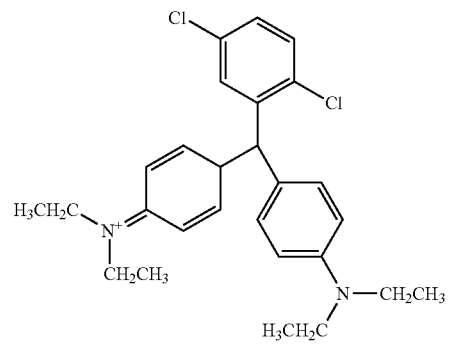

127
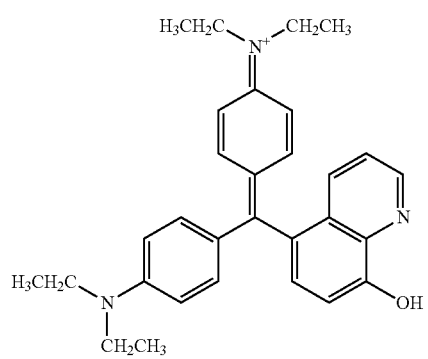
Hydroquinoline purple
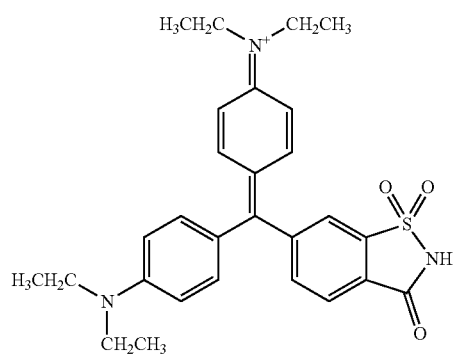
Saccharine green
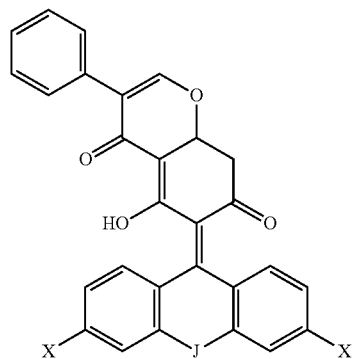
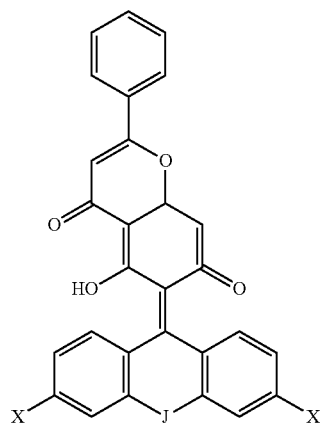
128
-continued
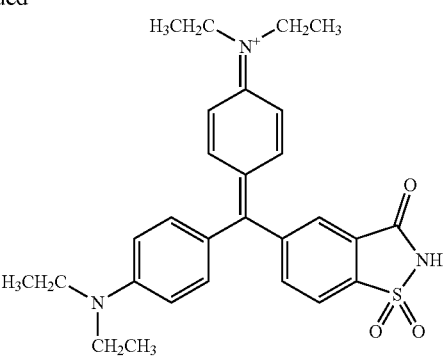
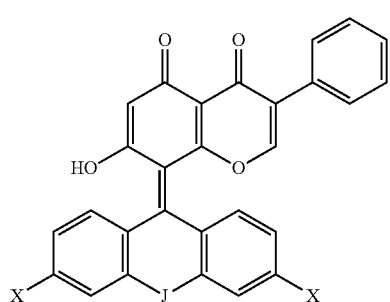
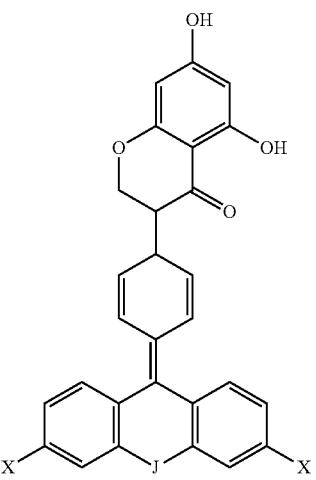
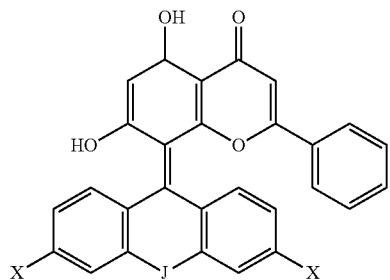

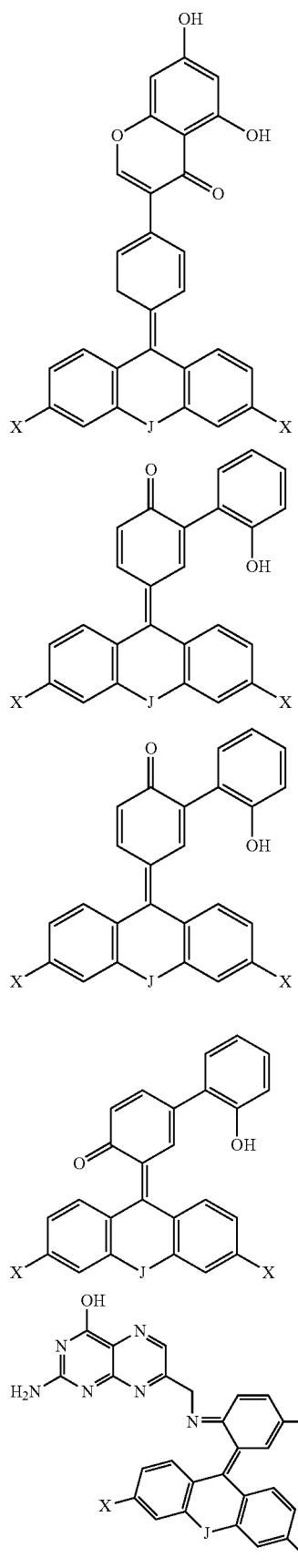
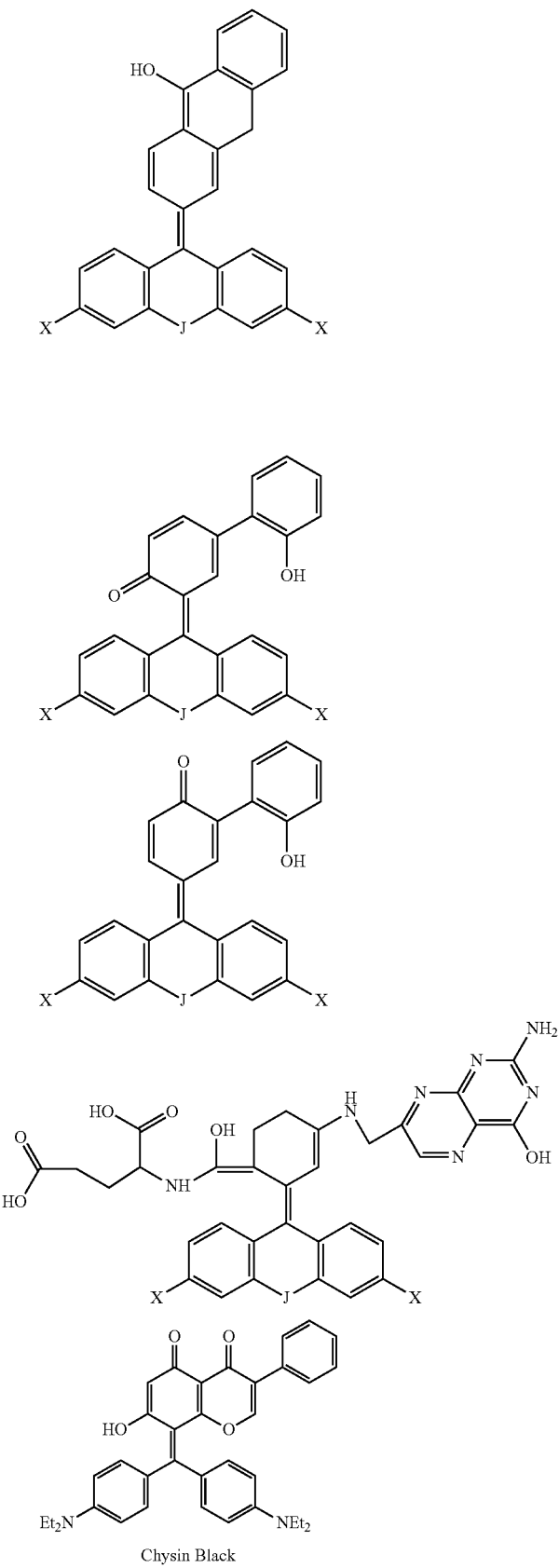
Chysin Black

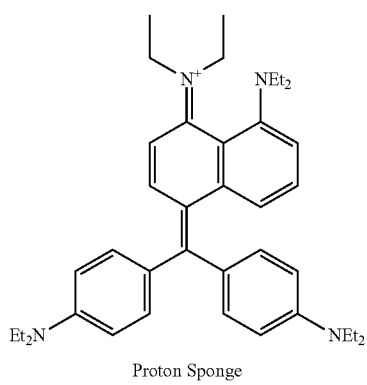

Proton Sponge where J and X are as defined above within this subsection.

Tautomeric forms of the compounds are also provided. For example, the compounds shown below can exist in both tautomeric forms:

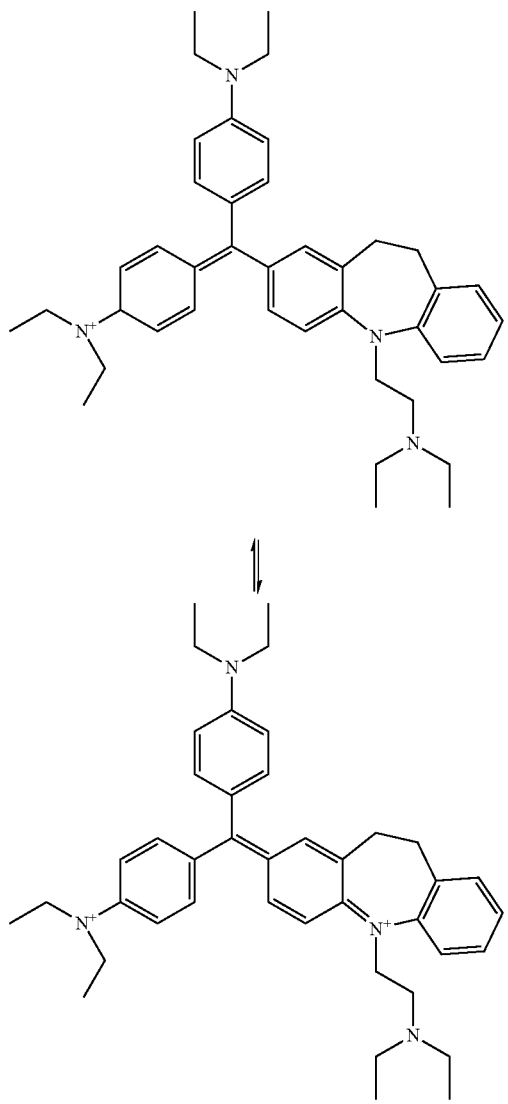

In some embodiments, the reduced compounds (prodrugs) have one or more free amine groups, which can be reacted with dichloroacetyl chloride to make one or more trichloroacetyl amide groups. Upon hydrolysis, the prodrugs will hydrolyze in vivo to form dichloroacetic acid salts ("DCA") and the triphenylmethane compounds.

For example, the prodrugs can be prepared by reacting quaternary ammonium groups with a reducing agent such as sodium cyanoborohydride to form amines. The amines can be reoxidized in vivo.

As discussed above within this subsection the amine groups can be converted to amide groups, which, upon hydrolysis, yield the amines, which can be oxidized to form the active compounds.

Prodrug forms of the compounds, in which the iminium group on certain triphenylmethanes are reduced, for example, with sodium cyanoborohydride, are also disclosed. One such compound is the reduced form of gentian violet (tris (dimethylaminophenyl)methane). The prodrugs can readily be reoxidized into the parent compounds, and offer various advantages over the drugs themselves. For example, the prodrug forms are less colored and more lipophilic (because the iminium salt is reduced to an amine). The compounds can be more easily taken up by cells than the parent drugs, and may be less irritating in vivo.

2. Functional Nucleic Acids Inhibitors of HIF-2α

The HIF-2α inhibitor can be a functional nucleic acid. Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Therefore the compositions can include one or more functional nucleic acids designed to reduce expression of the HIF-2α gene, or a gene product thereof. For example, the functional nucleic acid or polypeptide can be designed to target and reduce or inhibit expression or translation of HIF-2α mRNA; or to reduce or inhibit expression, reduce activity, or increase degradation of HIF-2α protein. In some embodiments, the composition includes a vector suitable for in vivo expression of the functional nucleic acid.

In some embodiments, a functional nucleic acid or polypeptide is designed to target a segment of the nucleic acid sequence of SEQ ID NO:1 or 38, or the complement thereof, or a genomic sequence corresponding therewith, or variants thereof having a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO:1 or 38.

In some embodiments, a functional nucleic acid or polypeptide is designed to target a segment of a the nucleic acid encoding the amino acid sequence of SEQ ID NO:2 or 39, or the complement thereof, or variants thereof having a nucleic acid sequence 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to a nucleic acid encoding the amino acid sequence of SEQ ID NO:2 or 39.

In some embodiments, the function nucleic acid hybridizes to the nucleic acid of SEQ ID NO:1 or 38, or a complement thereof, for example, under stringent conditions. In some embodiments, the functional nucleic acid hybridizes to a nucleic acid sequence that encodes SEQ ID NO:2 or 39, or a complement thereof, for example, under stringent conditions.

a. Antisense

The functional nucleic acids can be antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

b. Aptamers

The functional nucleic acids can be aptamers. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

c. Ribozymes

The functional nucleic acids can be ribozymes. Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

d. Triplex Forming Oligonucleotides

The functional nucleic acids can be triplex forming molecules. Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

e. External Guide Sequences

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

f. RNA Interference

In some embodiments, the functional nucleic acids induce gene silencing through RNA interference. Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404: 293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors having shRNA are available, such as, for example, Imgenex's GENESUPPRESSOR™ Construction Kits and Invitrogen's BLOCK-IT™ inducible RNAi plasmid and lentivirus vectors.

In some embodiment, the functional nucleic acid is siRNA, shRNA, miRNA. In some embodiments, the composition includes a vector expressing the functional nucleic acid. Methods of making and using vectors for in vivo expression of functional nucleic acids such as antisense oligonucleotides, siRNA, shRNA, miRNA, EGSs, ribozymes, and aptamers are known in the art.

g. Other Gene Editing Compositions

In some embodiments the functional nucleic acids are gene editing compositions. Gene editing compositions can include nucleic acids that encode an element or elements that induce a single or a double strand break in the target cell's genome, and optionally a polynucleotide. The compositions can be used, for example, to reduce or otherwise modify expression of HIF-2α.

i. Strand Break Inducing Elements CRISPR/Cas

In some embodiments, the element that induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, Science, 15:339(6121):819-823 (2013) and Jinek, et al., Science, 337(6096):816-21 (2012)). By transfecting a cell with the required elements including a Cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, Science, 15:339(6121):819-823 (2013) and Jinek, et al., Science, 337(6096):816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.upsud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence (such as HIF-2α) can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

Zinc Finger Nucleases

In some embodiments, the element that induces a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The most common cleavage domain is the Type IIS enzyme Fok1. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. Proc., Natl. Acad. Sci. USA 89 (1992):4275-4279; Li et al. Proc. Natl. Acad. Sci. USA, 90:2764-2768 (1993); Kim et al. Proc. Natl. Acad. Sci. USA. 91:883-887 (1994a); Kim et al. J. Biol. Chem. 269:31,978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

Transcription Activator-Like Effector Nucleases

In some embodiments, the element that induces a single or a double strand break in the target cell's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, Nucl. Acids Res. 1-11 (2011). US Published Application No. 2011/0145940, which discloses TAL effectors and methods of using them to modify DNA. Miller et al. Nature Biotechnol 29: 143 (2011) reported making TALENs for site-specific nuclease architecture by linking TAL truncation variants to the catalytic domain of Fok1 nuclease. The resulting TALENs were shown to induce gene modification in immortalized human cells. General design principles for TALE binding domains can be found in, for example, WO 2011/072246.

ii. Gene Altering Polynucleotides

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6× His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

C. Compounds for Increasing HIF-2α Bioavailability

Compounds for increasing the bioactivity of HIF-2α, and formulations formed therewith are provided. In some embodiments, the compound is small molecule, a HIF-2α polypeptide or protein, a fusion protein including a HIF-2α polypeptide or protein, an isolated nucleic acid encoding a HIF-2α polypeptide or protein or HIF-2α fusion protein, or an agent such as a transcription factor that increases endogenous expression of a HIF-2α polypeptide or protein. The compound can increase the expression or bioavailability of HIF-2α. In some embodiments, the compound is a transcription factor that increase endogenous expression of HIF-2α.

In other embodiments, muscle repair and regeneration is modulated by targeting a target of HIF-2α. The Examples below show that HIF-2α induces satellite cell quiescence by binding HREs in the Spry1 promoter and impedes SC proliferation by activating Spry1 transcription. Thus, in some embodiments the compound for use in the disclosed methods is activator or otherwise increases the bioavailability of Spry1.

In some embodiments, the compound is a wildtype HIF-2α protein such as SEQ ID NO:2 or 39, or a function fragment thereof, or a variant thereof with at least 50, 60, 70, 80, 85, 90, 95, 96, 97, 98, or 99% sequence identity to SEQ ID NO:2 or 39.

In some embodiments, the compound is a nucleic acid encoding a wildtype HIF-2α protein such as SEQ ID NO:2 or 39, or a function fragment thereof, or a variant thereof with at least 50, 60, 70, 80, 85, 90, 95, 96, 97, 98, or 99% sequence identity to SEQ ID NO:2 or 39.

In some embodiments, the compositions include a compound that increases bioactivity of endogenous HIF-2α. Such compounds include factors that increase the expression of or increase the half life of endogenous HIF-2α. Factors that increase expression of endogenous HIF-2α include, for example, HIF-2α transcription factors. HIF-2α transcription factors can be provided as a recombinant polypeptide, or an isolated nucleic acid encoding the transcription factor.

In some embodiments the factor that increases expression of endogenous HIF-2α or increase the half life of engodenous HIF-2α is a small molecule. See, for example, U.S. Published Application No. 2015/0218098, which is specifically incorporated by reference herein in its entirety), defined according to the following paragraphs found in this subheading, and provides prolyl hydroxylase inhibitors that can stabilize hypoxia inducible factor-1 alpha (HIF-1α), as well as hypoxia inducible factor-2 (HIF-2).

A compound having the formula:

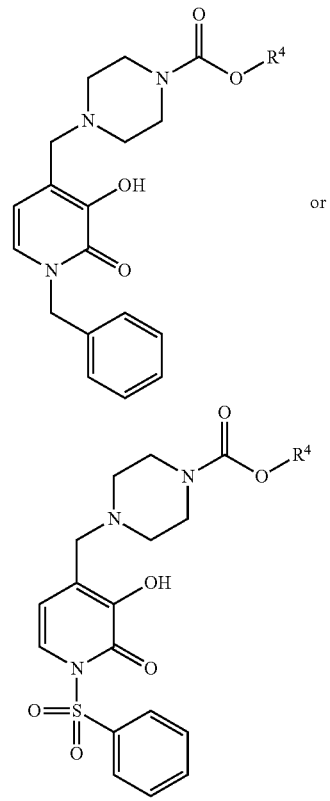

$R_4$ is $C_1$-$C_4$ linear alkyl or $C_3$-$C_4$ branched alkyl; or a pharmaceutically acceptable salt thereof. In some embodiments, $R_4$ is methyl, ethyl, or tert-butyl. In some embodiments, the compound is a pharmaceutically acceptable salt of an anion chosen from chloride, bromide, iodide, sulfate, bisulfate, carbonate, bicarbonate, phosphate, hydrogensulfonate, p-toluenesulfonate, methanesulfonate, formate, acetate, propionate, butyrate, pyruvate, lactate, oxalate, malonate, maleate, succinate, tartrate, fumarate, glycolate, or citrate. In some embodiments, the compound is tert-butyl 4-(1-benzyl-3-hydroxy-2-oxo-1,2-dihydropyridin-4-yl) methyl)piperazine-1-carboxylate, methyl 4-((1-benzyl-3-hydroxy-2-oxo-1,2-dihydropyridin-4-yl)methyl)piperazine-1-carboxylate; Ethyl 4-{[1-(3-chlorobenzyl)-3-hydroxy-2-oxo-1,2-dihydropyridin-4-yl]methyl}piperazine-1-carboxylate; Methyl 4-((3-hydroxy-2-oxo-1-(phenylsulfonyl)-1,2-dihydropyridin-4-yl)methyl) piperazine-1-carboxylate; Ethyl 4-((3-hydroxy-2-oxo-1-(phenylsulfonyl)-1,2-dihydropyridin-4-yl)methyl) piperazine-1-carboxylate; or tert-Butyl 4-((3-hydroxy-2-oxo-1-(phenylsulfonyl)-1,2-dihydropyridin-4-yl)methyl) piperazine-1-carboxylate.

D. Isolated Nucleic Acid Molecules

Isolated nucleic acid sequences encoding HIF-2α proteins, polypeptides, fusions fragments and variants thereof, as well as inhibitor nucleic acid, and vectors and other expression constructs encoding the foregoing are also disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-HIF-2α proteins). The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

The nucleic acid sequences encoding HIF-2α polypeptides include genomic sequences. Also disclosed are mRNA sequence wherein the exons have been deleted. Other nucleic acid sequences encoding HIF-2α polypeptides, such polypeptides that include the above-identified amino acid sequences and fragments and variants thereof, are also disclosed. Nucleic acids encoding HIF-2α polypeptides may be optimized for expression in the expression host of choice. Codons may be substituted with alternative codons encoding the same amino acid to account for differences in codon usage between the organism from which the HIF-2α nucleic acid sequence is derived and the expression host. In this manner, the nucleic acids may be synthesized using expression host-preferred codons.

Nucleic acids can be in sense or antisense orientation, or can be complementary to a reference sequence encoding a HIF-2α polypeptide. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Common modifications are discussed in more detail below.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

1. Vectors and Host Cells

Vectors encoding HIF-2α polypeptides, fusion, fragments, and variants and inhibitor nucleic acids thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the HIF-2α polypeptides or fusion polypeptides described herein.

The vectors can be used to express HIF-2α or nucleic acids inhibitory thereof in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo.

Nucleic acids may also be administered in vivo by viral means. Nucleic acid molecules encoding polypeptides or fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polyly sine.

In addition to virus- and carrier-mediated gene transfer in vivo, physical means well-known in the art can be used for direct transfer of DNA, including administration of plasmid DNA and particle-bombardment mediated gene transfer.

2. Oligonucleotide Composition

The disclosed nucleic acids nucleic acids can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides include uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents.

In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

a. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocyto sine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

b. Sugar Modifications

Oligonucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i–1 phosphate in the purine strand of the duplex.

In some embodiments, the nucleic acid is a morpholino oligonucleotide. Morpholino oligonucleotides are typically composed of two or more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

c. Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., *Organic. Chem.*, 52:4202, (1987)), and uncharged morpholino-based polymers having achiral intersubunit linkages (see, e.g., U.S. Pat. No. 5,034, 506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., *Chem. Biol.*, 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are composed of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527, 675, 5,623,049, 5,714,331, 5,736,336, 5,773,571 and 5,786, 571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

In some embodiments, the nucleic acid can be single stranded or double stranded.

E. Delivery Vehicles

The disclose compounds can be administered and taken up into the cells of a subject with or without the aid of a delivery vehicle. Appropriate delivery vehicles for the disclosed inhibitors are known in the art and can be selected to suit the particular inhibitor. For example, if the compound is a nucleic acid or vector, the delivery vehicle can be a viral vector, for example a commercially available preparation, such as an adenovirus vector (Quantum Biotechnologies, Inc. (Laval, Quebec, Canada). The viral vector delivery can be via a viral system, such as a retroviral vector system which can package a recombinant retroviral genome (see e.g., Pastan et al., (1988) *Proc. Natl. Acad. Sci.* U.S.A. 85:4486; Miller et al., (1986) Mol. Cell. Biol. 6:2895). The recombinant retrovirus can then be used to infect and thereby deliver to the infected cells nucleic acid encoding the compound inhibitor. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948 (1994)), adeno-associated viral (AAV) vectors (Goodman et al., *Blood* 84:1492-1500 (1994)), lentiviral vectors (Naidini et al., *Science* 272:263-267 (1996)), pseudotyped retroviral vectors (Agrawal et al., *Exper. Hematol.* 24:738-747 (1996)).

Physical transduction techniques can also be used, such as liposome delivery and receptor-mediated and other endocytosis mechanisms (see, for example, Schwartzenberger et al., *Blood* 87:472-478 (1996)). For example in some embodiments, the CTPS1 inhibitor is delivered via a liposome. Commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art are well known. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.). This disclosed compositions and methods can be used in conjunction with any of these or other commonly used gene transfer methods.

In some embodiments, the delivery vehicle is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the compound. In some embodiments, release of the drug(s) is controlled by diffusion of the compound out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

F. Protein Transduction Domains and Targeting Moieties

1. Protein Transduction Domains

Any of the compounds disclosed herein, including both HIF-2α inhibitors and compounds that increase the bioactivity of HIF-2α, and delivery vehicles including the compounds, can be modified to one or more domains for enhancing delivery of the compound across the plasma membrane in into the interior of cells. The compounds can be modified to include a protein transduction domain (PTD), also known as cell penetrating peptides (CPPS). PTDs are known in the art, and include, but are not limited to, small regions of proteins that are able to cross a cell membrane in a receptor-independent mechanism (Kabouridis, P., *Trends in Biotechnology* (11):498-503 (2003)). Although several of PTDs have been documented, the two most commonly employed PTDs are derived from TAT (Frankel and Pabo, *Cell*, 55(6):1189-93(1988)) protein of HIV and Antennapedia transcription factor from *Drosophila*, whose PTD is known as Penetratin (Derossi et al., *J Biol Chem.*, 269(14): 10444-50 (1994)).

The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRRR (SEQ ID NO:3)) of the parent protein that appears to be important for uptake. Additionally, the basic domain Tat(49-57) or RKKRRQRRR (SEQ ID NO:4) has been shown to be a PTD. TAT has been favored for fusion to proteins of interest for cellular import. Several modifications to TAT, including substitutions of Glutatmine to Alanine, i.e., Q→A, have demonstrated an increase in cellular uptake anywhere from 90% (Wender et al., *Proc Natl Acad Sci USA.*, 97(24): 13003-8 (2000)) to up to 33 fold in mammalian cells. (Ho et al., *Cancer Res.*, 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally, exemplary PTDs include, but are not limited to, poly-Arg—RRRRRRR (SEQ ID NO:5); PTD-5—RRQRRTSKLMKR (SEQ ID NO:6); Transportan GWTLNSAGYLLGKINL-KALAALAKKIL (SEQ ID NO:7); KALAWEAKLAKA-LAKALAKHLAKALAKALKCEA (SEQ ID NO:8); and RQIKIWFQNRRMKWKK (SEQ ID NO:9).

In some embodiments, the compounds includes an endosomal escape sequence that improves delivery of the compound to the interior of the cell. Endosomal escape sequences are known in the art, see for example, Barka, et al., *Histochem. Cytochem.*, 48(11):1453-60 (2000) and Wadia and Stan, *Nat. Med.*, 10(3):310-5 (2004).

2. Targeting Signal or Domain

Any of the compounds disclosed herein, including both HIF-2α inhibitors and compounds that increase the bioactivity of HIF-2α, and delivery vehicles including the compounds can be modified to include one or targeting signals or domains. The targeting signal or sequence can be specific for a host, tissue, organ, cell, organelle, an organelle such as the nucleus, or cellular compartment. Moreover, the compositions disclosed here can be targeted to other specific intercellular regions, compartments, or cell types.

In some embodiments, the targeting signal binds to a ligand or receptor which is located on the surface of a target cell such as to bring the compound and cell membranes sufficiently close to each other to allow penetration of the compound into the cell. Additional embodiments are directed to specifically delivering the compound to specific tissue or cell types.

Preferably, the targeting moiety enhances targeting to muscle, most preferably muscle satellite cells.

In a preferred embodiment, the targeting molecule is selected from the group consisting of an antibody or antigen binding fragment thereof, an antibody domain, an antigen, a cell surface receptor, a cell surface adhesion molecule, a viral envelope protein and a peptide selected by phage display that binds specifically to a defined cell.

Targeting domains to specific cells can be accomplished by modifying the disclosed compounds to include specific cell and tissue targeting signals. These sequences target specific cells and tissues, but in some embodiments the interaction of the targeting signal with the cell does not occur through a traditional receptor:ligand interaction. The eukaryotic cell includes a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the compound can be altered by changing the targeting signal.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest Another embodiment provides an antibody or antigen binding fragment thereof bound to the disclosed recombinant polypeptides acting as the targeting signal. The antibodies or antigen binding fragment thereof are useful for directing the fusion protein to a cell type or cell state. In one embodiment, the fusion protein possesses an antibody binding domain, for example from proteins known to bind antibodies such as Protein A and Protein G from *Staphylococcus aureus*. Other domains known to bind antibodies are known in the art and can be substituted. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting domain includes all or part of an antibody that directs the compound to the desired target cell type or cell state. Antibodies can be monoclonal or polyclonal, but are preferably monoclonal. For human gene therapy purposes, antibodies are derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

Additional embodiments are directed to specifically delivering the compound to intracellular compartments or organelles. Eukaryotic cells contain membrane bound structures or organelles.

For example, in some embodiments, the compounds include a nuclear localization signal. Most proteins transported across the nuclear envelope contain a nuclear localization signal (NLS). The NLS is recognized by a nuclear import complex, enabling active transport to the nucleus. Even the transport of small proteins that can diffuse through the nuclear pore is increased by an NLS. NLS domains are known in the art and include for example, SV 40 T antigen or a fragment thereof, such as PKKKRKV (SEQ ID NO:10). The NLS can be simple cationic sequences of about 4 to about 8 amino acids, or can be bipartite having two interdependent positively charged clusters separated by a mutation resistant linker region of about 10-12 amino acids. The cauliflower mosaic virus (CMV) major capsid protein, CP, possesses an amino-terminal NLS. Additional representative NLS include but are not limited to GKKRSKV (SEQ ID NO:11); KSRKRKL (SEQ ID NO:12); KRPAATKK-AGQAKKKKLDK (SEQ ID NO: 13); RKKRK-TEEESPLKDKAKKSK (SEQ ID NO:14); KDCVMNKHHRNRCQYCRLQR (SEQ ID NO:15); PAAKRVKLD (SEQ ID NO:16); and KKYENVVIKR-SPRKRGRPRK (SEQ ID NO:17).

G. Formulations

The disclosed compounds can be formulated in a pharmaceutical composition. Pharmaceutical compositions can be for administration by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes of administration or using bioerodible inserts and can be formulated in dosage forms appropriate for each route of administration.

The compositions can be administered systemically.

Drugs can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g. as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Formulations are typically prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, disintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et.al., (Media, Pa.: Williams and Wilkins, 1995) which provides information on carriers, materials, equipment and process for preparing tablets and capsules and delayed release dosage forms of tablets, capsules, and granules.

The compound can be administered to a subject with or without the aid of a delivery vehicle. Appropriate delivery vehicles for the compounds are known in the art and can be selected to suit the particular active agent. For example, in some embodiments, the active agent(s) is incorporated into or encapsulated by, or bound to, a nanoparticle, microparticle, micelle, synthetic lipoprotein particle, or carbon nanotube. For example, the compositions can be incorporated into a vehicle such as polymeric particles which provide controlled release of the active agent(s). In some embodiments, release of the drug(s) is controlled by diffusion of the active agent(s) out of the particles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing particles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

1. Formulations for Parenteral Administration

Compounds and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as POLY-SORBATE® 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Oral Immediate Release Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

3. Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form having single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

4. Delayed Release Dosage Forms

Delayed release formulations are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUDRAGIT®. L-100 (soluble at pH 6.0 and above), EUDRAGIT®. S (soluble at pH 7.0 and above, as a result of a higher degree of esterification), and EUDRAGITS®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Methods of Manufacturing

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or a drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert). For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, Pa.: Williams & Wilkins, 1995).

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

5. Formulations for Mucosal and Pulmonary Administration

Active agent(s) and compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions composed of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different active agents may be administered to target different regions of the lung in one administration.

6. Topical and Transdermal Formulations

Transdermal formulations may also be prepared. These will typically be gels, ointments, lotions, sprays, or patches, all of which can be prepared using standard technology. Transdermal formulations can include penetration enhancers.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) composed of the drug dispersed or dissolved in a mixture of surfactant(s) and lipophillic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components.

Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Additional agents that can be added to the formulation include penetration enhancers. In some embodiments, the penetration enhancer increases the solubility of the drug, improves transdermal delivery of the drug across the skin, in particular across the stratum corneum, or a combination thereof. Some penetration enhancers cause dermal irritation, dermal toxicity and dermal allergies. However, the more commonly used ones include urea, (carbonyldiamide), imidurea, N, N-diethylformamide, N-methyl-2-pyrrolidone, 1-dodecal-azacycloheptane-2-one, calcium thioglycate, 2-pyrrolidone, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly(10)oxyethylene ether), and BRIJ® 721 (stearyl poly (21) oxyethylene ether) (ICI Americas Inc. Corp.). Chemical penetrations and methods of increasing transdermal drug delivery are described in Inayat, et al., *Tropical Journal of Pharmaceutical Research,* 8(2):173-179 (2009) and Fox, et al., *Molecules,* 16:10507-10540 (2011). In some embodiments, the penetration enhancer is, or includes, an alcohol such ethanol, or others disclosed herein or known in the art.

Delivery of drugs by the transdermal route has been known for many years. Advantages of a transdermal drug delivery compared to other types of medication delivery such as oral, intravenous, intramuscular, etc., include avoidance of hepatic first pass metabolism, ability to discontinue administration by removal of the system, the ability to control drug delivery for a longer time than the usual gastrointestinal transit of oral dosage form, and the ability to modify the properties of the biological barrier to absorption.

Controlled release transdermal devices rely for their effect on delivery of a known flux of drug to the skin for a prolonged period of time, generally a day, several days, or a week. Two mechanisms are used to regulate the drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. Devices incorporating a reservoir will deliver a steady drug flux across the membrane as long as excess undissolved drug remains in the reservoir; matrix or monolithic devices are typically characterized by a falling drug flux with time, as the matrix layers closer to the skin are depleted of drug. Usually, reservoir patches include a porous membrane covering the reservoir of medication which can control release, while heat melting thin layers of medication embedded in the polymer matrix (e.g., the adhesive layer), can control release of drug from matrix or monolithic devices. Accordingly, the active agent can be released from a patch in a controlled fashion without necessarily being in a controlled release formulation.

Patches can include a liner which protects the patch during storage and is removed prior to use; drug or drug solution in direct contact with release liner; adhesive which serves to adhere the components of the patch together along with adhering the patch to the skin; one or more membranes, which can separate other layers, control the release of the drug from the reservoir and multi-layer patches, etc., and backing which protects the patch from the outer environment.

Common types of transdermal patches include, but are not limited to, single-layer drug-in-adhesive patches, wherein the adhesive layer contains the drug and serves to adhere the various layers of the patch together, along with the entire system to the skin, but is also responsible for the releasing of the drug; multi-layer drug-in-adhesive, wherein which is similar to a single-layer drug-in-adhesive patch, but contains multiple layers, for example, a layer for immediate release of the drug and another layer for control release of drug from the reservoir; reservoir patches wherein the drug layer is a liquid compartment containing a drug solution or suspension separated by the adhesive layer; matrix patches, wherein a drug layer of a semisolid matrix containing a drug solution or suspension which is surrounded and partially overlaid by the adhesive layer; and vapor patches, wherein an adhesive layer not only serves to adhere the various layers together but also to release vapor. Methods for making transdermal patches are described in U.S. Pat. Nos. 6,461,644, 6,676,961, 5,985,311, and 5,948,433.

EXAMPLES

Xie, et al., *J Clin Invest.* 2018 Jun. 1; 128(6):2339-2355. doi: 10.1172/JCI96208. Epub 2018 Apr. 30, and all supplementary materials and data associated there with (e.g., jci-128-96208-s009.pdf (13M)), is specifically incorporated by reference herein in its entirety.

Example 1

Satellite Cells are Hypoxic in the Niche and Have Stabilized HIF-2α in Quiescent but Not Activated State Materials and Methods Animal Experimental Procedures Animals were housed in a temperature-controlled (23° C.) environment with 12:12-hrs light:dark cycle and allowed food and water ad lithium. All mouse strains were purchased from the Jackson Laboratory: Pax7$^{creERT2}$ (JAX: 017763), R26R$^{CAG-Sun1/sfGFP}$ (JAX: 021039), R26R$^{CAG-tdTomato}$ (JAX: 007914) and Hif2α$^{flox}$ (JAX: 008407).

To induce Cre activity in mice with the Pax7$^{cre/ERT2}$ allele, tamoxifen (20 mg/ml in corn oil) was intraperitoneally administered for 3 consecutive days (100 mg/Kg/day). To assess myofiber damage, 1% Evan's blue (4 ml/Kg in saline) was intraperitoneally administered 1 day before the euthanasia. To trace proliferative cells, EdU (50 mg/Kg in DMSO) was intraperitoneally administered 1 day before the euthanasia. For CTX-induced muscle injury, CTX (0.5 nmol in saline) was injected into TA muscle.

Immunofluorescence Staining and Imaging

For staining muscle sections, muscle sections were fixed with 2% paraformaldehyde (PFA)/PBS for 10 mins, quenched with 50 mM glycine for 10 mins, permeabilized with 0.5% Triton X-100 for 10 mins. To reduce background fluorescence due to endogenous mouse IgG, Mouse on Mouse (M.O.M.) Blocking Reagent (Vector Lab) was used according to the manufactures' instruction. Muscle sections were blocked in 5% BSA/5% normal goat serum in PBS for 1 hr and incubated with primary antibodies: anti-Pax7 (1:5; DSHB), anti-HIF-2α (1:250; Novus Bio.), anti-HIF-1α (1:250; Novus Bio.), anti-Ki67 (1:1,000; Abcam), anti-Laminin B2 (1:1,000; Milipore), anti-embryonic MyHC (1:50, DSHB), anti-MyHC type I, IIA, or IIB (1:50, DSHB) overnight at 4° C. For EdU staining, Click-iT EdU Fluorescence Kit (Life technologies) was used according to the manufactures' instruction before the application of primary antibodies. Muscle sections were washed in PBS with 0.1% Tween-20, incubated with Alexa Fluor dye-labeled secondary antibodies at room temperature for 1 hr and washed. Sections were mounted with DAPI-containing mounting medium (Life technologies).

For staining myofibers and myoblasts, single myofibers/cells were fixed in 4% PFA, blocked in 5% BSA/5% normal goat serum in PBS for 1 hr and incubated with primary antibodies: anti-Pax7 (1:5; DSHB), anti-MyoD (1:125; Sigma), anti-HIF-2α (1:250; Novus Bio.), anti-HIF-1α (1:250; Novus Bio.), anti-cleaved Caspase-3 (Asp175; 1:400; Cell Signaling) and anti-GFP (1:1,000; 101Bio or Ablab). Mounted slides were imaged on a Zeiss LSM 710 confocal microscope.

Measurement of Muscle Maximal Contraction Force and Eccentric Contraction-Induced Injury Peak isometric torque of the ankle dorsiflexors (tibialis anterior, extensor digitorum longus and extensor hallicus longus muscles) was assessed in vivo as previously described (47). Briefly, mice were anaesthetized with 1.75% isoflurane mixed with oxygen. The left hindlimb was depilated and aseptically prepared before the foot was placed into a foot plate attached to a servomotor (Model 300C-LR; Aurora Scientific, Aurora, Ontario, Canada). Two Pt—Ir electrode needles (Model E2-12; Grass Technologies, West Warwick, R.I., USA) were inserted percutaneously on either side of the peroneal nerve. The ankle joint was secured at a 90° angle and body temperature was maintained at 37° C. throughout functional testing. Peak isometric torque was achieved by varying the current delivered to the peroneal nerve at a frequency of 200 Hz and a 0.1-ms square wave pulse. Torques (N·mm) were normalized by the body mass ($kg^{-1}$) to account for differences in body size among mice. Following peak isometric torque measurements, the dorsiflexors were subject to 100 electronically stimulated eccentric contractions in order to induce injury. During each contraction the foot was passively moved from the 0° position (perpendicular to tibia) to 20° of dorsiflexion. The dorsiflexors were stimulated at 200 Hz for a 100-ms isometric contraction followed by an additional 50 ms of stimulation while moving from 20° dorsiflexion to 20° plantarflexion at an angular velocity of 800°/s. Eccentric contractions were repeated every 10 seconds and the entire protocol lasted about 14 min.

Hypoxyprobe Injection and In Situ Detection of the Hypoxic State of Satellite Cells To assess $pO_2$ of muscle cells in vivo, Hypoxyprobe-1 (Pimonidazole Hydrochloride, Hypoxyprobe Inc.; 60 mg/kg in PBS) was intraperitoneally administrated to $Pax7^{cre/ERT2}$; $R26R^{CAG-tdTomato}$ mice at 1.5 hrs before the euthanasia. Because the anti-pimonidazole adducts antibody is the same isotype as anti-Pax7 antibody (IgG1κ), $Pax7^{cre/ERT2}$; $R26R^{CAG-tdTomato}$ mice were used to identify SCs on myofibers.

Statistics

All values in the figures represent mean±s.e.m with >=3 biological replicates. Statistical significance was determined by Prism GraphPad 6 using Student's t-test (two-sided). *: p<0.05, : p<0.01, *: p<0.005, N.S.: not significant (p>=0.05).

Study Approval

All animal studies were approved by the University of Georgia Institutional Animal Care and Use Committee (IACUC) and performed strictly following the guidelines.

Results

The partial oxygen tension ($pO_2$) of most adult tissues is between 2% to 9% (17). To assess the normoxic/hypoxic state of SCs in vivo, pimonidazole, a hypoxia indicator that forms adducts in hypoxic cells in situ (when $pO_2$<1.3%), was administered to tamoxifen-treated adult $Pax7^{cre/ERT2}$; $R26R^{CAG-tdTomato}$ mice (3 mo. old) that carry $tdTomato^+$ SCs in the muscle. After pimonidazole was fully metabolized in vivo, single myofibers with residing SCs were isolated from extensor digitorum longus (EDL) muscle and stained for pimonidazole adducts to evaluate $pO_2$ in SCs. Abundant pimonidazole adducts are detected in almost all (>99%) $tdTomato^+$ quiescent SCs but not in myonuclei or in sarcoplasm, indicating quiescent SCs are hypoxic in the niche.

To understand whether hypoxia leads to stabilization of hypoxia-inducible factors in quiescent SCs (QSCs), $O_2$-sensitive HIF-1α and HIF-2α were stained on myofibers and muscle cross-sections prepared from uninjured muscles of adult C57BL/6 mice (3 mo. old). $Pax7^+$ QSCs do not express HIF-1α; whereas QSCs and myonuclei express HIF-2α. This indicates that HIF-2α, not HIF-1α, is the mediator of hypoxia signaling in quiescent SCs.

Figure 1B:
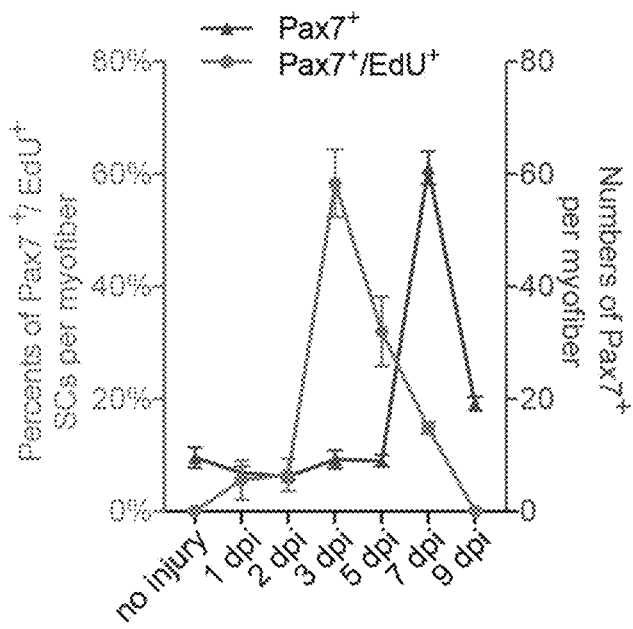
FIG. 1B is a line graph showing the numbers of Pax7$^+$ SCs per myofiber (-▲-) and percents of Pax7$^+$/EdU$^+$ SCs ((-●-); n>50 myofibers/group/time point).
Figure 1C:
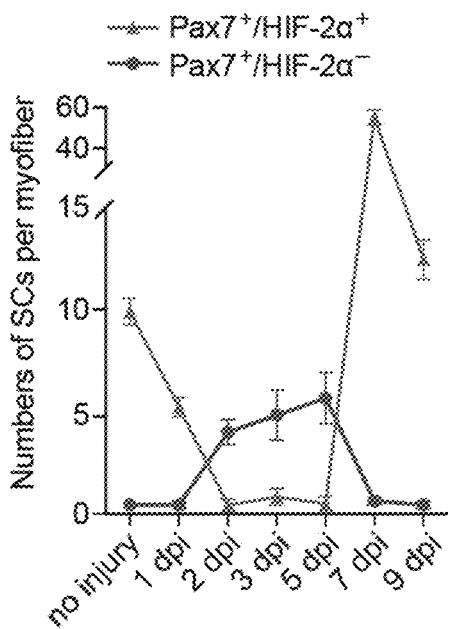
FIG. 1C Numbers of Pax7$^+$/HIF-2α$^+$ (-▲-) and Pax7$^+$/HIF-2α$^-$ (-●-) SCs per myofiber (n>50 myofibers/group/time point).

Quiescent SCs reenter cell cycle during muscle repair. To assess HIF-2α expression during physiological process of muscle repair, tibialis anterior (TA) and EDL muscles of adult C57BL/6 mice (3 mo. old) were injured by repetitive eccentric contraction and isolated the injured EDL myofibers from 1 to 9 days post injury (dpi; FIG. 1A). EdU and Evans blue dye were administrated (24 hrs before myofiber isolation) to assess cell proliferation and sarcolemma integrity in injured muscles, respectively. After eccentric contraction-induced injury, SC proliferation (percents of $Pax7^+$/$EdU^+$ SCs) peaks at 3 dpi on injured myofibers then declines afterwards and phases out at 9 dpi when sarcolemma integrity is restored (FIG. 1B). The quiescent/proliferative states of SCs are correlated with HIF-2α expression: at 2 dpi, HIF-2α diminishes in SCs prior to SC proliferation; at 7 dpi, HIF-2α reappears in SCs concomitant with SC returning to quiescence (FIG. 1C). Like QSCs, proliferative SCs (3 dpi) remain hypoxic (pimonidazole$^{+pos}$). Throughout the process of contraction-induced muscle injury, HIF-1α expression is not detectable in SCs, myonuclei or sarcoplasm, indicating HIF-1α is not related to SCs dynamics under physiological conditions.

Example 2

Genetic Ablation of HIF-2α in Quiescent Satellite Cells Leads to Spontaneous Activation/Proliferation and Loss of Homeostatic Self-Renewal Materials and Methods Myofiber Isolation, Culture and Transfection Myofibers were isolated from EDL muscles as described before (Pasut, et al., J Vis Exp., (73):e50074. doi: 10.3791/50074 (2013)). Briefly, EDL muscle was dissected and digested in 0.2% collagenase I in DMEM at 37° C. for 1.5 hr. Single myofibers were isolated by triturating the digested EDL muscle with polished Pasteur pipettes. For myofiber culture, single myofibers were cultured in horse serum-coated 24-well plates in DMEM (4.5 g/L glucose) supplemented with 20% FBS, 1% sodium pyruvate and 1% chicken embryo-extract and 1% penicillin-streptomycin under 21% $pO_2$ and 5% $CO_2$. For myofiber transfection, single myofibers were cultured as described above for 12 hrs, transfected with 2 μg pCMEGIP-HIF2αTM or control empty pCMEGIP plasmid by Lipofectamine 3000 (Thermo Fisher Scientific). 6 hrs after transfection, transfection reagent-containing medium was removed, washed and replaced with fresh myofiber culture medium. Myofibers were further cultured for 48 hrs before the fixation and staining.

Plasmid Construction

For expression of $O_2$-insensitive forms of HIFs, pcDNA3_mHIF-2α_MYC and pcDNA3_mHIF-1α_MYC plasmids containing HIF ORFs with triple mutations (TM) were acquired from Addgene (#44027, #44028). mHIF-2αTM and mHIF-1αTM ORFs were PCR amplified from above plasmids, sub-cloned downstream of the CMV promoter in pCDH-CMV-MCS-EF1-eGFP-IRES-Puro plasmid (pCMEGIP; System Biosciences) that also expresses eGFP from an EF1 promoter.

For transplantation of HIF-2αTM transfected SCs/myofibers, the mHIF-2αTM ORF was sub-cloned downstream of the CMV promoter in pCDH-CMV-MCS-EF1-Puro plasmid (pCMEP; System Biosciences), which does not express GFP.

Results

Figure 2A:
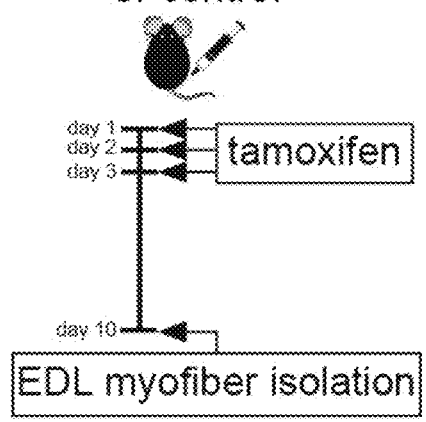
FIG. 2A is a diagram depicting the experimental scheme for tracing Stem Cell (SC) activation after HIF-2α ablation.
Figure 2B:
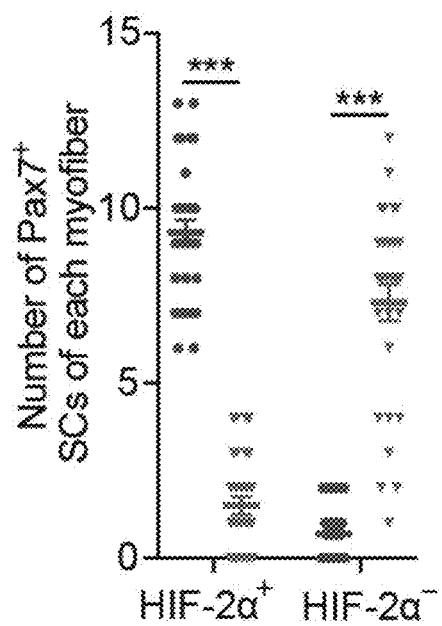
FIG. 2B is dot plot showing the numbers of Pax7$^+$/HIF-2α$^+$ and Pax7$^+$/HIF-2α$^-$ SCs per myofiber (n>50) ((-●-) control, (-▼-) SC-HIF2αKO).
Figure 2C:
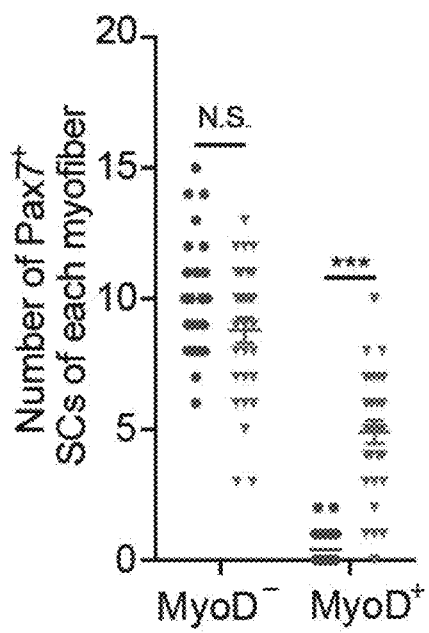
FIG. 2C is a dot plot showing the numbers of Pax7$^+$/MyoD$^-$ and Pax7$^+$/MyoD$^+$ SCs per myofiber (n>50) ((-●-) control, (-▼-) SC-HIF2αKO).

Upon contraction-induced injury, SC proliferation following diminished HIF-2α expression implicates a role of HIF-2α in the maintenance of satellite cell quiescence. To investigate this putative function, tamoxifen was administered to adult Pax7$^{cre/ERT2}$;Hif-2α$^{flox/flox}$ mice (hereafter called SC-HIF2αKO mice; 3 mo. old), which led to genetic ablation of HIF-2α specifically in SCs within adult muscles (FIG. 2A). One week after tamoxifen administration, HIF-2α expression is abolished in ~80% of QSCs on myofibers of EDL muscles (FIG. 2B). Myogenic transcription factor MyoD is absent in QSCs yet expressed in activated/proliferative satellite cells (Zammit, et al., J Cell Biol., 166(3): 347-57 (2004)). HIF-2α ablation leads to a significant increase of MyoD$^+$ SCs in uninjured/resting muscles (FIG. 2C), indicating a proportion of SCs in SC-HIF2αKO mice are spontaneously activated.

Figure 2D:
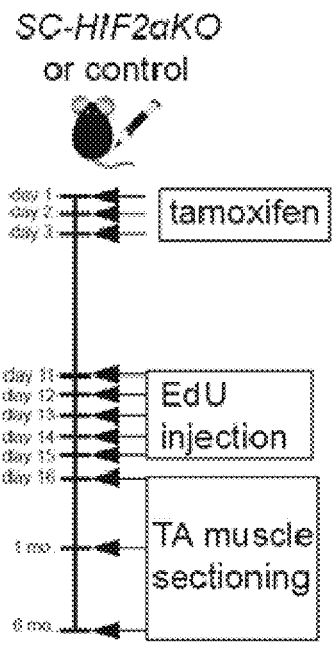
FIG. 2D is a diagram depicting the experimental scheme for tracing SC proliferation and homeostatic maintenance after HIF-2α ablation.
Figure 2E:
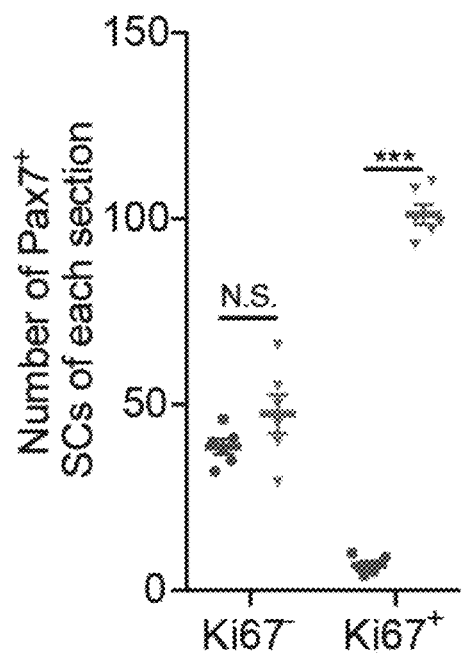
FIG. 2E is a dot plot showing the numbers of Pax7$^+$/Ki67$^-$ and Pax7$^+$/Ki67$^+$ SCs per TA section (n=6) ((-●-) control, (-▼-) SC-HIF2αKO).
Figure 2F:
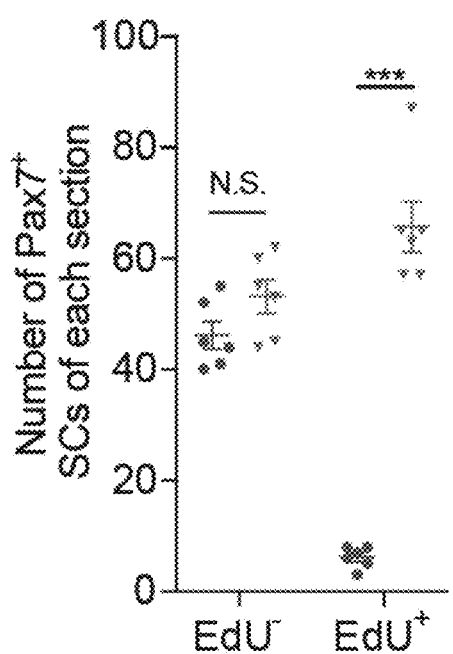
FIG. 2F is a dot plot showing the numbers of Pax7$^+$/EdU$^-$ and Pax7$^+$/EdU$^+$ SCs per TA section (n=6) ((-●-) control, (-▼-) SC-HIF2αKO).
Figure 2G:
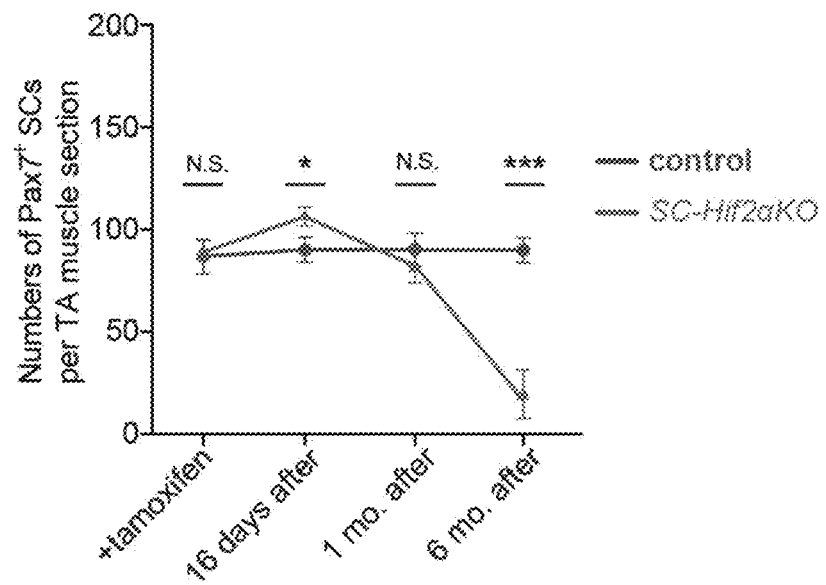
FIG. 2G is a line graph showing the numbers of Pax7$^+$ SCs per TA muscle section from SC-HIF2αKO mice and control littermates (n=3 mice/group) on the same day of tamoxifen induction (+tamoxifen), at 16 days, 1 month and 6 months after tamoxifen induction.

To confirm that satellite cells exit quiescence and proliferate after HIF-2α ablation, EdU was administered to SC-HIF2αKO mice at 11-15 days following tamoxifen-induced HIF-2α ablation (FIG. 2D). At 16 days after HIF-2α ablation in SCs, uninjured TA muscles of SC-HIF2αKO mice show increased numbers of Pax7$^+$/Ki67$^+$/EdU$^+$ SCs, compared to the control littermates (FIG. 2F). Proliferation markers Ki67 and EdU were detected only in Pax7$^+$ SCs, consistent with the specificity of HIF-2α ablation in SC compartment. The total SC number in TA muscle increases to ~110% at 16 days after HIF-2α ablation, returns to the normal level at 1 month and reduces to ~20% of the normal level after 6 months of HIF-2α ablation (FIG. 2E). The reduction of total SC number is not due to SC apoptosis as no cleaved Caspase 3 was detected in HIF-2α ablated SCs. Therefore, HIF-2α is important for the quiescence and long-term homeostatic maintenance of satellite cells in adult muscle.

Example 3

HIF-2α Stabilization Promotes Quiescence, Self-Renewal and Stemness of Satellite Cells, Yet Impairs Myogenic Differentiation Materials and Methods Satellite Cell/Myofiber Transplantation Myofibers were isolated from tamoxifen-induced Pax7$^{cre/ERT2}$;R26R$^{CAG-Sun1/sfGFP}$ (SC-INTACT) mice and cultured for 12 hrs. Single myofibers were then transfected with pcDNA3-HIF2αTM plasmid or control empty pcDNA3 plasmid using Lipofectamine 3000 (Thermo Fisher Scientific). 6 hrs after transfection, 10 transfected myofibers were briefly washed, loaded into a 28-gauge insulin syringe and injected into each TA muscle that was damaged by CTX 24 hrs before transplantation.

Myoblast Culture, Transfection and Differentiation

Primary myoblasts were isolated from 1 week old C57BL/6 male mice as described before (Motohashi, et al., J Vis Exp., 8(86). doi: 10.3791/50846 (2014)). Primary myoblasts were cultured on collagen-coated petri dishes (Roche) in HAM's F10 medium supplemented with 20% FBS, 50 μg/ml basic FGF and 1% penicillin-streptomycin-neomycin under 21% $pO_2$ and 5% $CO_2$. C2C12 myoblasts were purchased from ATCC and cultured in DMEM (4.5 g/L glucose) medium supplemented with 10% FBS and 1% penicillin-streptomycin-neomycin under 21% $O_2$ and 5% $CO_2$. C2C12 myoblasts were transfected with pCMEGIP-HIF2αTM or control empty pCMEGIP plasmids using TransIT-X2 (Mirus Bio.). To differentiate C2C12 myoblasts, cells were cultured to reach 80% confluency and further cultured in DMEM (4.5 g/L glucose) medium supplemented with 2% horse serum for 5 days.

Cell Cycle Analysis of Primary Myoblasts

Primary myoblasts were infected with lentivirus packaged from pCMEGIP-HIF2αTM plasmid or control pCMEGIP empty plasmid. 3 days after lentivirus infection, primary myoblasts were treated with puromycin (0.5 μg/ml) to select infected myoblasts. 1 week after puromycin selection, primary myoblasts were harvested, fixed with 70% ethanol for 10 mins and stained with Hoechst 33342 (10 μg/ml). Primary myoblasts were analyzed on a HyperCyAn flow cytometer (Beckman Coulter) equipped with 405 nm, 488 nm and 633 nm lasers (UGA CTEGD Cytometry Laboratory). Cells of different cell cycle phases were calculated by FlowJo v10 software.

Fluorescence Activated Cell Sorting (FACS)

Satellite cell sorting was performed on a MoFlo XDP cell sorter (Beckman Coulter) equipped with 405 nm, 488 nm, 561 nm and 633 nm lasers (UGA CTEGD Cytometry Laboratory). GFP$^+$ satellite cells (~$2 \times 10^5$) were FACS-sorted from 3 mo. old SC-INTACT and SC-INTACT-HIF2αKO mice (1 week after tamoxifen induction) following an established protocol (49).

Results

Figure 3A:
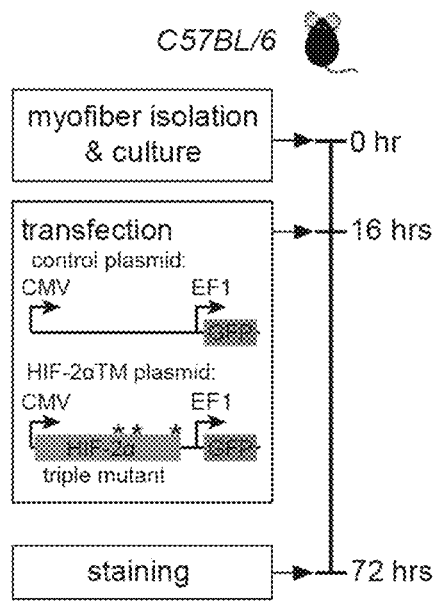
FIG. 3A is a diagram depicting the experimental scheme for stabilization of HIF-2α in SCs cultured under normoxia.
Figure 3B:
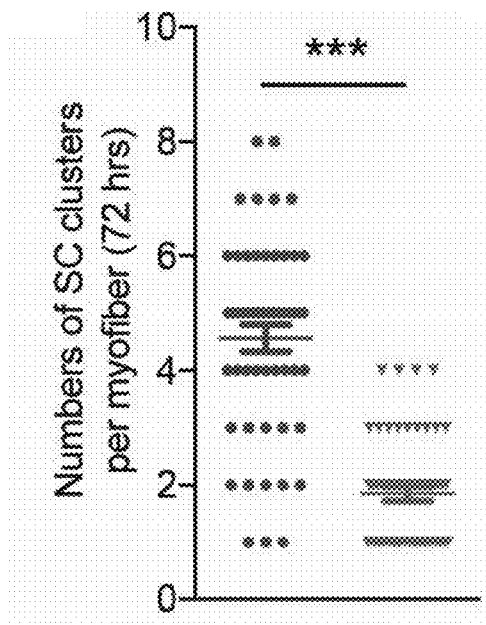
FIGS. 3B-3F are dot plots showing numbers of SC clusters (3B), Pax7$^+$ SC per cluster (3C), Pax7$^+$/MyoD$^-$ (3D), Pax7$^+$/MyoD$^+$ (3E), and Pax7$^-$/MyoD$^+$ (3F), SCs per SC cluster (n>50) ((-●-) control, (-▼-) HIF-2αTM+GFP).
Figure 3C:
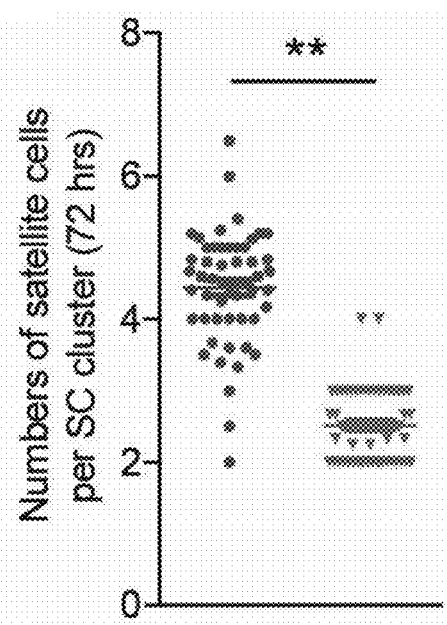
Figure 3D:
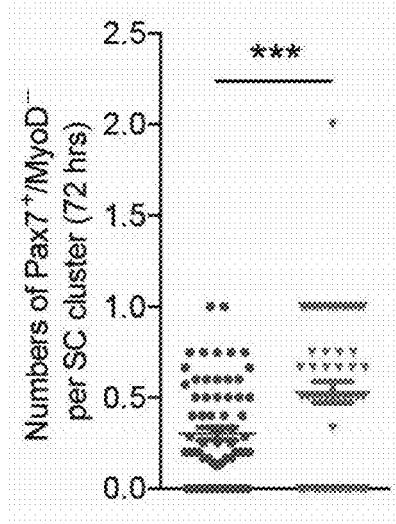
Figure 3E:
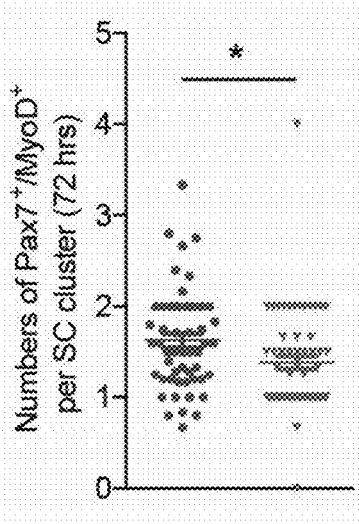
Figure 3F:
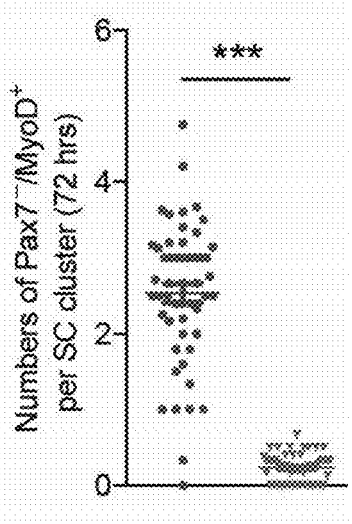
Figures 3J, 3K:
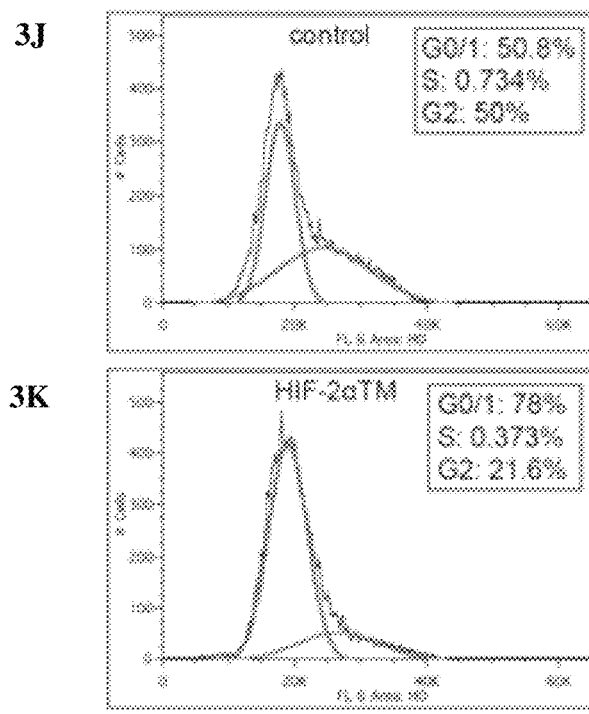
FIGS. 3J-3K are histograms of Hoechst 33258 intensity distribution in control (3J) and HIF-2αTM transfected primary myoblasts and results of cell cycle analysis (3K) (FlowJo).
Figure 3L:
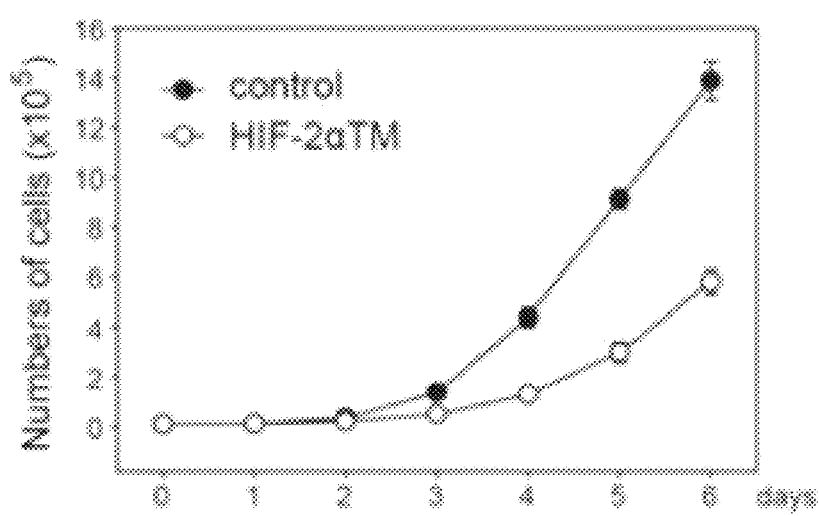
FIG. 3L is a line graph showing the numbers of control (-●-) and HIF-2αTM-transfected (-o-) primary myoblasts (1×10$^4$ seeded at day 0; n=6 replicates) after 1-6 days culture under normoxia.

Cultured satellite cells (myoblasts) have increased doubling time and engraftment efficiency (stemness), yet impaired myogenic potential under hypoxia (Liu, et al., Development, 2012; 139(16):2857-65 (2012); Majmundar, et al., Mol Cell Biol., 32(1):36-49 (2012)). Whether HIF-2α mediates the profound hypoxic effects remains unclear. Thus, experiments were designed to investigate whether stabilization of HIF-2α in SCs on single myofibers cultured under normoxia (21% $pO_2$) is sufficient to mimic the hypoxic effects. After 72-hrs of normoxic culture, SC clusters form on single myofibers due to the activation and proliferation of individual SCs originally on the myofibers. Unlike the nuclear localization of Pax7 and MyoD transcription factors, HIF-2α localizes in the cytoplasm of cultured SCs, consistent its degradation under normoxic conditions. To stabilize HIF-2α under normoxia, SCs on cultured single myofibers were transfected with a plasmid expressing green fluorescent protein (GFP) and a triple mutated form of HIF-2α (HIF-2αTM, carrying P405A, P530V and N851A mutations of mouse HIF-2α), which is resistant to oxygen-induced hydroxylation and proteasome degradation (Hu, et al., Mol Biol Cell, 18(11):4528-42 (2007)) (FIG. 3A). After 72-hours of normoxic culture, control myofibers transfected with GFP only have attached clusters of GFP+ SCs (~4.6 clusters per myofiber and ~4.3 GFP+ SCs per cluster on average; FIG. 3B). In contrast, myofibers that were transfected with HIF-2αTM have markedly reduced number and size of GFP+ SC clusters (~1.9 clusters per fiber and ~2.5 SCs per cluster on average; FIGS. 3B-C). This indicates that HIF-2α maintains quiescene by impeding SC activation and proliferation. Consistent with this, transfection of HIF-2αTM in primary myoblasts under normoxic culture increases the percent of cells in G0/G1 phases, while decreasing the percent of cells in G2/S phases (FIGS. 3J-3K), resulting in a significantly decreased proliferation rate (FIG. 3L).

To assess the impact of HIF-2α stabilization on SC self-renewal and differentiation, SC clusters cultured on single myofibers (72 hrs) were stained with Pax7 and MyoD (FIGS. 3A-3F). Compared to the control myofibers, HIF-2αTM-transfected myofibers have increased numbers of Pax7+/MyoD− self-renewing SCs (HIF-2αTM: 0.6 vs. control: 0.35 cells per cluster) yet decreased numbers of Pax7−/MyoD+ committed myogenic SCs (HIF-2αTM: 2.6 vs. control: 0.4 cells per cluster). These differences indicate that HIF-2α stabilization impairs myogenic differentiation but promotes self-renewal in SCs.

To confirm the negative impact of HIF-2α on myogenic differentiation, C2C12 myoblasts were transfected with the plasmids expressing HIF-2αTM and GFP or GFP alone, differentiated in 2% horse serum for 5 days and stained for Pax7 and myosin heavy chain (MyHC). Myoblasts transfected with the control plasmid (GFP+) are either Pax7+/MyHC− (self-renewed reserve cells) or Pax7−/MyHC+ (differentiated myocytes). In contrast, cells transfected with HIF-2αTM (GFP+) are almost exclusively Pax7+/MyHC−, indicating stablized HIF-2α expression impedes myogenic differentiation.

The improved quiescence and self-renewal of satellite cells/myoblasts after HIF-2αTM transfection suggest that modulating HIF-2α activity may facilitate the engraftment efficiency of satellite cells after transplantation (maintenance as stem cells). To assess this potential effect, single myofibers (and residing SCs as donor cells) were isolated from tamoxifen-induced Pax7$^{cre/ERT2}$;R26R$^{CAG\text{-}Sun1/sfGFP}$ mice (hereafter called SC-INTACT mice). The specific presence of nuclear membrane located GFP (nmGFP) in SCs of SC-INTACT mice allows us to trace the location and fates of transplanted SCs (Deal, et al., Dev Cell, 18(6):1030-40 (2010)). The myofibers were transfected with control and HIF-2αTM plasmids (no GFP expression) and transplanted into cardiotoxin (CTX)-injured TA muscles (1 dpi) of cognate C57BL/6 host mice (3 mo. old; FIG. 3G).

Figure 3M:
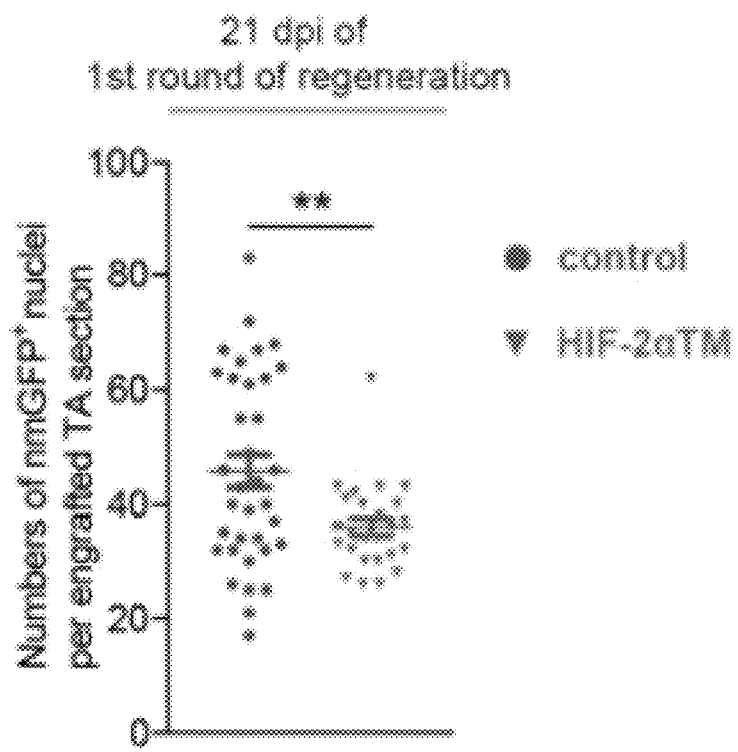
FIG. 3M is a dot plot showing the numbers of nmGFP+ nuclei (derived from donor SCs transfected with control or HIF-2αTM plasmids) per TA muscle section after SC/myofiber engraftment (at 21 dpi of 1st round of regeneration).

Twenty-one days after transplantation, nmGFP+ nuclei locate in both niche-residing Pax7+ self-renewed SCs (immediately adjacent to Laminin B2+ basal lamina) and Pax7− differentiated myonuclei (at the center of the sections of regenerated myofibers), representing two distinct fates of donor SCs. HIF-2α transfection results in increased percentages of nmGFP+/Pax7+ engrafted SCs in total SC pool (control: 2.5% vs. HIF-2α: 4.8%; FIG. 3H), indicating HIF-2α improves the stemness of SCs. The total number of nmGFP+ engrafted nuclei (including SC nuclei and myonuclei) after HIF-2αTM transfection is slightly lower than the control (control: 45 per section vs. HIF-2αTM: 38 per section; FIG. 3M), consistent with functions of HIF-2α in promoting SC quiescence. To further confirm that HIF-2α improves SC stemness and their function in supporting muscle repair, regenerated TA muscles that received SC engraftment (at 30 dpi) with CTX were injured for a second time. Thirty days after the second round injury, the TA muscles that originally engrafted HIF-2αTM-transfected SCs have a pronounced increase of nmGFP+/Pax7+ donor-originated SCs in the total SC pool (control: 2.1% vs. HIF-2αTM: 11.6%; FIG. 3I). This indicates that engrafted donor SCs are able to proliferate, self-renew and support muscle repair.

Example 4

Genetic Ablation of HIF-2α Promotes SCs Expansion During Muscle Regeneration

Figure 4A:
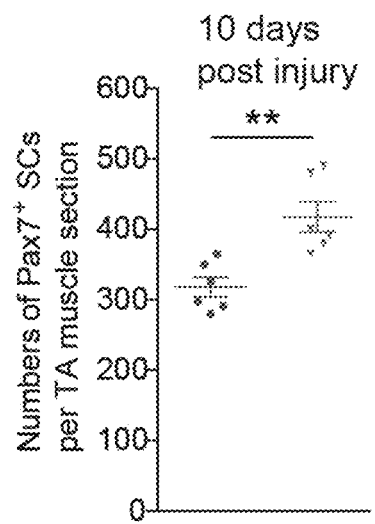
FIGS. 4A-4B are dot plots showing Pax7$^+$ SCs per TA muscle section at 10 dpi (4A) and 21 dpi (4B) (n=6) ((-●-) control, (-▼-) SC-HIF2αKO).
Figure 4B:
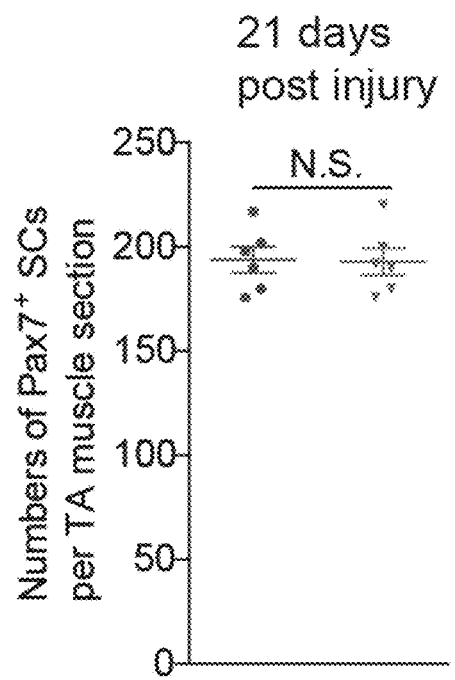
Figures 4C, 4D, 4E:
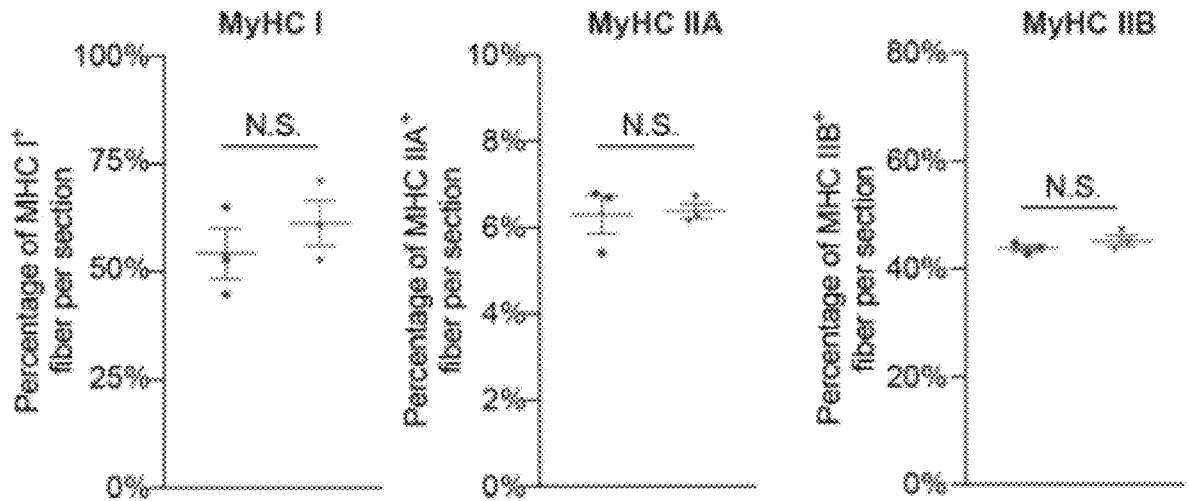
FIGS. 4C-4E are dot plots showing the percentages of myofibers positive for type I MyHC (4C), type IIA MyHC (4D), or type IIB MyHC (4E) ((-●-) control, (-▼-) SC-HIF2αKO).

Next, the impact of HIF-2α ablation on muscle regeneration was investigated. Eccentric contraction-induced injury is of physiological relevance; however, the universally diminished HIF-2α expression in SCs after injury negates the necessity of genetic HIF-2α ablation in this injury model. Unlike contraction-induced injury, HIF-2α expression dampens but is still weakly present in many SCs at 3 days post CTX-induced injury (3 dpi; C57BL/6 mice, 3 mo.); meanwhile, most SCs (along with many Pax7− cells) express HIF-1α. Thus, TA muscle regeneration was examined following CTX-induced injury in SC-HIF2αKO mice and their control littermates. SC-specific HIF-2α ablation in SC-HIF2αKO mice leads to increased number of Pax7+ SCs at 10 dpi, compared to control littermates (control: ~320 SCs vs. SC-HIF2αKO: ~420 SCs per TA section; FIGS. 4A-B). The numbers of Pax7+ SCs are comparable between SC-HIF2αKO and control mice at 21 dpi (FIGS. 4A and 4B), indicating that augmented myogenic differentiation of SCs occurs following a better SC expansion. Consistently, embryonic myosin heavy chain (eMyHC), which transiently expresses in newly formed/regenerating myofibers, exists abundantly in many myofibers in the control mice at 10 dpi, yet already diminishes in most myofibers in SC-HIF2αKO mice. The percentage of myofibers expressing myosin heavy chain isoforms I, IIA and IIB are comparable between SC-HIF2αKO and control mice (FIGS. 4C-4E), indicating that SC-specific HIF-2α ablation does not alter myofiber type composition during muscle regeneration.

Example 5

Pharmacological Inhibition of HIF-2α Accelerates Muscle Regeneration

Materials and Methods
Sirius Red Staining
Muscle sections were stained with Sirius red solution (0.1% in picric acid) for 15 mins, washed with 1% acetic acid for 3 times. Sections were mounted with Cytoseal™ 60 mounting medium (Thermo Fisher Scientific), followed with imaging.
HIF-C2
HIF-C2 (N-(3-chloro-5-fluorophenyl)-4-nitrobenzo[c][1,2,5]oxadiazol-5-amine) is a potent and selective allosteric inhibitor of hypoxia inducible factor-2 (HIF-2). It binds within the internal cavity of HIF-2α PAS-B (Kd of 81 nM) and disrupts heterodimerization of the full-length HIF-2 transcription factor. HIF-C2 functions effectively as a HIF-2 inhibitor in living cells, disrupting HIF-2 DNA binding and inhibiting the transcription of its target genes. Moreover, HIF-C2 is selective for the HIF-2 isoform and has no activity to antagonize HIF-1.

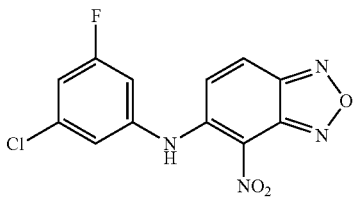

HIF-2C

```
HIF-2α shRNA #1 oligo
                                      (SEQ ID NO: 18)
5'TGCTGTTGACAGTGAGCGAACACTTGATGTGGAAACGTATTAGTGA
AGCCACAGATGTAATACGTTTCCACATCAAGTGTGTGCCTACTGCCT
CGGA-3'

HIF-2α shRNA #2 oligo
                                      (SEQ ID NO: 19)
5'TGCTGTTGACAGTGAGCGATCCAACAAGCTGAAGCTAAAGTAGTG
AAGCCACAGATGTACTTTAGCTTCAGCTTGTTGGACTGCCTACTGCCT
CGGA-3'
```

Results

Figure 5A:
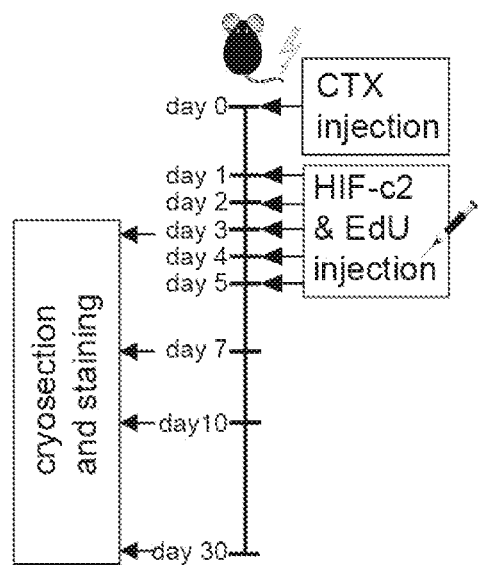
FIG. 5A is diagram depicting the experimental scheme for pharmacological inhibition of HIF-2α in muscle regeneration.
Figure 5B:
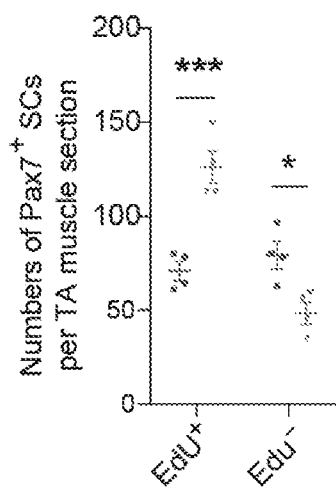
FIG. 5B is a dot plot showing the numbers of Pax7+/EdU+ and Pax7+/EdU− SCs per TA muscle section at 3 dpi (n=4) ((-●-) DMSO, (-▼-) HIF-c2).
Figure 5C:
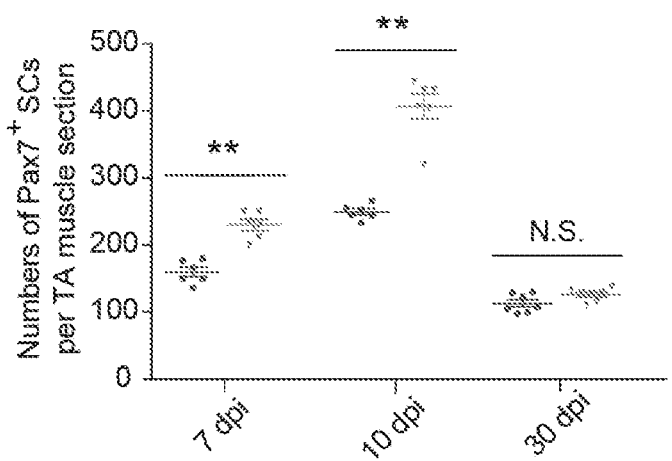
FIG. 5C is a dot plot showing the numbers of total Pax7+ SCs per TA muscle section at 7 dpi (n=6), 10 dpi (n=6) and 30 dpi (n=7) ((-●-) DMSO, (-▼-) HIF-c2).

A transient inhibition of HIF-2α following muscle injury may benefit muscle regeneration by promoting SC proliferation, yet lessening the side-effect on SC self-renewal. To transiently inhibit HIF-2α in muscle, a HIF-2α inhibitor was administered intramuscularly (HIF-c2, CAS #:1422955-31-4; 5 mg/injection/day, 3 consecutive days), which reduced HIF-2α expression in muscle (including SCs) as reported (Scheuermann, et al., Nat Chem Biol., 9(4):271-6 (2013)). To investigate effects of HIF-2α inhibition on muscle regeneration, HIF-c2 or the carrier solution (1% DMSO) was administered into CTX-injured TA muscles of C57BL/6 mice (daily injections between 1-5 dpi; FIG. 5A). EdU was administrated in the same mice to trace cell proliferation. HIF-c2 treatment results in increased Pax7$^+$/EdU$^+$ activated SCs at 3 dpi and increased total number of Pax7$^+$ SCs at 7 dpi and 10 dpi (FIGS. 5B-5C). At 7 dpi, HIF-c2 treated muscles show reduced expression of HIF-2α, MyoD and eMyHC as well as improved myofiber regeneration.

Figure 5D:
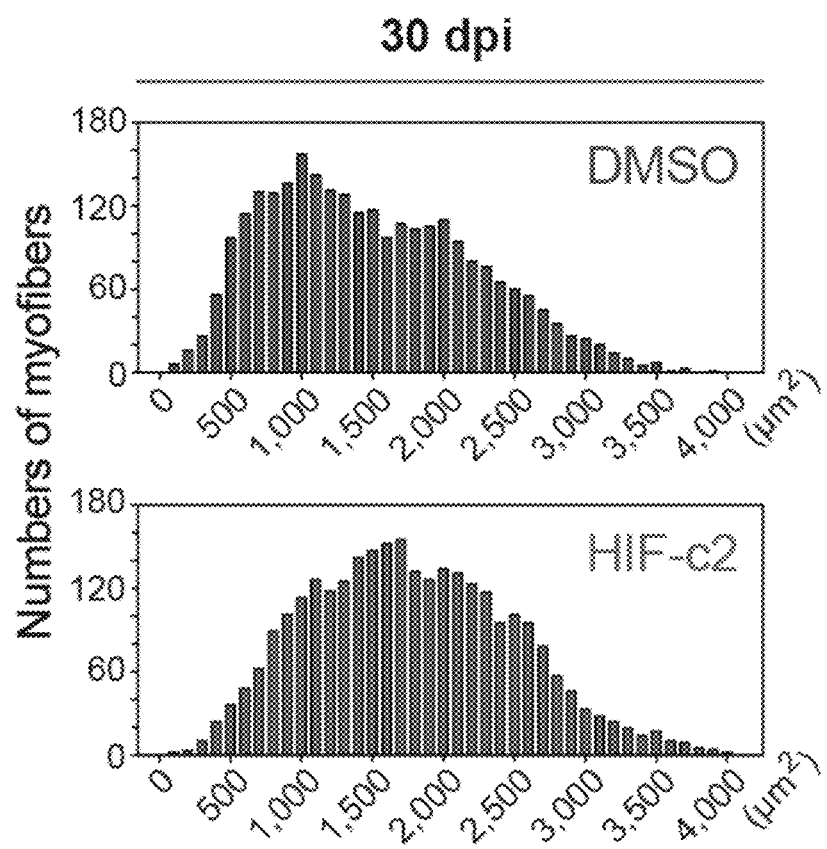
FIG. 5D is a pair of graphs showing the distribution of myofiber cross-sectional areas of HIF-c2 or DMSO treated TA muscles at 30 dpi (n=3).
Figure 5E:
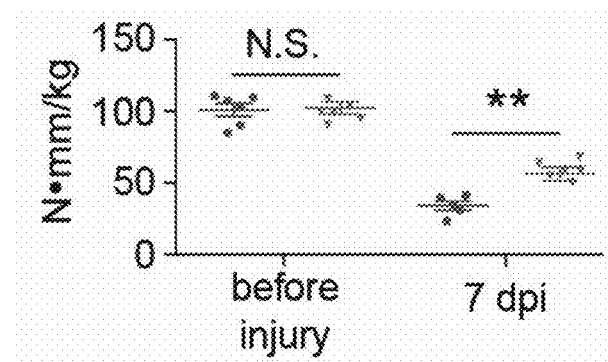
FIGS. 5E-5G are dot plots showing maximal torque of uninjured TA muscles and HIF-c2 or DMSO treated TA muscles at 7 dpi (n=6) (5E), 10 dpi (n=3) (5F) and 30 dpi (n=3) (5G).
Figure 5F:
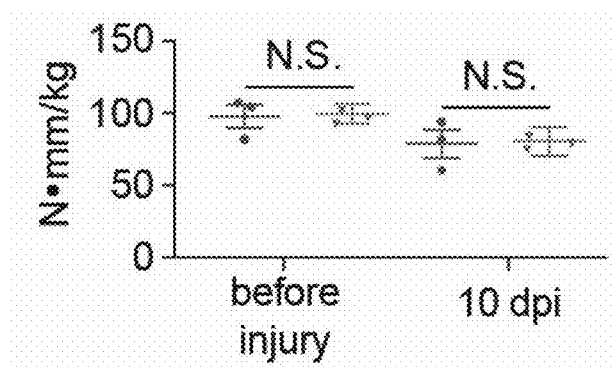
Figure 5G:
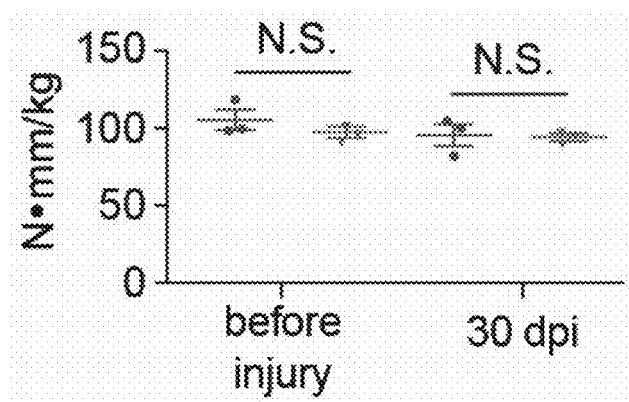
Figures 5H, 5I, 5J:
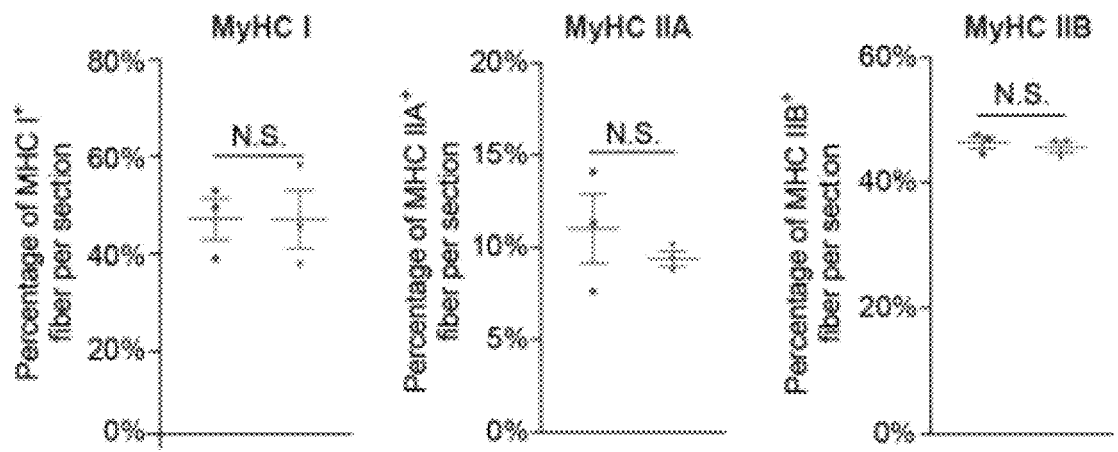
FIGS. 5H-5J are dot plots showing the percentages of myofibers positive for type I MyHC (5H), type IIA MyHC (5I), or type IIB MyHC (5J) ((-●-) control, (-▼-) HIF-c2).

To prove HIF-c2 treated muscles have improved contractile function, maximal torque generated by the regenerating muscles was measured following peroneal nerve stimulation (Call, et al., Methods Mol Biol., 1460:3-18 (2016)). At 7 dpi, HIF-c2 treated muscles (n=6) recover ~53% of the maximal torque measured before injury; whereas the control muscles only recover ~32% of the torque (FIG. 5E-5G). At 30 dpi, when muscle regeneration is close to completion, both HIF-c2 treated and control muscles (n=3) contain comparable numbers of Pax7$^+$ SCs and recover ~90% of the strength (FIGS. 5C and 5E-5G), indicating transient HIF-c2 treatment does not affect SC self-renewal or future contractile capacity of regenerated muscle. At 30 dpi, HIF-c2 treated muscles have no overt sign of fibrosis (Sirius red staining for collagen) and similar myofiber type composition as the control muscle (FIGS. 5H-5J), although HIF-c2 treated muscle have increased myofiber cross sectional areas (FIG. 5D). Therefore, transient inhibition of HIF-2α accelerates muscle regeneration.

Example 6

HIF-2α Binds to HREs in Spry1 Promoter and Activates Spry1 Expression

Materials and Methods

Plasmid Construction

For HIF-2α knockdown, HIF-2α shRNA oligos (see below) was synthesized (Integrated DNA Technologies) and cloned into pMSCV-P2GM retrovirus plasmids acquired from Addgene (#19750).

Satellite Cell Nuclei Isolation by Isolation of Nuclei Tagged in Specific Cell Types (INTACT)

SC-INTACT mice were administrated with tamoxifen 1 week before nuclei isolation to induce the expression of sfGFP and myc-tagged Sun1 on satellite cell nuclear membrane. One day before nuclei isolation, 2.5 μg GFP and 2.5 μg Myc antibodies were incubated with protein A Dynabeads (from 50 μl 50% slurry) in 100 μl PBST (PBS containing 0.1% Tween 20) on a rotating platform at 4° C. overnight. To crosslink HIF-2α in situ on chromatin of satellite cells in vivo, SC-INTACT mice were transcardially perfused with 30 ml 0.5% PFA and 30 ml 125 mM glycine as described before (Gage, et al., J Vis Exp., (65) pii: 3564. doi: 10.3791/3564. (2012)). Skeletal muscle was dissected from limbs and trunk regions, grinded in liquid nitrogen in a mortar with matched pestles, and homogenized (15 ml Wheaton dounce, loose pestle) in homogenization buffer (250 mM sucrose, 2 mM MgCl$_2$, 25 mM KCl, 1% NP40) for 30 strokes. Homogenized muscle was filtered by 100 μm and 40 μm cell strainers (Thermo Fisher Scientifics) and centrifuged at 1,000×g, 4° C. for 5 min to collect crude nuclei. Nuclei were resuspended in 10 ml homogenization buffer and loaded on top of a two-step buffer cushion (lower cushion buffer: 500 mM sucrose, 2 mM MgCl$_2$, 25 mM KCl and 40% glycerol; upper cushion buffer: 340 mM sucrose, 2 mM MgCl$_2$, 25 mM KCl and 40% glycerol). The nuclei were centrifuged through buffer cushions in a swing bucket rotor at 1,000×g, 4° C. for 10 min. Nuclei enriched at the interface of upper/lower buffer cushions were collected by long-neck glass Pasteur pipettes and checked under an EVOS fluorescent microscope (Thermo Fisher Scientifics). The above homogenization/centrifugation procedure was repeated until most GFP$^+$ SC nuclei were physically separated from tissue debris or other GFP$^-$ nuclei in the crude nuclei preparation. Crude nuclei were incubated with washed anti-GFP/anti-Myc-coated Dynabeads in INTACT IP buffer (340 mM sucrose, 2 mM MgCl$_2$, 25 mM KCl and 5% glycerol) on a rotating platform (8 rpm/min) at 4° C. for overnight. Immunoprecipitated nuclei (tethered on Dynabeads) were isolated on magnetic stands and washed (~6 times) with PBS to remove the non-bound GFP$^-$ nuclei. After each round of washing, the yield and purity of GFP$^+$ SC nuclei were assessed under the fluorescent microscope (see Figure S6B, after INTACT purification). GFP$^+$ SC nuclei from multiple preparations were pooled and used for HIF-2α chromatin immunoprecipitation (ChIP).

Chromatin Immunoprecipitation (ChIP) Assay and ChIP-qPCR

Satellite cell nuclei purified by INTACT method together with Dynabeads were resuspended in 100 μl lysis buffer (1% SDS, 10 mM EDTA, 50 mM Tris.HCl pH 8.1, 1× protease inhibitor cocktail) and sonicated at 4° C. in a Bioruptor® Pico sonication device (Diagenode) using 5 on/off cycles of 30:30 seconds for 3 rounds (15 on/off sonication cycles in total to reach the average chromatin size ~300 bp). Between each sonication round, sample tubes were vortexed and spinned briefly. The sheared chromatin was 1:10 diluted in IP dilution buffer (50 mM HEPES-KOH pH7.5, 140 mM NaCl, 1 mM EDTA, 1% Triton X-100, 0.1% sodium deoxycholate, 0.1% SDS) and centrifuged at 20,000×g, 4° C. for 10 min. The supernatant was transferred to siliconized tubes and incubated with 2 µg HIF-2α antibody (rabbit, Novurs Bio.) or 2 µg rabbit IgG (Santa Cruz) on a rotating platform at 4° C. overnight. On the next day, PBS-washed protein A Dynabeads (from 30 µl 50% slurry) were added to the chromatin/antibody mix and incubated on a rotating platform at 4° C. for 4 hrs. All ChIP beads were sequentially washed with low salt, high salt, lithium and TE buffer for 2 times/each and reverse-crosslinked with 1M NaCl for 6 hrs at 65° C. Decrosslinked samples were sequentially treated with 10 µg RNase A (Thermo Fisher Scientific) at 37° C. for 0.5 hr and 20 µg Proteinase K (Thermo Fisher Scientific) at 55° C. overnight. ChIPed genomic DNA was purified by phenol/chloroform/isoamyl alcohol (25:24:1) extraction followed by precipitation with 100% isopropanol and glycol blue (Thermo Fisher Scientific) at −20° C. overnight. The following primers were used to quantify relative enrichment levels at HRE flanking regions in the Spry1 promoter:

```
Spry1_promoter S:
                                    (SEQ ID NO: 20)
5'-GAGTGTCCTGGGTTCCTTGC-3'

Spry1_promoter AS:
                                    (SEQ ID NO: 21)
5'-GGCATAATGCATTTGCAAGC-3'
```

The following primers were designed for PCR amplification of gene-lacking regions on chromosome 5 and 6 of mouse genome, which serve as inner reference controls in calculation of relative enrichment levels:

```
Chr5_S:
                                    (SEQ ID NO: 22)
5'-CCCGTCACTCAACCATTTCA-3'

Chr5_AS:
                                    (SEQ ID NO: 23)
5'-CTTATCAATGGGGGCTCTGG-3'

Chr6_S:
                                    (SEQ ID NO: 24)
5'-AGATATGGCTGGCTTTGTGC-3'

Chr6_AS:
                                    (SEQ ID NO: 25)
5'-GAACTCGCTCAGGTTCTGC-3'
```

Reverse Transcription and Quantitative Real-Time PCR

For measure relative expression levels, total RNA was isolated from C2C12 myoblasts using TRIzol or from FACS sorted satellite cells using PicoPure RNA Isolation Kit (Thermo Fisher Scientific). 1 µg total RNA from C2C12 myoblasts (or 0.2 µg total RNA from satellite cells) was used in 20 µl reverse transcription reactions (Maxima; Life technologies) and diluted into 100 µl. 2 µl diluted cDNA was used in 8 µl quantitative PCR reactions (SsoAdvanced™ Universal SYBR Green mix; Bio-Rad) on a BioRad CFX384™ Real-Time PCR Detection System. Cq-values were determined and expression values were calculated by BioRad CFX Manager™ Software. Relative expression values were normalized to inner reference genes Rps18 and Tbp of each biological sample. The following primers were used for quantifying expression levels:

```
HIF-2α_S
                                    (SEQ ID NO: 26)
5'-ACATGGCCCCCGATGAAT-3'

HIF-2α_AS
                                    (SEQ ID NO: 27)
5'-CAGGTAAGGCTCGAACGATG-3'

Spry1_S
                                    (SEQ ID NO: 28)
5'-GGATTTGGCCGAGAGTTGTT-3'

Spry1_AS
                                    (SEQ ID NO: 29)
5'-CGGCTAGGAGAAGGACACTA-3'

Calcr_S
                                    (SEQ ID NO: 30)
5'-CGGCGGGATCCTATAAGTTG-3'

Calcr_AS
                                    (SEQ ID NO: 31)
5'-GCGTGGATAATGGTTGGCA-3'

Cd36_S
                                    (SEQ ID NO: 32)
5'-TCCTCTGACATTTGCAGGTC-3'

Cd36_AS
                                    (SEQ ID NO: 33)
5'-AAGGCATTGGCTGGAAGA-3'

Rps18_S
                                    (SEQ ID NO: 34)
5'-CGCCATGTCTCTAGTGATCC-3'

Rps18_AS
                                    (SEQ ID NO: 35)
5'-GGTCGATGTCTGCTTTCCTC-3'

Tbp_S
                                    (SEQ ID NO: 36)
5'-ACTTCGTGCAAGAAATGCTGA-3'

Tbp_AS
                                    (SEQ ID NO: 37)
5'-TCTGGATTGTTCTTCACTCTTGG-3'
```

Protein Extraction and Immunoblotting

Whole cell lysates were prepared by lysing cells in RIPA buffer supplemented with 1×proteinase inhibitor cocktail (Thermo Fisher Scientific). Protein concentration was quantified by BCA assays (Thermo Fisher Scientific). Protein lysates (30 µg) were loaded on 8% SDS-PAGE, transferred to PVDF membrane. Membrane was blocked with 5% non-fat milk/TBST, probed with primary antibodies: HIF-2α (1:1,000; Thermo Fisher Scientific), and β-tubulin (1:5,000; Sigma), incubated with ECL reagents (Santa Cruz) and exposed to x-ray films.

Luciferase Assay

A Spry1 promoter region spanning −341 bp to +39 bp (relative to TSS) was PCR amplified from mouse genomic DNA (from a C57BL/6 male) and cloned into a luciferase plasmid pGL4.18 (Promega). The resultant pGL4.18-Spry1 promoter luciferase plasmid (200 ng) was co-transfected with pcDNA3-HIF1αTM, pcDNA3-HIF2αTM or control empty pcDNA3 plasmid (200 ng) into C2C12 myoblasts by TransIT-X2. pcDNA-LacZ (100 ng) expressing β-gal was co-transfected as internal transfection control. 48 hrs later, C2C12 myoblasts were lysate with Luciferase Cell Lysis Buffer (NEB), followed with firefly luciferase/β-gal assay with homemade luciferase and β-gal solutions. Luciferase assay solution: 0.11M Trizma pH7.8, 0.5M $MgCl_2$, 0.1M ATP and 10 mM Luciferin. β-gal solution: 4 mg/ml o-nitrophenyl-β-D-galactoside, 60 mM $Na_2HPO_4$, 40 mM $NaH_2PO_4$, 10 mM KCl, and 1 mM $MgSO_4$.

Results

Figure 6A:
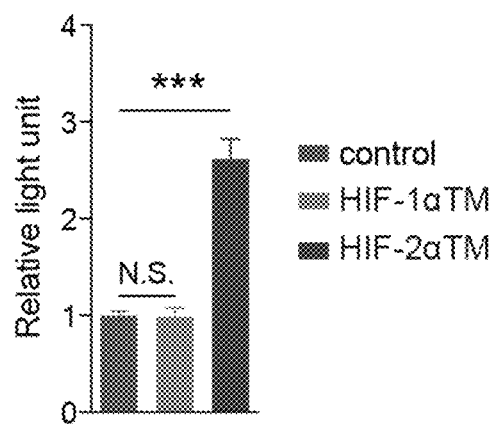
FIG. 6A is a bar graph showing the results of a luciferase assay (measure by relative light unit) indicating that stabilized HIF-2α, but not HIF-1α, transactivates the Spry1 promoter (left-to-right bars represent: control, HIF-1α, HIF-2α).

Next, the molecular mechanism underlying functions of HIF-2α in SC self-renewal was investigated. Recent studies showed that Spry1, a negative regulator of FGF signaling, maintains a functional pool of muscle stem cells by promoting SC self-renewal (Shea, et al., Cell Stem Cell, 6(2):117-29 (2010); Chakkalakal, et al., Nature, 490(7420):355-60 (2012)). Three conserved HREs within the proximal promoter of Spry1 gene were identified. To confirm the Spry1 promoter is responsive to HIF-2α, Spry1 promoter sequence (−361~+39 bp, mouse genome) was cloned upstream to a luciferase ORF and transfected C2C12 myoblasts with this plasmid together with the HIF-2αTM, HIF-1αTM or control empty plasmids. In the luciferase assay, HIF-2α, but not HIF-1α, increases the transcription activity of the Spry1 promoter (FIG. 6A).

Figure 6B:
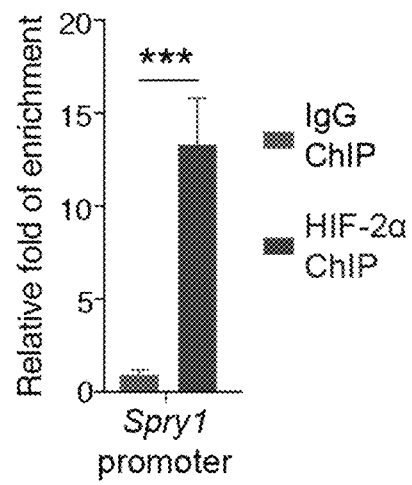
FIG. 6B is a bar showing the results of a chromatin IP and qPCR assay (measured by fold of enrichment) indicating that HIF-2α binds to Spry1 promoter in quiescent SCs in vivo (left-to-right bars represent: IgG ChIP, HIF-2α).

To confirm HIF-2α directly binds to the Spry1 promoter in vivo, HIF-2α chromatin immunoprecipitation (ChIP) was performed using 2×10$^6$ nmGFP$^+$ SC nuclei that were fixed in vivo and isolated from SC-INTACT mice (Methods). ChIP-qPCR revealed ~13-fold of enrichment for HIF-2α on the Spry1 promoter compared to a IgG control (FIG. 6B), indicating HIF-2α directly binds to Spry1 promoter in quiescent SCs in vivo.

Figure 6C:
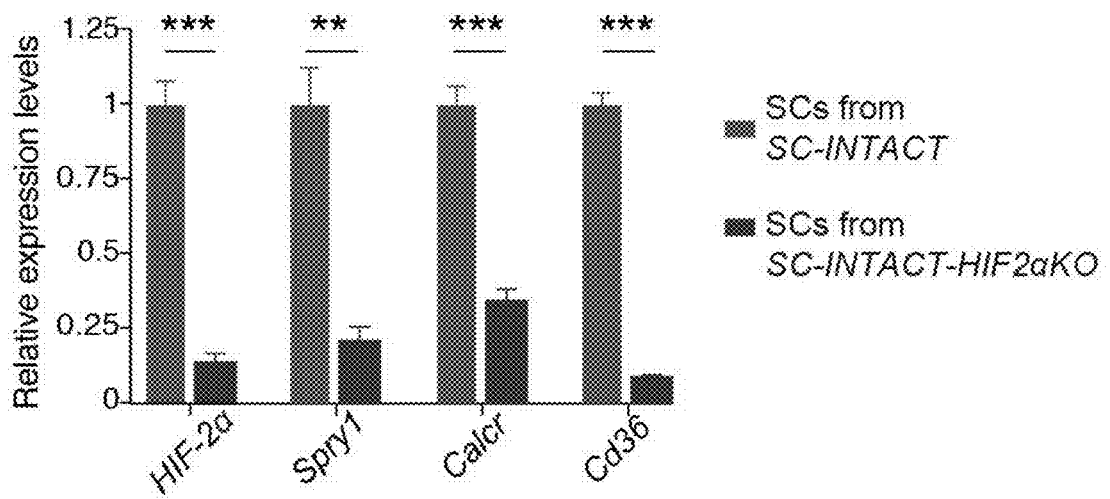
FIG. 6C is a bar graph showing RT-qPCR assays which reveal reduced mRNA levels of HIF-2α, Spry1, Calcr and Cd36 in SCs after HIF-2α ablation (for each pair: SCs from SC-INTACT (left bar), SCs from SC-INTACT-HIP2αKO (right bar)).
Figure 6D:
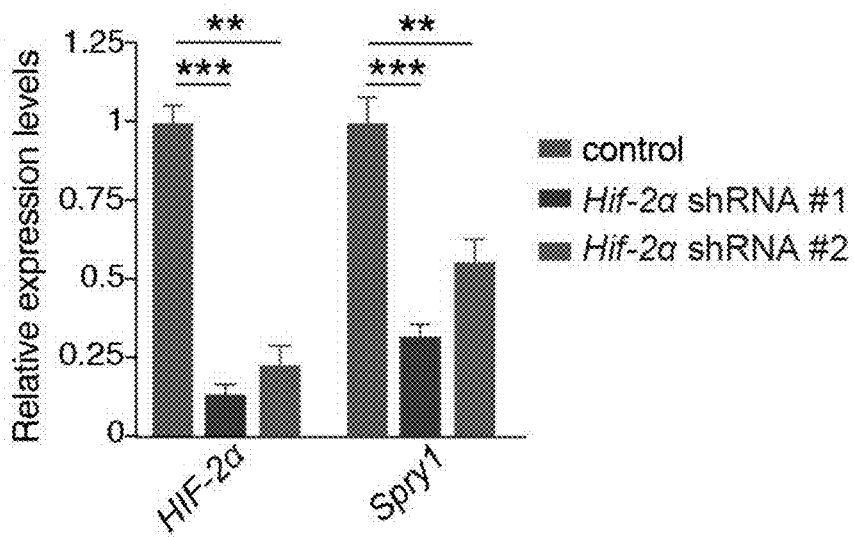
FIG. 6D is a bar graph showing the results of RT-qPCR assays which reveal reduced mRNA levels of HIF-2α and Spry1 in C2C12 myoblasts after HIF-2α shRNA expression (for each group: control (left bar), HIF-2α shRNA #1 (center bar), HIF-2α shRNA #2 (right bar)).
Figure 6E:
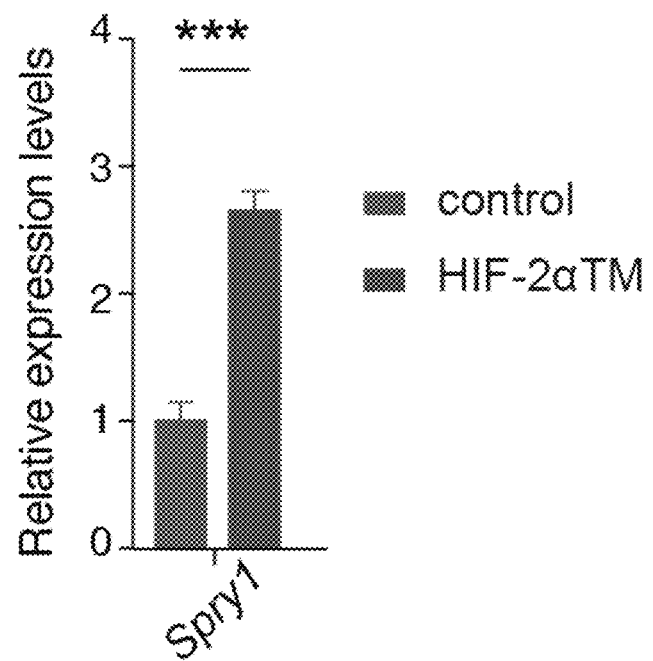
FIG. 6E is a bar graph showing RT-qPCR assays reveal increased mRNA levels of Spry1 after HIF-2α stabilization in C2C12 myoblasts.
Figure 6F:
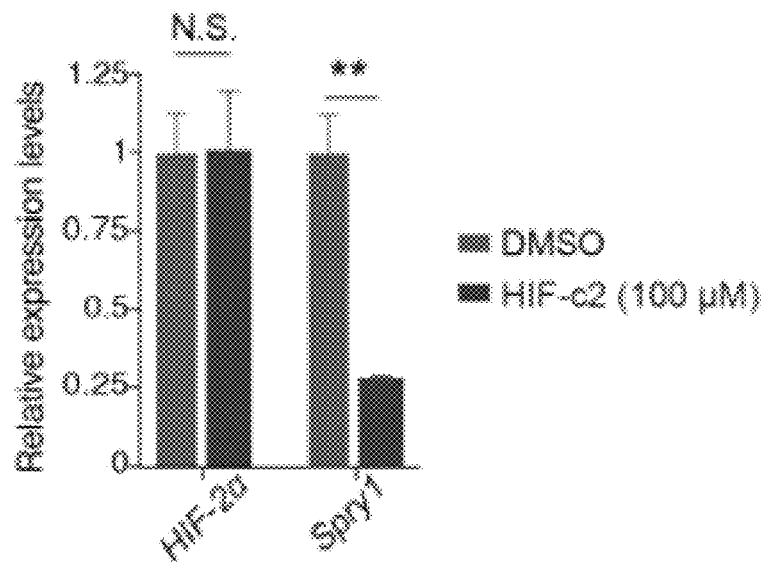
FIG. 6F is a bar graph showing the results of RT-qPCR assays that reveal unchanged HIF-2α mRNA and decreased Spry1 mRNA levels in HIF-c2 (100 μM) treated C2C12 myoblasts (for each pair: SCs from HIF-2α (left bar), SCs from Spry1 (right bar)).
Figures 9A, 9B, 9C, 9D:
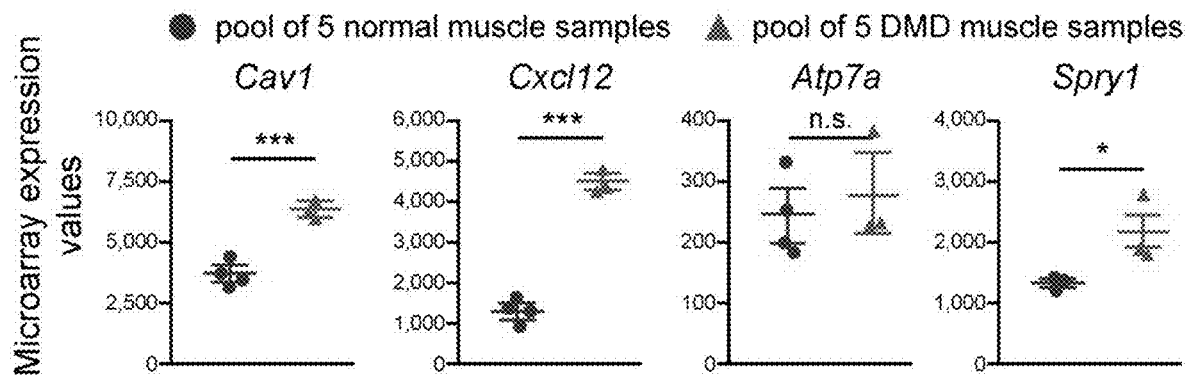
FIGS. 9A-9H are dot plots showing the expression values of HIF-2α-specific target genes in published microarray datasets: Cav1 (9A), Cxc12 (9B), Atp7a (9C), Spry1 (9D) (GSE465 (Chen, et al., *J. Cell Biol.,* 11;151(6):1321-36 (2000)); Cav1 (9E), Cxc12 (9F), Atp7a (9G), Spry1 (9H) (GSE1004 (Haslett, et al., *PNAS,* 99(23):15000-5 (2002)).
Figures 9E, 9F, 9G, 9H:
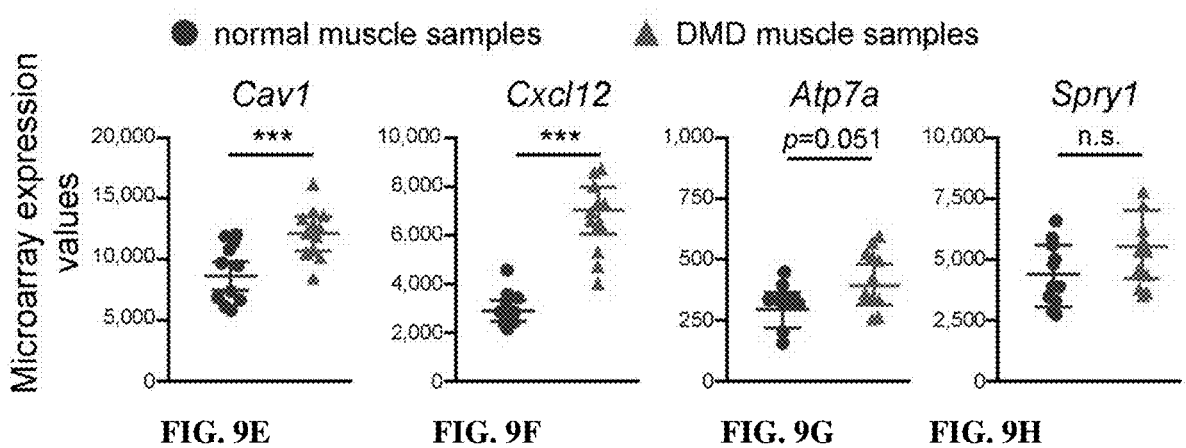

To confirm HIF-2α activates Spry1 expression in SCs, nmGFP$^+$ SCs were isolated from SC-INTACT and SC-INTACT-HIF2αKO mice by Fluorescence Activated Cell Sorting. RT-qPCR detected reduced expression of HIF-2α, Spry1 and two other quiescent SC markers Calcr and Cd36 in SCs from SC-INTACT-HIF2αKO mice comparing to the control SCs from SC-INTACT mice (FIG. 6C) (Ryall, et al., Cell Stem Cell, 16(2):171-83 (2015); Yamaguchi, et al., Cell Rep.,13(2):302-14 (2015)). Under normoxia, C2C12 myoblasts express a low level of HIF-2α; knockdown of HIF-2α expression by siRNAs or inhibition of HIF-2α by HIF-c2 leads to reduced mRNA levels of Spry1 (FIGS. 6D and 6F). Reversely, overexpressing HIF-2αTM in C2C12 myoblasts results in increased mRNA levels of Spry1 (FIG. 6E). Therefore, HIF-2α may regulate SC quiescence and self-renewal through activating Spry1 expression.

The Examples herein uncovers a previously unappreciated hypoxic state of SCs in their native niche and the expression of hypoxia signaling mediator HIF-2α in this adult stem cell population. These findings illuminate roles of HIF-2α in SC function and homeostasis. By temporally-controlled, cell-specific genetic ablation, HIF-2α loss-of-function in adult Pax7$^+$ SCs disrupts their quiescent states and results in failed homeostatic maintenance of adult SCs. Through a pharmacological approach, results show that transient inhibition of HIF-2α immediately after muscle injury benefits muscle regeneration by augmenting SC proliferation and accelerating their differentiation. In normoxic culture, HIF-2α gain-of-function is sufficient to promote SC quiescence, self-renewal and stemness after engraftment. Mechanistically, HIF-2α may function as a transcription factor to activate Spry1 expression in quiescent/self-renewing SCs. Together, these results support a model that HIF-2α is a pivotal mediator of hypoxia signaling that profoundly impacts muscle stem cell behaviors. It has been determined that pO$_2$ in healthy resting skeletal muscle ranges from 25-34 mmHg (Boekstegers, et al., Adv Exp Med Biol.,277: 507-14 (1990); Ikossi, et al., J Trauma, 61(4):780-8; Discussion 8-90 (2006)), which is consistent with the pimonidazole$^{-neg}$ states of myonuclei and sarcoplasm in this study. In contrast, adult SCs are pimonidazole$^{+pos}$, indicating their intracellular pO$_2$ is less than 1.3% (or 10 mmHg) (Das, et al., Stem Cells, 30(8):1685-95 (2012)). In skeletal muscle, SCs are closely adjacent to myofibers and the abundant muscle vasculature (Christov, et al., Mol Biol Cell, 18(4):1397-409 (2007)). Thus, the hypoxic state of SCs is likely not due to the extracellular milieu but rather due to an unknown intracellular mechanism. Intriguingly, SCs retain their viability and regenerative potential under extreme hypoxia/anoxia (Latil, et al., Nat Commun.,3:903 (2012)), implying SCs are adapted to hypoxia.

Mammalian cells sense and cope with hypoxia by stabilizing hypoxia-inducible factors (HIF-1/2/3α). It has been shown that HIF-2α controls chronic hypoxic gene activation under medium-level hypoxia, whereas HIF-1α transiently mediates acute hypoxic responses under extreme hypoxia (Holmquist-Mengelbier, et al., Cancer Cell, 10(5):413-23 (2006)). The Examples herein show that in skeletal muscle, HIF-2α, but not HIF-1α, is stabilized in quiescent SCs; after cardiotoxin-induced injury, HIF-2α expression reduces while HIF-1α is stabilized in activated SCs; yet after contraction-induced muscle injury, HIF-2α expression decreases in activated SCs without HIF-1α stabilization. This distinct expression patterns of HIFs likely reflect differential hypoxic states of SCs in vivo; however, it is important to note that O$_2$-independent mechanisms also should contribute to HIF expression in skeletal muscle. In support of this view, activated SCs remain hypoxic (pimonidazole$^{+pos}$) when HIF-2α expression decreases. Additionally, myonuclei are pimonidazole$^{-neg}$, yet abundant for HIF-2α. O$_2$-independent regulatory mechanisms for HIFs have been reported before: for example, the translation of HIF-2α mRNA (but not HIF-1α mRNA) has been shown to be regulated by insulin receptor-PI3K-mTORC2 pathway and iron response element binding protein 1 (IREBP1) (Mohlin, et al., Cancer Res., 75(21):4617-28 (2015); Toschi, et al., J Biol Chem., 283(50):34495-9 (2008)). Given pivotal functions of HIF-2α in SCs, it would be interesting to further explore regulatory mechanisms of HIF-2α expression in SCs in future studies.

The hypoxic state of adult SCs in their niche implicates that a hypoxic culture condition may more closely mimic the native microenvironment of quiescent SCs. Indeed, previous studies have demonstrated that hypoxic (1% pO$_2$) culture promotes the quiescence, self-renewal and engraftment efficiency of rodent and human myoblasts (Chaillou, et al., FASEB J., 30(12):3929-41 (2016)). Intriguingly, in the present study, these hypoxic effects are replicated by stabilizing HIF-2α expression under normoxia. This favors the hypothesis that a hypoxic niche and HIF-2α expression constitute causal factors for the self-renewal/quiescence of adult SCs in vivo.

Previous studies indicate that HIF-2α (but not HIF-1α) promotes stem cell characteristics in multiple types of cancer stem cells and HIF-2α re-expression suppresses the growth of soft tissue sarcoma (Holmquist-Mengelbier, et al., Cancer Cell, 10(5):413-23 (2006); Koh, et al., Cancer Res., 71(11):4015-27 (2011); Nakazawa, et al., Nat Commun., 7:10539 (2016)). In addition, HIF-2α enhances the stemness of human embryonic stem cells and the reprogramming efficiency of human induced pluripotent stem cells (Das, et al., Stem Cells, 30(8):1685-95 (2012); Mathieu, et al., Cell Stem Cell, 14(5):592-605 (2014)).

Besides identifying a function of HIF-2α in adult stem cells, this study also reveals a mechanistic link between HIF-2α and Spry1, a negative regulator of receptor tyrosine kinase (RTK) signaling and cell proliferation. Previous studies showed that Spry1 plays a central role in inducing self-renewal/quiescence in activated SCs during muscle regeneration (Shea, et al., Cell Stem Cell, 6(2):117-29

(2010); Chakkalakal, et al., Nature, 490(7420):355-60 (2012)). The results suggest that HIF-2α promotes SC self-renewal by directly binding to HREs in the Spry1 promoter and activating Spry1 transcription. Interestingly, HIF-1α does not transactivate the Spry1 promoter—a difference corroborating previous findings that HIF-1α and HIF-2α require distinct co-activators for transcriptional activation (Chen, et al., Mol Cell Biol., 34(6):1085-99 (2014); Pawlus, et al., Oncogene, 33(13):1670-9 (2014)). Notably, genetic ablation of HIF-2α, but not Spry1, leads to a failure of SC homeostatic maintenance (FIG. 2) (Shea, et al., Cell Stem Cell, 6(2):117-29 (2010)). Thus, HIF-2α plausibly activates other targets to maintain SC quiescence. It has been shown that angiopoietin receptor Tie-2 is highly expressed in quiescent SCs and Ang1 binding to Tie-2 restricts the cell cycle entry of SCs (Abou-Khalil, et al., Cell Stem Cell, 5(3):298-309 (2009)). Thus, HIF-2α may maintain the quiescence of SCs via activating Tie-2 expression, a known HIF-2α target in endothelial cells (Takeda, et al., Circ Res., 95(2):146-53 (2004); Tian, et al., Genes Dev.,11(1):72-82 (1997)).

Various types of muscle injury involve distinct levels of damage to muscle vasculature (Hardy, et al., PLoS One,11 (1):e0147198 (2016)) and expectedly differ in hypoxic signals and HIF expression in SCs. The data supports a conclusion that vasculature in regenerative muscle coordinates with SCs via hypoxia signaling to meet distinct needs for SC proliferation. Understanding the hypoxia signaling in regenerative muscle sheds light on specific therapeutic strategies for muscle injuries complicated with different levels of hypoxia and ischemia. In this study, demonstrates that HIF-2α loss-of-function benefits muscle regeneration after cardiotoxin-induced injury, which involves vasculature damage/remodeling and heterogeneous HIF-2α reduction in activated SCs. HIF-2α ablation or transient inhibition augments SC proliferation and accelerates myogenic differentiation, apparently alleviates a negative impact of hypoxia/ischemia on muscle regeneration capacity. The total number of self-renewed SCs is not affected by HIF-2α ablation/inhibition after one round of muscle regeneration, which is likely owing to increased SC expansion.

In comparison, SC-specific HIF-1α ablation has been shown to increase myogenic differentiation without an effect on SC expansion following ischemic muscle injury (Majmundar, et al., Development, 142(14):2405-12 (2015)). In addition, SC-specific ablation of both HIF-1α and HIF-2α has been shown to impair muscle regeneration with reduced SC expansion and self-renewal (Yang, et al., J Biol Chem., 292(14):5981-91 (2017)). The findings that HIF-2α stabilization promotes SC quiescence and self-renewal are consistent with these previous observations, and together, support that HIF-1α and HIF-2α play distinct roles in SCs during muscle regeneration. This corroborates the emerging notion that HIF-1α and HIF-2α, although both induced by hypoxia, exert distinct and sometimes opposite functions (Keith, et al., Nat Rev Cancer, 12(1):9-22 (2011)). Previous studies have reported that Myogenin Cre-mediated HIF-2α ablation during embryonic myogenesis results in myofiber switching from slow to fast types (Rasbach, et al., Proc Natl Acad Sci USA, 107(50):21866-71 (2010)) and muscle regeneration with HIF-1α ablation ends in muscle fibrosis (Majmundar, et al., Development, 142(14):2405-12 (2015)). In this study, these side-effects following transient HIF-2α inhibition in regenerative muscle were not observed. Given the accelerated recovery of muscle strength, the evidence supports a conclusion that transient HIF-2α inhibition represents an appealing strategy to improve muscle regeneration.

Example 7

HIF-2α Inhibitor Completely Reversed the Detrimental Effects of Hypoxia on Muscle Regeneration For data presented in Examples 7-11, the all values in the figures represent mean±s.e.m with >=3 biological replicates. Statistical significance was determined by Prism GraphPad 6 using Student's t-test (two-sided). *: p<0.05, : p<0.01, *: p<0.005, n.s.: not significant (p>=0.05).

Previous studies showed that hypobaric hypoxia (10% pO2, 0.48 atm) impairs muscle regeneration; on the other hand, episodic hyperbaric hyperoxia (100% pO2, 2.5 atm) improves SC proliferation and muscle regeneration (Chaillou et al., Pflugers Arch 466, 587-598, doi:10.1007/s00424-013-1336-7 (2014), Horie et al., J Appl Physiol (1985) 116, 149-155, doi:10.1152/japplphysiol.00235.2013 (2014)). To gain insights on hypoxic effect on muscle regeneration, wildtype B6 mice (12-week old) were treated with eubaric hypoxia (17% pO2, 1 atm) in hypoxia chamber for 4 weeks and injected with CTX (0.5 nmol, 100 µL) into tibialis anterior (TA) muscles at day 18. Mice under normoxia (21% pO2, 1 atm) were injured with CTX as a control.

To assess if HIF-2α inhibition benefits regeneration under experimental hypoxia, HIF-2α inhibitor HIF-C2 (5 mg in 0.1% DMSO) or vehicle (0.1% DMSO) were intramuscularly administered to the injured muscles at days 2, 3 and 4 post-injury (2-4 dpi). The results show that hypoxia exposure impaired muscle regeneration as evidenced by the presence of necrotic/degenerative myofibers and reduced number of MuSC at 10 dpi (FIG. 8A). Importantly, HIF-C2 treatment increased MuSC number and improved the regeneration under hypoxia (FIG. 8A). Consistent with satellite cell numbers, hypoxia reduced the percentage of Ki67+ proliferating satellite cells in regenerative muscle whereas HIF-C2 treatment under hypoxia not only negated the hypoxia effect but also even improved satellite cell proliferation under hypoxia to a level better than the normoxic condition (FIG. 8B). These results indicate that HIF-2α inhibition is a promising therapeutic strategy to treat hypoxia-impaired muscle regeneration in muscular dystrophy.

Example 8

HIF-2α is Abnormally Stabilized in Muscles of Mouse Models with Severe Types of Muscular Dystrophy To understand whether muscle tissue hypoxia is a latent co-morbidity of muscular dystrophy, immunoblotting was performed on gastrocnemius (GA) muscle samples collected from mdx/utrn+/− and mdx/utrn−/− mice (14-week old) as well as age-matched mdx mice (littermate controls from mdx/utrn+/− mating pairs in B6.129 background) and B6.129 wildtype mice. The resuls show that HIF-2α was abundantly expressed in GA muscles of both male and female of mdx/utrn+/− and mdx/utrn−/− dKO mice, but not in control B6.129 mice or even mdx mice, indicating HIF-2α is abnormally stabilized in the muscle of mice with severe dystrophic phenotypes. In contrast, HIF1A was highly expressed in B6.129 wildtype mice, mdx male mice, and mdx/utrn+/− female mice, but not in mdx/utrn+/− male mice or mdx/utrn−/− dKO mice, consistent with the results discussed above showing HIF1A and HIF-2α have opposite effects on satellite cell proliferation and differentiation.

To understand whether HIF-2α stabilization is a common co-morbidity of many severe types of muscular dystrophy, the immunoblotting was repeated with GA muscle samples collected from Myf5-Cre;FktnL/L mice (14-week old), which also showed severe muscular dystrophy pathologies as mdx/utrn+/− and mdx/utrn−/− dKO mice. Consistently, HIF-2α was abnormally stabilized in both male and female Myf5-Cre;FktnL/L mice, but not in the littermate controls. HIF1A also showed the converse expression patterns. Thus, these results indicate that HIF-2α stabilization, a result of muscle tissue hypoxia, is a common co-morbidity of severe types of muscular dystrophy.

To implicate HIF-2α stabilization in human patients, expression values of HIF-2α-specific target genes (Cav1, Cxcl12, Atp7a, and Spry1 intoduced above), from published microarray datasets (GSE465, GSE1004) for DMD patients (FIGS. 9A-9H) were analyzed. HIF-2α mRNA level were not a focus because HIF-2α is regulated at protein stability level. All HIF-2α target genes showed elevated expression in DMD patient muscle samples, comparing to normal people (FIGS. 9A-9H). This analysis indicates that HIF-2α stabilization also occurs in human DMD patients.

Example 9

Intramuscular HIF-2α Inhibitor Administration Augmented the Regeneration Capacity in Dystrophy Muscle To reveal the potential therapeutic effects of HIF-2α inhibition on muscular dystrophy, the HIF-2α inhibitor HIF-C2 was intramuscularly injected (5 mg/injection; total 3 doses on day 1, day 4, and day 7) into tibialis anterior (TA) muscles of mTR/Mdx mice (2nd generation; males: n=3 and females: n=3; 16-week old). The contralateral TA muscles received vehicle (0.1% DMSO) injections followed the same injection regime. HIF-C2 and vehicle-treated TA muscles were collected for histological examinations at 28 days after the first treatment.

Figures 10A, 10B:
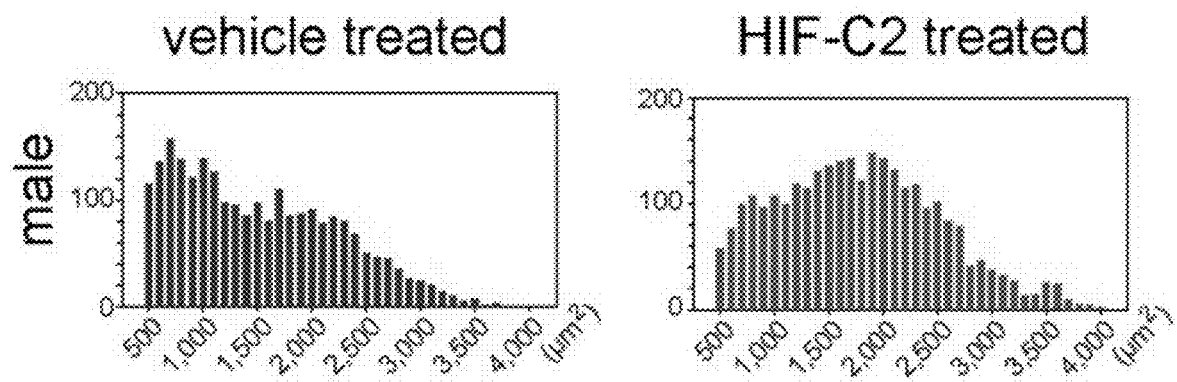
FIGS. 10A-10D are histograms showing the distributions of myofiber cross-sectional areas (CSA) in HIF-C2 (10B, 10D) or vehicle-treated (10A, 10C) TA muscles of male (10A, 10B) and female (10C, 10D) mice.
Figure 10C:
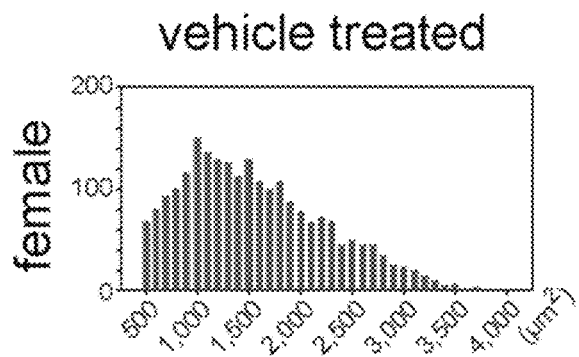
Figure 10D:
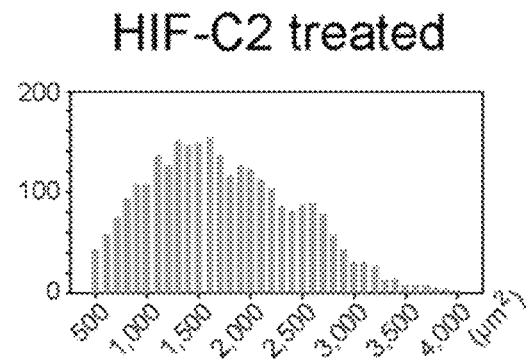
Figure 10E:
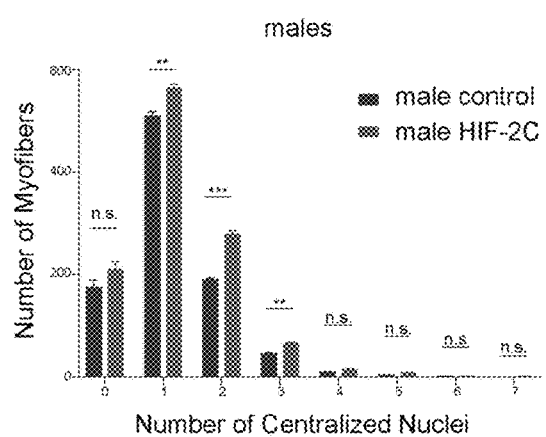
FIGS. 10E and 10F are histograms showing the numbers of myofibers with 0-7 centralized myonuclei in HIF-C2 (right-hand bar for each pair) or vehicle-treated (left-hand bar for each pair) TA muscles in male (10E) and female (10F) mice.
Figure 10F:
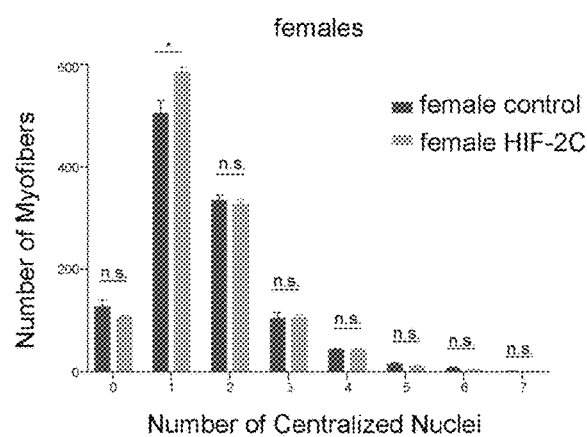
Figure 11A:
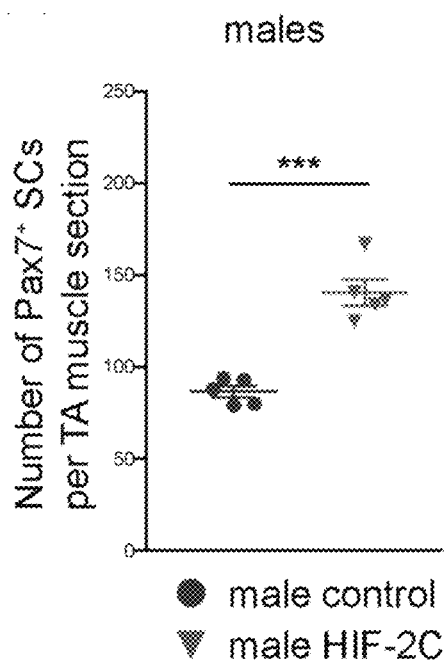
FIGS. 11A-11D are dot plots showing the total numbers of Pax7$^{+pos}$ MuSCs in HIF-C2 or vehicle-treated TA muscles of mTR/Mdx male (11A) and female (11B) mice, and the percentages of Ki67+pos MuSCs in HIF-C2 or vehicle-treated TA muscles of mTR/Mdx male (11C) and female (11D) mice.
Figure 11B:
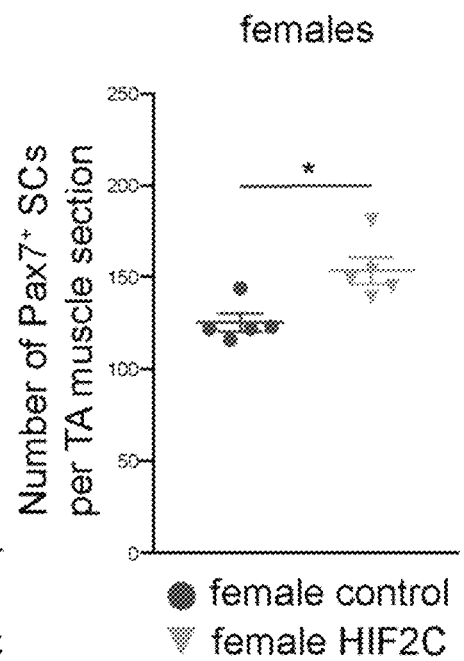
Figure 11C:
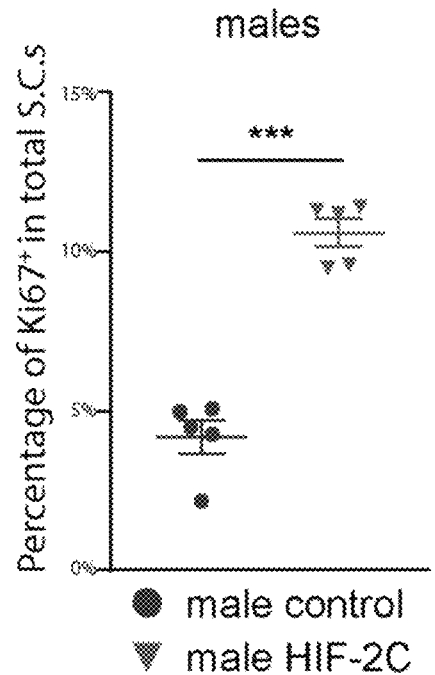
Figure 11D:
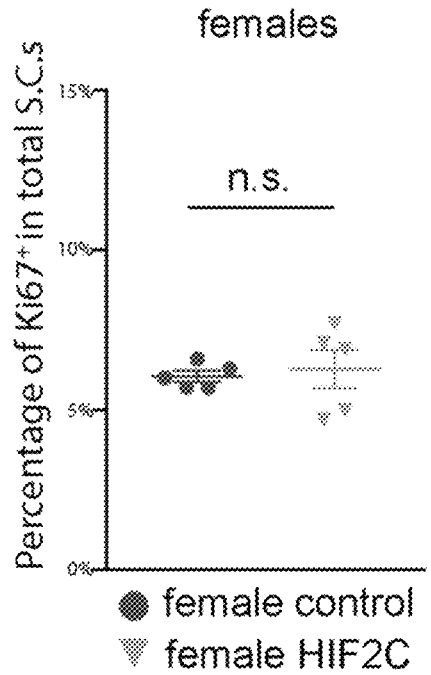

H&E staining of muscle cross-sections showed that the vast majority of myofibers in both HIF-C2 and vehicle-treated TA muscles (from either males or females) contained centralized nuclei, indicative of extensive regeneration activity in these dystrophic muscles. Compared to vehicle-treated control muscles, HIF-C2 treated muscles overtly contained larger myofibers (both males and females). ImageJ analysis of myofiber cross-sectional area (CSA) confirmed the increase of myofiber caliber in HIF-C2 treated myofibers (FIGS. 10A-10D). Intriguingly, the enumeration of the number of centralized nuclei in a myofiber revealed that HIF-C2 treatment also increased the number of centralized nuclei in male but not in female mTR/Mdx mice (FIGS. 10E-10F). As centralized nuclei were derived from the nuclei of differentiated satellite cells, the above increase of centralized nuclei indicated that HIF-C2 treatment augmented the regeneration capacity of dystrophic muscle in male mTR/Mdx mice.

Example 10

Intramuscular HIF-2α Inhibitor Administration Improved Satellite Cell Proliferation in Dystrophic Muscle To investigate whether HIF-C2 improves satellite cell function in mTR/Mdx mice, Pax7 (the definitive marker of satellite cells) and Ki67 (a proliferation marker) immunostaining were carried out on muscle cross-sections and the number of Pax7+pos cells (total number of satellite cells) and Pax7+pos/Ki67+pos cells (proliferative satellite cells) per muscle section were enumerated. For male mTR/Mdx mice, HIF-C2 significantly increased both the total number of satellite cells and the number of proliferative satellite cells (FIGS. 11A-11D). For female mTR/Mdx mice, the total number of satellite cells was elevated in HIF-C2 treated muscle, yet the number of proliferative satellite cells was comparable between HIF-C2 and control muscles at 28 days post-treatment (FIGS. 11A-11D). The above data indicate that HIF-2α inhibition improves satellite cell proliferation in male mdx mice, which is concordant with the augmented regeneration capacity in these mice.

Example 11

Intramuscular HIF-2α Inhibitor Administration Prevented Fibrosis Development in Dystrophic Muscle Muscle fibrosis is one of the characteristic pathological changes of Duchenne muscular dystrophy (Klingler et al., *Acta Myol* 31, 184-195 (2012)). A study showed that endomysial fibrosis was the only myopathologic parameter that significantly correlated with poor muscle strength and the age of the loss of ambulation in DMD patients. The H&E staining of HIF-C2-treated and control muscle sections revealed that the vehicle-treated control muscle had overtly increased endomysial space compared to HIF-C2 treated muscles (particularly in male mTR/Mdx mice), indicative of a difference in endomysial fibrosis. Thus, Masson's trichrome staining was performed to reveal the amount of collagen in endomysium. Indeed, HIF-C2 treated muscles had a remarkably reduced amount of collagen in endomysial space compared to vehicle-treated control muscles. Therefore, HIF-2α inhibition also prevented fibrosis development in dystrophic muscles.

There is an urgent need for treatment to delay the progression of heterogeneous dystrophic and myopathic genetic diseases and improve patients' lifespan and quality of life. This disclosed experiments demonstrates that muscle hypoxia is a common co-morbidity in two non-related types of muscular dystrophies, which strongly supports that the hypothesized vicious circle (FIG. 7) is a common disease mechanism for many severe types of muscular dystrophies and myopathic diseases. Understanding this latent disease mechanism substantiates the therapeutic application of HIF-2α inhibition for these devastating diseases.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of enhancing, increasing, accelerating or/and otherwise improving skeletal muscle generation or regeneration in a subject in need thereof comprising administering the subject an effective amount of HIF-2α inhibitor.

2. The method of claim 1, wherein the HIF-2α inhibitor is effective to increase muscle satellite cell proliferation, differentiation, or a combination thereof in a subject.

3. The method of claim 1, where the HIF-2α inhibitor is effective to increase or accelerate differentiation of satellite cells into myoblasts in the subject.

4. The method of claim 1, wherein the HIF-2α inhibitor is a small molecule or a functional nucleic acid.

5. The method of claim 4, wherein the HIF-2α inhibitor is the small molecule PT2385, PT2977, PT-2399, or a derivative, stereoisomer, or pharmaceutically acceptable salt thereof.

6. The method of claim 4, wherein the HIF-2α inhibitor is a functional nucleic acid selected from the group consisting of antisense molecules, siRNA, miRNA, aptamers, ribozymes, triplex forming molecules, RNAi, and external guide sequences that targets the HIF-2α gene or a gene product thereof.

7. The method of claim 1, wherein the HIF-2α inhibitor is targeted to skeletal muscle.

8. The method of claim 1, wherein the HIF-2α inhibitor is administered to the subject by an oral, parenteral, transdermal, or transmucosal administration.

9. The method of claim 1, wherein the HIF-2α inhibitor is administered to the subject locally or systemically.

10. The method of claim 1 wherein the subject has a skeletal muscle injury.

11. The method of claim 1 wherein the subject has a skeletal muscle disease or disorder.

12. The method of claim 1, wherein the method increases myofiber number, length, density, cross sectional area, or a combination thereof, increases muscle strength or volume, or any combination thereof in the subject.

13. The method of claim 1, wherein the subject has a muscular dystrophy or myopathogenic disorder, fibrosis, poor respiration, or a combination thereof.

14. The method of claim 13, wherein the muscular dystrophy or myopathic disorder is one or more of a dystrophin-glycoprotein complex (DGC)-related dystrophy, a congenital muscular dystrophy, a muscle-eye-brain disease, a facioscapulohumeral dystrophy, a limb-girdle muscular dystrophy, ocular muscular dystrophy, and oculpharyngeal muscular dystrophy, a myotonic dystrophy an oculopharyngeal muscular dystrophy, a congenital myopathy, a toxic myopathy, an inflammatory myopathy, an endocrine or metabolic myopathy, a vitamin D deficiency, a mitochondrial myopathy, glycogenoses, a lipid storage myopathy, a myotonic disease, and periodic paralyses.

15. The method of claim 13, wherein the muscular dystrophy or myopathic disorder is Bethlem myopathy, Bethlem congenital muscular dystrophy (CMD), Duchenne Muscular Dystrophy, Becker dystrophy, Fukuyama CMD, Ullrich CMD, Walker-Warburg syndrome, Emery-Dreifuss Muscular Dystrophy, a limb-girdle muscular dystrophy 2 (2A-2L), myotonic dystrophy type 1, myotonic dystrophy type 2, rigid spine syndrome, or myasthenia gravis.

16. A method of increasing skeletal muscle generation or regeneration comprising administering to a subject with a skeletal muscle injury, disease, or disorder an effective amount of a small molecule HIF-2α inhibitor to increase skeletal muscle generation or regeneration.

17. The method of claim 16, wherein the small molecule is PT2385, PT2977, PT-2399, or pharmaceutically acceptable salt thereof.

18. The method of claim 17, wherein the small molecule is administered orally to the subject.

19. The method of claim 17, wherein the small molecule is administered to a muscle in need of skeletal muscle generation or regeneration.

20. The method of claim 18, wherein the disease a muscular dystrophy.

* * * * *